(12) United States Patent
Sadik et al.

(10) Patent No.: US 11,091,597 B2
(45) Date of Patent: Aug. 17, 2021

(54) PACKAGING MATERIAL AND METHODS OF USING THE SAME

(71) Applicant: The Research Foundation for The State University of New York, Albany, NY (US)

(72) Inventors: Omowunmi A. Sadik, Vestal, NY (US); Idris Yazgan, Johnson City, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 315 days.

(21) Appl. No.: 15/987,198

(22) Filed: May 23, 2018

(65) Prior Publication Data
US 2018/0340049 A1 Nov. 29, 2018

Related U.S. Application Data

(60) Provisional application No. 62/509,919, filed on May 23, 2017.

(51) Int. Cl.
| | |
|---|---|
| *C08J 5/18* | (2006.01) |
| *C08L 79/08* | (2006.01) |
| *A01N 37/24* | (2006.01) |
| *B65D 65/46* | (2006.01) |
| *G01N 33/02* | (2006.01) |

(Continued)

(52) U.S. Cl.
CPC .............. *C08J 5/18* (2013.01); *A01N 25/10* (2013.01); *A01N 37/24* (2013.01); *B65D 65/466* (2013.01); *C08J 3/24* (2013.01); *C08K 5/07* (2013.01); *C08K 5/175* (2013.01); *C08L 79/08* (2013.01); *G01N 33/02* (2013.01); *B32B 2307/7163* (2013.01); *B32B 2367/00* (2013.01); *B32B 2379/00* (2013.01); *B32B 2439/80* (2013.01); *B65B 25/001* (2013.01); *B65B 25/02* (2013.01); *B65B 25/04* (2013.01); *B65B 25/041* (2013.01); *B65B 25/062* (2013.01); *B65B 25/067* (2013.01); *B65D 81/24* (2013.01); *B65D 81/28* (2013.01); *C08J 2367/04* (2013.01); *C08J 2379/08* (2013.01); *C08K 5/0025* (2013.01); *C08K 5/0058* (2013.01); *C08K 5/053* (2013.01); *C08K 5/13* (2013.01); *C08K 5/1545* (2013.01);
(Continued)

(58) Field of Classification Search
None
See application file for complete search history.

(56) References Cited

U.S. PATENT DOCUMENTS

| | | | | |
|---|---|---|---|---|
| 6,326,364 B1 * | 12/2001 | Lin | ...................... | A61P 31/04 514/154 |
| 6,495,368 B1 * | 12/2002 | Wallach | ................ | G01N 31/221 422/421 |

(Continued)

FOREIGN PATENT DOCUMENTS

| | | | |
|---|---|---|---|
| CN | 101643544 A | * | 2/2010 |
| CN | 101947415 A | * | 1/2011 |

(Continued)

*Primary Examiner* — Vivian Chen
(74) *Attorney, Agent, or Firm* — Scully, Scott, Murphy & Presser, P.C.

(57) ABSTRACT

The present disclosure is directed to films. The films can include polyamic acid (PAA). Methods of making and using the film for food product coverings is also included.

17 Claims, 96 Drawing Sheets
Specification includes a Sequence Listing.

(51) Int. Cl.

| | | |
|---|---|---|
| C08J 3/24 | (2006.01) | |
| A01N 25/10 | (2006.01) | |
| C08K 5/17 | (2006.01) | |
| C08K 5/07 | (2006.01) | |
| C08K 5/00 | (2006.01) | |
| C08L 67/04 | (2006.01) | |
| C08K 5/13 | (2006.01) | |
| C08K 5/053 | (2006.01) | |
| C08K 5/1545 | (2006.01) | |
| C08K 5/375 | (2006.01) | |
| B65D 81/28 | (2006.01) | |
| B65D 81/24 | (2006.01) | |
| B65B 25/04 | (2006.01) | |
| B65B 25/06 | (2006.01) | |
| B65B 25/00 | (2006.01) | |
| B65B 25/02 | (2006.01) | |

(52) U.S. Cl.
CPC .............. *C08K 5/375* (2013.01); *C08L 67/04* (2013.01); *C08L 2203/16* (2013.01)

(56) References Cited

U.S. PATENT DOCUMENTS

| | | | | |
|---|---|---|---|---|
| 2004/0018278 | A1* | 1/2004 | Popplewell | B32B 27/08 426/132 |
| 2004/0253451 | A1* | 12/2004 | Kawashima | C23C 16/30 428/411.1 |
| 2008/0296225 | A1* | 12/2008 | Ho | B01D 67/0006 210/640 |
| 2009/0280266 | A1* | 11/2009 | Komada | B32B 27/08 427/527 |
| 2013/0052277 | A1* | 2/2013 | Weiss | B01D 69/148 424/618 |
| 2013/0108678 | A1* | 5/2013 | Santra | B82Y 30/00 424/409 |
| 2014/0205729 | A1* | 7/2014 | Didzbalis | A23L 27/21 426/537 |
| 2015/0108061 | A1* | 4/2015 | Chi | B01D 69/125 210/490 |
| 2015/0114907 | A1* | 4/2015 | Gong | B01J 20/267 210/660 |
| 2017/0143022 | A1* | 5/2017 | Wicker | A23L 27/20 |

FOREIGN PATENT DOCUMENTS

| | | | |
|---|---|---|---|
| CN | 103589153 A | * | 2/2014 |
| JP | 2008-308645 A | * | 12/2008 |
| WO | WO 2007/084921 A | * | 7/2007 |

\* cited by examiner

| Membrane/Film | Modulus Elasticity, GPa | Tensile Strength, MPa | Elongation at Break, % |
|---|---|---|---|
| Polyvinyl chloride | 2.4-3.2 | 66.6 | 8.75 |
| Polycarbonate | 2.4-3.0 | 64.9 | 42.2-82.7 |
| Polyethylene terephtalate | 2.76-4.14 | 48.3-79.6 | - |
| Polystyrene | 2.28-3.34 | 35.9-56.5 | - |
| Mesoporous silica | 2.3 | 60.9 | 7.3 |
| C-ATH | 2.3 | 47.1 | 2.1 |
| SPI-PLA | 1.6 | 13.7 | 1.3 |
| PLA | 2.6 | - | 3.5 |
| PLA film | 0.9 | 20.5 | 246 |
| PHBV3-PEG | 1.6 | 39.0 | 3.4 |
| PAA-I-GA | 2.2 | 59.9 | 70.4 |
| PAA-A-GA | 2.7 | 66.9 | 5.8 |
| PAA-BB-GA | 2.2 | 68.9 | 40.9 |
| PAA-I-pAS-GA | 2.6 | 84.8 | 13.8 |
| PAA-SA-pAS-5AS-GA | 3.9 | 91 | 85 |
| PAA-pAS-SA-GA | 4.1 | 95.1 | 88.9 |

C-ATH: chitosan-anthocyanins intelligent films; SPI-PLA: isolated soy protein-poly(lactic)acid; PLA; Poly(lactic)acid; PHBV3-PEG: polyhydroxybutyrate (PHB) and a polyhydroxybutyrate-co-valerate copolymer with 3% valerate content (PHBV3)-Polyethyleneglycol (PEG); PAA: poly(amic)acid; A: L-alanine; GA: glutaraldehyde; BB: 2-benzylbenzoil; I: L-isoleucine; pAS; p-aminosalicylic acid. All of these membranes given here were from FIG. 1b.

FIG. 66

PACKAGING MATERIAL AND METHODS OF USING THE SAME

CROSS REFERENCE TO RELATED APPLICATIONS

The present application claims benefit of U.S. Provisional Application 62/509,919, filed on May 23, 2017, the contents of which are incorporated by reference.

STATEMENT REGARDING FEDERALLY SPONSORED RESEARCH OR DEVELOPMENT

This invention was made with government support under grants CBET 1230189 and DMR 1007900 awarded by the National Science Foundation. The government has certain rights in the invention.

INCORPORATION BY REFERENCE OF SEQUENCE LISTING

The Sequence Listing in the ASCII text file, named as 34570_SequenceListing.txt of 32 KB, created on May 21, 2018, and submitted to the United States Patent and Trademark office via EFS-Web, is incorporated herein by reference.

BACKGROUND OF THE DISCLOSURE

Smart packaging requires the packaging materials to provide simultaneous active protection and intelligent communication with food and other perishable materials. In that respect, packaging materials should perform the dual role of sensing and packaging.

Smart packaging requires that the packaging materials provide active protection and intelligent communication about the packaged food. Package materials add extra protection for the food by providing information about time and past conditions of the food. Intelligent packaging advances communication capabilities of traditional packaging materials by providing information about the integrity and quality of the packaged foods and its surrounding environment from packaging, to storage, transport and market shelves. Current smart packaging uses radio frequency identification, and indicators of environmental factors such as pH and heat. Even though these are commercially available, the cost is still high for large scale applications.

In contrast to intelligent packaging, active packaging does not provide information about the condition of packaged food, but enhances the shelf-life through a variety of mechanisms, including, but not limited to, moisture absorption, antimicrobial packaging material, antioxidants, carbon dioxide emitters and oxygen scavengers.

Further, most food packaging materials in use are derived from starting materials that are either obtained from petrochemicals or they require the use of organic toxic solvents. The resulting polymers are not biodegradable.

Currently, there is no practical food packaging system that integrates intelligent and active capabilities and is also biodegradable.

Therefore, what is desired is a film and film material that can be used for, among other uses, food packaging, that provides intelligent and active capabilities.

Embodiments of the present disclosure provide devices and methods that address the above and other issues.

SUMMARY OF THE DISCLOSURE

The present disclosure is directed to films. The films can include polyamic acid (PAA). Methods of making and using the film for food product coverings is also included.

BRIEF DESCRIPTION OF THE DRAWINGS

The file of this application contains at least one drawing executed in color. Copies of this patent with color drawing(s) will be provided by the Patent and Trademark Office upon request and payment of the necessary fee.

The present disclosure will be better understood by reference to the following drawings of which:

FIG. 66 is a table of various PAA films' properties.

DETAILED DESCRIPTION OF THE DISCLOSURE

Figure 1A:
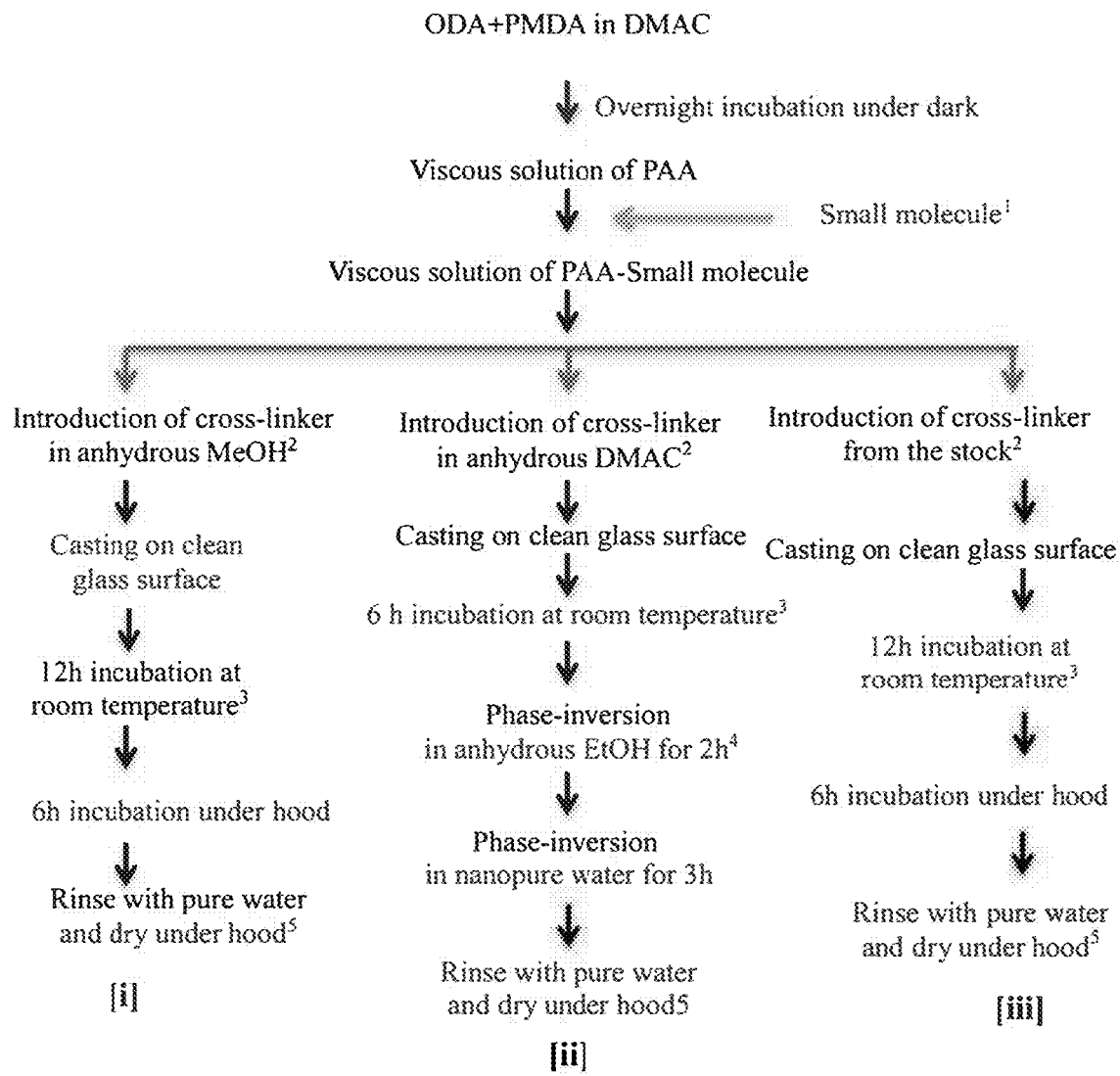
FIG. 1a is an illustration of the synthesis of PAA and ternary PAA copolymers.

In the discussion and claims herein, the term "about" indicates that the value listed may be somewhat altered, as long as the alteration does not result in nonconformance of the process or structure to the illustrated embodiment. For example, for some elements the term "about" can refer to a variation of ±0.1%, for other elements, the term "about" can refer to a variation of ±1% or ±10%, or any point therein.

As used herein, the term "substantially", or "substantial", is equally applicable when used in a negative connotation to refer to the complete or near complete lack of an action, characteristic, property, state, structure, item, or result. For example, a surface that is "substantially" flat would either completely flat, or so nearly flat that the effect would be the same as if it were completely flat.

As used herein terms such as "a", "an" and "the" are not intended to refer to only a singular entity, but include the general class of which a specific example may be used for illustration.

As used herein, terms defined in the singular are intended to include those terms defined in the plural and vice versa.

Reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes whole numbers of 5, 6, 7, 8, 9, and 10, and fractional numbers 5.1, 5.2, 5.3, 5.4, 5.5, 5.6, 5.7, 5.8, 5.9, etc.

As used herein, the term "film" refers to a thermoplastic film made using a film extrusion and/or foaming process, such as a cast film or blown film extrusion process. For the purposes of the present invention, the term includes nonporous films as well as microporous films. Films may be vapor permeable or vapor impermeable, and function as liquid barriers under normal use conditions.

As used herein, the term "thermoplastic" refers to polymers of a thermally sensitive material, which flow under the application of heat and/or pressure.

As used herein, the term "polymers" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

Biodegradable Ternary Co-polymers of Conducting Electroactive PAA Membranes hereby referred to as membranes or films. For descriptive purposes, the term membrane has the same definition as that of the term "film" discussed above.

Polyamic acid (PAA) is a polymer that has many novel properties. PAA is electroactive, substantially biodegradable and has free carboxyl and amide groups that can act as molecular anchors. PAA can also be used in conjunction with both organic and inorganic solvents due to its substantial chemical resistance. PAA is a generic name of use for the polycondensation product of dianilines and dianhydrides synthesized in anhydrous organic aprotic polar solvents.

The present disclosure is directed to PAA films and PAA films as food packaging materials that can provide both active-packaging qualities and intelligent-packaging qualities. These PAA films and PAA films as food packaging materials can be formed without any petroleum based or petrochemical ingredient and/or any ingredient formed from a hydrocarbon and/or without an organic solvent.

The PAA films were created from compositions including biological compounds (e.g. amino acids, sugars) and one or more of intrinsic antimicrobial agents (e.g. sulfanilic acid, p-aminosalicylic acid), and cross-linkers (e.g. glutaraldehyde, carbodiimidazole) in the presence of other substances, for example diamines and dianhydrides. Also, PAA can be further modified into polyimide depending on the processing conditions or employed as stabilizing agents during nanoparticles synthesis.

H DOSY NMR studies showed that the average molecular weight of PAA films were between about $10^6$ and about $10^7$ Da while average molecular weight of regular PAA polymer was about $1.43 \times 10^5$ Da.

PAA has advanced mechanical properties in the range of about 2.2-about 2.7 GPa modulus elasticity comparable to strong plastics (2.4 to 3.2 GPa).

PAA also demonstrates stability in common solvents, high optical transparency, impermeability to gas exchange, oil and water vapor transfer.

FIG. 66 is a table of modulus elasticity, tensile strength and elongation of six films of the present disclosure (bottom six films on the list) as compared to other non-PAA films.

Non-crude oil-based plastic PAA films illustrate voltage changes in response to pH change. Showing a trend in response to pH change demonstrates the intelligent properties of the packaging material of the present disclosure, which does not require complicated sensor electronics to indicate food freshness/quality. In the table below, it can be also seen that there is a voltage change in the disclosed films as a function of their thickness.

TABLE A

| Membrane Type | Thickness [mm] | DC Voltage [mV] |
|---|---|---|
| PAA-A-GA | 0.02 | −0.7 |
| PAA-W-GA | 0.02 | 1.2 |
| PAA-BB-GA | 0.02/0.06 | −0.4/0.4 |
| PAA-PCl-GA | 0.06 | 0.9 |
| PAA-C-GA | 0.02 | 1.8 |
| PAA-DA-GA | 0.03 | 0.1 |
| PAA-PCl-GA | 0.06/0.12 | −0.6/−1.1 |
| PAA-W-GA | 0.02 | 2.4 |
| PAA-A-GA | 0.05 | 0.4 |
| PAA-DP-GA | 0.05 | −0.4 |
| PAA-pAB-W-GA | 0.06 | −0.9 |
| PAA-pAB-GA | 0.06 | −0.5/−0.4 |
| PAA-A-GA | 0.09 | −0.6 |

In Table A PAA: Poly (amic) acid; GA: Glutaraldehyde and the letters in the middle refer to different small molecules such as A-alanine and W-tryptophane. As referred to herein, the term small molecule can refer to any organic molecule having a low molecular weight of less than about 900 Daltons) that may regulate a biological process, with a size on the order of about 1 nm. Type of small molecule and concentration of glutaraldehyde affect voltage of dry PAA membrane's potential, and its behavior against changes as a function of pH and salt concentrations.

Microbiological tests showed that there was no bacterial development which means that PAA copolymer films developed in connection with the present disclosure worked as a strong active packaging material. As a packaging material, the PAA films can be provided on a roll, the film provided with a predetermined width and a predetermined length. An example of an existing roll of this type would be a roll of Saran™ Wrap, having a width of about 12" and a length of tens or hundreds of feet. Rolls of the disclosed PAA films can be wider or narrower, and can also be longer or shorter than this example, as desired.

The disclosed PAA films can be applied so as to cover an entire food product, or a portion thereof. The PAA films can also be provided so as to contact the entire food product or a portion of the food product, or so as to not contact any portion of the food product due to an intervening material or a space between the food product and the PAA film. The disclosed PAA films can be applied by a user and/or the disclosed PAA films can be applied by a packaging device/machine.

As discussed below, packaged food products did not include color changes or fungal development, this is related to the non-porous nature of PAA film, which did not allow air and water vapor entry. Measured voltage (0.2 mV) did not show any changes which means that there was no food spoilage and decomposition during the tested times.

The utilization of organic solvents such as ethanol is generally not preferred in the synthesis of PAA since they are nucleophiles and can compete with the dianiline component to attack the dianhydride resources. In the present disclosure, the use of ethanol and even water as part of the solvent system did not show any effect on the formation of the PAA polymer when solid dianhydride was added to an already dissolved dianiline. This represents a major deviation from standard chemistry of PAAs and one that has led to the preparation of a new class of stable polymeric compositions and novel processing procedures as reported here. We however, observed the (FIGS. 2a-2q) formation of ester and alteration in the repeating units of PAA. As shown in Table B, the utilization of ethanol as part of the solvent system significantly improved the mechanical properties of the synthesized films/membranes.

TABLE B

Selection of solvent and formation of viscous PAA solution.

| Mixture of solvent | Observation |
|---|---|
| 50:50 or 35:65, DMAC:EtOH | High viscosity, require warming (i.e. 50° C.), resulting in membranes that are strong but limited colors (no blue color obtained) |
| 25:75, DMAC:EtOH | Medium viscosity, require warming (i.e. 60° C.), resulting in membranes that are strong, but limited colors |
| 35:50:15 or 30:50:20, DMAC:EtOH:Water | Medium viscosity, require warming (i.e. 60° C.), produces membranes with broad range of colors. The color intensity is stronger than those prepared using DMAC. |
| 60:40, DMAC:Water | Did not form PAA viscous solution but resulted in yellow precipitate. This did not result in any membrane formation. |
| 60:30:10, DMAC:Water:AcOH | Did not form PAA viscous solution but resulted in yellow precipitate. This did not result in any membrane formation. Acetic acid limits the role of GA. |

It should be noted that heating was not continuous; rather it was stopped right after PMDA was added to the dissolved 4,4'-oxydianiline (ODA). Continuation of heating resulted in highly viscous PAA solution which does not allow membrane formation.

Another important observation noted here was that the average molecular size of PAA polymers decreased when the solvent system changed from DMAC to DMAC/Ethanol, and further decreases were observed for DMAC/Ethanol/Water system.

Parameters relating to the synthesis of FIG. 1a membranes were evaluated at four aspects(1)-(4).

(1) Formation of Amorphous, Glassy and Plasticized Membranes

When pure PAA viscous solution (either from ODA+PMDA or PDA+PMDA) was casted on glass to form membrane, the fate of the membrane was shown to be determined by evaporation mediated solvent elimination and solvent-nonsolvent exchange in coagulation bath.

TABLE C

Effect of evaporation period on PAA membrane preparation

| Incubation time(h)[1] | Texture | Character |
|---|---|---|
| <4 h | Amorphous | Similar to phase inverted PAA membrane in coagulation-bath |
| 4-8 h | Glassy | The outer surface is shiny, but not totally plasticized. The membrane turns into brittle form within 2 h right after being taken out from the coagulation-bath |
| 6-10 h | Mix | Mostly the outer layer is fully plasticized while the inner part is amorphous. The membranes are durable, and never turn into a glassy form |
| >12 h | Plasticized | Plastic-like transparent membrane, durable and flexible. Coagulation-bath doesn't affect appearance of the membrane |

Incubation time refers to the time-period when membranes were incubated under a hood at 80 rpm/min face-shield. In all cases, the coagulation bath employed was pure-water. [1]Thickness and viscosity of the casted PAA solution affected the time requirement, but 12 h or over were enough to obtain plasticized membranes for the casted solutions at up to 2 mm (beyond this point, thicker membranes were not tested) thickness. For thin membranes (e.g. below 50 μm), 6 h was enough to obtain fully plasticized membranes. Evaporation of the solvent is the main element determining the fate of the membrane's texture. This is further discussed below. However, the most prominent parameter is the humidity of the surrounding environment. However, pre-heating the casted PAA solution decreases the negative effect of the humidity, which can lead to accelerated removal of DMAC coupled with enhanced GA activity.

(2) Crosslinker Effect on Membrane Formation

In accordance with the present disclosure, glutaraldehyde (GA) was used as the cross-linker due to the fact that GA provided the most pronounced effect on PAA membrane formation.

TABLE D

Effect of evaporation period on PAA-GA membrane preparation

| Incubation time (h)[1] | Texture | Character |
|---|---|---|
| <2 h | Amorphous | Similar to phase inverted PAA membrane in coagulation-bath |
| 4-6 h | Glassy | The outer surface is shiny, but not totally plasticized while the edges are totally plastic-like. The membrane turns into brittle form within 1 h right after taken out from the coagulation-bath. The brittle form shows very high glassy character. |
| 4-8 h | Mix | The outer layer is fully plasticized while the inner part is amorphous. Only thicker membranes (e.g. over 2 mm) forms this type of membranes. These ultimately turns into glassy-brittle form within days. |
| >8 h | Plasticized | Plastic-like transparent membrane, durable, flexible and non-soluble in common organic solvents. Coagulation-bath does not affect appearance of the membrane |

[1]Viscosity of the casted solution is determined by GA activity. Other than GA, other crosslinkers were also used as detailed below.

The time difference between transformations from amorphous to glassy texture were linked to the degree of cross-linking. This is attributed to the fact that the cross-linker is becoming an element in determining the fate of the membrane in terms of color and texture. It is not critical that the membrane loses a higher proportion of the DMAC in order to form the plasticized PAA membranes. This is related to cross-linking of individual PAA membranes with crosslinker (i.e. glutaraldehyde). For example, in the case of p-phenylenediamine (PDA)-PMDA based PAA membrane, 30 min incubation is sufficient to provide the plasticized PAA membranes unlike the ODA-PMDA based PAA membrane that requires over 4 h incubation. This is expected because PDA has two amino groups which enhance its cross-linking with GA. Even though, no chemical treatment was performed in DMAC, the final forms of the membranes even for relatively lower GA concentrations (pre-diluted in DMAC) were still obtained in the plasticized form. This was not common for the GA concentrations that were directly added from stock. For example, in the case of PAA-CS-GA membrane, the same amount of GA when dissolved in water produced an amorphous membrane while GA that was pre-diluted in DMAC provided plasticized membrane. Further, heat treatment to GA/PAA membranes resulted in plasticized membranes, which can be related to the promotion of cross-linking and faster evaporation of solvent. Further details are provided below.

(3) Small-Molecule Effect

None of the small molecules showed any strong impact on membrane formation when added to the casted PAA solution without the co-addition of the cross-linker. Increase in viscosity related to the addition of small molecule (excluding the cross-linker GA) did not affect the overall membrane formation (amorphous, glassy or plasticized) as detailed below. However, the use of small molecules in the presence of the cross-linkers significantly impacts the structure, the plasticity and other notable physical attributes of the resulting membranes.

As shown below, while certain small molecules with PAA copolymers ended up as plasticized membranes, others were amorphous in nature. Similarly, the mechanical properties of the membrane under same conditions showed direct dependence on type of the small molecule employed.

Figure 70:
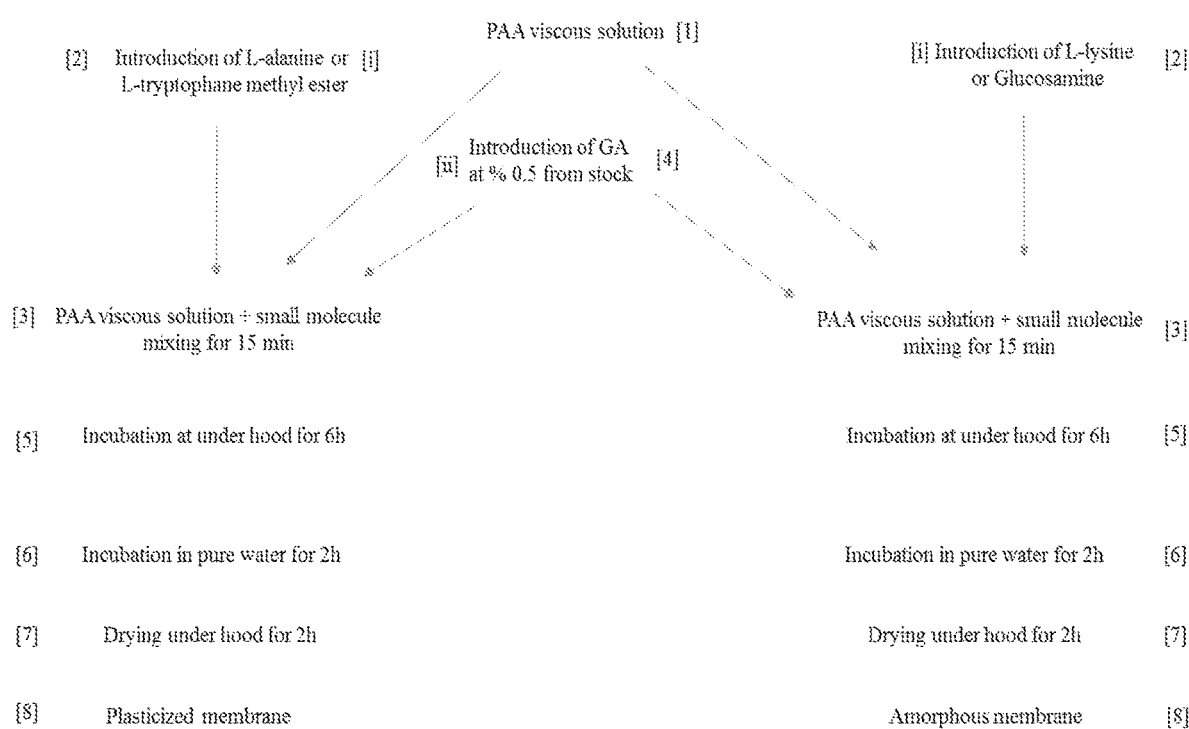
FIG. 70 is a graphical illustration of the effect of small molecules on membrane formation.
Figure 71:
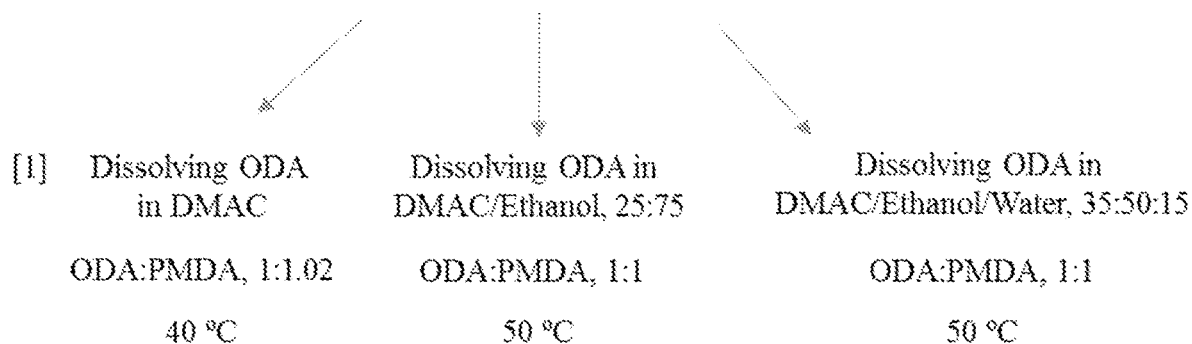
FIG. 71 is a graphical illustration of the steps in the synthesis of a PAA polymer.

FIG. 70 illustrates the effect of small molecule on membrane formation. (i) Selection of small molecule is not limited to these small molecules; (ii) GA concentration has strong influence on the final form of the membrane apart from the small molecule used in the study.

The addition of glutaraldehyde is an element in the kinetics of membrane formation. For example, at 0.5% GA concentration, the time needed to form a stand-alone membrane diminishes. This change is believed to be coming from the alteration in the characteristics of the solution itself. For example, PAA alone requires 12 h to form a membrane of PAA alone; PAA-GA requires 8 h while PAA-GA-SA requires 4 h to give stand-alone (FIG. 1a) membranes. The time requirement for providing stand-alone membrane is subject to change in response to thickness of the casted solution. However, it should be noted that obtaining stand-alone membrane in shorter period may not be related to faster drying.

When the stand-alone membrane is first obtained, its mechanical property is poorer than the membranes that are fully dried. The modulus of elasticity and tensile strength are the main parameters that improved dramatically when the membrane is fully dried. In contrast to this, % elongation decreases at least two-times upon total drying, which was observed for PAA-I-GA, PAA-K-GA, PAA-CA-GA or thicker PAA-GA (over 2 mm casted solution) membranes; when they get dry, they show very high glassy character which makes them as brittle as glass.

L-alanine and L-cysteine in all cases of provided plasticized PAA membranes, and L-tryptophan-methyl ester also provided plasticized-membranes if the conditions are controlled in terms of humidity and heat. However, utilizing higher concentrations of GA (i.e. 2% or higher) for any type of small molecule co-polymerized with PAA resulted in plasticized PAA membranes. These also affect the formation of colorful membranes. Here, for example, L-alanine gives green membrane while PAA-GA gives chestnut color membrane. Actually, PAA-A-GA provided the membranes which were the best examples of plasticized membranes for FIG. 1a membranes, which was also comparable to the membranes obtained from FIG. 1b. Regarding color formation, even for PAA-small molecule co-polymers, the age of GA can influence the results.

(4) Final Step of Coagulation Bath

TABLE E

Effect of coagulation bath on membrane surface characteristics.

| Coagulation-bath | Surface-characteristics |
| --- | --- |
| Pure-water | Shiny, porous or non-porous |
| Methanol[1, 2] | Sponge, nano-fabric or porous |
| Ethanol[1, 3] | Sponge, nano-fabric or porous |
| Ethanol-water mixture[1] | Sponge and non-porous |

In Table E, [1]For extended evaporation times, sonication might be required in order to obtain nano-fabric and/or sponge surfaces. [2]The membranes, which are giving glassy texture/form in the case of pure-water coagulation bath, give sponge or non-porous surfaces and durable membranes. [3]In the case of pure-water coagulation bath, the membranes becomes brittle within times.

Membranes possessing nano-porous, sponge, nano-fabric, non-porous and featureless surfaces can be obtained using the method depicted in FIG. 1a, which are detailed below.

Figure 1B:
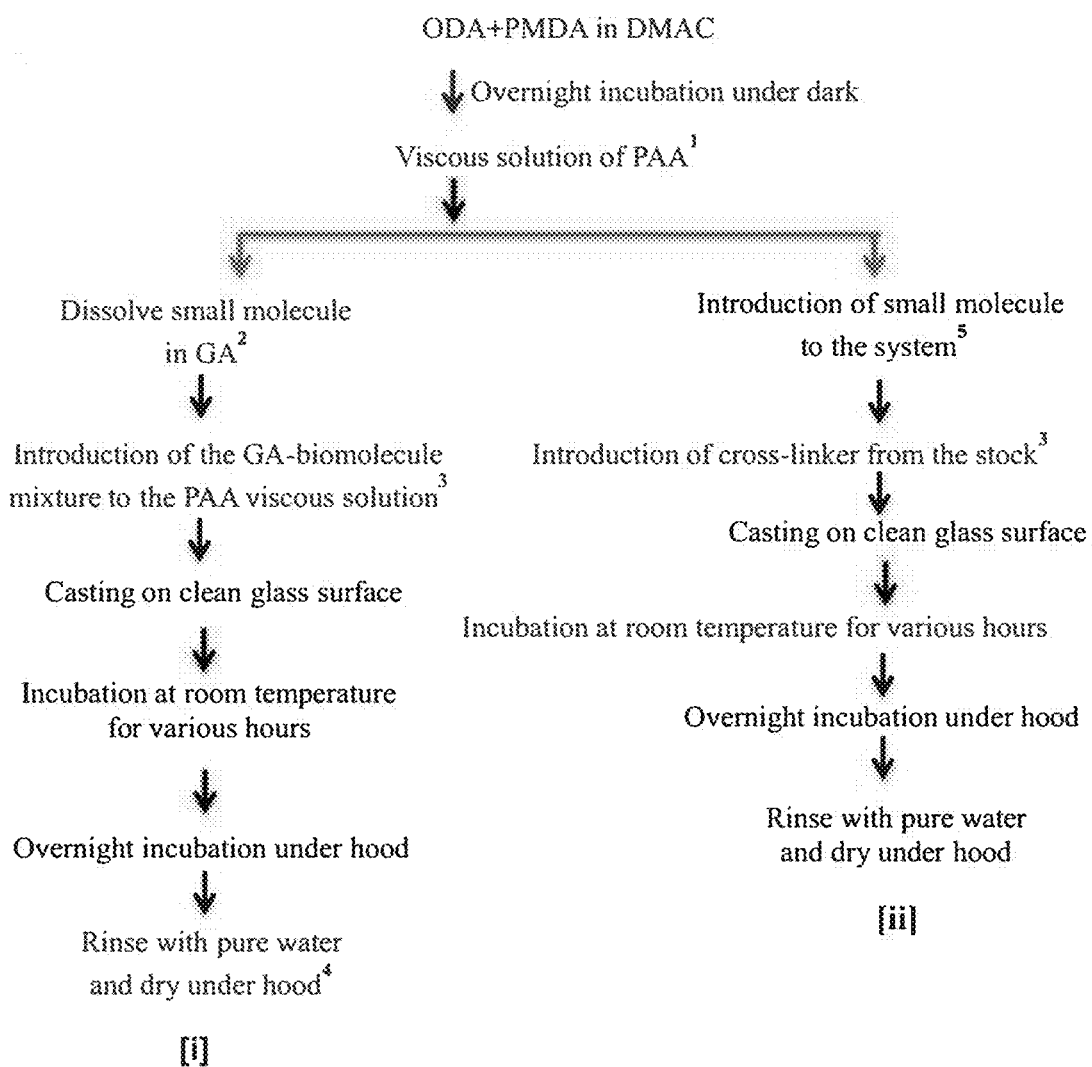
FIG. 1b is an illustration of the synthesis of PAA.

Characteristic differences exist between the methods depicted in FIG. 1b and FIG. 1a. These differences are discussed below and throughout the application. These include (i) evaporation is the main driving force for phase-inversion, (ii) small-molecules, which are co-polymerized with PAA are dissolved in PAA viscous solution or pre-dissolved in a solvent prior to being co-polymerized with PAA, (iii) small-molecule can be cross-linked with the cross-linker in order to adapt the overall properties of the resulting membrane, and (iv) flexible design via combination of small molecules and/or the order of the addition of the small molecule or cross-linker.

GA is a cross-linker. Since GA can exist in different chemical forms in aqueous and organic solvents (as detailed below) it is adapted for the objectives met by the present disclosure. For example, GA can be polymerized into a water-soluble and non-soluble forms based on the objective. Here, GA was first aged through incubating the solution at 70° C. for hours. Optimization was followed with NMR characterization. As detailed below, the following manipulations were performed for GA to obtain the desired membranes;

i. Utilization of aged or non-aged GA. While aged GA is used in order to obtain fluorescently active membranes, non-aged GA was preferential to obtaining physically strong membranes.

ii. Quenching GA activity with methanol or ethanol is needed in order to obtain physically strong membranes. The addition of methanol results in physically strong and non-soluble membranes.

iii. Concentration of GA or heat-treatment of GA before it is introduced to PAA solution has strong effect on membrane formation with respect to color and time-requirement for stand-alone membrane formation.

iv. Very high concentrations of GA (i.e. over 2%) prevent the formation of ideal long-lasting membranes; higher GA makes PAA membranes brittle and even in some cases disrupts proper membrane formation. In the case of imidazole, concentrations can vary as described below.

As used herein, the term "fresh" or "non-aged" GA refers to GA purchased from companies, which were used as received and stored at all times at about −20° C. The term "aged" GA refers to GA that was kept in an oven for about 1-2 hours (e.g. 50-70° C.) prior to use. The term "over-aged" refers to GA that was stored at room temperature for about 2 weeks or longer.

The data and discussion below presents the development, processing, characterization and novel applications of the disclosed films. Due to the organic solvents being environmental pollutants, replacing them with substantially environmentally benign solvents are desired.

1D and 2D NMR techniques indicated that DMAC/EtOH and DMAC/EtOH/Water solvent mixtures were applicable for generating PAA polymers synthesized in DMAC. Reducing the use of DMAC by about 75% did not affect the PAA synthesis. However, the repeating units were altered as cis-/trans-ratio and the average molecular weights of the PAA polymers decreased by up to 5 times. The use of crosslinkers, especially GA, was utilized to alter the kinetics of the phase-inversion. GA is a component in the synthesis leading to the formation of amorphous and plasticized membranes. Small molecules were co-polymerized with PAA to manipulate the overall properties of the membrane with respect to their plasticity, antimicrobial properties and mechanical strengths, as discussed in detail below.

The methods, apparatus and compositions of the present disclosure will be better understood by reference to the following Examples, which are provided as exemplary of the disclosure and not by way of limitation.

Example 1.1—Materials and Methods

All of the reagents used in this and the following examples were purchased from Sigma-Aldrich (St. Louis, Mo.). *Escherichia coli* ATCC® 25922™ *Citrobacter freundii*, ATCC® 8090 and *Staphylococcus epidermidis* ATCC® 12228™ were purchased from American Type Culture Collection (ATCC) (Manassas, Va., USA). Dimethyl sulfoxide (DMSO)-$d_6$ was purchased from Cambridge Isotope Laboratories (Andover, Mass. USA). Unless otherwise specified, phosphate saline (PBS) buffer was used as 50 mM pH 7.2. All solutions were prepared with triply distilled Nanopure water with resistivity of 18 MΩ.

FIG. 7l illustrates the steps in the synthesis of a PAA Polymer of the present disclosure using optional solvent systems: The ratio of 4,4'-oxydianiline (ODA):PMDA was tested from 1.20:1.00 to 1.00:1.05. The ratio given for each solvent was used through the examples.

The synthesis of PAA films in accordance with the present disclosure is shown in FIG. 1a. In the process of FIG. 1a, crosslinkers serve as a reactive transforming agent that crosslinks re-organize the kinetics of the membrane formation and define the fate of the membrane.

The superscript numbers herein refer to the steps of the corresponding superscript numbers in FIG. 1a. In FIG. 1a, the preparation of PAA and Ternary PAA co-polymers is illustrated. MeOH refers to methanol and DMAC refers to N,N'-dimethylacetamide. [1]Examples include D-glucosamine, L-lysine, L-alanine and other amino acids. [2]Glutaraldehyde stock was obtained in water, but throughout the study it was added as pre-dissolved in methanol or DMAC to possibly alter its activity by changing the working microenvironment. [3]Since pre-treating GA with MeOH or DMAC affected the activity; their incubation at room temperature was taken at periodic intervals. But incubation time was changed just to alter the resulting surface properties of the PAA membrane. [4]Phase-inversion in ethanol/water mixture was applied to alter the surface properties of the resulting membrane. [5]The last step of phase-inversion took place in nano-pure water, followed by drying under hood.

Further synthesis of PAA films is shown in FIG. 1b. The superscript numbers herein refer to the steps of the corresponding superscript numbers in FIG. 1b. [1]Methanol can be added to the system at this stage; [2]This procedure was only used for amino acids and glucosamine; [3]Methanol can be added to the system immediately after the introduction of GA-biomolecule; [4]The membrane can be sonicated in methanol/ethanol/methanol-water mixture. [5]The small molecules, 4-amino-2-chlorobenzoic acid, p-aminobenzoic acid and aminosalycilic acid, could be added to the system during PAA synthesis. Films generated using the synthetic method of FIG. 1b were used for food-packaging throughout the examples.

Example 1.2—Structural Characteristics of PAA Films

The PAA film and the functionalized derivatives were dissolved in DMSOd6 (unless otherwise stated) and then subjected to 1H Nuclear Magnetic Resonance (NMR), 13C NMR, and 1H-correlation spectroscopy (COSY), 1H 13C Heteronuclear Single Quantum Coherence (HSQC), 1H 15N HSQC, 1H 13C Heteronuclear Multiple Bond Coherence (HMBC) and 1H 15N HMBC characterizations. A Bruker AM 600 spectrometer operated by Topspin™ 3.0 NMR software was used for spectra measurement and analysis.

In order to fully annotate structure of phase inverted PAA and the designed PAA, NMR and IR experiments were performed. NMR was also used to monitor the possibility of Bisphenol A formation in relation to heat treatment and exposure time.

To move step by step, ACD/ChemSketch (Freeware) academic edition was used to draw the PAA structures, and PAA-GA interaction. This was due to the fact that in all cases, GA was used as an element in preparation of PAA films.

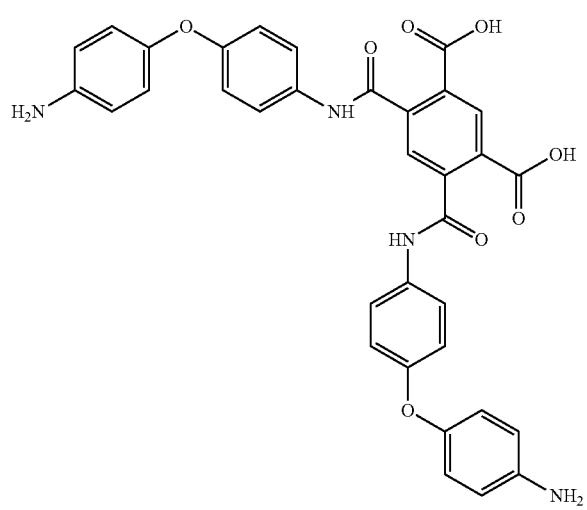

[A]

-continued

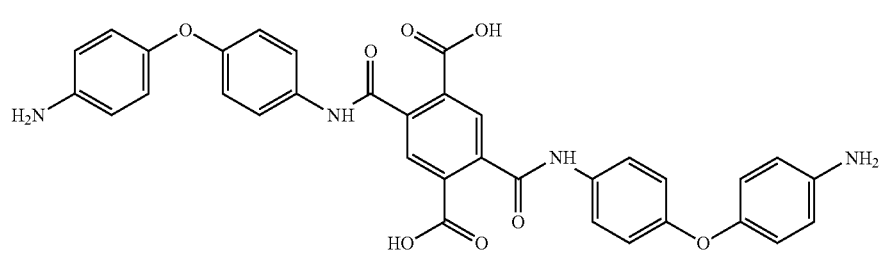
[B]

In the above structures, the proposed structure of PAA polymers are shown. $[A]_a\text{-}[B]_b\text{-}[A]_c\text{-}[B]_d$ [a,b,c and d can be 1 or more, and can be the same or different]. In the case of PAA synthesized in DMAC, $[A]_2\text{-}[B]_3\text{-}[A]_2\text{-}[B]_3$ is proposed as the possible structure.

TABLE F $^1$H NMR of PAA and ternary PAA Films

| Film | Carboxyl group | Amino group | Carbonyl group | Aromatic protons | Aliphatic proton |
|---|---|---|---|---|---|
| PAA | 13.05 | 10.56/10.53 | N/A | 8.35/8.00/7.74 7.72/7.05 | N/A |
| PAA[1] | Not visible | 10.57/10.54 | N/A | 8.37/8.02/7.77 7.73/7.06 | N/A |
| PAA-GA | 13.33 | 10.55/10.52 | 9.26 | 8.34/7.99/7.74 7.71/7.05 | Not clear |
| PAA-GA[2] | 13.54 | 10.65/10.54 10.52 | 9.30/9.22/9.1/8.75 | 8.33/7.97 7.70/7.04 | 5.00/4.92/4.87 4.68/1.77/1.23 |
| PAA-GA-SA[1,2] | Not visible | 10.66/10.55 10.53 | 9.32/9.28 | 8.35/8.00 7.72/7.05 | 4.68/3.51 1.66/1.22 |
| PAA-GA-SA-pAS[2] | 13.00 | 10.65/10.54 10.51 | 9.32/9.30 | 8.33/7.97/7.76 7.70/7.04 | 5.26/2.03/1.23 0.93/0.83 |
| PAA-GA-SA-pAS-A | 13.19 | 10.65/10.53 10.51 | 9.32/9.31/9.29 9.06/9.04 | 8.33/7.98/7.72 7.70/7.04 | 2.03/1.91/1.90 1.39/1.23 |
| PAA-GA-SA-pAS[2,3] | 13.19 | 10.65/10.53 10.51 | 9.39/8.74 | 8.33/7.97 7.70/7.04 | 5.74/2.08/1.23 |
| PAA-GA-SA[4] | 13.16 | 10.66/10.54 10.51 | 9.29/9.22 | 8.33/7.97/7.72 7.70/7.04 | 6.09/5.97/4.32 3.69/3.45/1.32 1.23/1.05 |

TABLE G $^{13}$C NMR of PAA and ternary PAA film

| Film | Carbonyl | Carboxyl | Amide | aromatic | Aliphatic |
|---|---|---|---|---|---|
| PAA | 165.79/165.69 | 166.73/166.42 | 152.95 | 141.20/139.08/134.81 133.12/129.83/128.86 127.56/121.53/118.83 118.81 | N/A |
| PAA[1] | 165.89/165.79 | 166.81/166.51 | 152.05 | 141.29/139.18/134.87 133.99/133.18/130.90 129.1/128.95/127.64 121.63/120.33/118.91 117.61/116.58 | N/A |
| PAA-GA | 165.77/165.66 | 166.68/166.38 | 152.94 | 141.21/139.08/134.79 133.06/129.05/128.83 127.53/121.51/118.81 118.29 | Not seen |
| PAA-GA[2] | 165.70/165.59 167.59/167.30 | 166.62/166.31 | 152.86 | 141.14/139.01/134.74 133.71/129.02/128.77 127.49/121.44/121.35 118.74/118.72 | Not seen |
| PAA-GA- | 165.86/165.75 167.28/167.89 | 166.75/166.46 166.36 | 153.02 | 141.28/140.68/139.16 136.52/134.84/133.18 | 37.57 |

TABLE G-continued

$^{13}$C NMR of PAA and ternary PAA film

| Film | Carbonyl | Carboxyl | Amide | aromatic | Aliphatic |
|---|---|---|---|---|---|
| SA[1, 2] | | | | 130.83/129.13/128.91 121.60/118.88 | |
| PAA-GA-SA-pAS-A | 165.72/165.61 | 166.63/166.33 | 152.89 | 141.17/140.45/139.04 134.75/133.02/130.72 129.03/128.78/127.49 121.47/120.06/118.76 118.74 | Not seen |
| PAA-GA-SA-pAS[2, 3] | 165.73/165.63 167.60/167.27 | 166.63/166.33 | 152.89 | 141.18/140.47/139.05 134.75/131.66/130.72 129.04/127.49/121.48 120.05/118.77/118.74 | 37.47 |
| PAA-GA-SA[4] | 165.72/165.62 | 166.65/166.34 | 152.88 | 141.16/139.03/134.76 133.05/130.75/129.02 128.79/127.50/121.62 121.46/118.76/118.74 | 13.78 |

The following superscript numbers refer to the tables above: [1]very high concentration (150 mg/mL) of PAA; [2]GA used high concentration 2%. [3]high concentration (80-100 mg/mL) of pAS. [4]PAA was synthesized in 65:35, Ethanol: DMAC. Protons of N,N'-dimethylacetamide were not listed on the table since they are only impurities.

Tables F and G provide a comparison for PAA alone vs. various PAA films. Since GA and small molecules were used at very low amount in comparison to PAA, $^1$H and $^{13}$C NMR techniques did not provide the presence of new peaks for each group. However, at higher amount of sulfanilic acid and glutaraldehyde, the characteristic peaks related to these were observed.

Figure 2A:
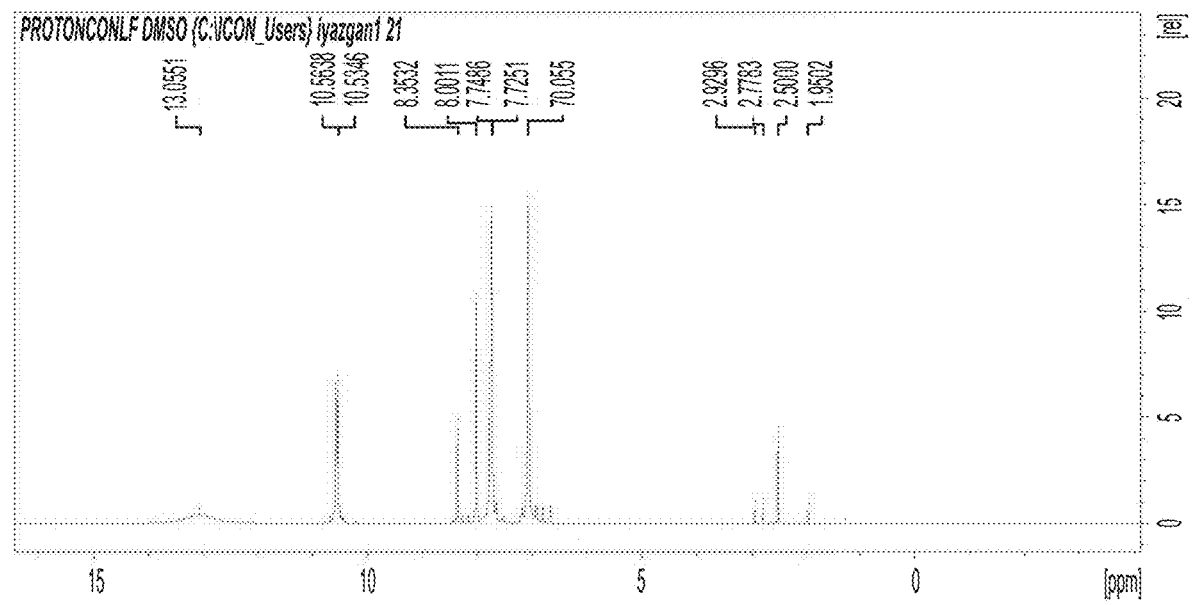
FIGS. 2a-2q are illustrations of NMR data.
Figure 2B:
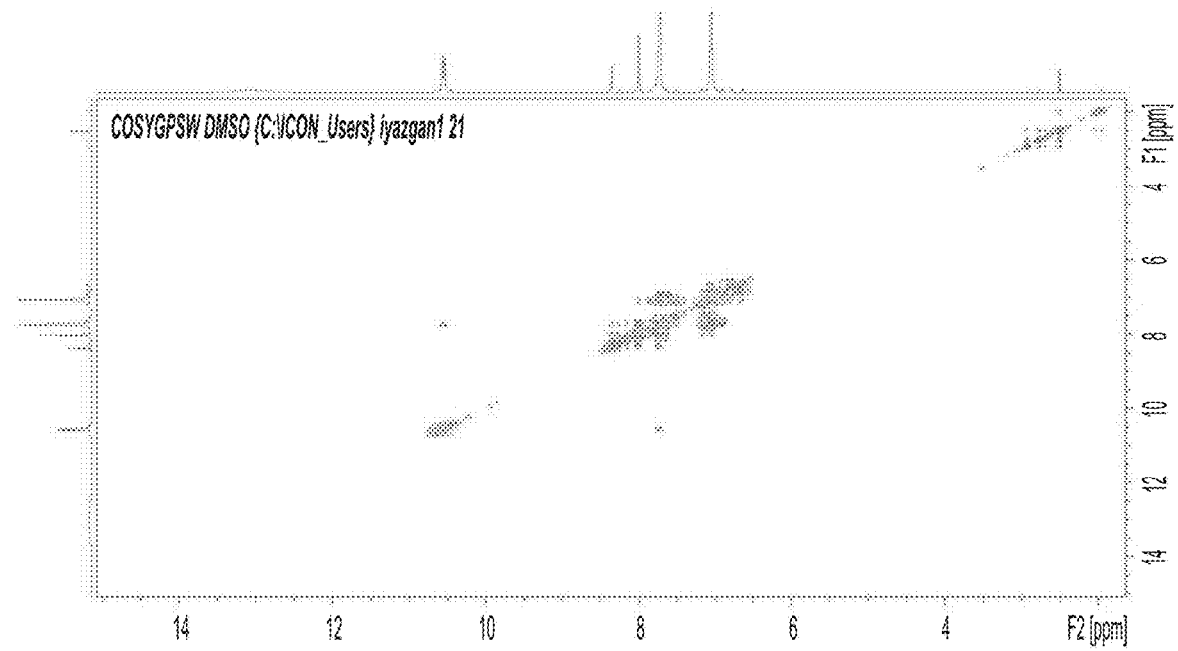
Figure 2C:
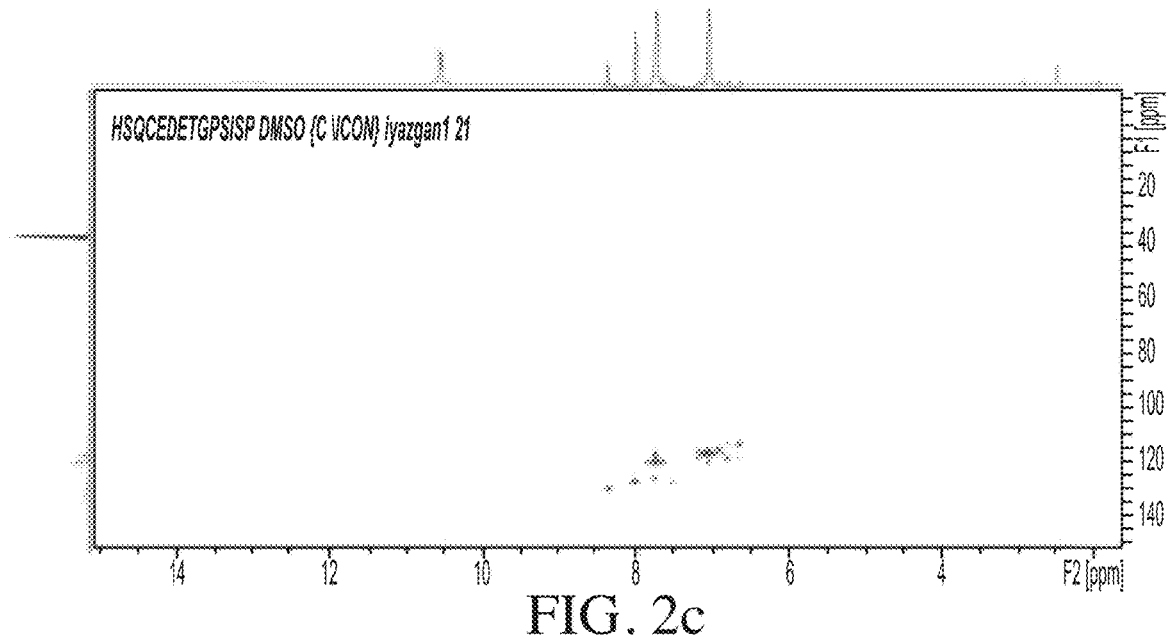
Figure 2D:
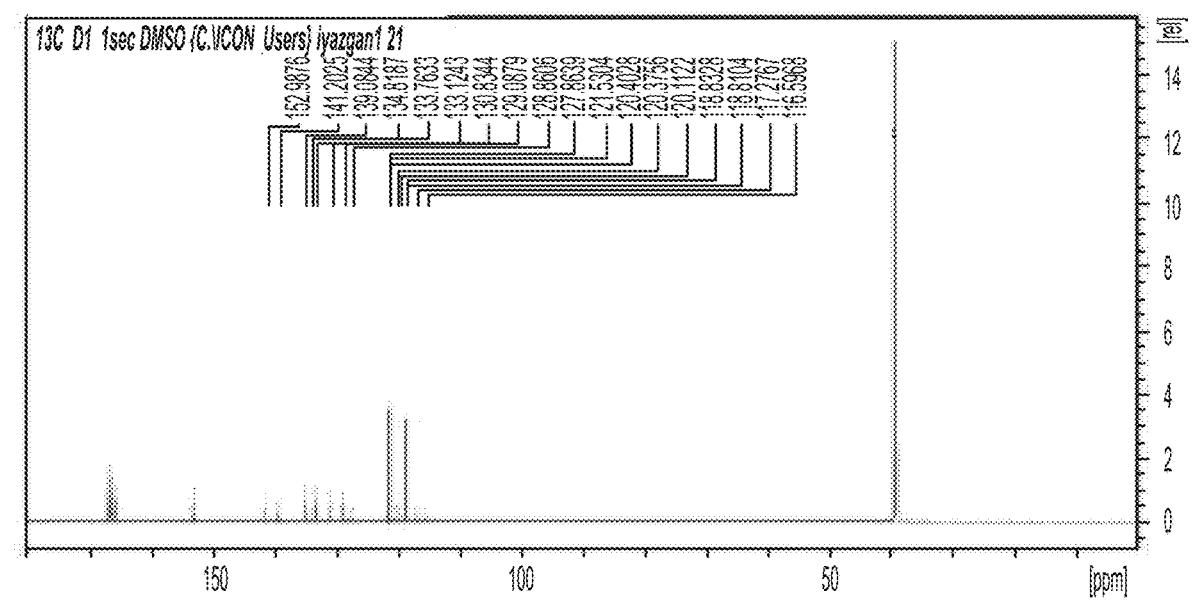
Figure 2E:
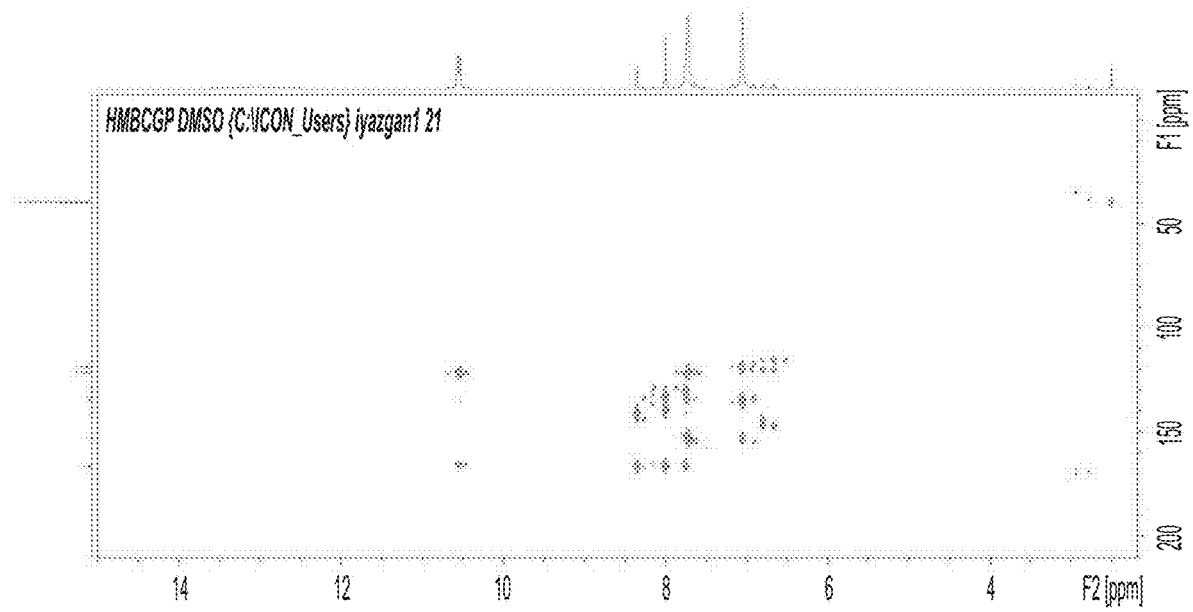
Figure 2F:
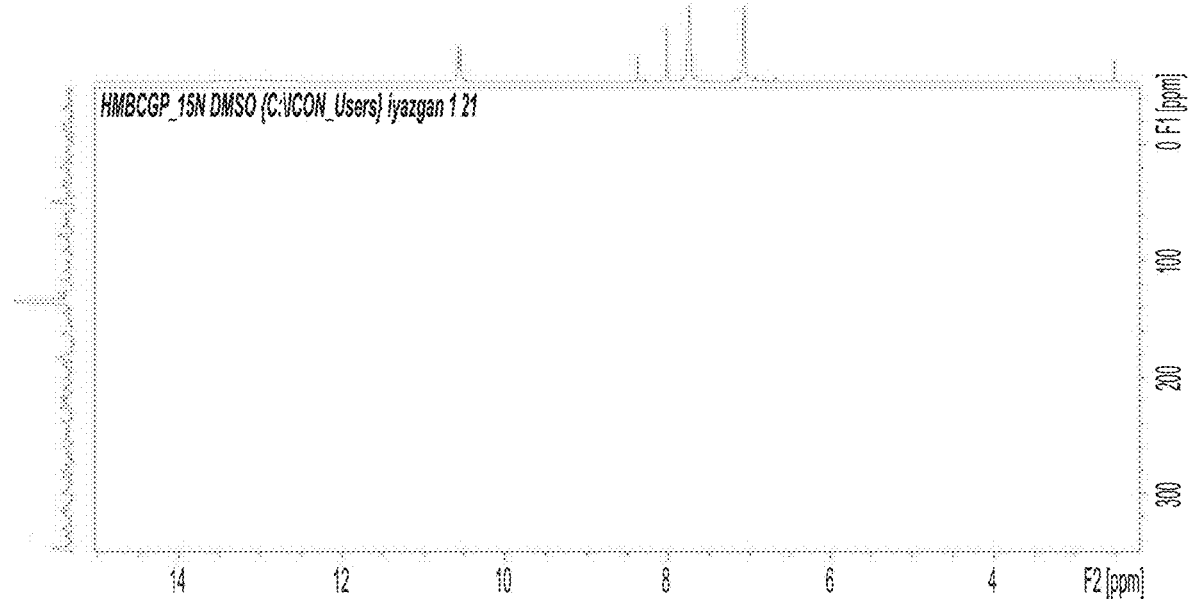
Figure 2G:
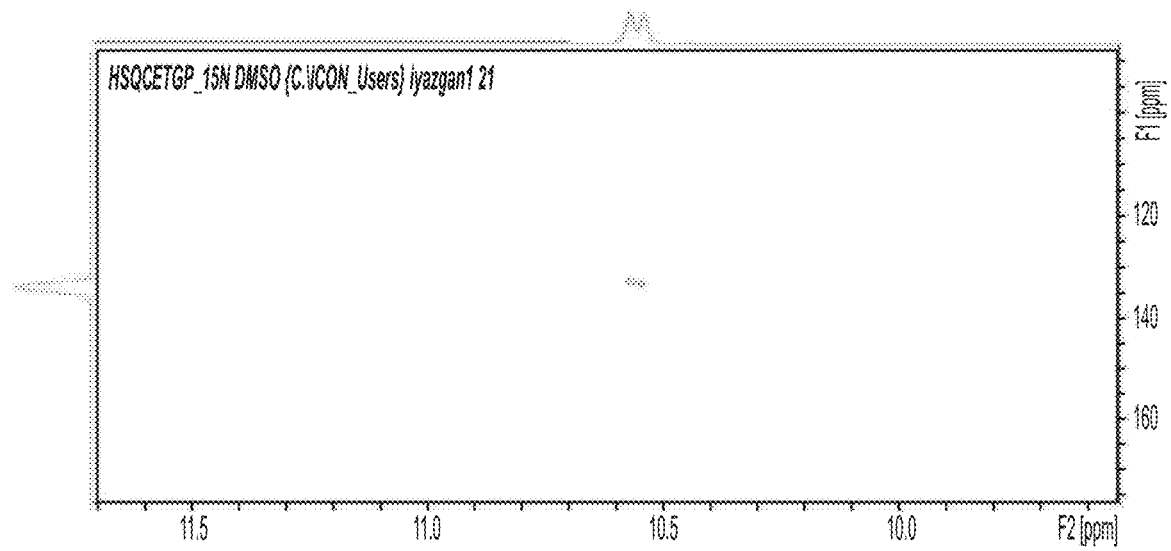
Figure 2H:
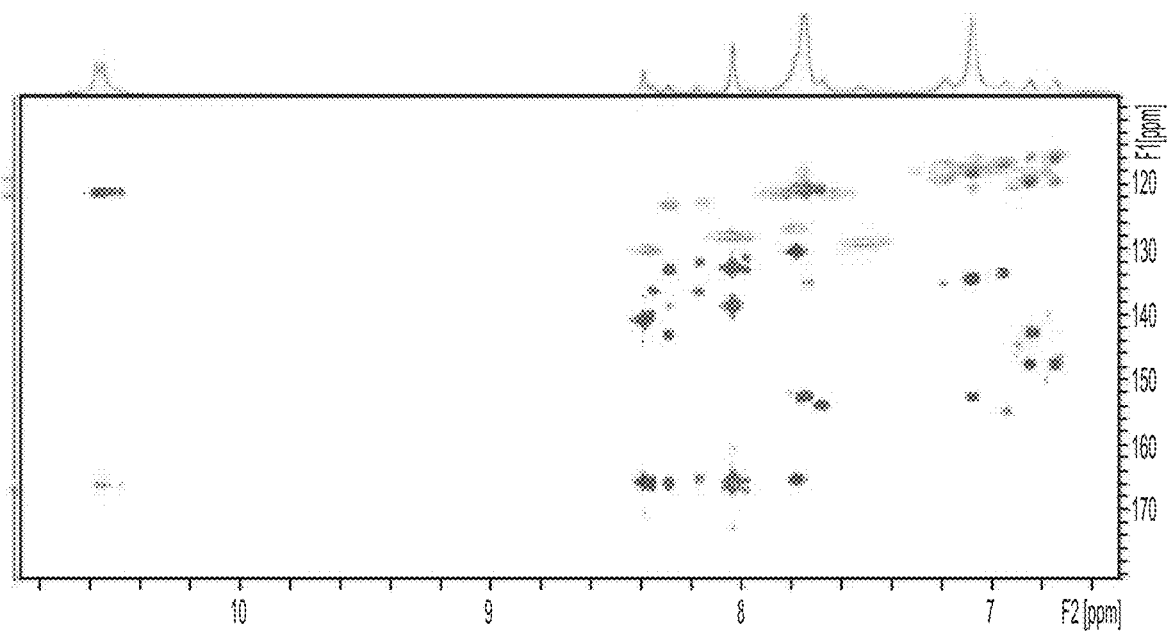
Figure 2I:
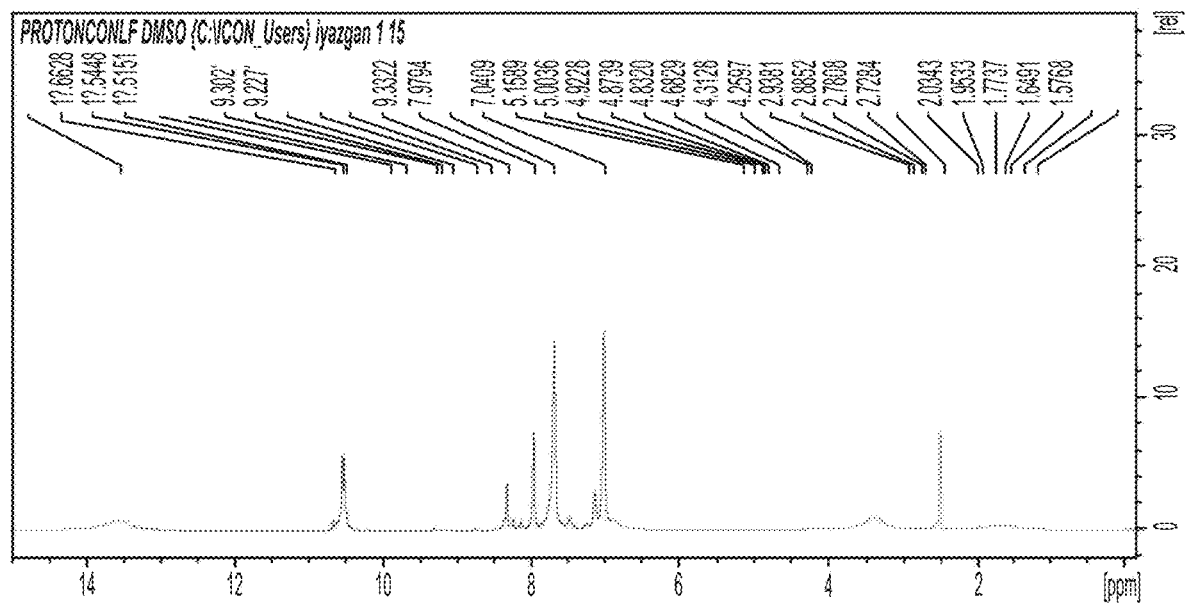
Figure 2J:
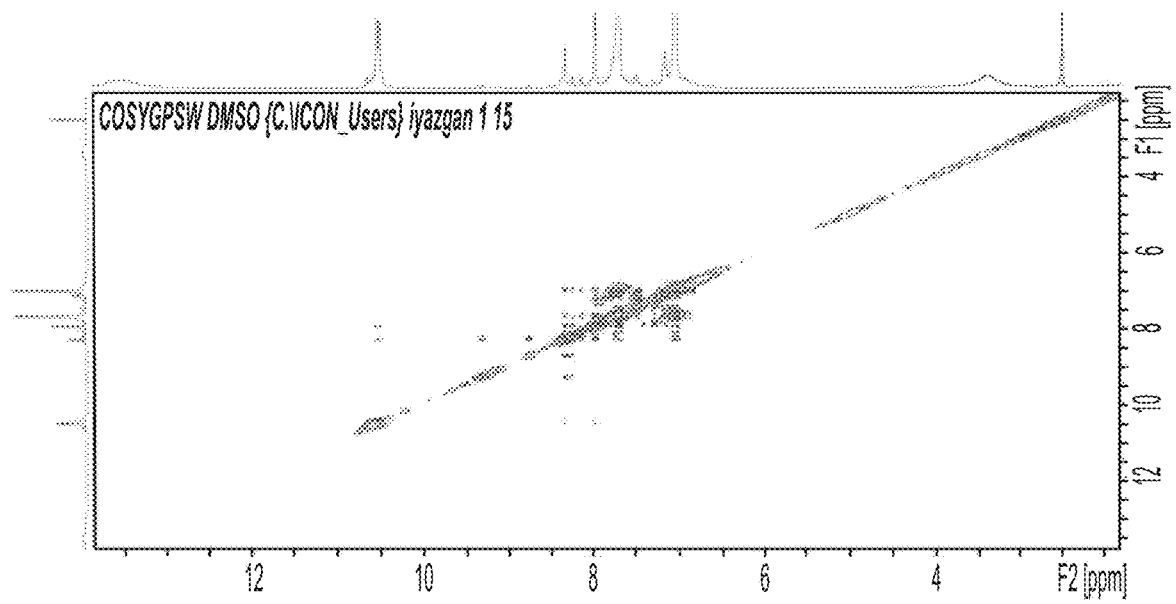
Figure 2K:
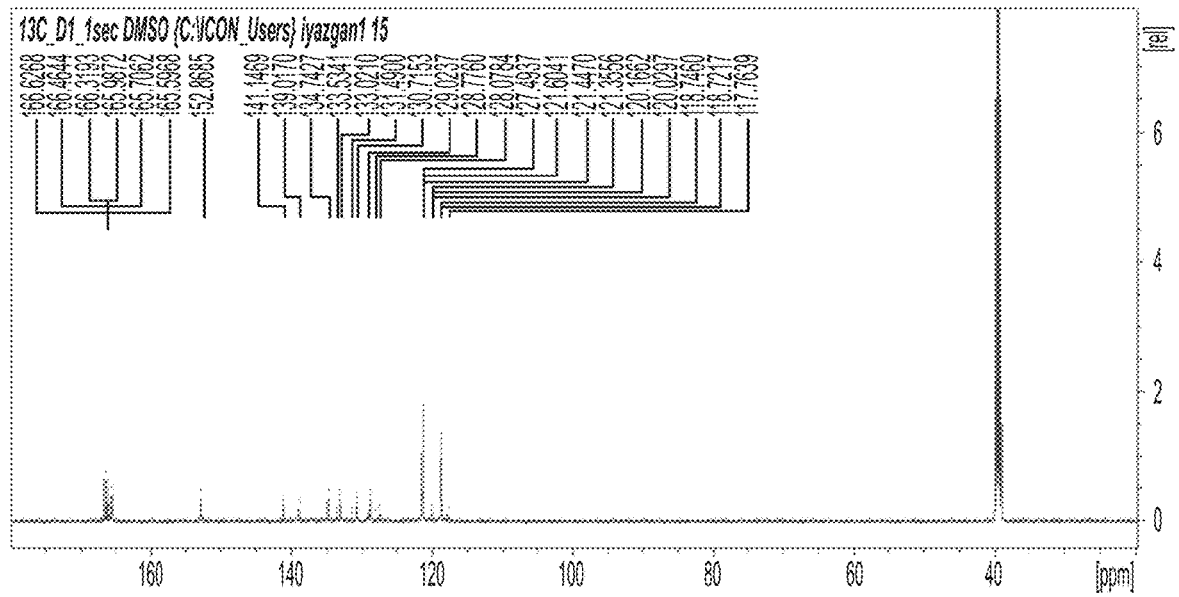
Figure 2L:
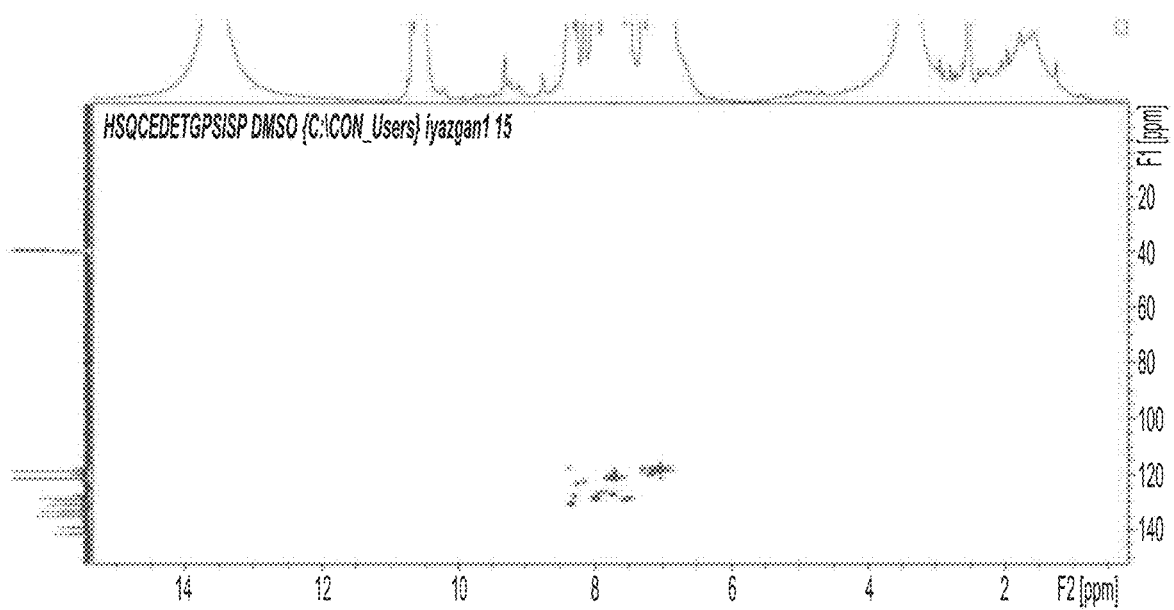
Figure 2M:
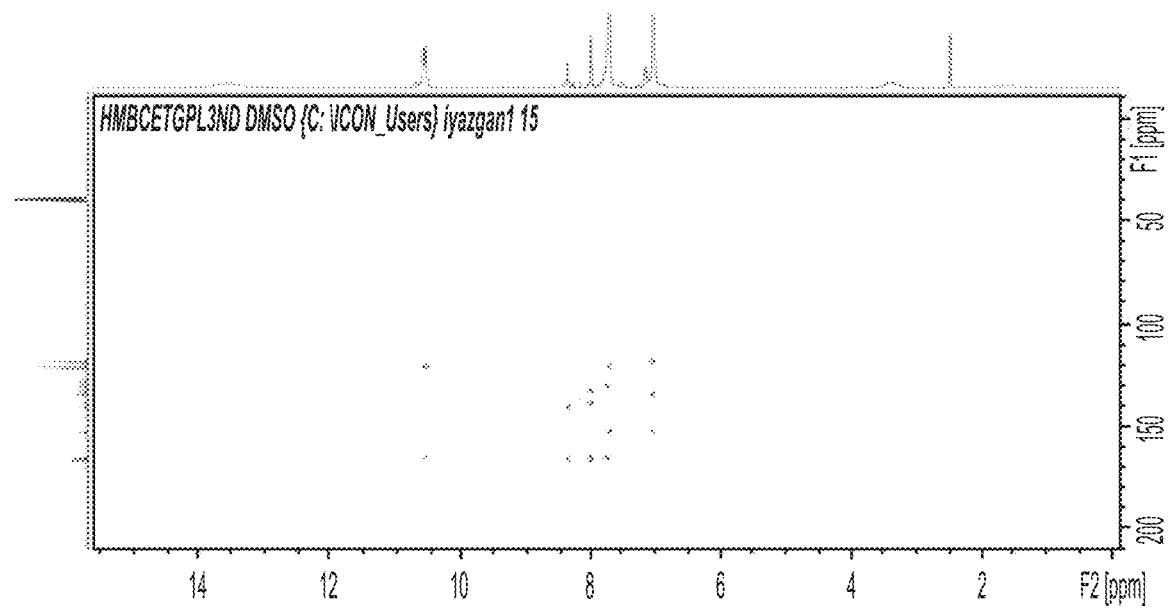
Figure 2N:
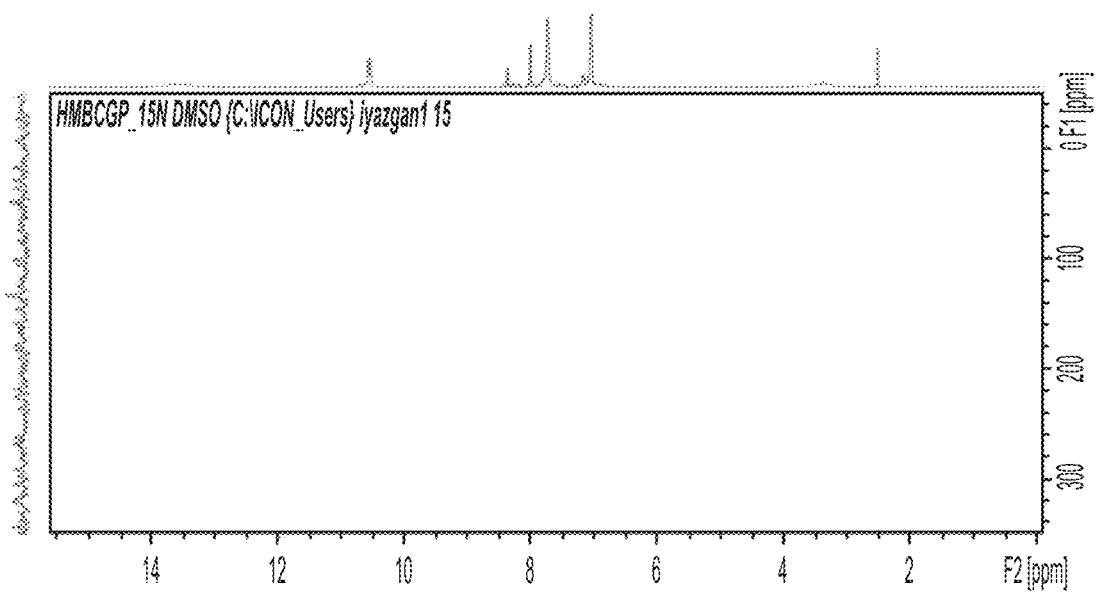
Figure 2O:
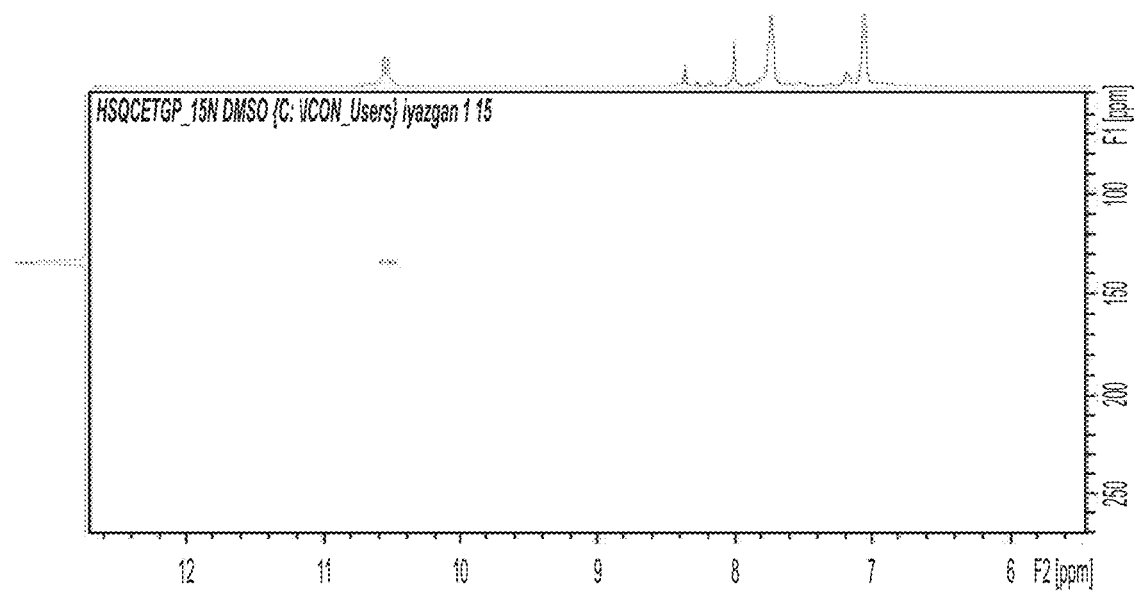
Figure 2P:
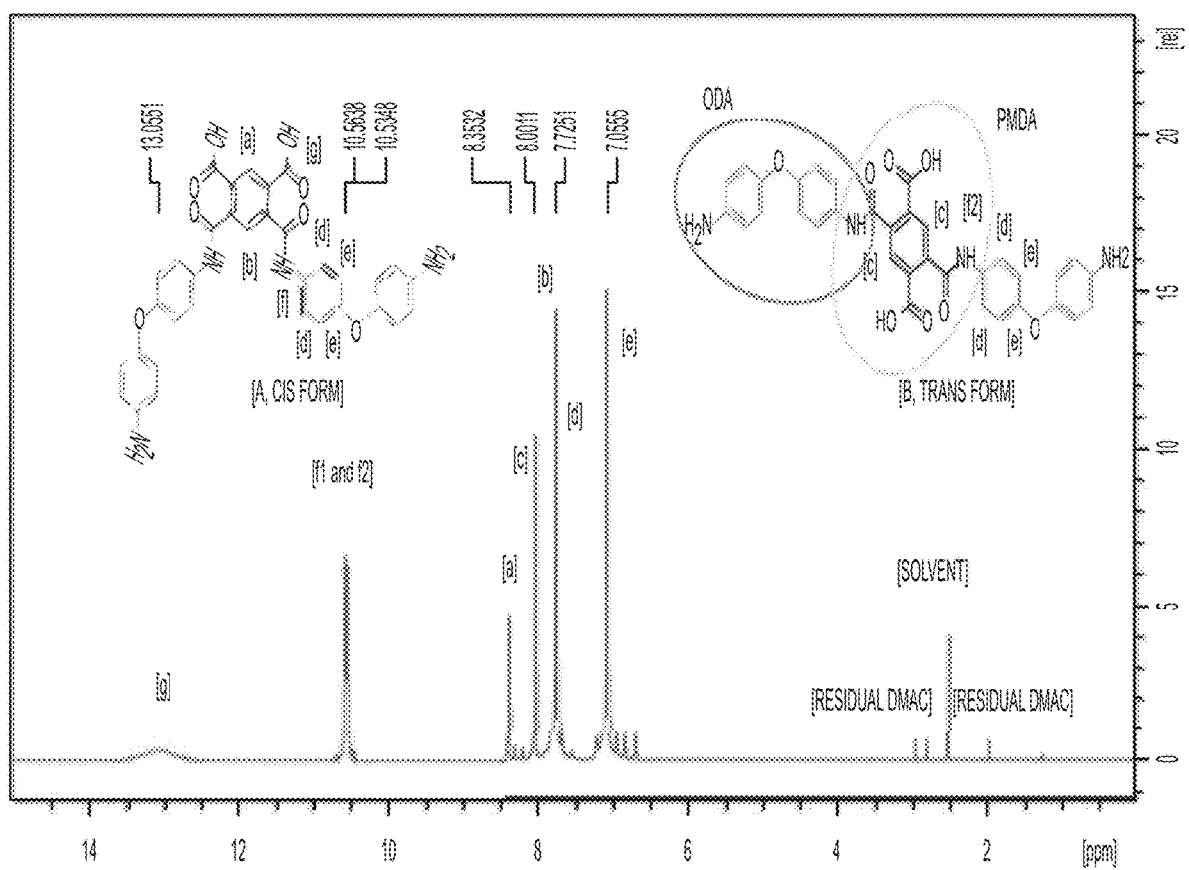
Figure 2Q:
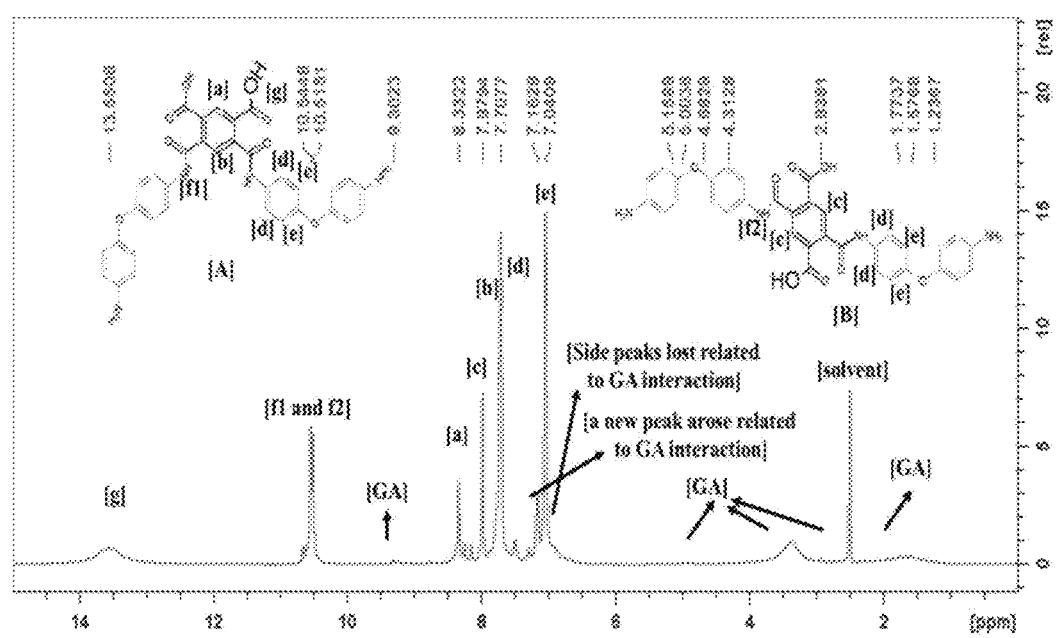

NMR data is shown in FIGS. 2a-2q. Specifically FIG. 2a is NMR data for $^1$H, FIG. 2b is NMR data for $^1$H COSY, FIG. 2c is NMR data for $^1$H-$^{13}$C HSQC, FIG. 2d is NMR data for $^{13}$C, FIG. 2e is NMR data for $^1$H-$^{13}$C HMBS, FIG. 2f is NMR data for $^1$H-$^{15}$N HSQC, FIG. 2g is NMR data for $^1$H-$^{15}$N HMBC and FIG. 2h is NMR data for co-presentation of $^1$H-$^{13}$C HMBC and $^1$H-$^{13}$C HSQC spectra (blue HMBC and red HSQC). Further NMR data for PAA membrane phase-inverted in pure-water in FIG. 2i, which is NMR data for $^1$H, FIG. 2j is NMR data for $^1$H COSY, FIG. 2k is NMR data for $^1$H-$^{13}$C HSQC, FIG. 2l is NMR data for $^{13}$C, FIG. 2m is NMR data for $^1$H-$^{13}$C HMBS, FIG. 2n is NMR data for $^1$H-$^{15}$N HSQC and FIG. 2o is NMR data for $^1$H-$^{15}$N HMBC of PAA-GA membrane prepared according to the method of FIG. 1b.

In this disclosure, NMR data is used to obtain physical, chemical, electronic and structural information of the disclosed of organic compounds. It is due mostly to the chemical shift on the resonant frequencies of the nuclei present in the compound compared to a reference magnetic field (usually tetramethylsilane or TMS). Chemical shift is the function of the nucleus and its environment, which is measured relative to a reference compound (i.e. TMS). As for the specific NMR data presented in the figures of this disclosure, PAA does not give peaks at the following region including aliphatic region (single or double bond). So, any missing PAA signature peak is an indication that the polymer is not present or is degrading. The NMR images also provide how GA binds to the PAA molecules.

The disclosed data is used to provide detailed information on the topology, dynamics and three-dimensional structure of molecules. The NMR data in FIGS. 2a-2o compare the NMR spectra of PAA and PAA-GA. The figures generally illustrate the chemical interaction of GA with PAA being due to cross linking between GA and PAA.

$^1$H NMR spectrum (FIG. 2a) of PAA depicts presence of carboxyl, amino and aromatic protons. The aliphatic protons are from residual N,N'-dimethylacetamide (DMAC). According to the depicted $^1$H spectrum, only one type of carboxyl group is present in PAA polymer while two carboxyl carbons present in PAA were revealed by $^{13}$C spectrum (FIG. 2b). Since the microenvironment of protons in the carboxyl group is more isolated, it was observed as single carboxyl group.

However, an amino group proton was obtained as an overlap of two peaks (FIG. 2a); according to $^1$H-$^{15}$N HSQC (FIG. 2f) there is only one type of nitrogen, but the nitrogen locates in two slightly distinct environments which explains the presence of the overlapped peak. This was further supported by $^1$H-$^{15}$N HMBC (FIG. 2g) spectrum where long-range couplings of the two overlapped amino protons showed the same long-range couplings. The overlapped peaks at 7.75 ad 7.72 ppm were from two different carbon atoms which was supported by $^1$H-$^{13}$C HSQC (FIG. 2c) and $^1$H-$^{13}$C HMBC (FIG. 2g); the peak 7.75 ppm gave cross-peak with carbon peak at 128.92 ppm while the peak at 7.72 ppm gave cross-peak with carbon peak at 121.57 ppm. According to $^1$H-$^{13}$C HMBC (FIG. 2g) spectrum, both the protons gave peak at 7.75 ppm and 7.7.72 ppm showed two distinct long range couplings, which could not be obtained by just one proton on proton. Further, three long-range couplings were observed for amide carbon, which were linked to the protons on pyromellitic dianhydride (PMDA) group. Therefore, all these results indicate that several PAA structures can be produced in accordance with the present disclosure.

Glutaraldehyde (GA) can bind at different positions to PAA. According to $^1$H (FIG. 2i) and $^{13}$C (FIG. 2j), inclusion of GA did not affect PAA structure, rather added new groups; particularly, the presence of carbonyl proton and aliphatic protons around 5 ppm and 1-2 ppm revealed that GA chemically bound to PAA. Further indications that GA was chemically bound to PAA was obtained from $^1$H COSY, $^1$H-$^{13}$C HSQC, $^1$H-$^{13}$C-HMBC and $^1$H-$^{15}$N HMBC NMR spectra. 1H COSY spectrum gave new peaks related to the presence of GA. For pure PAA, there is no long range coupling for the amino groups with the shift at ~8 ppm while it is strong for GA modified PAA. Similarly, new and strong long-range couplings were observed for carbonyl proton and the free protons on PMDA, particularly which locates between two free carboxyl groups. $^1$H-$^{13}$C HSQC revealed that GA interaction nearly eliminated the presence of adjacent peaks nearby the peak at ~7 ppm, which could be related to that GA attacked on the phenyl ring of 4,4'-oxydianiline (ODA).

Similarly, the long-range couplings for the adjacent peaks got lost via GA interaction. According to $^1$H-$^{15}$N HMBC NMR spectral data, nearly all of the long range couplings were lost between the amide nitrogen and the protons on phenyl ring of ODA; particularly proximal to the amino group. However, at the same time, one of the amino peaks seen in the $^1$H-$^{15}$N HMBC NMR spectrum was lost; this peak stayed the same for low GA concentrations. A new amino peak was observed at ~10.65 ppm (FIG. 2i). Therefore, for low levels of GA, GA prefers to attach on phenyl rings of PAA while at high levels, GA attaches on amino groups in addition to phenyl rings.

GA preferentially binds to phenyl ring of PAA. In particular, it binds to the ODA ring of PAA polymer. FIG. 2q illustrates that GA interaction eliminated the presence of small side peaks at aromatic region, which belongs to the proton of ODA. This is because PMDA has more steric hindrance and hence, the GA preferentially binds onto the ODA portion of the PAA molecule.

GA preferentially binds to phenyl ring of PAA. In particular, it binds to the ODA ring of PAA polymer. This is partially illustrated in FIG. 2p, which illustrates aromatic peaks of PAA being at 7.07 ppm, 7.74 ppm, 8.01 ppm and 8.36 ppm. Amino peaks of PAA are at 10.54 ppm and 10.57 ppm. Carboxyl peak of PAA is at 13.51 ppm. ODA residue is shown in left circle and PMDA is shown in the right circle.

FIG. 2q illustrates that GA interaction eliminated the presence of small side peaks at aromatic region, which belongs to the proton of ODA. This is because PMDA has more steric hindrance and hence, the GA preferentially binds onto the ODA portion of the PAA molecule. In FIG. 2q, the used GA concentration was less than 5% of the PAA concentration when PAA-GA membrane was prepared.

Figure 3A:
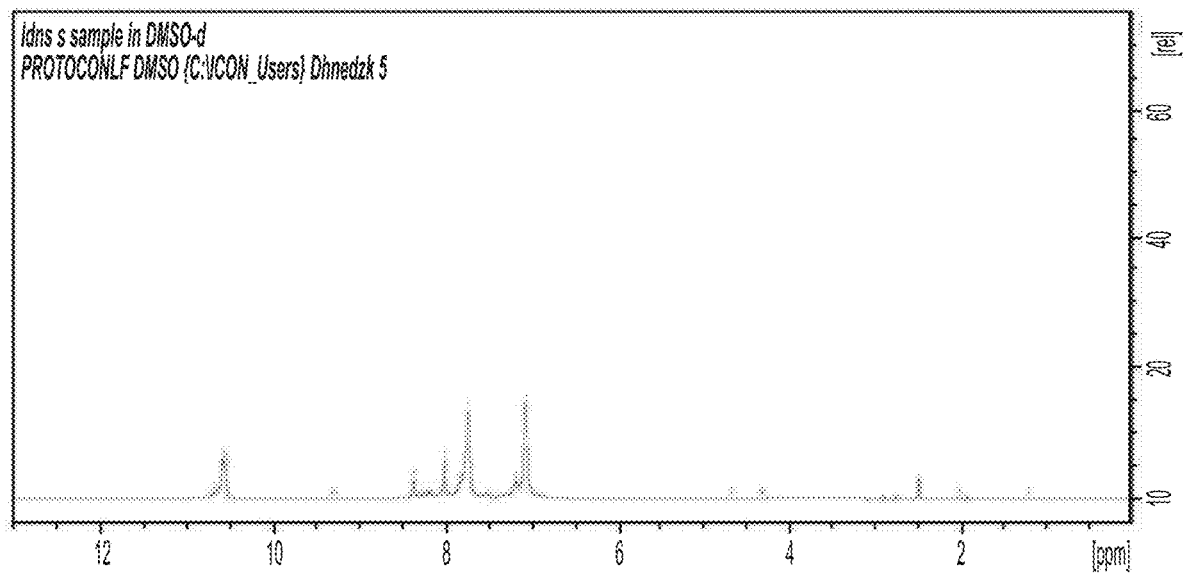
FIGS. 3a-3f are illustrations of NMR data.
Figure 3B:
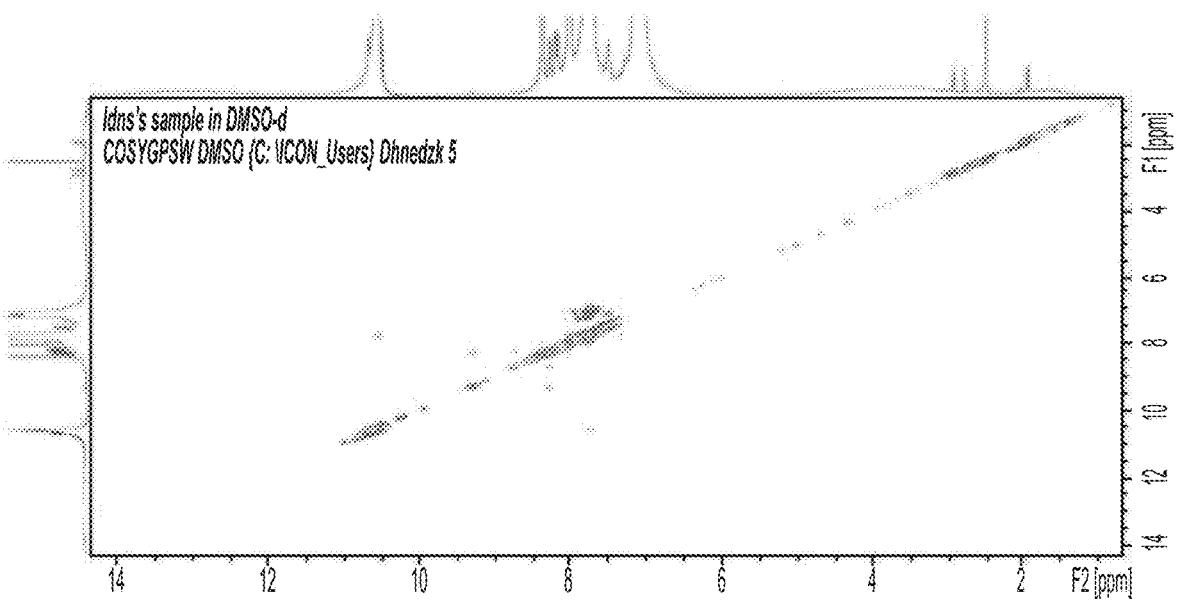
Figure 3C:
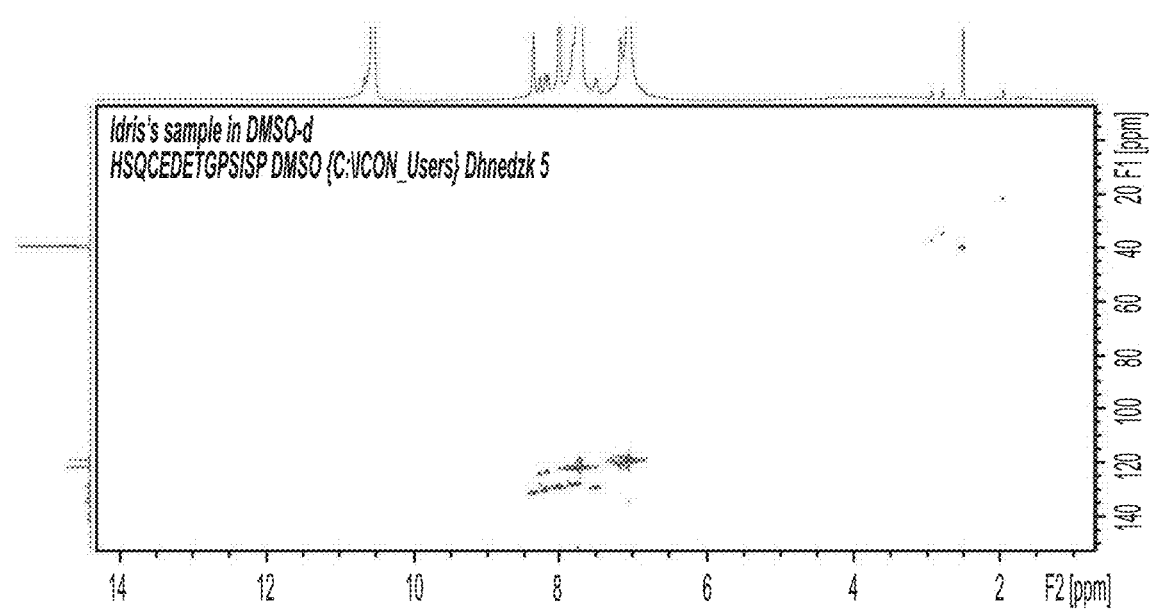
Figure 3D:
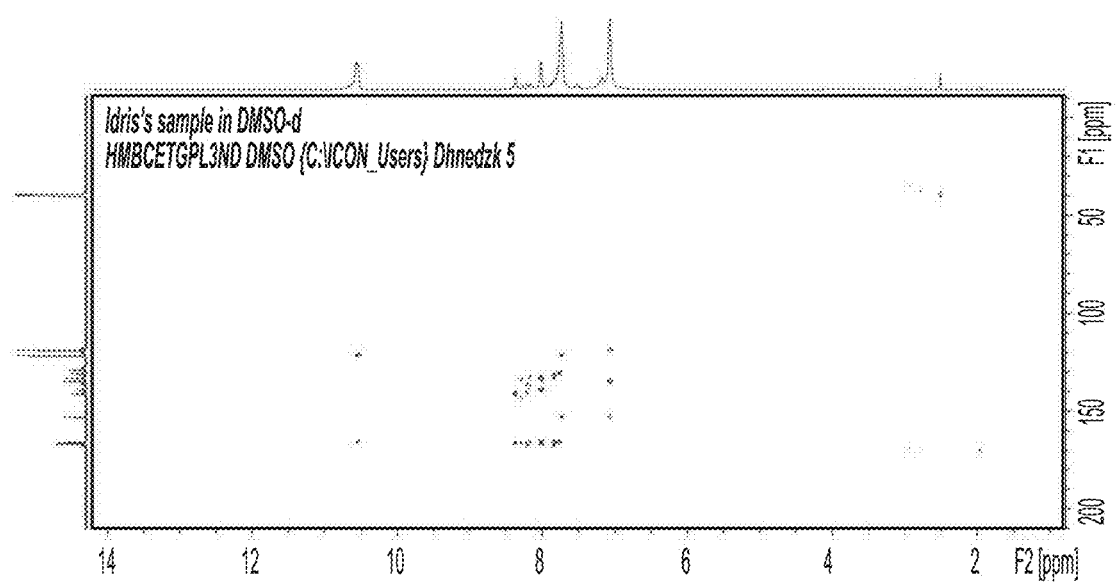
Figure 3E:
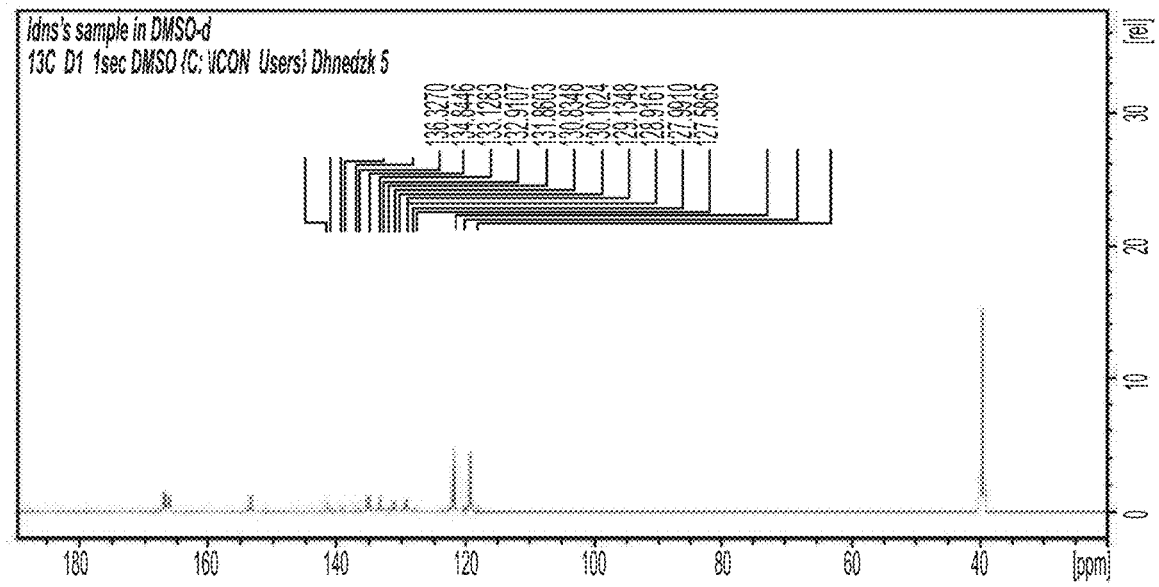
Figure 3F:
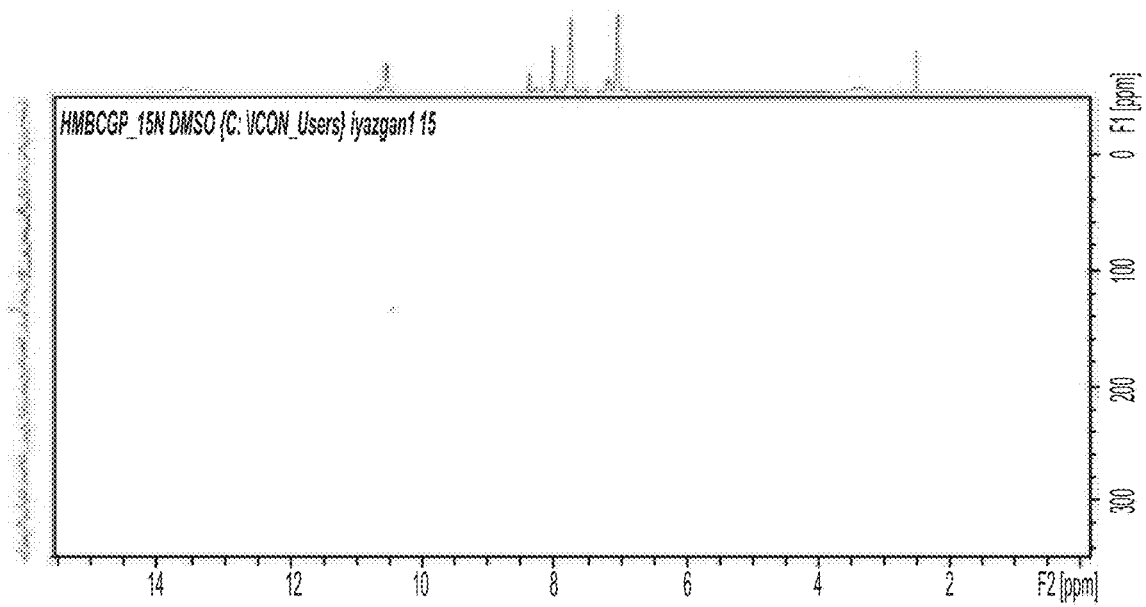

NMR data is shown in FIGS. 3a-3f. Specifically FIG. 3a is NMR data for $^1$H, FIG. 3b is NMR data for COSY, FIG. 3c is NMR data for $^1$H-$^{13}$C HSQC, FIG. 3d is NMR data for $^{13}$C, FIG. 3e is NMR data for $^1$H-$^{13}$C HMBS, FIG. 3f is NMR data for $^1$H-$^{15}$N HSQC spectra of a PAA-SA-GA membrane synthesized according to the method shown in FIG. 1b.

Introduction of sulfanilic acid (SA) to PAA did not produce any additional peaks. However, some of the interactions observed in the COSY spectrum of PAA-GA were not observed for PAA-SA-GA. For $^1$H-$^{13}$C HSQC, one additional minor peak was observed at 8.21-130.18 ppm in addition to PAA-SA-GA. Similarly, $^1$H-$^{13}$C HMBC gave additional minor extra interactions for the protons at 8.16 and 7.82 ppm, which were more of long-range couplings shifted to more down-field, but simultaneously were protected. However, the cross-peak at 7.82-167.9 ppm could be speculated that it was from SA, rather GA. $^1$H-$^{15}$N HSQC spectrum did not show any differences. Overall, it can be said that, sulfanilic acid peaks were not clear in the membrane, while minor differences were observed in 2D NMR spectra.

Figure 4:
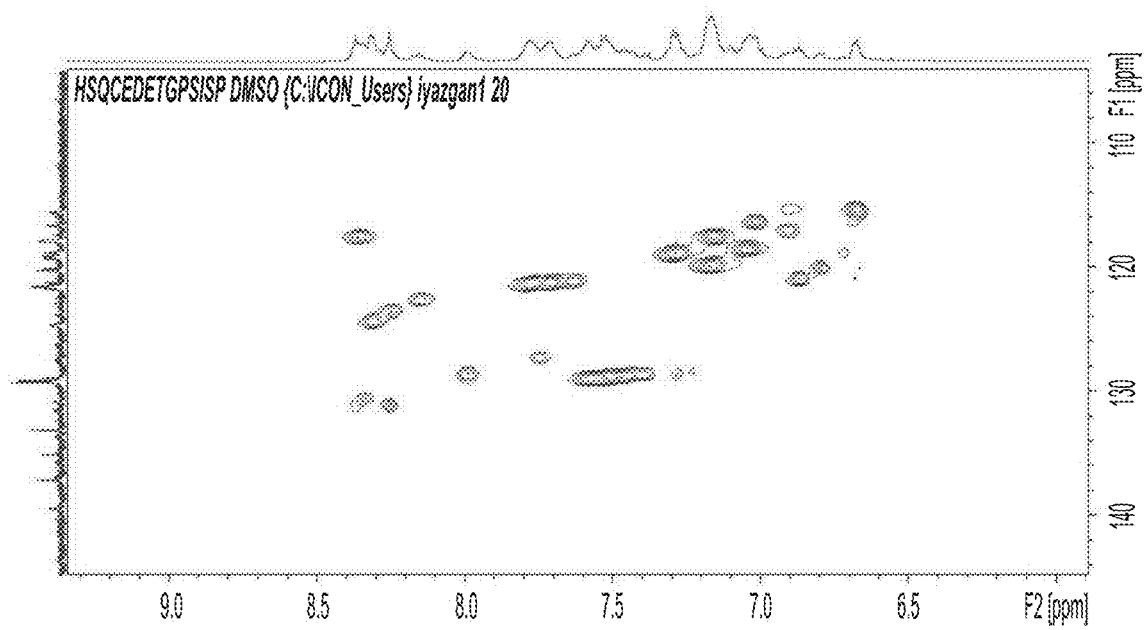
FIG. 4 is an illustration of NMR data.

As can be seen in FIG. 4 PAA-GA was incubated under sun-light for over 3 years in an airtight glass-container. Then, the film was dissolved in DMSO. 1H-13C HSQC spectrum clearly shows that the PAA-GA membrane lost its structural integrity, but no Bisphenol A (BPA) formation was observed.

BPA is primarily used to make plastics such as water bottles. There are studies showing that BPA might mimic natural receptors in the body and thereby cause an irreversible change at the genetic levels. Based on this potential effect, BPA and a host of other compounds were classified as endocrine disrupting chemicals. Certain plastics may not have BPA at the outset but with time, they may produce BPA after extensive usage and breakdown. The disclosed films did not produce BPA during study of their degradation and are therefore considered substantially safe for human health and the environment.

Figure 5A:
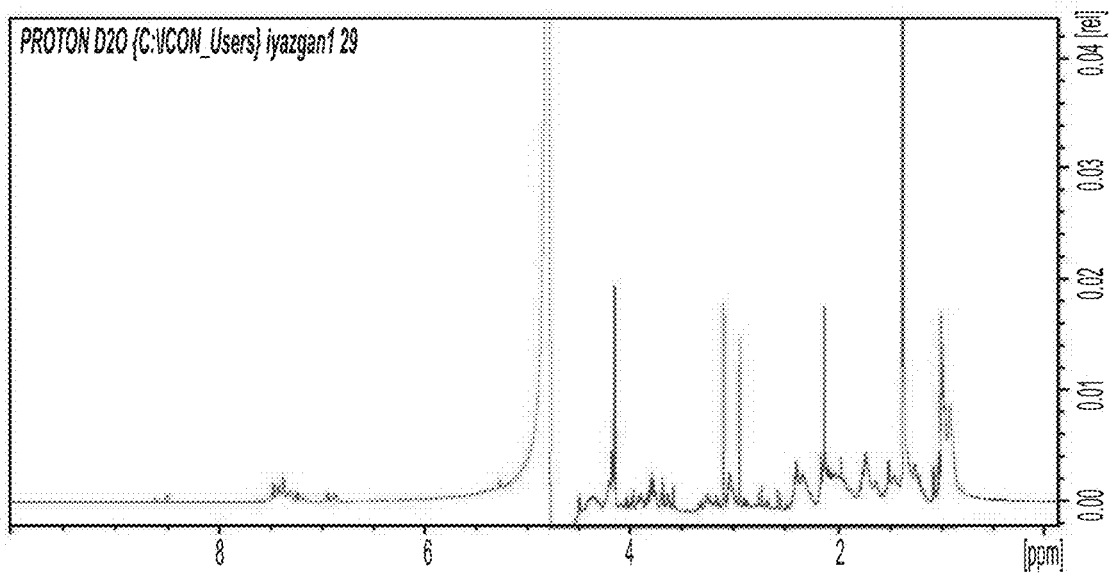
FIGS. 5a-5b are illustrations of NMR data.
Figure 5B:
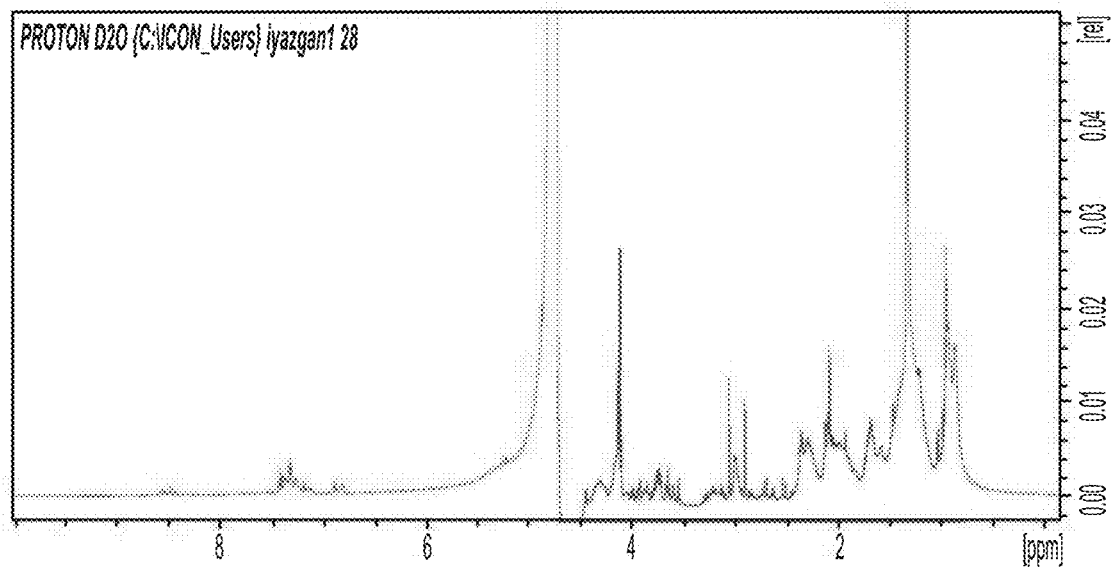

Further, Cabot sharp cheddar cheese was wrapped in a PAA-pAS-SA-GA membrane of the present disclosure for three months. Subsequently, we compared the proton $^1$H NMR of freshly purchased cheese (FIG. 5a) and the cheese kept in the membrane (FIG. 5b). There was no peak related to DMAC or PAA. Before the membrane was used to wrap the cheese, it was rinsed with tap water 10 times, and then rinsed with 70% Ethanol; in order to remove residual ethanol, the membrane was kept in pure water for 3 h.

As seen from FIGS. 2a-2q, pure poly(amic)acid did not have any aliphatic groups while it did possess carboxyl, amino, carbonyl and aromatic groups. Due to the two ways of ODA-PMDA interactions, carboxyl, carbonyl and amino groups showed two different environments.

Insets in FIG. 2a show the cis- and trans-forms of PAA. These two chemical environments affect proton shifts seen in NMR spectra. They have an impact on structural characterization.

Even though two amino protons were observed, only one carboxyl proton was observed; this difference is related to the fact that the carboxyl proton is more isolated despite the fact that two carboxyl carbons were observed. However, in the case of very high amount of PAA membrane dissolved in DMSO-$d_6$ to run NMR, the carboxyl proton was not observed even though carboxyl protons were present; similar results were observed for PAA-GA-SA membranes.

Further, introduction of GA to PAA resulted in the presence of proton peaks related to carbonyl and aliphatic groups. In parallel to the increase in GA concentrations, the peaks became sharper and more visible. As seen from FIGS. 3a-3f, GA can give peaks between 4-6 ppm due to the presence of double bonds. Therefore, the aliphatic protons provided in the Table I can be speculated as coming from GA. GA also showed its presence via the alterations in the aromatic region; higher concentrations of GA eliminate presence of the peak at about 7.74 ppm while the carbon peak related to that group remained same. As seen from FIGS. 3a-3f $^1$H COSY, $^1$H $^{13}$C HSQC and $^1$H $^{13}$C HMBC, the protons peak remained same. However, the adjacent peaks around the major PAA aromatic protons decreased, which is a sign of GA interaction to the phenyl ring of ODA.

Amino groups did not show any change in response to GA action while the presence of new peak at 10.65 ppm was observed in the cases of sulfanilic acid (SA). However, $^1$H $^{15}$N HSQC and $^1$H $^{15}$N HMBC did not show the presence of new amino groups; there was only one type of amino group. This can be speculated to mean that either SA content was not enough to be seen or prior treatment of SA with GA resulted in secondary amino group formation. $^1$H COSY reveals the presence of aromatic proton and amino proton of SA interacting each other. Therefore, it is clear that SA chemically bonded to the PAA backbone.

Overall, GA chemically binds to the PAA backbone from phenyl ring of ODA located at the edges of the individual PAA polymers. Prior treatment of SA with GA results in the elimination of primary amino groups, and made them visible as secondary amino groups with PAA-SA-GA polymers.

NMR was also used to characterize the chemical stability of PAA-GA polymer. The polymer was kept in an air-tight flask under sun-light for over 3 years. As seen from FIG. 4, PAA polymer lost its structural integrity, and gave fragmentation and oxidation peaks; this was supported by presence of multiple aromatic protons and amino protons, and loss of carboxyl proton. Besides, the adjacent peaks, particularly, around 7 ppm gave the same integral of the major peak which is a sign of fragmentation of individual PAA polymers as shown in FIGS. 2a-2q.

Example 1.2.1-Molecular Weight Characterization of PAA Polymers by NMR

Molecular weight (MW) characterization of the PAA polymers by NMR was performed using two approaches $^1$H DOSY and $T_1$-relaxation times.

$^1$H Diffusion ordered NMR Spectroscopy ($^1$H DOSY) is a two-dimensional NMR technique which relies on the relation between molecular mass of a molecule/polymer and its self-diffusion. The technique has been shown to be useful in determining the average molecular weight of a polymer. It is based on the theory of the Stokes-Einstein equation. In all DOSY experiments samples was 1.2-1.4 mg/mL in DMF-d$_7$ unless stated otherwise. In DOSY NMR experiments (a technique giving information about the average molecular weight of the molecules), concentration of the molecule/polymer should be low enough (1.2-1.4 mg/mL) to avoid viscosity related biased results.

Figure 6:
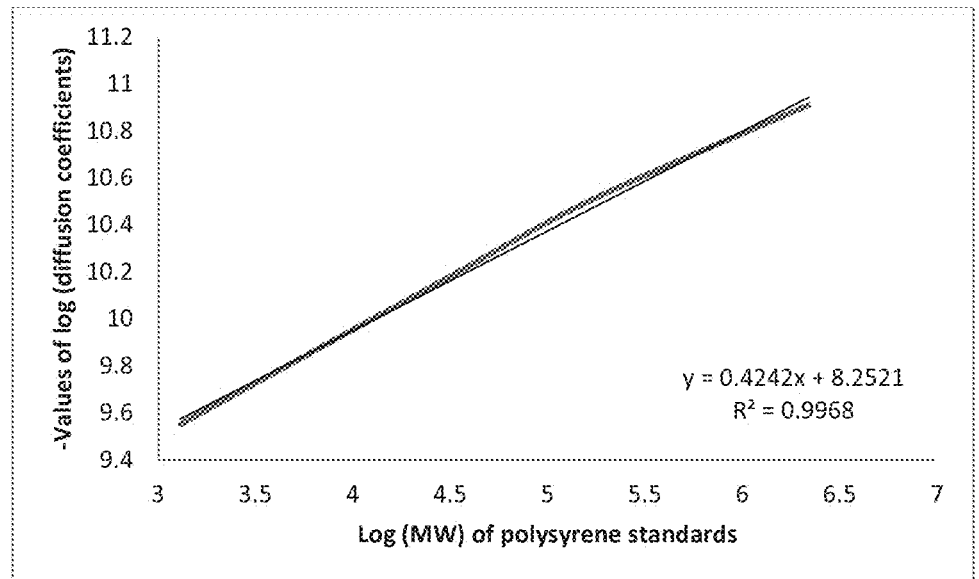
FIG. 6 is a graphical illustration of diffusion coefficients.

As can be seen from FIG. 6, which illustrates the standard graphics of $^1$H DOSY, Polystyrene standards at $10^{3.114}$ Da, $10^{4.455}$ Da, $10^{5.236}$ Da and $10^{6.34}$ Da MWs were used to draw the standard graphic. All standards were prepared ~1 mg/mL in DMF-d7.

DOSY results of some PAA synthesized in the study are shown in Table H below.

| Polymer | $^1$H DOSY MW (Da) |
|---|---|
| PAA-DA-GA (0.12M) | $1.6 \times 10^5$ |
| PAA-pAB-GA (fresh) (0.12M) | $1.22 \times 10^5$ |
| *Standard mixture 1 | $4.49 \times 10^5$ |
| #Standard mixture 2 | $1.01 \times 10^6$ |
| +Standard mixture 3 | $1.44 \times 10^5$ |
| PAA-I-W-GA (0.12M) | $1.76 \times 10^5$ |
| PAA (0.14M) 40° C. | $3.01 \times 10^5$ |
| PAA (0.16M) | $1.68 \times 10^5$ |
| PDA-PAA (0.16M) | $1.49 \times 10^4$ |
| PAA (0.12M) | $2.11 \times 10^5$ |
| PAA-IZ (0.12M) | $1.78 \times 10^5$ |
| PAA (0.10M) | $5.28 \times 10^5$ |
| PAA (0.14M) | $2.33 \times 10^5$ |
| 0.12M PAA-pAS-GA (fresh) | $1.36 \times 10^5$ |
| 0.08M PAA (1:1.03) 40° C. | $5.28 \times 10^5$ |
| 0.08M PAA-GA (aged) 1:1.03 40° C. | $3.41 \times 10^5$ |
| 0.08M PAA-GA (fresh) 1:1.03 40° C. | $4.02 \times 10^5$ |
| 0.16M PAA (1:1.03) | $3.81 \times 10^5$ |
| 0.12M PAA in 65:35 Ethanol:DMAC, 40° C. | $2.61 \times 10^5$ |
| 0.12M PAA in 50:15:35 Ethanol:H$_2$O:DMAC 40° C. | $1.14 \times 10^5$ |
| PAA (0.14M) 30° C. | $2.33 \times 10^5$ |
| 0.12M PAA in 60:40 Ethanol:DMAC, 40° C. | $1.78 \times 10^5$ |
| GA-autopolymer | Less than $10^{3a}$ |
| GA-SA | Less than $10^{3a}$ |
| 0.12M PAA, 1:1, Room temperature-cleaned | $1.35 \times 10^5$ |
| 0.12M PAA-GA, 1:1 Room temperature-cleaned | $6 \times 10^5$ |
| 0.12M PAA-GA-SA, 1:1 Room temperature-cleaned | $7.35\ 10^5$ |

In Table H, *Polymer mixture 1 [23% of $10^{3.114}$; 58% of $10^{5.236}$ and 19% of $10^{6.34}$]; #Polymer mixture 2 [14% of $10^{6.34}$, 2.6% of $10^{3.114}$]; +Polymer mixture 3 [38% of 3.11, 14% of $10^{4.455}$ 19% of $10^{5.236}$, 29% of $10^{6.34}$]. IZ: Carbodiimizole; 1:1.03 refers to ODA:PMDA ratio; I: isoleucine; W: L-tryptophane methylester; pAS: p-aminoscalicylic acid; PDA-PAA refers to p-phenylenedianiline+pyromellitic dianhydride PAA; SA: sulfanilic acid. $^a$ Refers to the value was below lowest MW of standard, so it was not calculated.

$^1$H DOSY is a technique to identify average MW of polymer mixtures. Four individual polystyrene standards and three mixtures of them were used in order to generate the standard graphic shown in FIG. 6, and evaluate the parameters of DOSY experiments. As seen from the standard graphic, $^1$H DOSY has less than 0.01% uncertainty. Table 3 shows that $^1$H DOSY provides highly satisfactory results for revealing the average MW of the polystyrene polymer mixtures.

Typically, crosslinked PAA polymers are supposed to show higher molar masses (MS). $^1$H DOSY experiments showed that even individual PAA polymers showed higher MS than glutaraldehyde (GA) crosslinked PAA. Further tests include aged GA-crosslinked PAA, (fresh) GA-crosslinked PAA, GA autopolymers, and GA-small molecule co-polymers gave more clues about the size of the membranes. Among the cross-linked PAA polymers, fresh GA-PAA gave the highest value while PAA-W-GA (aged) gave the lowest MW. Since it is not possible to apply a strict control on the activity of GA, there can be a variety of co-polymers which could be generated from just the GA autopolymer-PAA, GA autopolymer, GA-small molecule copolymer, PAA-GA-PAA copolymers etc.

Comparison of different concentrations of PAA and the solvent systems showed that the average PAA size was not changed. However, heat treatment and ODA:PMDA ratio affected the MW. Based on $^1$H DOSY data along with the observed viscosity, 0.12 M PAA prepared with Ethanol/DMAC mixture at 40-50° C. was employed as the standard film condition for any type of application described throughout the present disclosure.

NMR data provided additional information about the MW of polymers based on $T_1$-relaxation times, which relies of spin-lattice relaxation. Due to the fact that PAA polymers possess aromatic protons, $T_1$ relaxation times were compared in order to compare the MWs of the synthesized polymers. According to $T_1$ relaxation time test, heavy cross-linking by GA increases the MW of PAA polymers in accordance with the present disclosure.

IR Characterization—Functional groups on PAA and PAA-copolymers were determined with a Spectrum 65 FT-IR spectrometer [Perkin Elmer, Waltham, Mass.]. Membranes at solid-state was used to perform IR study. The results are tabulated in Table I.

TABLE I

Effect of GA on shifts in IR functional groups

| Film | O—H | NH$_2$/NH | C=O | C—N | C=C |
|---|---|---|---|---|---|
| Phase inverted-PAA | 3688/ 3222/2680 | 3422/3161/ 1624/1578 | 1692/ 1769 | 1352/ 1287/ 1306 | 1352/1452/ 1520/1580 |
| All of the modified PAAs | 3224/2700 | 3432/ 3164/1578 | 1812/ 1170/ 1668 | 1352/ 1308/ 1289 | 1636/1444/ 1464/1526/ 1574-1578 |

Stand-alone membranes were directly used for IR-characterization; the membranes were not crushed into powder or located onto IR cards.

Functional groups on PAA and PAA-copolymers were determined with a Spectrum 65 FT-IR spectrometer [Perkin Elmer, Waltham, Mass.]. Membranes at solid-state were used to perform IR study.

Figure 7:
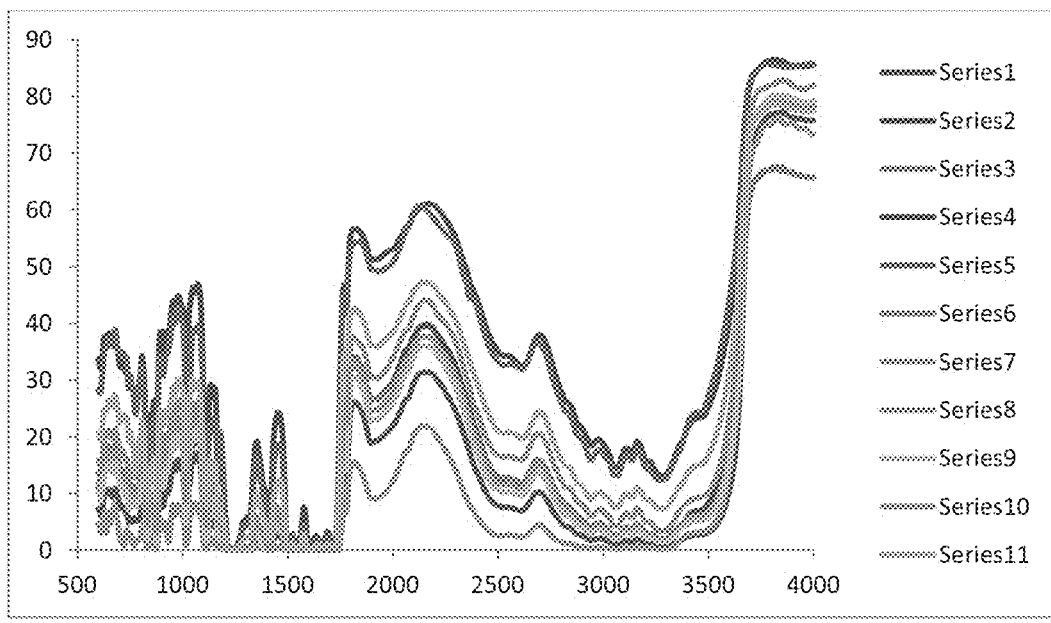
FIG. 7 is a graphical illustration of the IR spectrum of different PAA co-polymers.

FIG. 7 illustrates the IR spectrum of different PAA co-polymers. Series: 1: PAA-A-GA; 2: PAA-pAB-GA; 3: PAA-PC1-GA; 4: PAA-PC1-GA (direct hood); 5: PAA-DPC-GA; 6: PAA-C-GA; 7: PAA-BB-GA; 8: PAA-W-GA; 9: PAA-A-GA (direct hood); 10: PAA-A-GA (partially dissolved A); 11: PAA-pAB-GA (direct hood). Stand-alone membranes were directly used for IR-characterization; the membranes were not crushed into powder or located onto IR cards.

As seen from Table I, GA modification shifted the IR peaks to slightly higher frequencies for a majority of the PAA functional groups which is a sign of increases in mass of the polymers, which was depicted by $^1$H DOSY results as GA increased MW of PAA polymers up to 5 times. Besides, abundant peaks for C=C and C=O bonds were observed while O—H and —NH showed less peaks. Due to some groups overlapping in these polymers, characteristics of certain added groups were not observed in IR spectrometry. As seen from NMR characterization, introduction of GA and small molecules reveal more peaks correlated to —C=O and —C=C— groups, so it implies that the extra peaks seen are from GA and the small molecules. Decreases in O—H and —NH peaks could be related to the data that shows that cross-linking with GA might be shifting the amino groups resulting in overlapped and/or non-differentiable in IR spectra, whose spectrums are provided in FIG. 7.

Figure 8A:
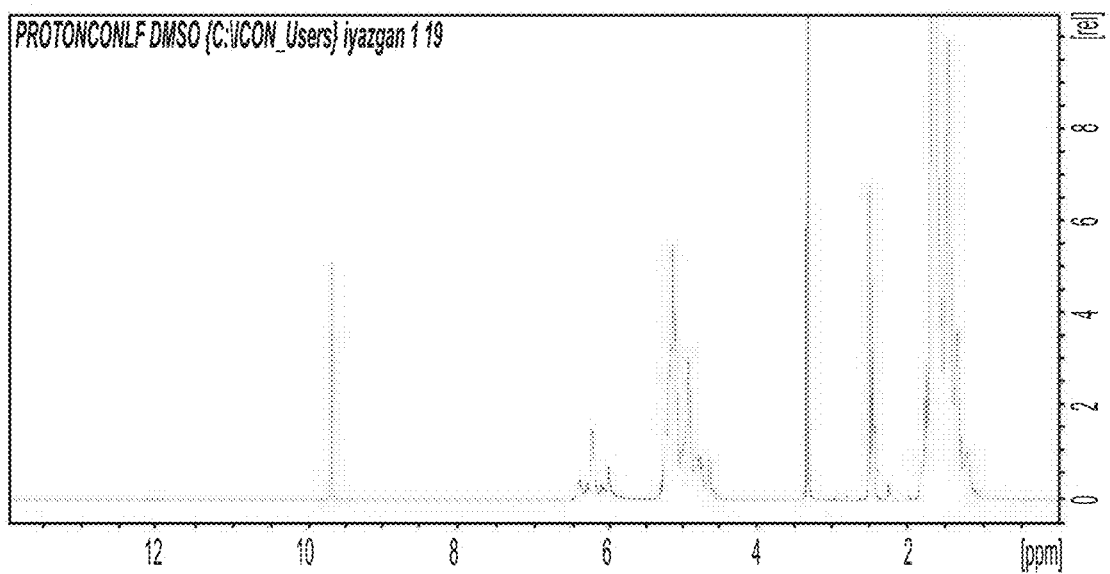
FIGS. 8a-8h are illustrations of NMR data.
Figure 8B:
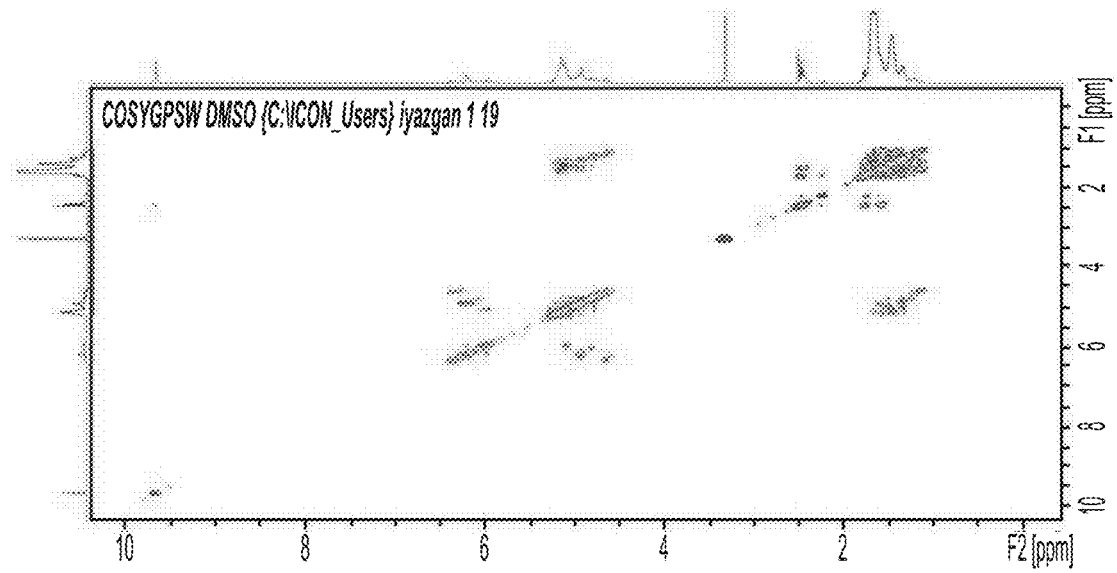
Figure 8C:
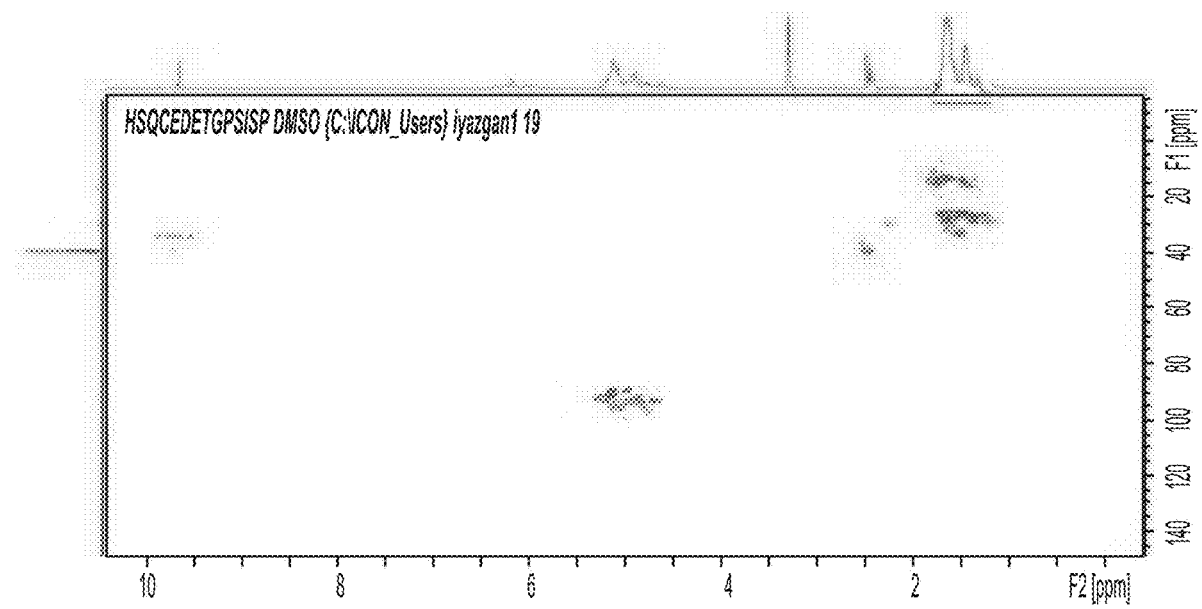
Figure 8D:
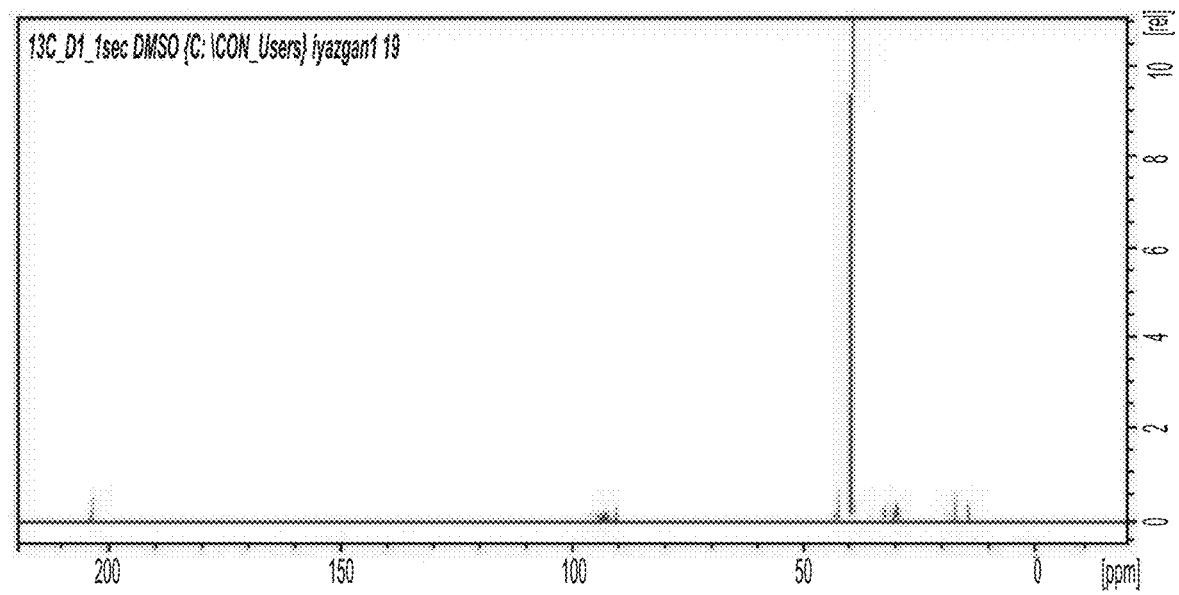
Figure 8E:
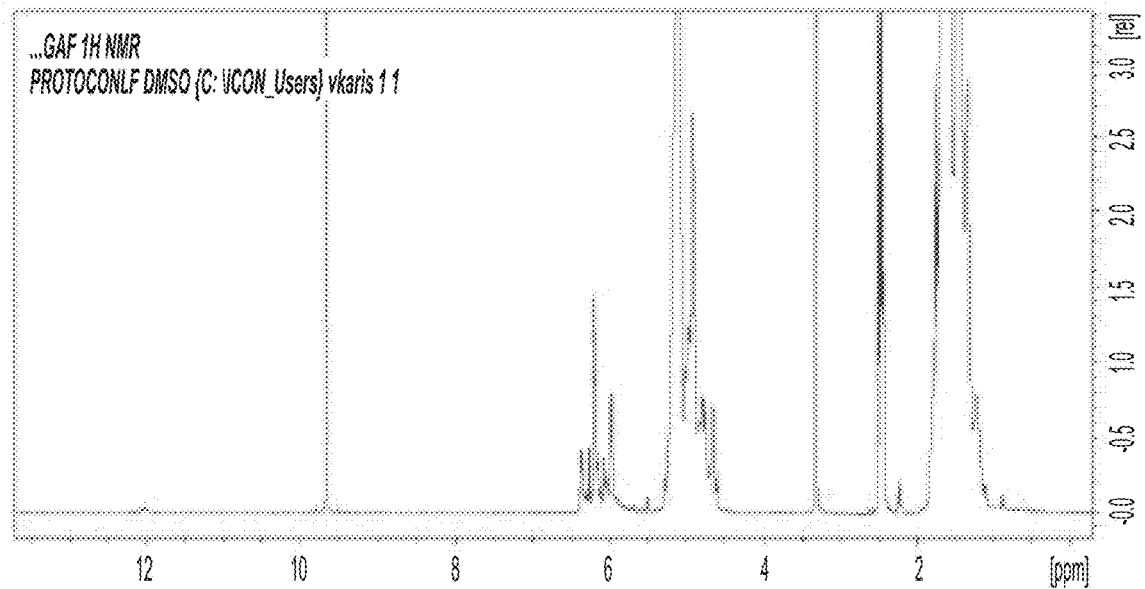
Figure 8F:
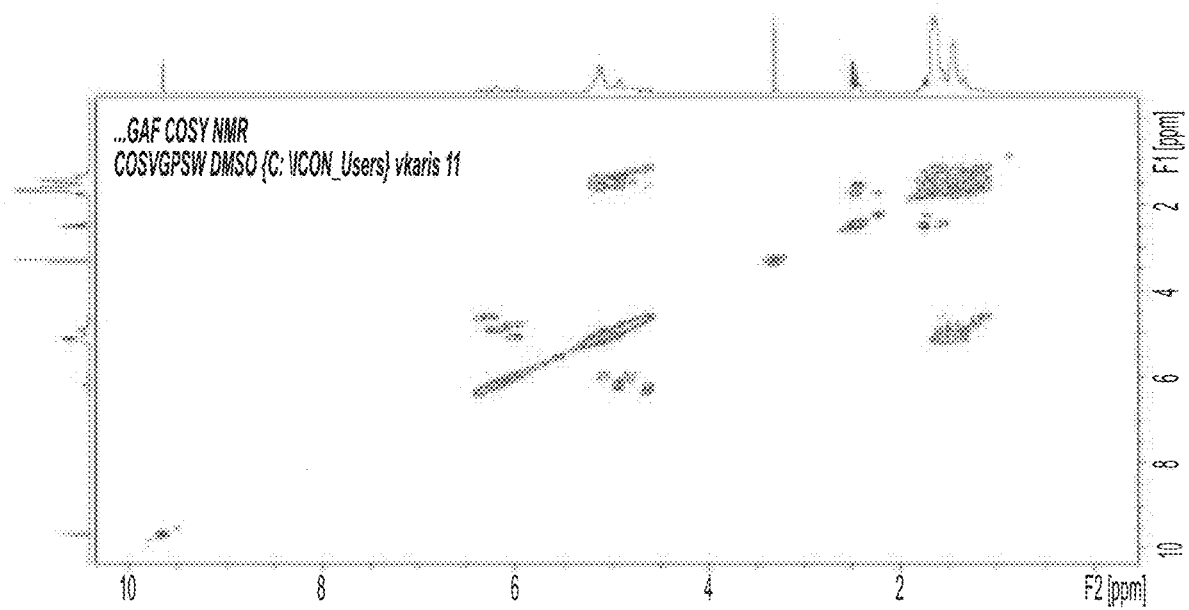
Figure 8G:
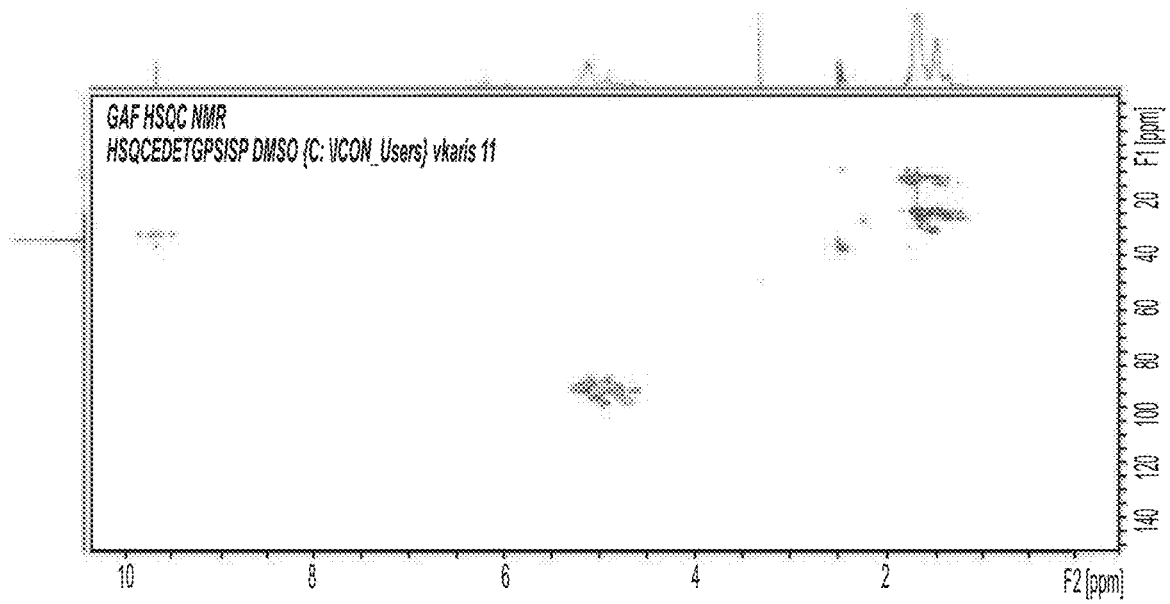
Figure 8H:
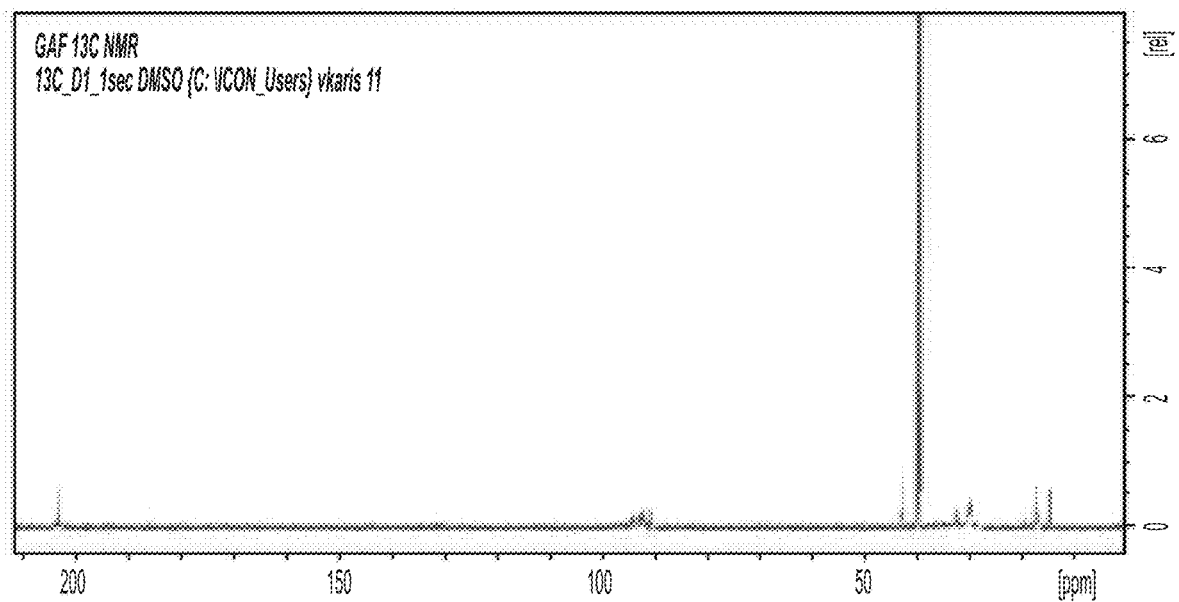

FIG. 8a is NMR data for FIG. 8b is NMR data for $^1$H COSY, FIG. 8c is NMR data for $^1$H $^{13}$C HSQC and FIG. 8d is NMR data for $^{13}$C NMR spectra of the aged GA while FIG. 8e is NMR data for $^1$H, FIG. 8f is NMR data for $^1$H COSY, FIG. 8g is NMR data for $^1$H $^{13}$C HSQC and FIG. 8h is NMR data for $^{13}$C NMR spectra of stock GA did not show characteristic alterations in groups.

$^1$H COSY showed that the interaction at 0.9-0.9 ppm, 1.45-2.43 ppm, 2.47-9.65 ppm and 4.08-6.47 ppm were only seen for stock GA. Actually, the interaction at 0.9 ppm shows that the peak at 0.9 ppm of stock GA was not seen in the aged GA.

Comparison shows that $^1$H $^{13}$C has some differences as well such as the aged GA has more interaction at 1.2-1.7 (H) 13-35 (C) ppm and 4.6-5.2 (H) −93-97 (C) ppm ranges.

Figure 9:
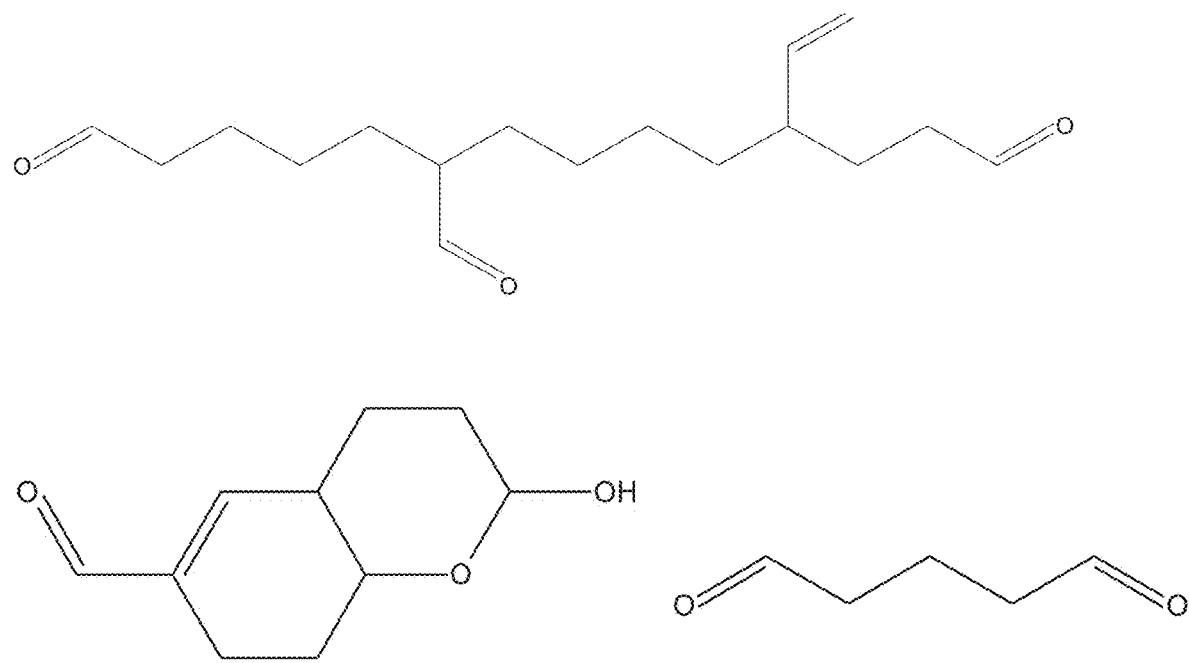
FIG. 9 is illustrations of different chemical structures.

Integration of the characteristic peaks in $^1$H showed that aging decreased free available carbonyl groups. GA can have different forms in aqueous solutions, some of them are shown in FIG. 9. The peaks at 12 ppm, 9.6 ppm, 6.0-6.5 ppm range, 4.5-5.2 ppm range, 1.0-2.0 ppm were accepted as that these peaks are from hydroxyl groups, carbonyl groups, cyclic groups, the protons of double bond containing C groups and hydrogen of saturated carbons, respectively. Carbonyl group has the function of GA to show its cross-linking potency; that's why, its integration was calibrated to 1, and the rest was calculated relative to the carbonyl integrals. For the aged integrations were obtained as 0.057 (—OH), 1 (HC=O), 3 (H-cyclic), 16.1 (HC=C) and 50 (—CH$_3$) while the integrations of the stock (fresh) GA were obtained as 0.04 (—OH), 1 (HC=O), 2.14 (H-cyclic), 14.26 (HC=C) and 44 (—CH$_3$). This shows the aging decreased the percentage of free carbonyl group around 30% in comparison to stock GA. Presence of doublet C=C bonds and cyclic C-residues increased. This could be the reason of getting colored and fluorescent active PAA with aged GA in comparison to the stock GA. However, it should be mentioned that it is not required to use aged GA to get colorful and fluorescent active PAA; the stock GA can be dissolved in DMAC, followed by introduced to PAA or PAA-small molecule mixture to get colorful and fluorescent active membranes.

Example 1.3—Scanning Electron Microscopy/Optical Characterization

Characterization of the PAA membrane morphology was carried out on a Zeiss Supra 55 VP field emission scanning electron microscope (SEM). The membranes were imaged both before and after filtration. All samples were coated with 2-5 nm gold layers for SEM imaging.

Only the membranes produced according to FIG. 1b were characterized for optical properties. Uv-vis properties were evaluated using HP Agilent 8452 spectrometry while Shimadzu RF 6000 fluorometer was utilized to characterize fluorescence properties. Uv-vis characterization was only performed for the stand-alone films while both stand-alone membranes and their dissolved forms were utilized for fluorescence characterizations.

Digital images of ternary PAA membranes from FIGS. 1a and 1b. a-PAA; b-PAA-DA; c-PAA-A; d-PAA-A was incubated in 30 min at 70° C. in addition to overnight incubation; e-PAA-A similar to d but higher GA concentration; f-PAA-A same GA concentration to e, but just incubated in room temperature; FIG. 1a. GA was applied at different concentrations to the PAA solutions. g-PAA-A with %0.3 GA; h-PAA-A with %0.9 GA; i-PAA-CA with %0.3 GA; j-PAA-CS with % 0.3 GA; k-PAA with % 0.3 GA; l-PAA with %0.9 GA, and m-PAA-DA with % 0.9; FIG. 1a i. n-PAA-A 3 h incubation; o-PAA-A; p-PAA-C; q-PAA and r-PAA-DA. FIG. 1a iii with 0.9% GA from 70% GA stock. s-PAA with %0.3 GA; FIG. 1a ii. This showed woven-like surface as shown by SEM imaging. The images "t" and "u" are synthesized with FIG. 1a iii with 0.35% GA concentration. In 6 h, PAA-CS gave green membrane [t] which could be peeled off from glass surface, which gave gel-like structure. The gel like membrane [t] was then phase-inverted in pure water and incubated overnight under hood [u]. The following membranes were prepared according to FIG. 1b; v: PAA-5AS-GA, w: PAA-4AS-GA-MeOH, x: PAA-AcOH-CA-GA, y: PAA-pAB-GA, z: PAA-AcOH-Ser-GA-MeOH, aa: PAA-PC1-GA, ab: PAA-AcOH-A-GA-MeOH, ac: PAA-5AS-GA but this is just incubated in RT, ad: PAA-5AS-GA but direct hood evaporation, ae: PAA-PC1-GA-MeOH [right after GA], af: PAA-MeOH-Ammonium Nitrate-GA [direct hood], ag:PAA-PC1-GA, ah:PAA-5AS-GA, ai:PAA-A-GA. Even though the images v, ac, ad and ah are made out of PAA-5AS, 5AS content and incubation procedure affect the color formation; ah has the lowest 5AS concentration. aj-PAA-I-GA.

Digital images of some films from FIG. 1b are shown in FIGS. 11a-11l. All the films were prepared according to FIG. 1b, and GA concentration was 0.1% while PAA was 0.12 M; a: PAA phase inverted under hood; b: pAB-GA-PAA; c: W-GA cross-linking for 15 min then introduced into PAA solution; d: pAB dissolved in DMAC incubated with GA for 15 min, followed by introduced into PAA solution; e: pAB was added to PAA solution, followed by addition of GA; f: W-GA cross-linking for 5 min then introduced into PAA solution; h: pAB dissolved in DMAC incubated with GA for 30 min, followed by introduced into PAA solution; i:W was crosslinked with aged GA, followed by introduced into PAA; j: pAS and W were added into PAA solution, followed by addition of GA; k: pAS was dissolved in DMAC, and then added into PAA solution, followed by added 0.2% pAB-GA (at that moment the incubation was passed already 30 min); j: W cross-linked with fresh GA (stock 70%), followed by added into PAA.

Figure 10A:
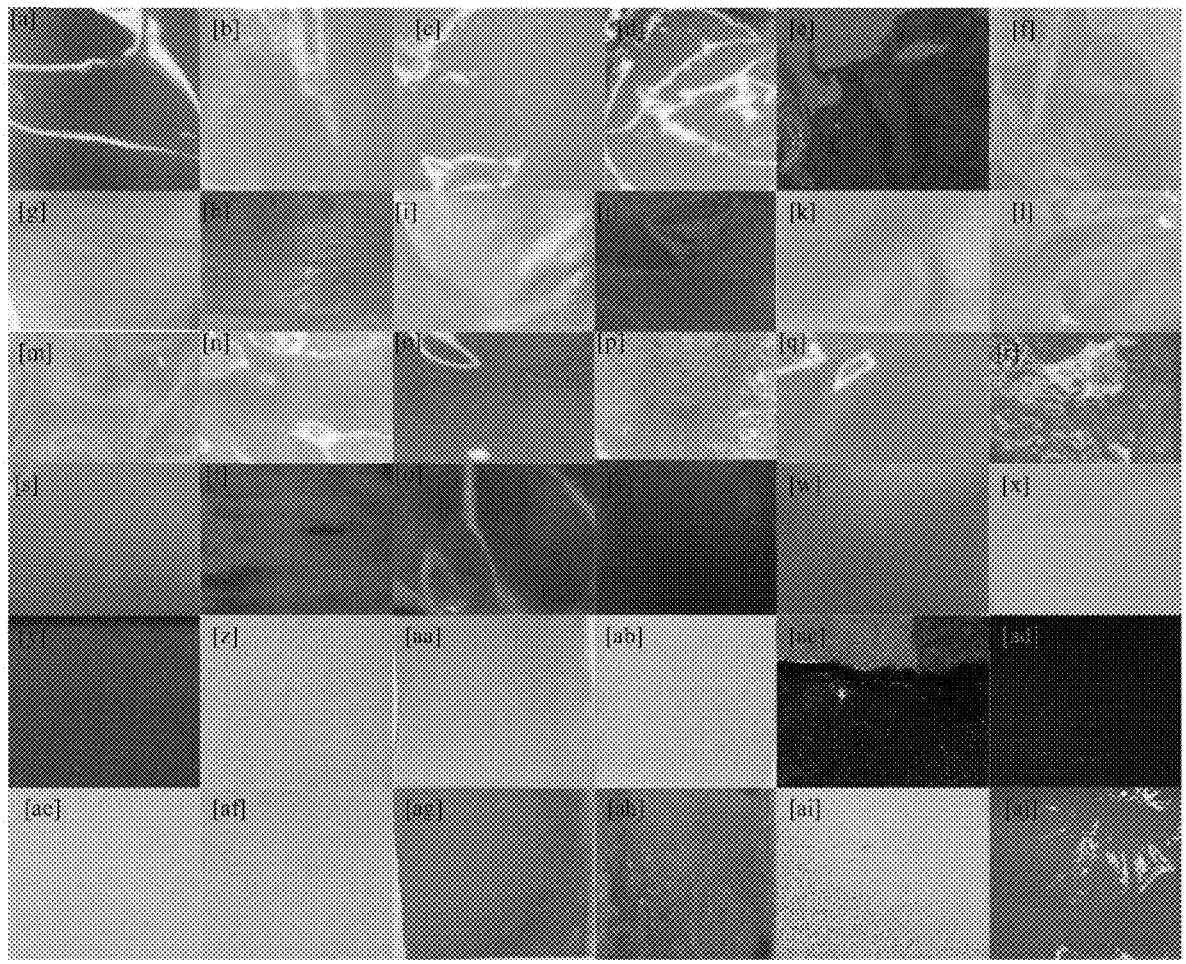
FIGS. 10a-10aj is photographs of various PAA films.

A discussion of FIGS. 10a-10aj and FIGS. 11a-11l follows. As seen in FIGS. 10a-10aj, PAA-DA gave some blue region but the rest is yellowish due to the fact that high amount of GA stacked in localized places because of high viscosity-related quenched stirring. Similarly, FIG. 10ac, FIGS. 10ah-10ai and FIG. 11b and FIG. 11h possessed uneven surfaces. Interestingly, increased incubation time and high GA concentration form colorful plastic like membranes in FIG. 1a, these parameters didn't show any significant effect on formation of different colored membranes with plastic-like structures. However, for both FIGS. 1a and 1b, treating GA with DMAC alters the formed color as well as affecting on the other parameters such as contact angle and mechanical strength. For example, the membranes FIGS. 10 m and 10r were from PAA-DA. Even though, the membrane FIG. 10m is plastic-like transparent while the membrane FIG. 10r is opaque and dark-blue color with possessing higher contact angle; top/bottom contact angles of the membranes FIGS. 10m and 10r were 62.35/55.7 45.3/47.3, respectively. Due to the aggressive nature of GA, it can make excessive cross-linking in PAA solution.

Comparing FIG. 1 a i and iii for same GA concentration and incubation periods, it was shown that pre-dissolving GA in DMAC makes it much more active; this can be resulted from that dissolving GA from stock in dry DMAC partially or totally altering GA microenvironment, which then might change binding preferences and/or rate of binding. Formation of transparent membrane also strongly depends on the small molecule added to the PAA solution. For example, L-Alanine added PAA membranes always formed transparent plastic like membranes if a special treatment was not applied even for FIG. 1a.

However, L-Tryptophan methyl ester, L-Isoleucine and some other small molecules resulted in opaque membranes. Individual PAA, PAA-DA and PAA-CS are the ones gave distinctly different membrane formations by just shifting the procedure, FIG. 1a i to iii. It should be noted that the membranes of FIG. 1a were partially or totally formed before rinsing step. Unless the membrane is totally formed, rinsing with water forms partially or totally opaque membranes, which can be explained with the model proposed elsewhere. However, further drying (after rinsing step) turns the opaque membranes into transparent forms within 24 h under hood for relatively higher GA concentrations such as %1; but mostly these are brittle. For example, the membrane FIG. 10u couldn't be turned into a transparent membrane even at 48 h incubation. This could be related to the high DMAC content formed thicker interacted with non-solvent.

In contrast to this, it is possible to synthesize substantially transparent and durable membranes of FIG. 1a for all of PAA-small molecules even PAA-I if the GA concentration is higher 2% with pre-dissolved GA in DMAC. Using low GA concentration as 0.35% still can provide substantially transparent and durable membranes, but the incubation time should be 12 h at room temperature and 12 h under hood. 12 h incubation does not totally remove DMAC, but further rinsing does not cause any opaque-structure formation.

Figures 12M, 12N, 12O, 12P:
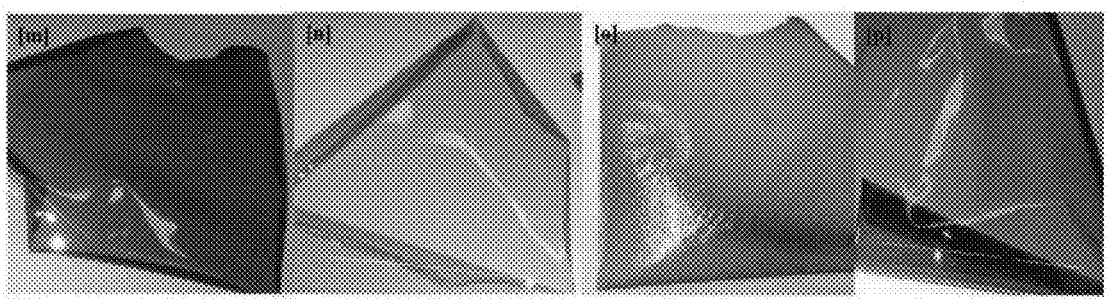
FIGS. 12m-12p is photographs of various PAA films.

FIG. 12m is photographs of PAA-SA (warmed)-pAS-5AS-GA, FIG. 12n PAA-SA-pAS-5AS-GA, FIG. 12o PAA-SN-GA, FIG. 12p PAA-SN-pAS-GA. Color change of the same films can also be manipulated by heating the small molecule, or introducing other small molecules at very low quantity. Warming up SA before it was pre-treated with GA changed the resultant film color from yellow to brown while FIG. 12p has only 0.1 mg/mL pAS in addition to FIG. 12o, but the color did changed.

Figures 11A, 11B, 11C, 11D, 11E, 11F, 11G, 11H, 11I, 11J, 11K, 11L:
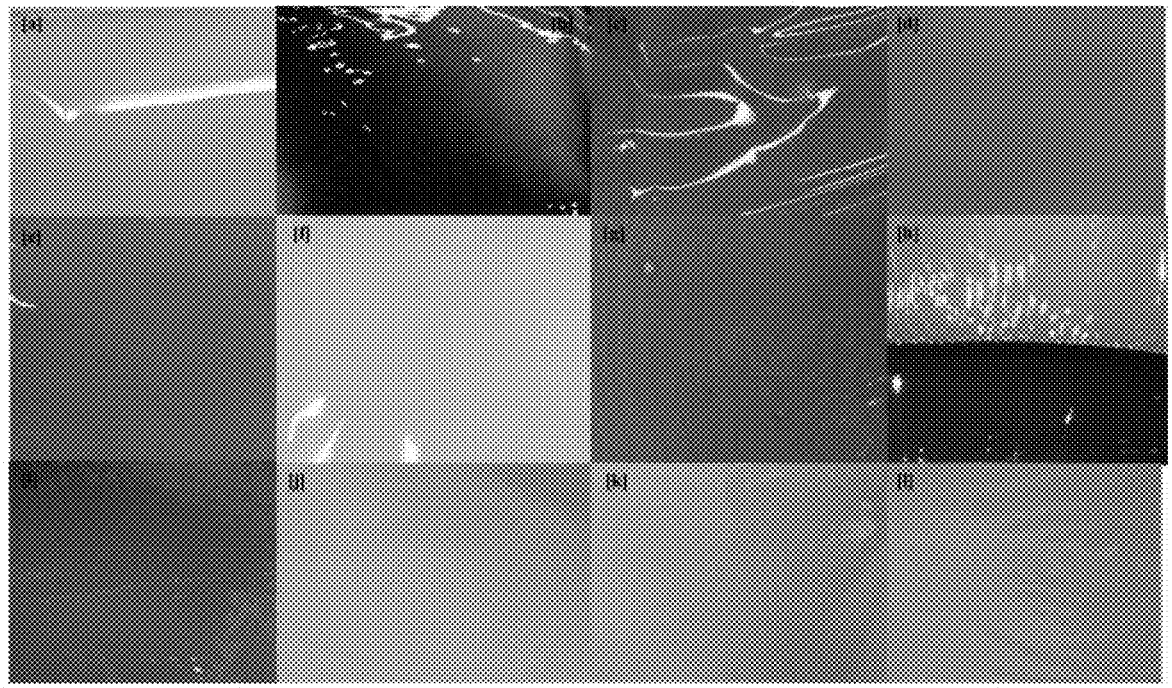
FIGS. 11a-11l is photographs of various PAA films.

Color formation in FIG. 1b is distinctly different from FIG. 1a. Pretreatment of small molecule with GA, GA condition (aged or fresh) and presence of cross-linking quenchers are the predominant parameters which can be even confirmed by only FIG. 10al. For instance, pretreatment pAB with aged GA provided blueish membrane formation while adding pAB directly into PAA-GA mixture formed slightly maroon color membrane. Another example is that using fresh GA instead of aged GA resulted in shifting the color from green (FIG. 11i) to yellow (FIG. 11l).

Example 1.3.1—UV-Vis Spectra of PAA and Ternary PAA Membranes

UV-Vis spectroscopic properties of PAA membranes were evaluated to determine the effect of small molecule and GA on formed membranes. PAA phase-inverted membranes that were processed in the hood were compared with the PAA that were synthesized according to FIG. 1a.

Figure 13A:
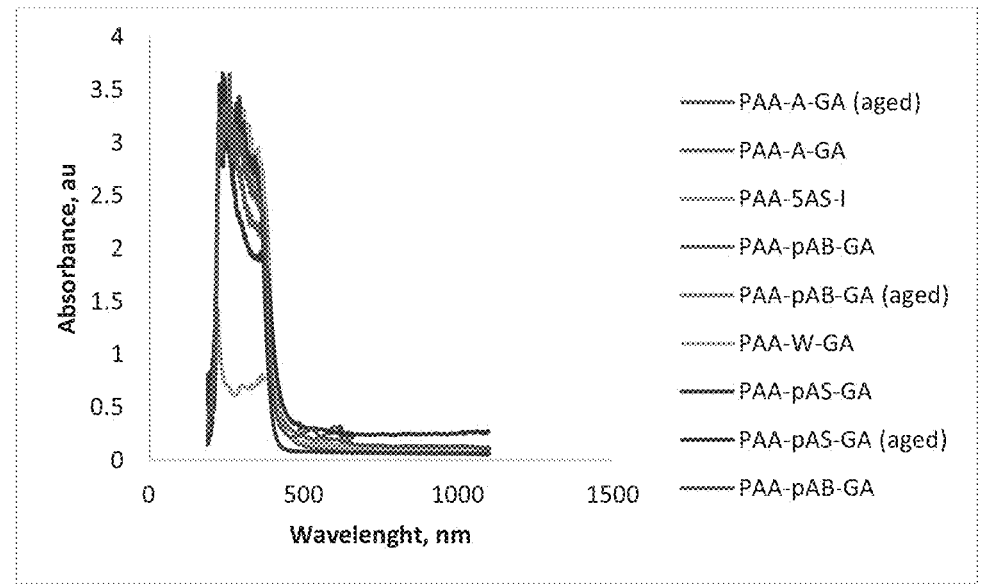
FIGS. 13a-13b are graphical illustrations of absorbance and transmittance values of various PAA films.

FIG. 13a illustrates UV-vis of some of the synthesized membranes. PAA: Poly(amic)acid; A: L-alanine; GA: glutaraldehyde; 5AS: 5-aminosalycylic acid; I: L-isoleucine; pAB: p-aminobenzoic acid; W: L-tryptophan-L-methyl-ester; pAS: p-aminosalycylic acid.

Figure 13B:
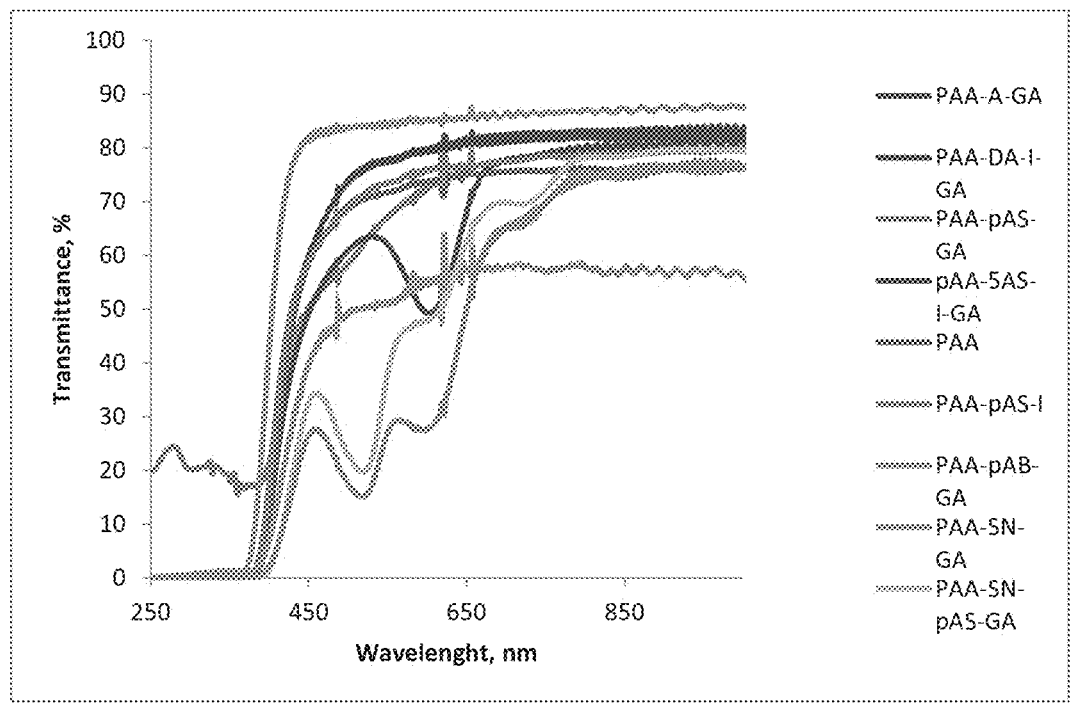

FIG. 13b illustrates ransmittance of some of the membranes synthesized in the study. PAA: Poly(amic)acid; A: L-alanine; GA: glutaraldehyde; 5AS: 5-aminosalycylic acid; I: L-isoleucine; pAB: p-aminobenzoic acid; DA; glucosamine; pAS: p-aminosalycylic acid; SN: sulfanilamide.

In FIG. 13a, there is no PAA peak from 400 to 700 nm range. The peaks are related to a small molecule being introduced to a PAA molecule. Even though the overall color of the membranes showed strong dependence on the condition of GA and GA pretreatment of small molecule, UV-Vis characterization did not provide any significant difference.

Transmittance of the membranes is important for food packaging material applications. All of the membranes showed over 65% transmittance between 450 to 700 nm. The used membranes (i.e. PAA-I-GA, PAA-I provided good visibility for monitoring food conditions. However, PAA-SA-pAS-5AS-GA and PAA-SN-pAS-5AS-GA have lower % transmittance at certain wavelengths such as ~510 nm and 650 nm. It should be mentioned that these are not affecting the overall visibility of the packaged food.

Unlike UV-Vis properties, fluorescence characteristics of PAA membranes showed strong dependence on GA condition, incubation period, GA pretreatment with small molecules and the presence of methanol and ethanol. However, it should be noted that optimizing the conditions are challenging due to the fact that GA can crosslink a variety of other groups including primary/secondary amino groups, thiol groups, hydroxyl groups of sugars and aromatic carbons.

Figure 14A:
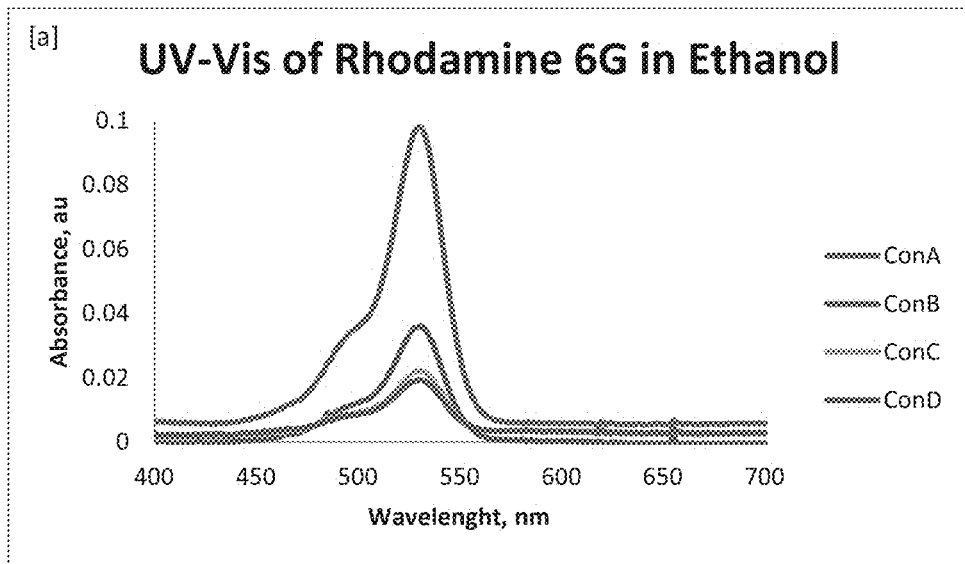
FIGS. 14a-14b are graphical illustrations of absorbance and emission values of various PAA films.
Figure 14B:
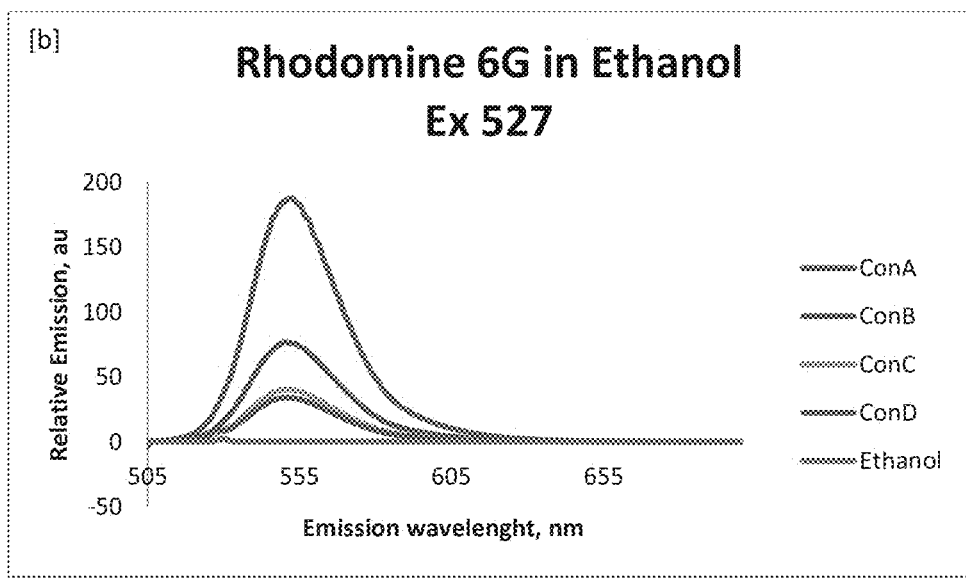
Figure 15A:
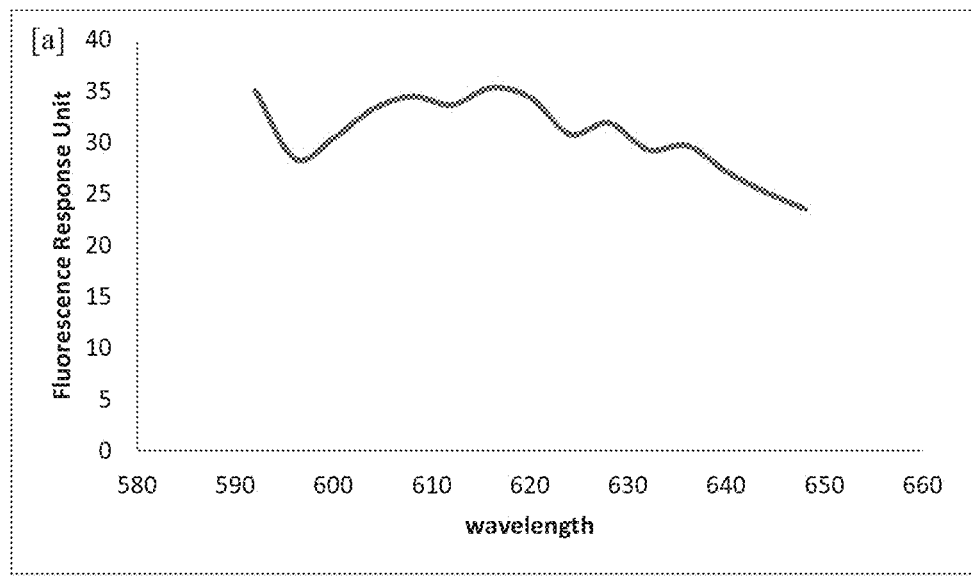
FIGS. 15a-15e are graphical illustrations of fluorescence values of various PAA films.
Figure 15B:
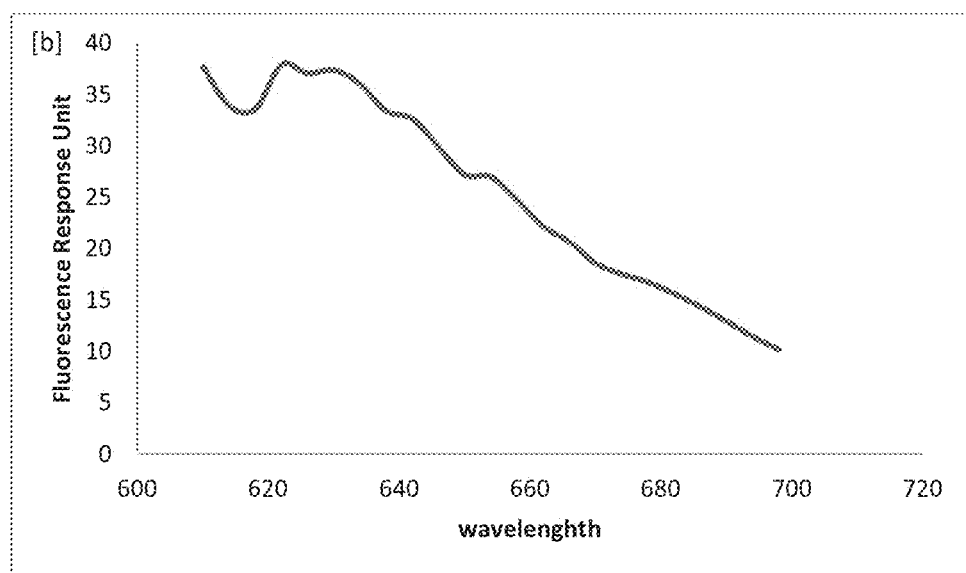
Figure 15C:
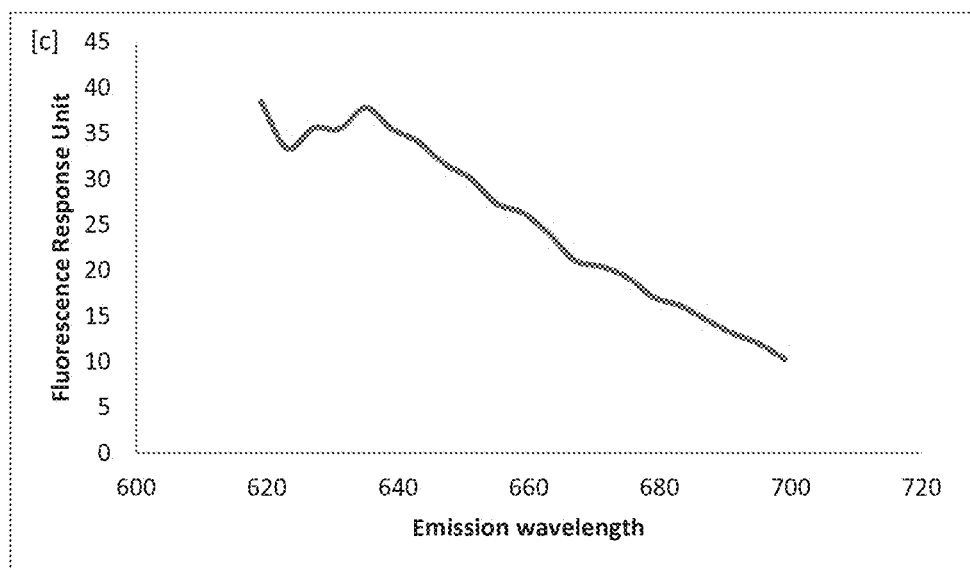
Figure 15D:
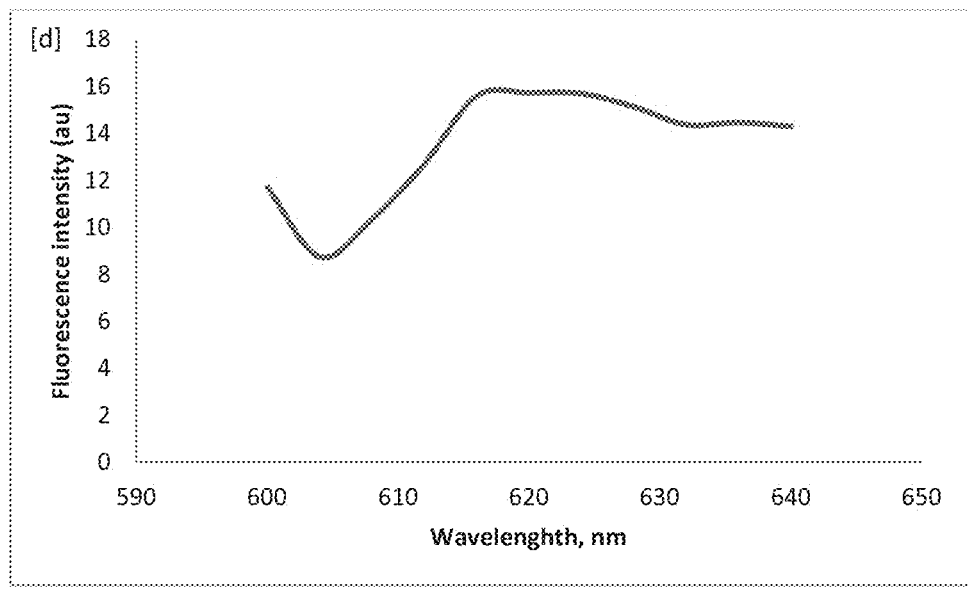
Figure 15E:
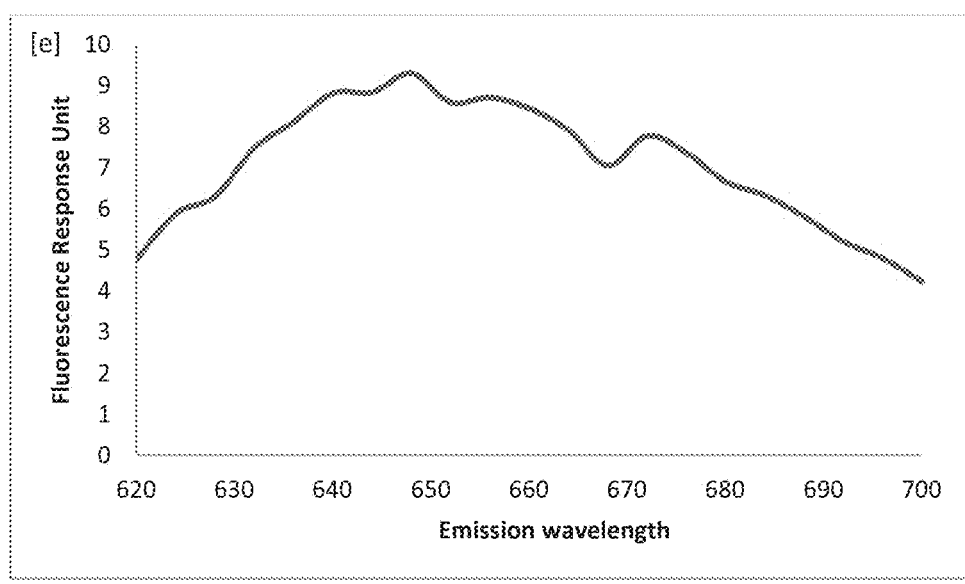

The Fluorescence Characteristics of several films are discussed below. FIGS. 14a and 14b illustrate Rhodamine 6G standards.

FIGS. 15a-15e illustrate several spectra. The spectra seen in "a" and "b" belong to yellowish PAA-A-GA membranes while the spectrums seen in "c" and "d" belong to the greenish PAA-A-GA membrane. The spectrum "e" belongs to PAA-GA. All of the membranes were synthesized according to FIG. 1a, and standalone membranes were used during fluorescence run. Excitation wavelengths were 581 nm, 598 nm, 608 nm and 596 nm for a-d membranes, respectively. Emission ranges were 592-648 nm, 610-698 nm, 619-699 nm and 600-640 nm for a-d membranes, respectively. Absorbance was kept below 1 for all, and during fluorescence measurement sensitivity was kept high. As it is seen, for all membranes, fluorescence intensity started with a decreasing trend, followed by increases in the intensity. However, PAA-GA showed an increasing trend for fluorescence intensity from the starting point, whose excitation was 612 nm while the emission range was between 620 nm and 700 nm. More than one maximum-emission peak was observed for all. The fluorescence quantum yields of these membranes were below 0.1.

Figure 16A:
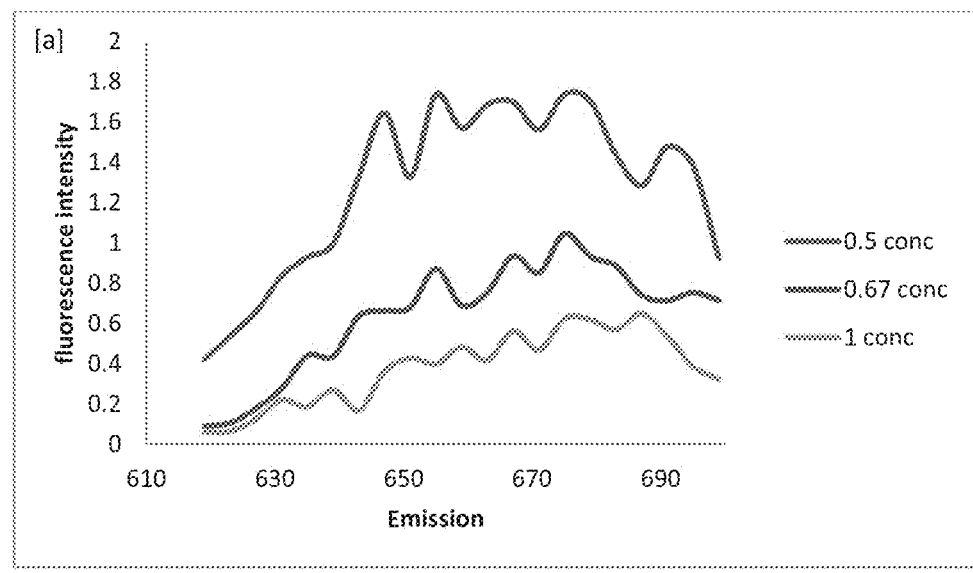
FIGS. 16a-16b are graphical illustrations of fluorescence values of various PAA films.
Figure 16B:
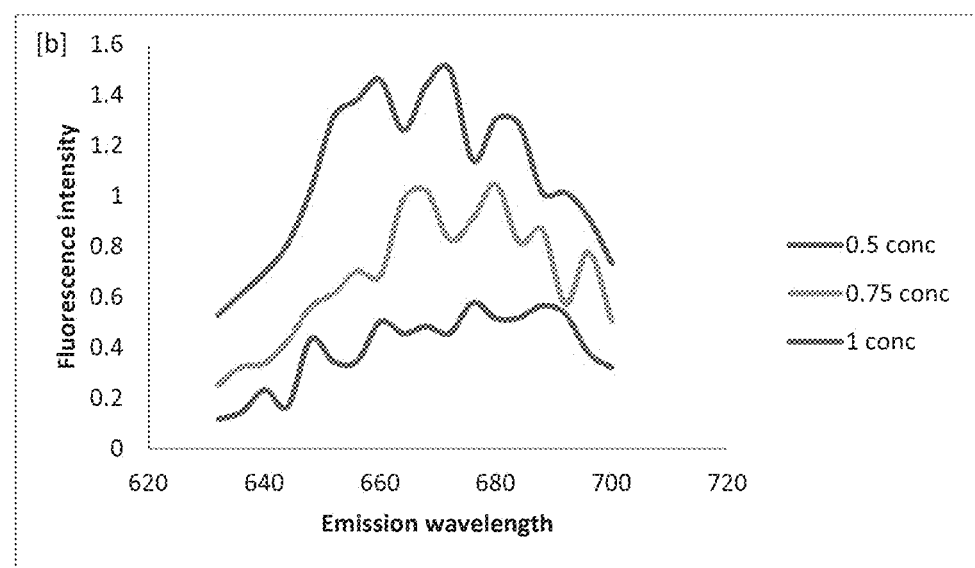
Figure 17A:
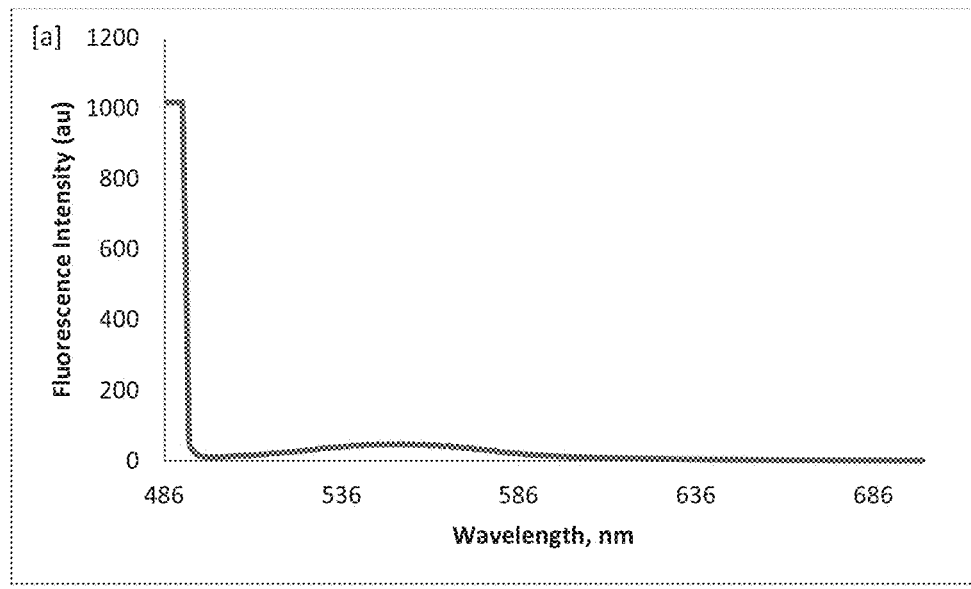
FIGS. 17a-17e are graphical illustrations of fluorescence values of various PAA films.
Figure 17B:
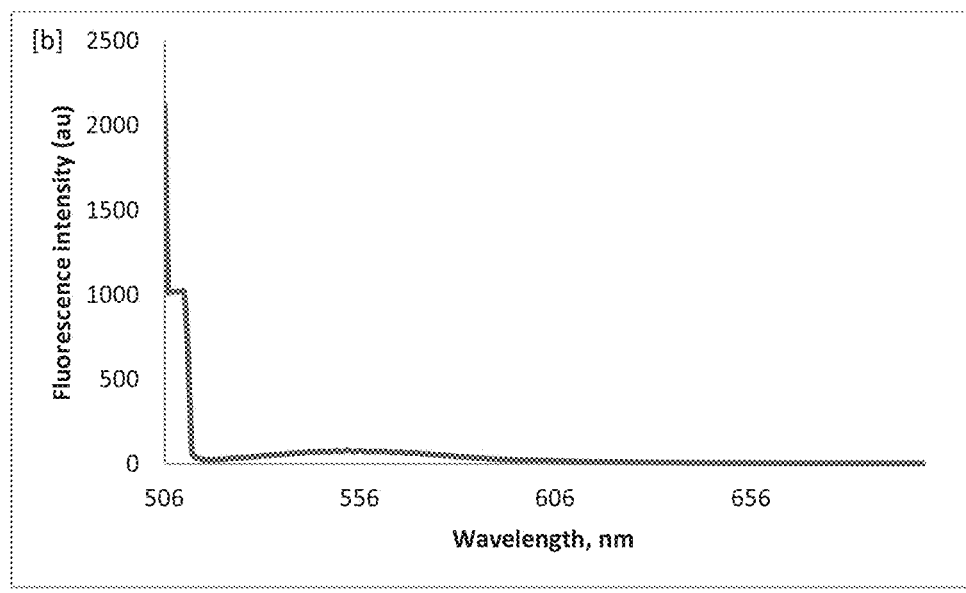
Figure 17C:
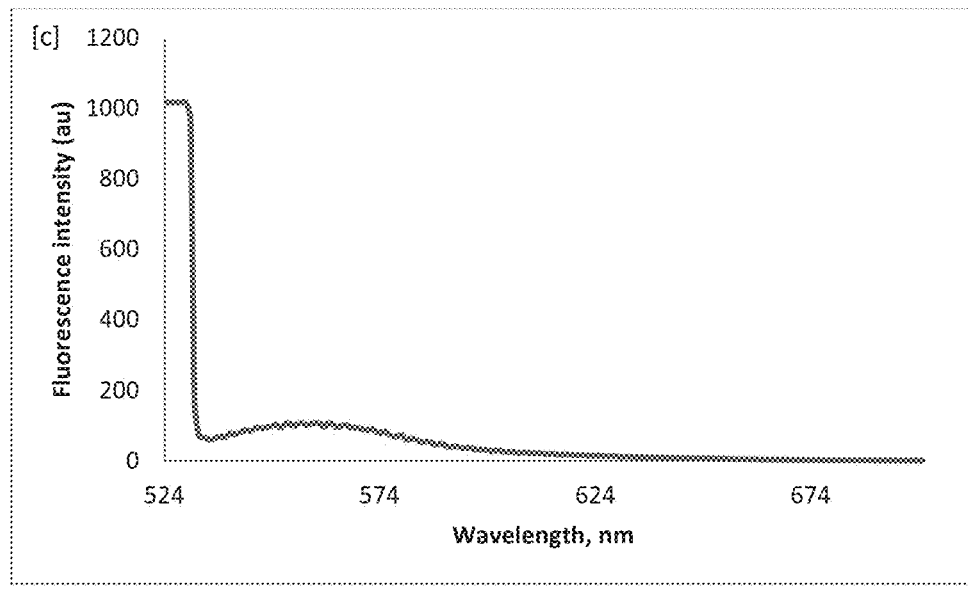
Figure 17D:
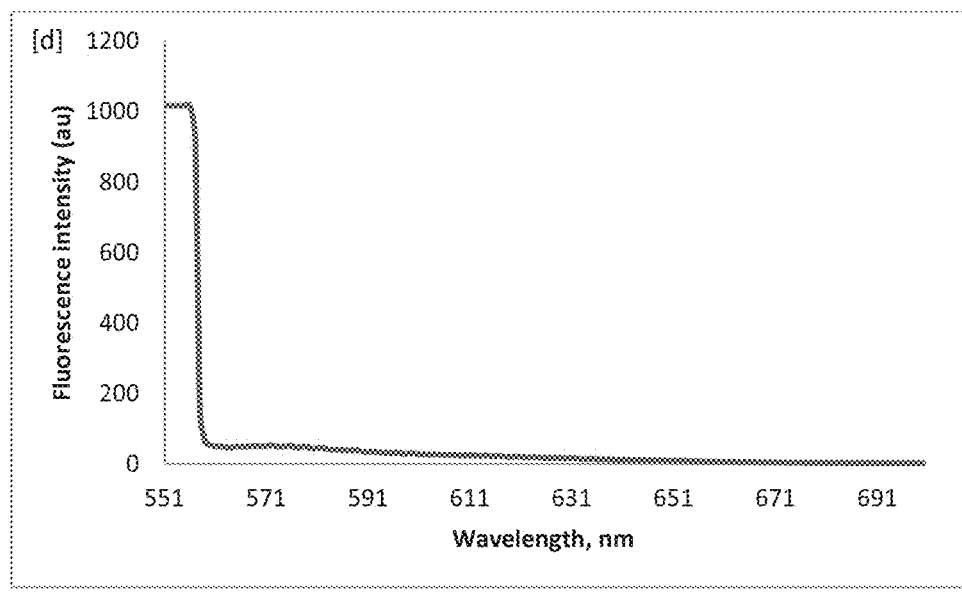
Figure 17E:
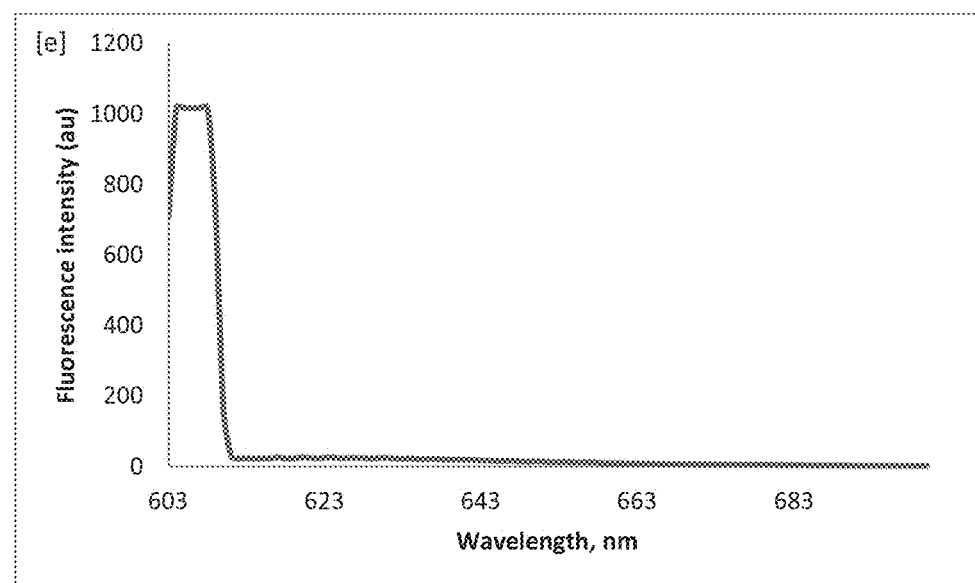
Figure 18A:
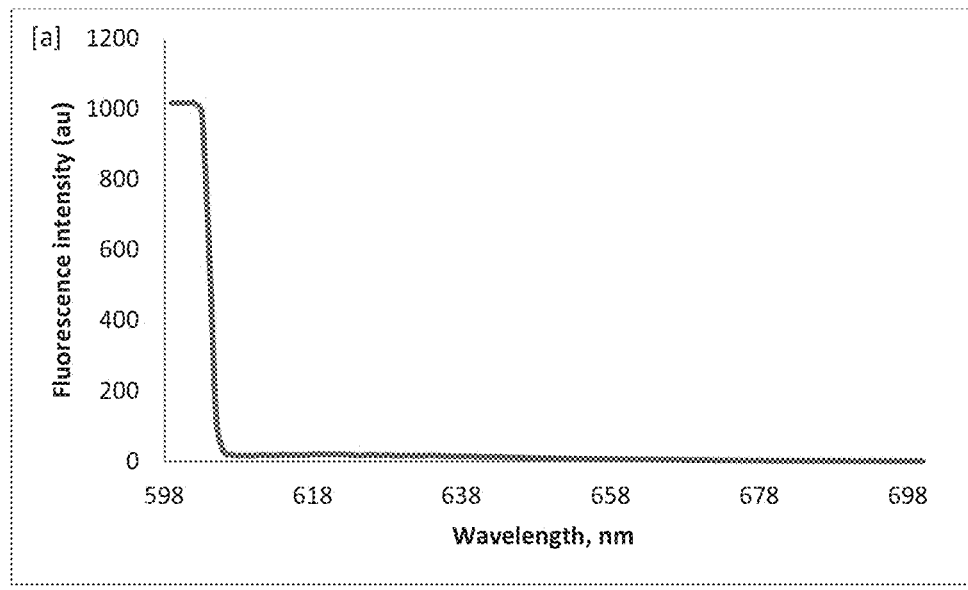
FIGS. 18a-18d are graphical illustrations of fluorescence values of various PAA films.
Figure 18B:
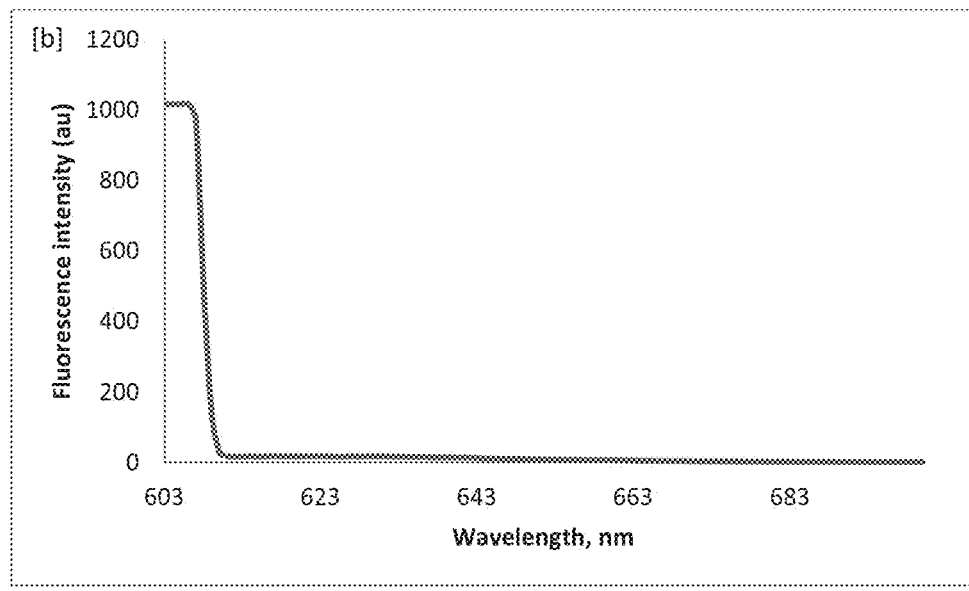
Figure 18C:
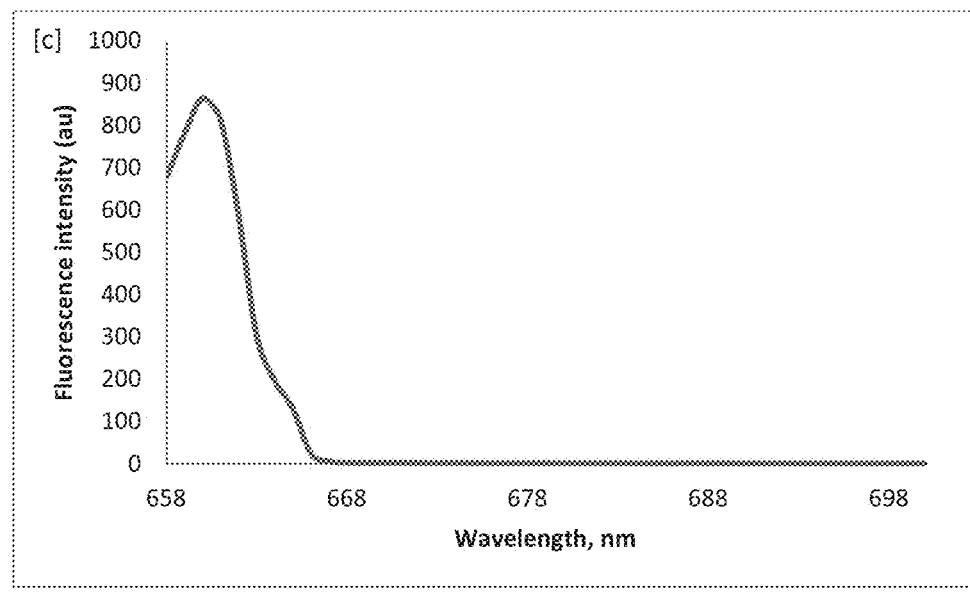
Figure 18D:
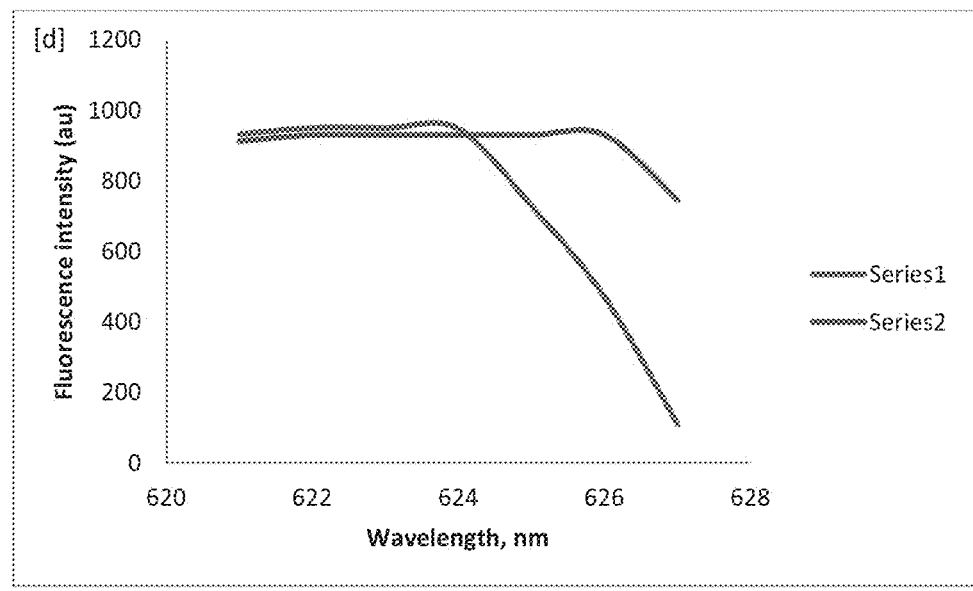
Figure 19A:
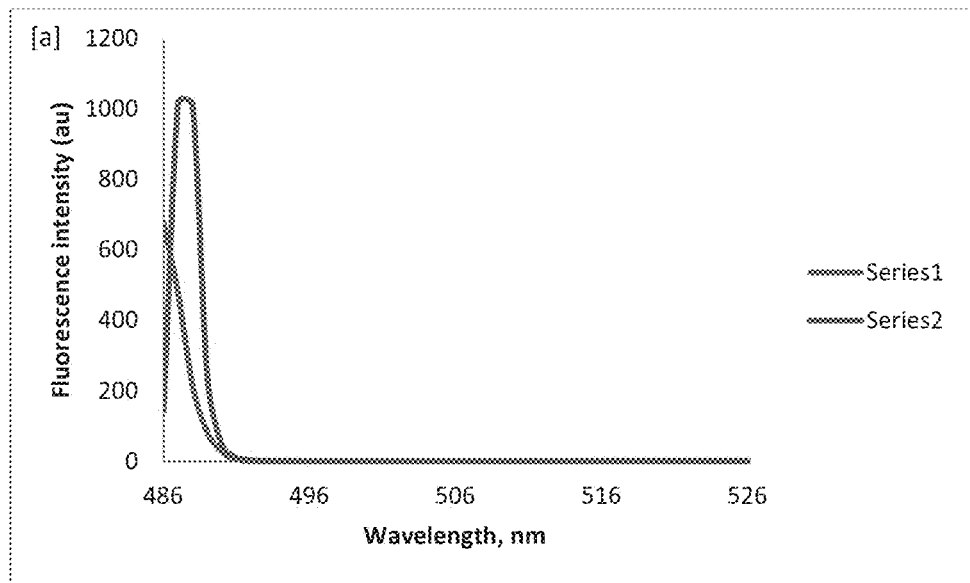
FIGS. 19a-19d are graphical illustrations of fluorescence values of various PAA films.
Figure 19B:
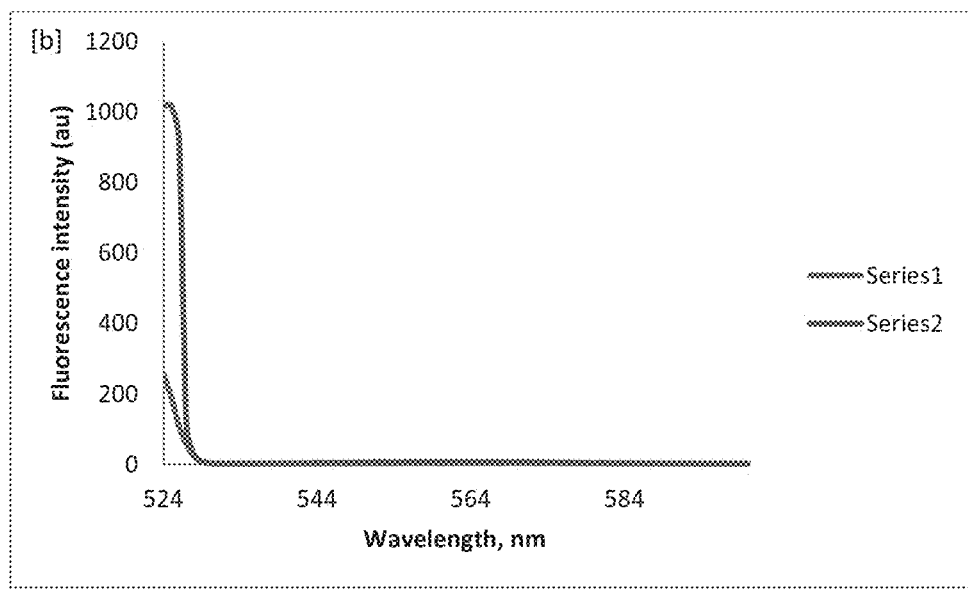
Figure 19C:
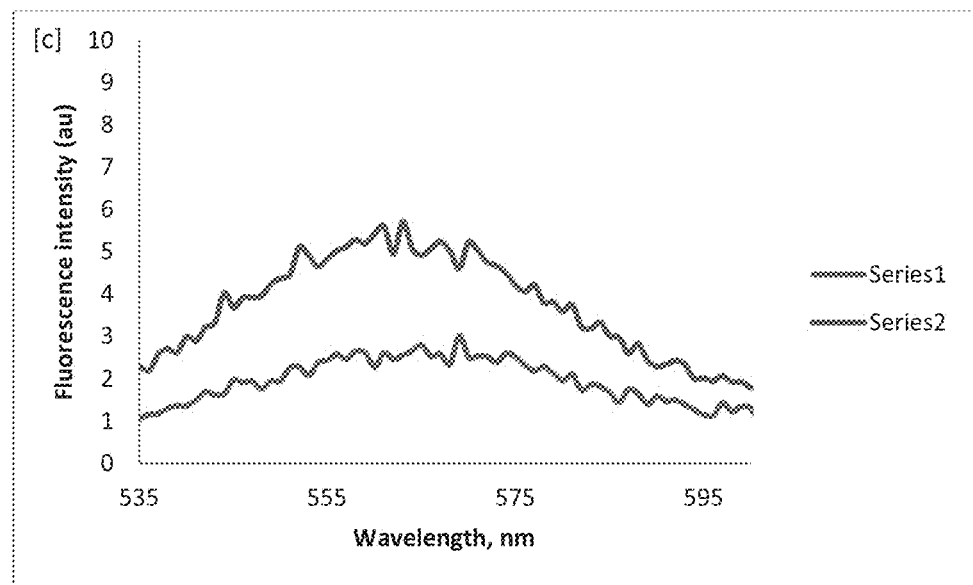
Figure 19D:
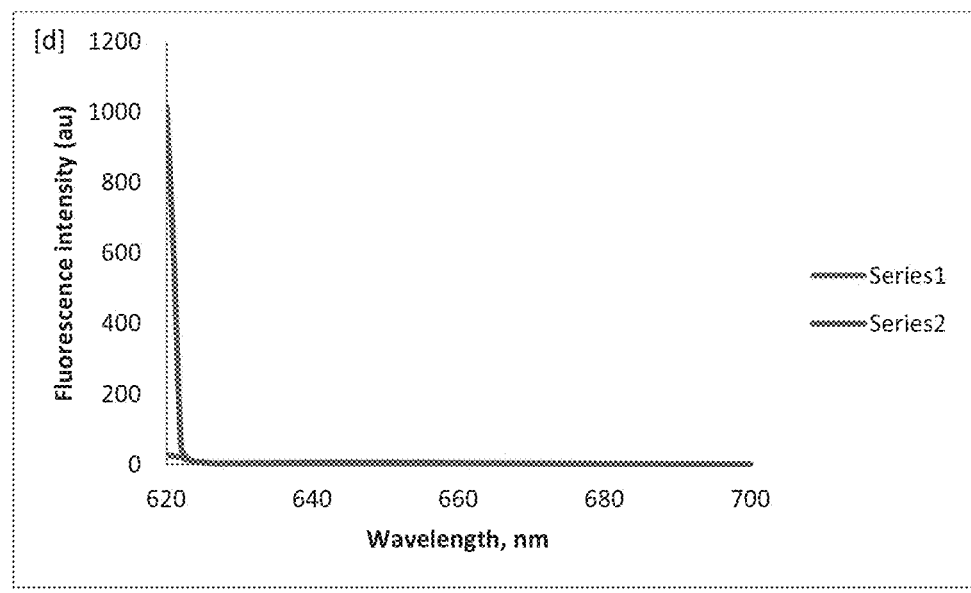
Figure 20A:
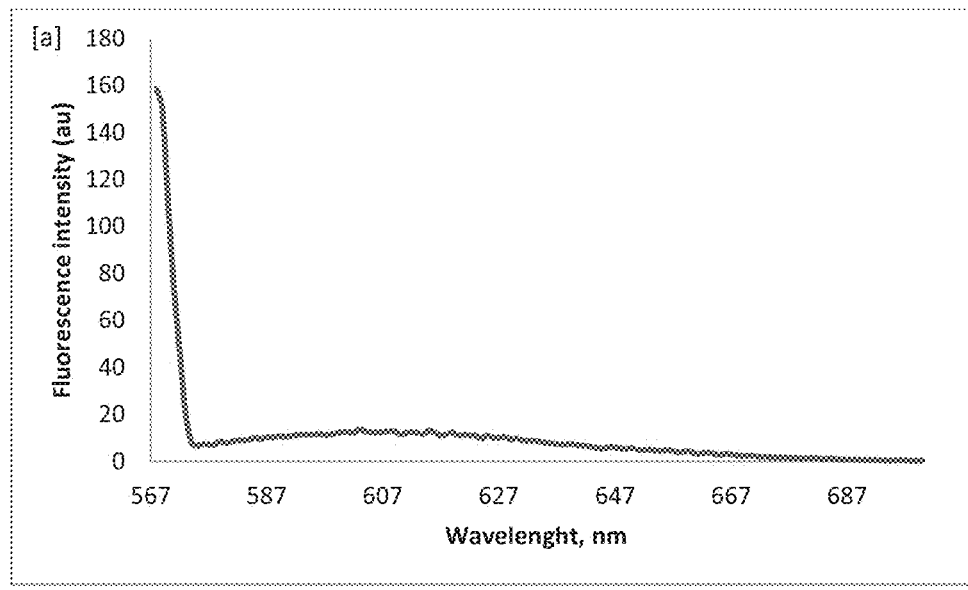
FIGS. 20a-20d are graphical illustrations of fluorescence values of various PAA films.
Figure 20B:
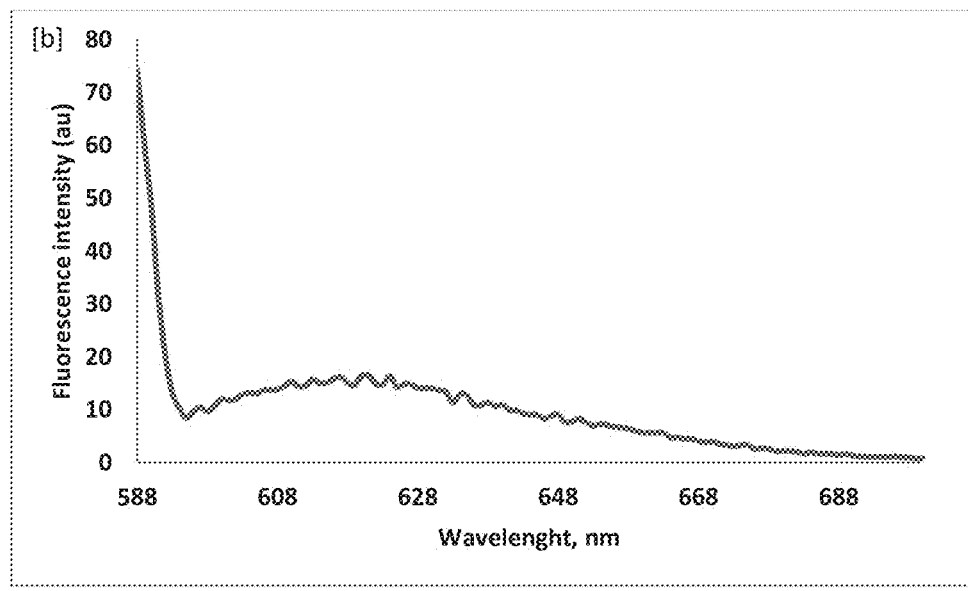
Figure 20C:
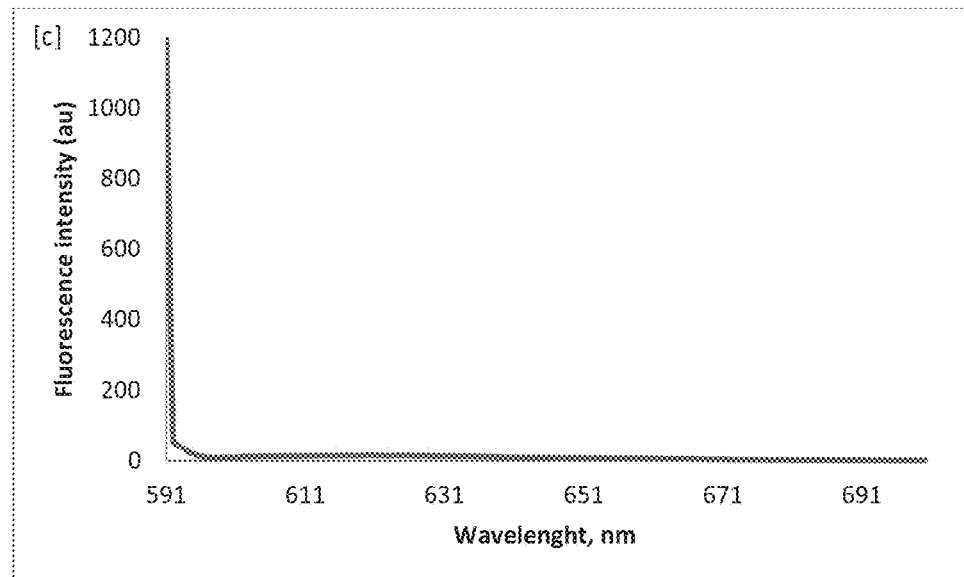
Figure 20D:
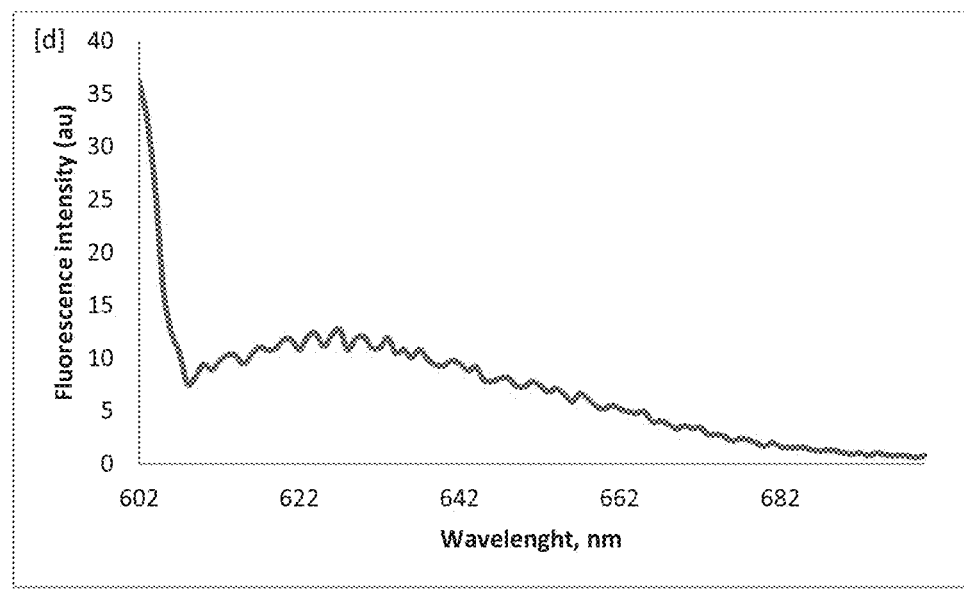
Figure 21A:
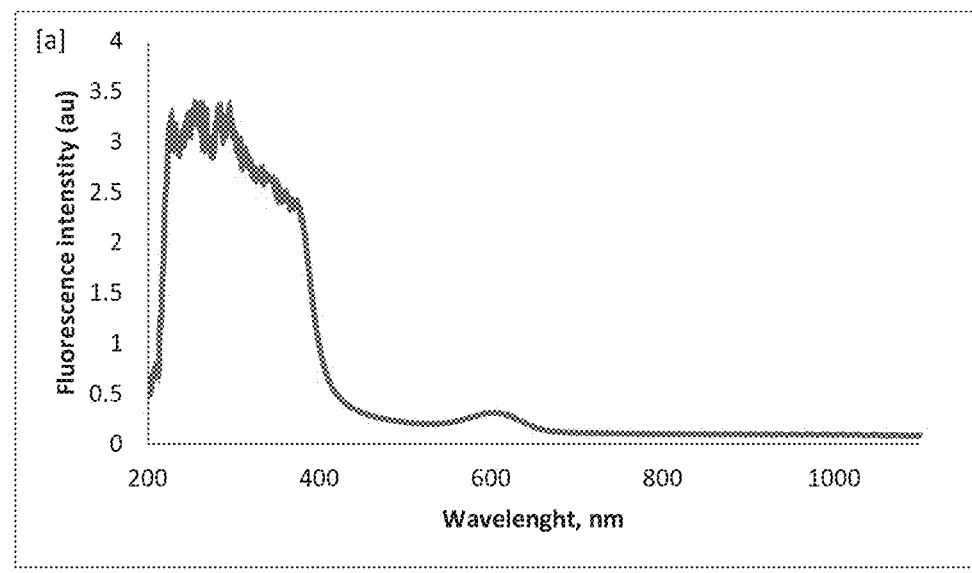
FIGS. 21a-21d are graphical illustrations of fluorescence values of various PAA films.
Figure 21B:
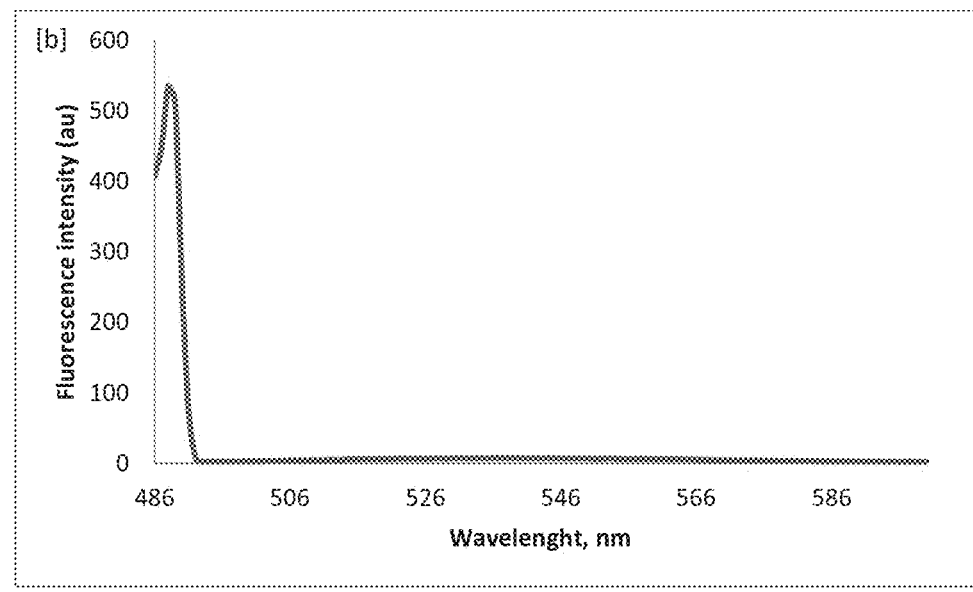
Figure 21C:
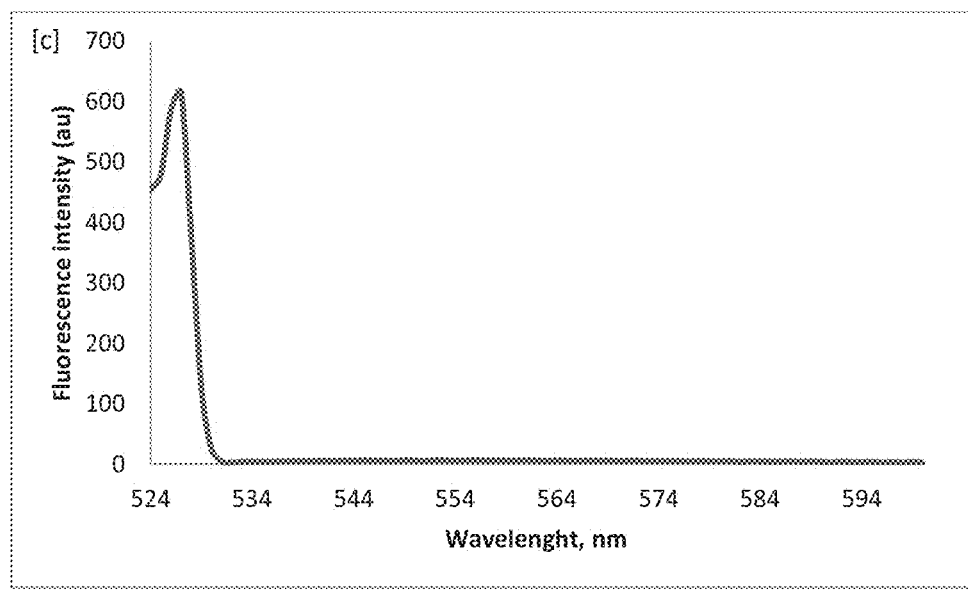
Figure 21D:
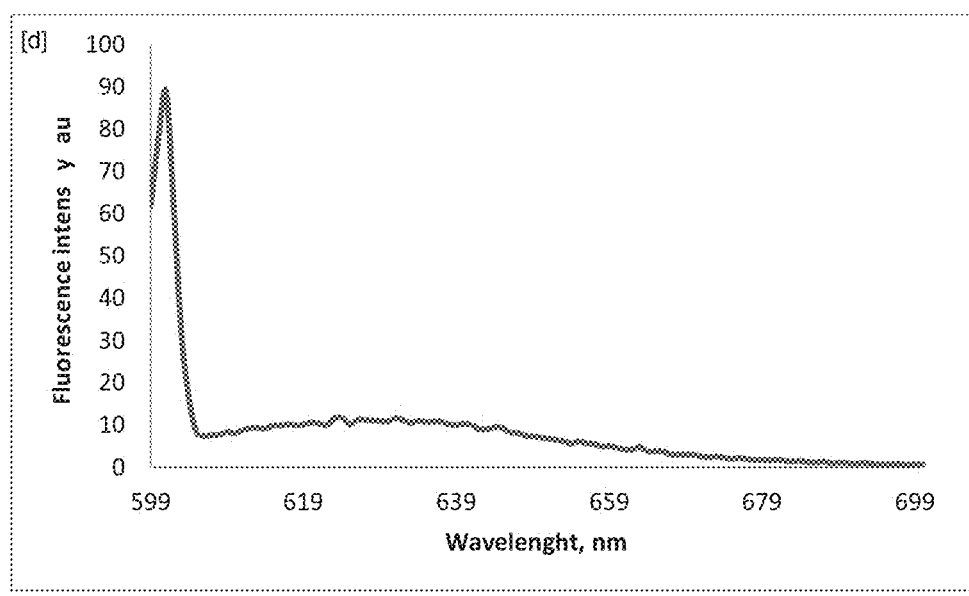
Figure 22A:
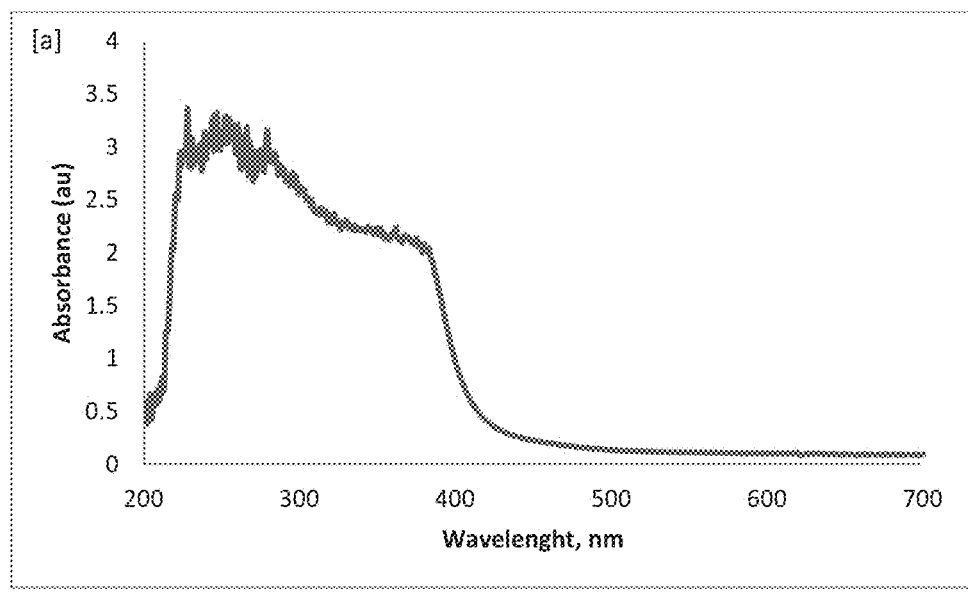
FIGS. 22a-22d are graphical illustrations of absorbance and fluorescence values of various PAA films.
Figure 22B:
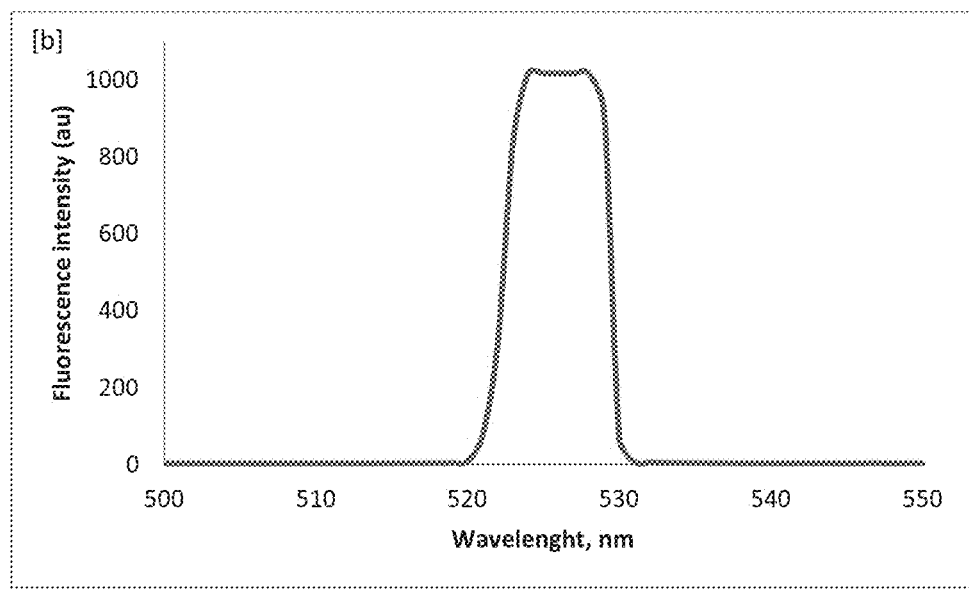
Figure 22C:
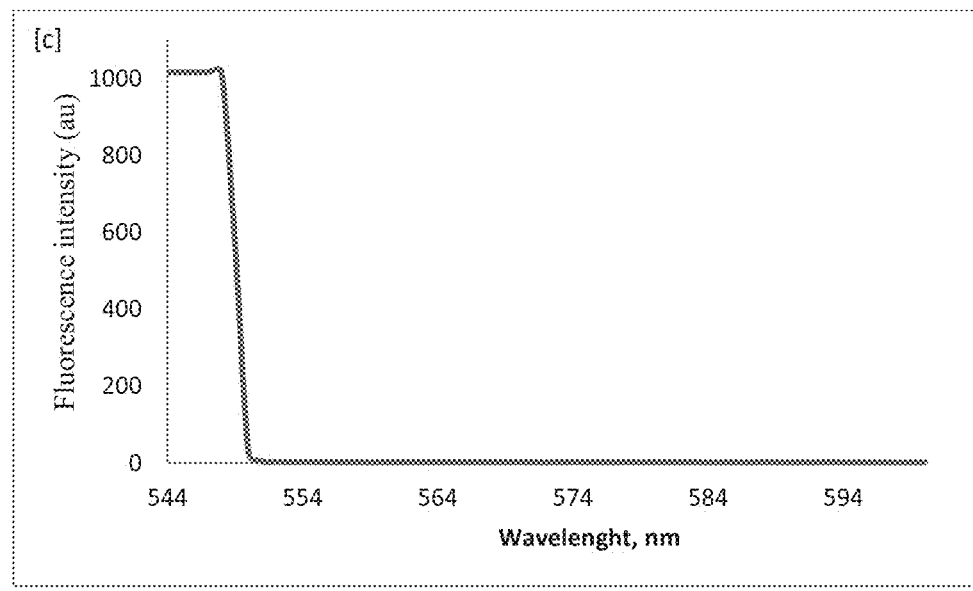
Figure 22D:
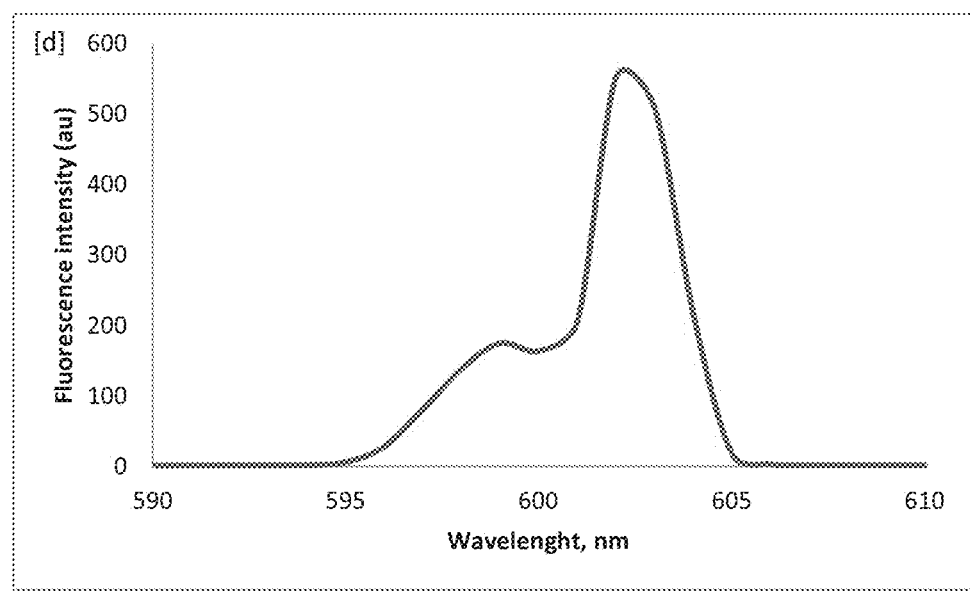
Figure 23A:
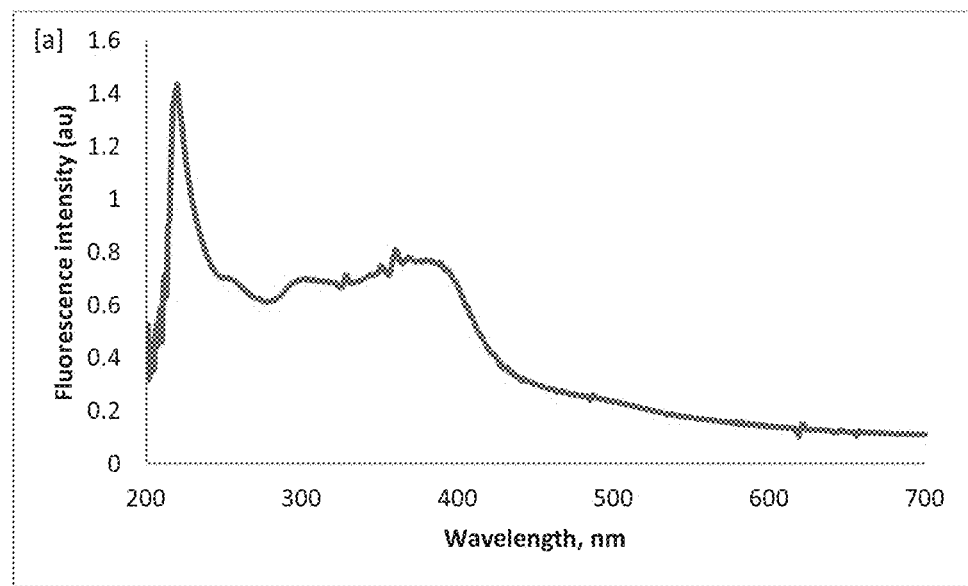
FIGS. 23a-23e are graphical illustrations of fluorescence values of various PAA films.
Figure 23B:
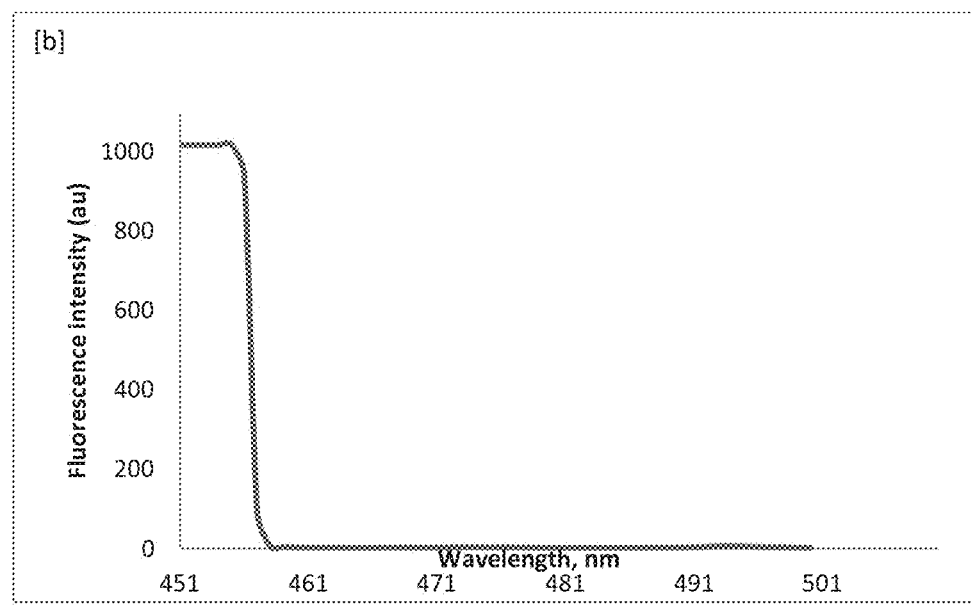
Figure 23C:
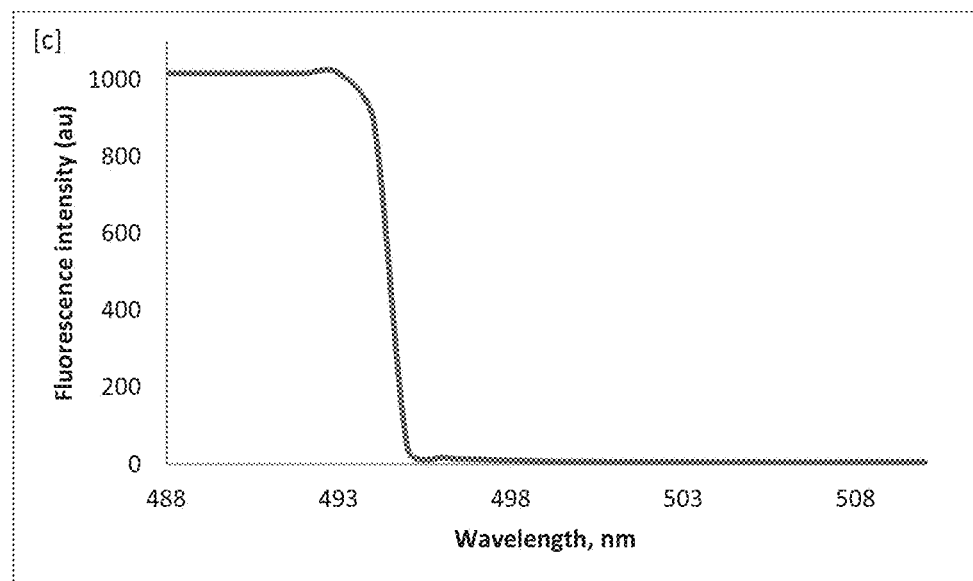
Figure 23D:
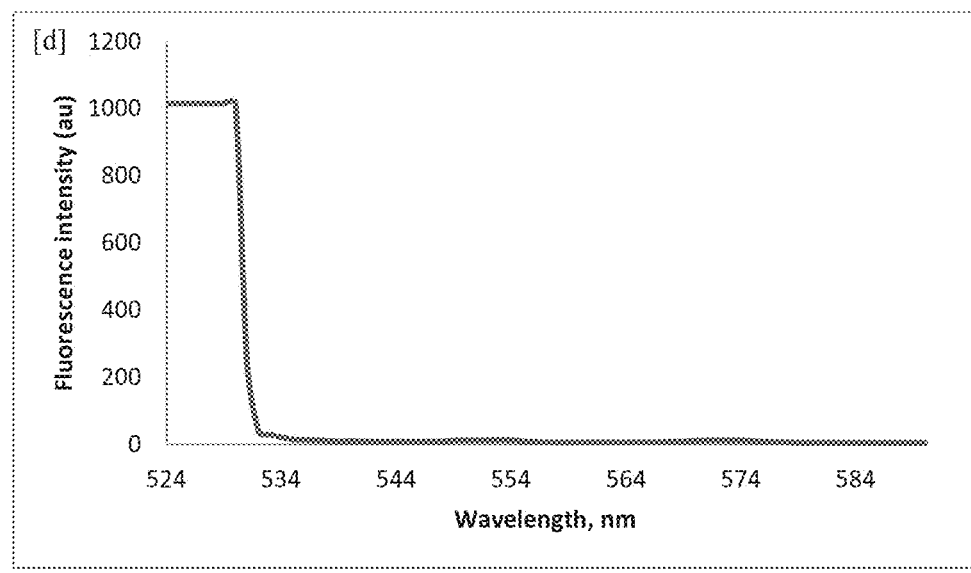
Figure 23E:
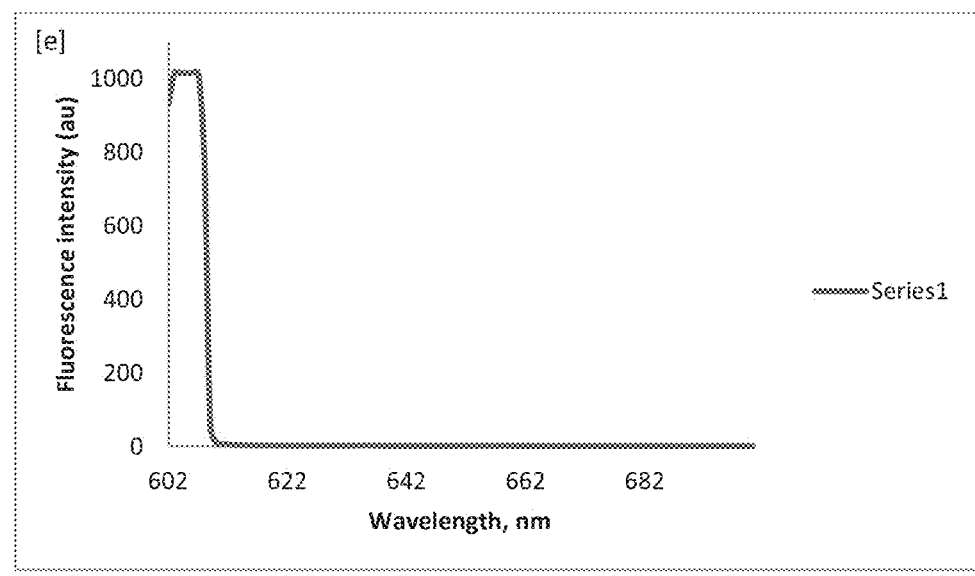

FIGS. 16a and 16b illustrate fluorescence intensity vs. emission and emission wavelengths. The membrane seen in FIG. 16a was dissolved in DMF at three different concentrations as 1, 0.67 and 0.5 for spectrum "a" while 1, 0.75 and 0.5 for spectrum "b". Excitation/Emission wavelengths were 608 nm/619-699 nm range and 621 nm/632-700 nm range for the spectrum "a" and "b", respectively. Similar to FIG. 16b of solid membrane, more than one maximum emission peaks were observed. Dilution enhanced the observed fluorescence intensity, while the dilutions decreased the UV-Vis absorbance of the corresponding solutions.

FIGS. 17a-17e are wavelength illustrations. In these figures 2 mg/mL pC1 was introduced into 10 mL of PAA viscous solution, followed by 200 μL GA from aged 25% stock was introduced to the PAA-pC1 solution. The mixture was casted on glass to prepared PAA-pC1-GA membrane according to FIG. 1b. (a) Ex 485 nm/Em 486-700; (b) Ex 505 nm/Em 506-700 nm; (c)Ex 523 nm/Em 524-700 nm; (d) Ex 550 nm/Em 551-700; (e) Ex 602/Em 603-700 nm. The best quantum yield was 0.2 (Ex 523/Em 524-700), for the rest was between 0.17-0.19.

FIGS. 18a-18d are wavelength illustrations. In these figures 20 mg pC1 and 200 μL of aged 25% GA were simultaneously dissolved in 2 mL DMAC, and mixed for 5 min. The solution was then added to 8 mL PAA solution, which was mixed for 10 min before casting on the glass to prepare the membrane according to FIG. 1b. (a) Ex 598 nm/Em 599-700 nm; (b) Ex 602/Em 603-700 nm; (c) Ex 657 nm/658-700 nm; (d) Ex 621 nm/Em 620 nm/Em 621-627 nm. The best quantum yield was 0.1 (Ex 598 nm/Em 599-700 nm).

FIGS. 19a-19d are wavelength illustrations. In these figures 20 mg pAB and 200 μL of aged 25% GA were simultaneously dissolved in 2 mL DMAC, and mixed for 10 min. The solution was then added to 8 mL PAA solution, which was mixed for 10 min before casting on the glass to prepare the membrane according to FIG. 1b. (a) Ex 485 nm/Em 486-650 (but shown 486-526 nm); (b) Ex 523 nm/Em 524 nm-700 nm (shown 524-600 nm); (c) range between 535 nm to 600 nm of b; (d) Ex 619/Em 620-700 nm. Series 1 always refer to the thicker PAA-pAB-GA while series 2 depicts the thinner PAA-pAB-GA (aged). The best quantum yield obtained was 0.1 (Ex 485 nm/Em 486-650 nm of Series 2).

FIGS. 20a-20d are wavelength illustrations. In these figures 10 mg I was dissolved in 200 μL of aged 25% GA, which was then vortexed for 10 min. I-GA mixture was then introduced to 10 mL PAA viscous solution, and mixed for 10 min, followed by casted on glass surface to prepare PAA-I-GA membrane according to FIG. 1b. (a) Ex 567 nm/Ex 568-700 nm; (b) Ex 587 nm/Em 588-700 nm; (c) Ex 590/591-700 nm; (d) Ex 601 nm/Em 602-700 nm. The best quantum yield obtained was 0.08 (Ex 590/591-700 nm).

FIGS. 21a-21d are wavelength illustrations. In these figures 20 mg pAS and 200 μL, of aged 25% GA were simultaneously dissolved in 2 mL DMAC, and mixed for 10 min. The solution was then added to 8 mL PAA solution, which was mixed for 10 min before casting on the glass to prepare the membrane according to FIG. 1b; (a) Ex 485 nm/Em 486-600 nm; (b) Ex 523 nm/Em 524-600 nm; (c) Ex 550 nm/Em 551-600 nm; (d) Ex 598 n/Em 599-700 nm. The best quantum yield obtained was 0.08 (Ex 523 nm/Em 524-600 nm).

FIGS. 22a-22d are wavelength illustrations. In these figures 10 mg I was dissolved in 200 μL of aged 25% GA, which was then vortexed for 10 min and 2 min heated at 70° C. sequentially. I-GA mixture was then introduced to 10 mL PAA viscous solution, and mixed for 10 min, followed by casted on glass surface to prepare PAA-I-GA membrane according to FIG. 1b. (a) UV-Vis of the solid membrane; (b) Ex 523 nm/Em 500-550 nm; (c) Ex543/Em 544-610; (d) Ex598/Em 590-610 nm. The best quantum yield obtained was 0.1 (Ex543 nm/Em 544-610 nm).

FIGS. 23a-23e are wavelength illustrations. In these figures 10 mg DA was dissolved in 200ℓ of aged 25% GA, which was then vortexed for 10 min. DA-GA mixture was then introduced to 10 mL PAA viscous solution, and mixed for 10 min, followed by casted on glass surface to prepare PAA-I-GA membrane according to FIG. 1b. (a) PAA-DA-GA (aged) UV-Vis of the solid membrane; (b) Ex450/Em451-500; Ex487/Em488-510; (c) Ex523/Em524-590; (d) Ex601/Em602-700. Ex543/Em 544-610. The best quantum yield obtained was 0.24 (Ex487/Em488-510) while at the other excitations quantum yields were observed between 0.1-0.17.

Then a series of films were synthesized to test the fluorescence properties with Synchronous Fluorescence Spectroscopy. PAA-pAS-GA, PAA-pAB-GA, PAA-W-GA and PAA-W-GA combined with GA treated pAS.

Figure 24:
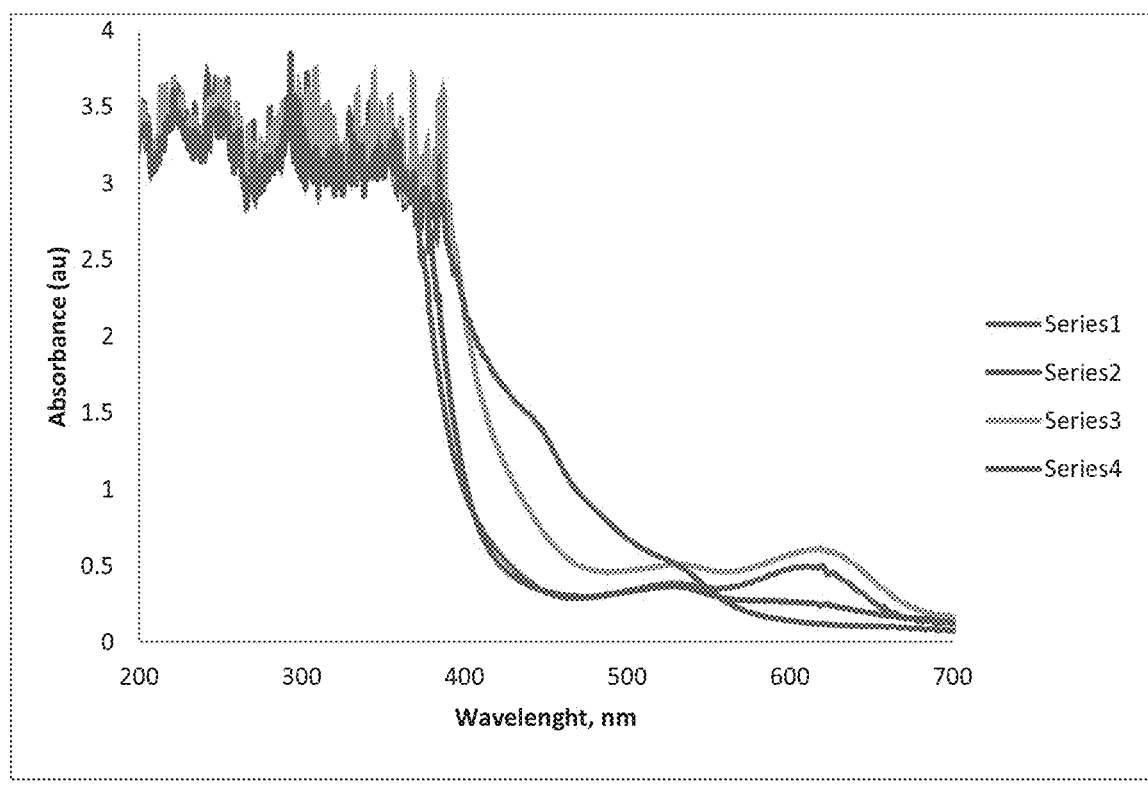
FIG. 24 is a graphical illustration of absorbance values of various PAA films.

In FIG. 24, Series 1-4: (1) PAA-pAB-GA (aged); (2) PAA-pAS-GA (aged)-purplish; (3) PAA-pAS-GA (aged)-greenish; (4) PAA-W-GA (aged)-reddish.

Figure 25A:
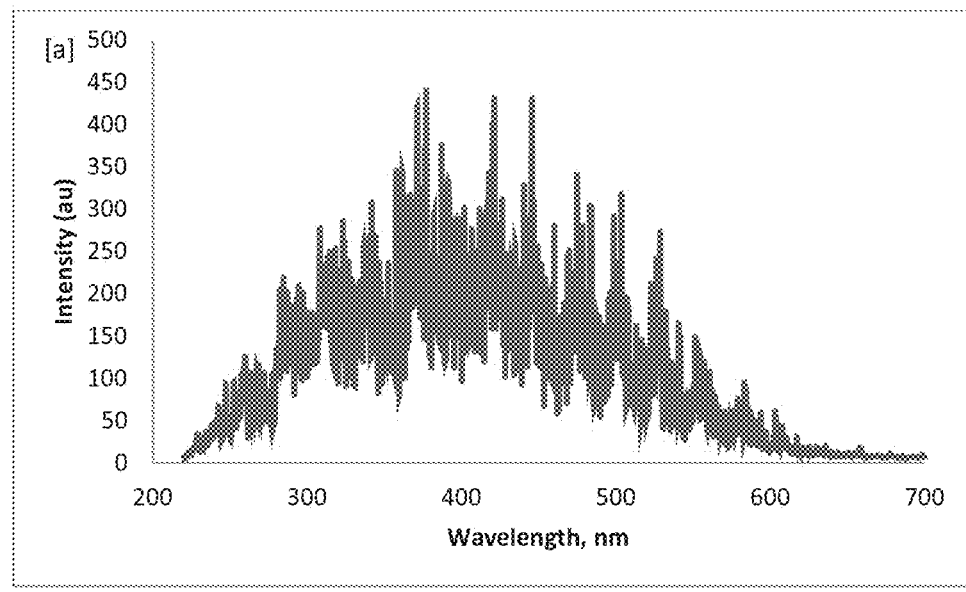
FIGS. 25a-25c are graphical illustrations of intensity values of various PAA films.
Figure 25B:
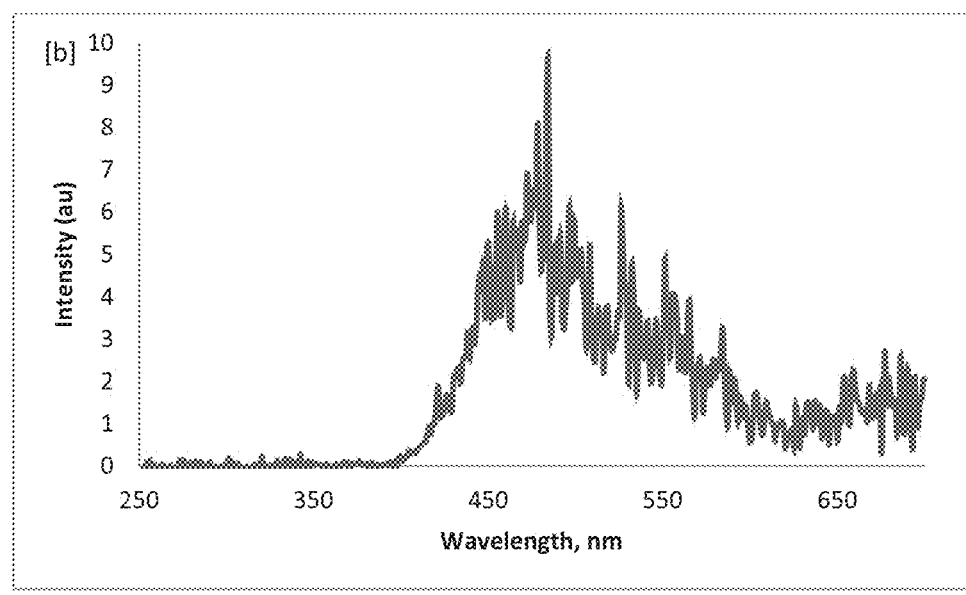
Figure 25C:
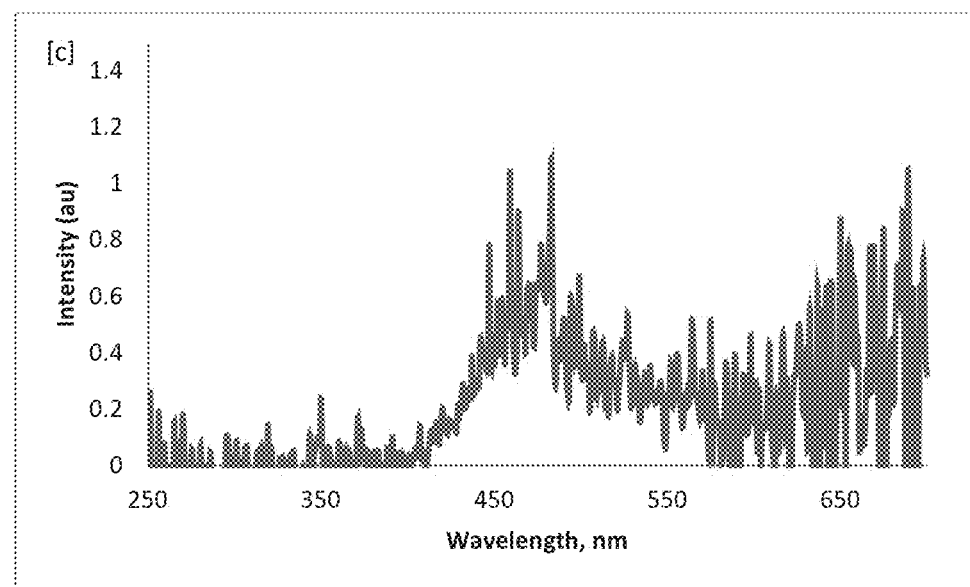
Figures 26A, 26B, 26C, 26D, 26E, 26F, 26G:
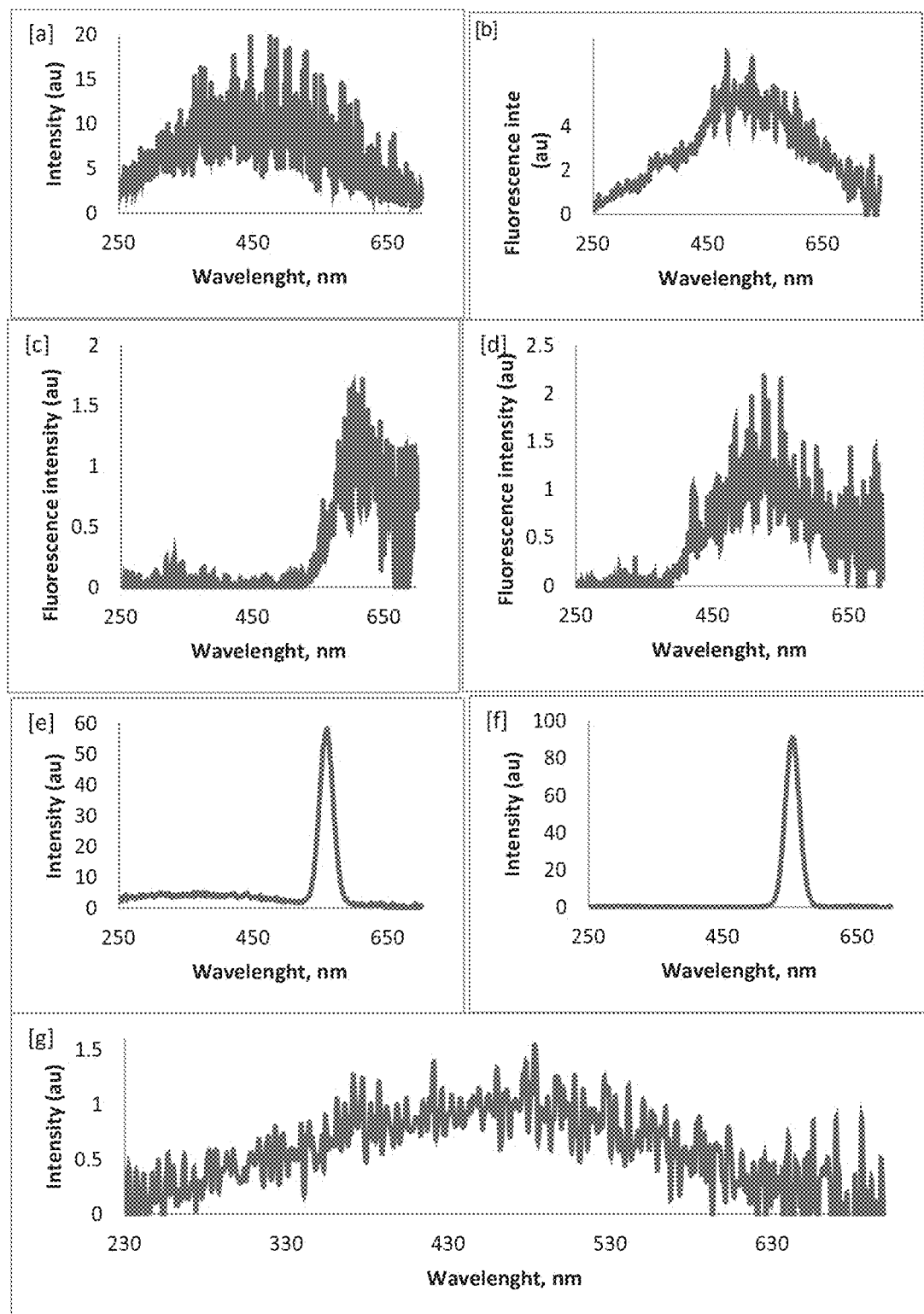
FIGS. 26a-26g are graphical illustrations of intensity values of various PAA films.

FIGS. 25a-25c are wavelength illustrations. In these figures PAA-pAB-GA (aged) greenish. First, pAB was cross-linked with aged GA in DMAC for 20 min, followed by introduced to PAA solution which was then strongly mixed for 10 min. The solution was then casted on glass, and incubated at room temperature for 6 h, followed by incubated under hood for 6 h. Then, the resulted standalone membrane was rinsed with nano-pure water. Experimental conditions for fluorescence was as described follow; room temperature, quartz fluorescence cuvette, standalone membrane itself, 1.5 slit width, excitation filter auto, emission filter auto, at synchronous mode, delta 0 nm, run mode was slowest (30 nm/min), start 220 nm, stop 700 nm. The instrument was Cary Eclipse run with Eclipse software. PAA-pAB-GA, slit 1.5, speed normal, delta 0.1 (b) and 1 nm (c).

FIGS. 26a-26g are wavelength illustrations. In these figures Synchronous fluorescence of modified PAA and Rhodamine B. (a) PAA-pAS-GA (purplish); (b) PAA-pAS-GA (greenish); (c) PAA-W-GA (reddish); (d) PAA-W-pAS-GA (purplish); Rhodamine B with delta 0 nm (e) and 10 nm (f); (g) formed PAA-pAS-GA membrane was dissolved in DMF, and 0.1 mg/mL 2-aminopyridine was added to the dissolved PAA-W-pAS-GA, which was then casted on glass for evaporation mediated membrane formation. In all cases experiments were performed for standalone membranes in quartz fluorescence cuvette at room temperatures. The fluorimeter was set to auto mode for excitation filter and open-mode for emission filter while scanned region was kept between 250 nm and 700 nm under slowest run which was 30 nm/min for the instrument. Slit width for excitation and emission were selected as 1.5 for "a", "c", "d" and "g" while they were set to 2.5 for "b", "e" and "f". Delta was selected 0 nm if not specified otherwise. All of the membranes were prepared according to FIG. 1b. To make PAA-pAS-GA green, pAS and GA were simultaneously dissolved in DMAC where GA cross-linked pAS for 20 min. Then, mixture of PAA-pAS-GA was introduced to viscous PAA solution containing 0.5 mg/mL pAS for 20 min mixing which was then casted on glass to form membrane according to FIG. 1b. Reddish PAA-W-GA was synthesized through introducing 20 min GA-crosslinked W into viscous PAA solution.

In the above reference figures, increasing delta from 0 to 10 nm, improved fluorescence intensity was observed as expected since possessing too close excitation and emission wavelengths causes decreases in fluorescence intensity. However, for the membranes increasing delta from 0 to 1 nm, disrupted the observed fluorescence intensity. This was most probably from that over-load of fluorophore in the medium; fluorophores within the membranes can show FRET which then diminished the observed fluorescence intensity. This idea was supported through adding more diverse fluorescent active molecules in the membrane. Introduction of pAS into PAA-W-GA decreased the observed fluorescence. Similarly, introduction of GA cross-linked pAS into PAA-pAS diminished the fluorescence intensity. PAA-pAS-W-GA did not provide enough fluorescence intensity when the slit width was 1.5; the highest peak was around 0.5 (not shown). However, dissolving PAA-pAS-W-GA in DMF, and introduction of 2-aminopyridine to the membrane gave a visible spectrum even at 1.5 slit width. However, if the PAA membrane was used without dilution, the intensity was not visible at 1.5 slit width.

As seen from FIGS. 14a and 14b, Rhodamine 6G provides very smooth excitation and emission curves while the PAA membranes did not provide any smooth curves. PAA films can be synthesized as fluorescence active, but the best quantum yield was obtained around 0.1 leaving 10 nm gap between excitation and the starting emission wavelengths. These figures were used to compare two things; (i) that the dyes can be introduced into the PAA membrane, where their presence is strong and similar to the original dyes molecules, (ii) FIGS. 14a and 14b represent the graphical illustrations of absorbance and emission values of various PAA film and these were used to calculate the quantum yields of the dye-modified PAA membranes.

Besides the selection of the emission range, the conditions must be controlled for reproducible results:

(1) Glutaraldehyde must be aged to obtain fluorescence active membranes, which was determined experimentally in the study. NMR spectroscopy can be used to keep the best conditions. (2) The presence of methanol end ethanol during membrane formation prevents fluorescence active membrane formation, which can be overcome with addition of water. (3) Humidity and longer incubation at room temperature disrupts UV-Vis and Fluorescence properties of PAA membranes. The humidity was not measured experimentally. (4) Care required during the addition of GA into the PAA-small molecule mixture. It should be drop by drop; sudden addition of high amount of GA prevents membrane formation.

Due to possessing unique properties and low cost, conjugated polymers are preferred as a sensor support material or direct sensing agent from electrical to optical sensors.

pAS was introduced into different polymers, and its fluorescent activity was shown dependent on the chemical and physical properties of the polymer, including ionization of side groups within the polymer, allowed volume and polarization properties of the groups within the molecules. Above, pAS is becoming part of the membrane itself. So, it is quite normal that fluorescence characteristics of pAS will show change. Besides the environment itself, the solvent also possesses strong effect on excitation and emission spectra, and quantum yield as well. For example, pAS itself gives only one emission in aprotic solvents, it gives more than one peak in protic solvents.

PAA itself is inherently not fluorescence-active, but introducing side groups to PAA was shown as a method to add fluorescence character to PAA such as grafted PAA with toluene-2,4-diisocyanate and straight alkyl chains showed fluorescence properties. Maximum absorption and excitation wavelengths of the high purity Rhodamine 6G in anhydrous ethanol were obtained at −527 nm and −550 nm, which refers to the stoke shift is over 20 nm which matched the literature. This shows there was only one fluorophore in the medium, and the working conditions only allowed possessing one broad peak. However, this was not valid for the stand-alone membranes and the dissolved membranes due to the fact that the membranes were composed of more than one fluorophore. As detailed in the examples below, GA can cross-link individual PAA polymers as well as it can cross-link PAA-small molecule and small molecule-small molecule, which can allow possessing fluorophore. FIGS. 26a-26g depict synchronous fluorescence run of Rhodamine B and PAA-pAB-GA, PAA-W-GA (reddish membrane), PAA-pAS-GA, respectively. SRB, as expected, provide a sharp peak which depicts that SRB in anhydrous ethanol has only one characteristics excitation and emission peaks while PAA-pAB-GA and PAA-pAS-GA have more than one.

As seen from FIGS. 26a-26g, when there is 0 nm difference (delta), under same conditions, between excitation and emission wavelengths for SRB, the fluorescence intensity is lower than the one in the case the delta was 10 nm. However, this situation is distinctly different for the membranes.

As seen from the FIGS. 26a-26g, when the delta is 0, the fluorescence intensity is the highest while the intensity decreased 400 times when delta was 1 nm. When the delta was selected 0.1 nm, the intensity decreased 20 times in comparison to the case of delta was 0 nm.

Quantum yield of a fluorophore is more influenced by the environment in comparison to molecular extinction coefficients. Fluorescence quenching is the process of reduction in fluorescence quantum yield, which can be resulted from collisional quenching and/or occurrence of vibrations of non-fluorescent ground-state species. Self-quenching is, also, a common problem seen in fluorescence, which is arisen from over-load of fluorophores presence. Fluorescence resonance energy transfer (FRET) is a fluorescence technique in which emission of a fluorophore is absorbed by another fluorophore as the excitation. The technique is distance-dependent, and the yield of FRET is proportional to the distance, which makes it sensitive.

FIG. 1b films can provide fluorescent active under strictly controlled conditions. However, current results are not allowing them to be used as a sensor material for FRET applications due to the fact that extensive fluorophore presence results in loss of quantum yield. However, studies related to metals and oxygen concentrations, the synthesized fluorescent active membranes can be a candidate for metal and oxygen sensors.

Figure 27:
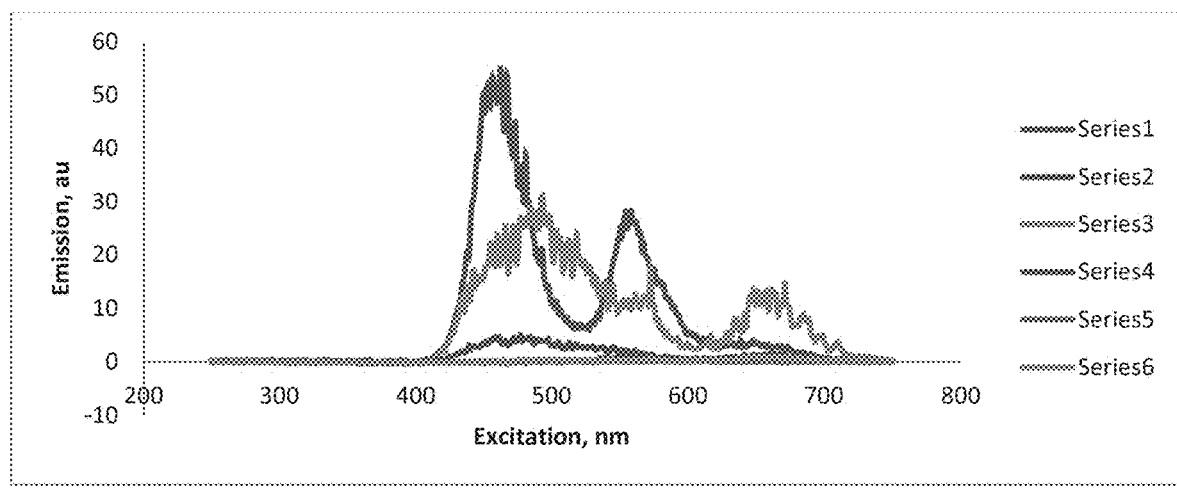
FIG. 27 is a graphical illustration of emission values of various PAA films.

FIG. 27 illustrates excitation data for several films. Specifically, Series 1-6, respectively; PAA-Sulfanilamide-GA (Ex-Ee=1 nm); PAA-Sulfanilamide-GA (Ex-Em=5 nm); pAS in PAA (Ex-Em=5 nm); pAS in PAA (Ex-Em=10 nm); pAS+W in PAA (Ex-Em=5 nm); W in PAA (Ex-Em=5 nm).

Figures 28A, 28B, 28C:
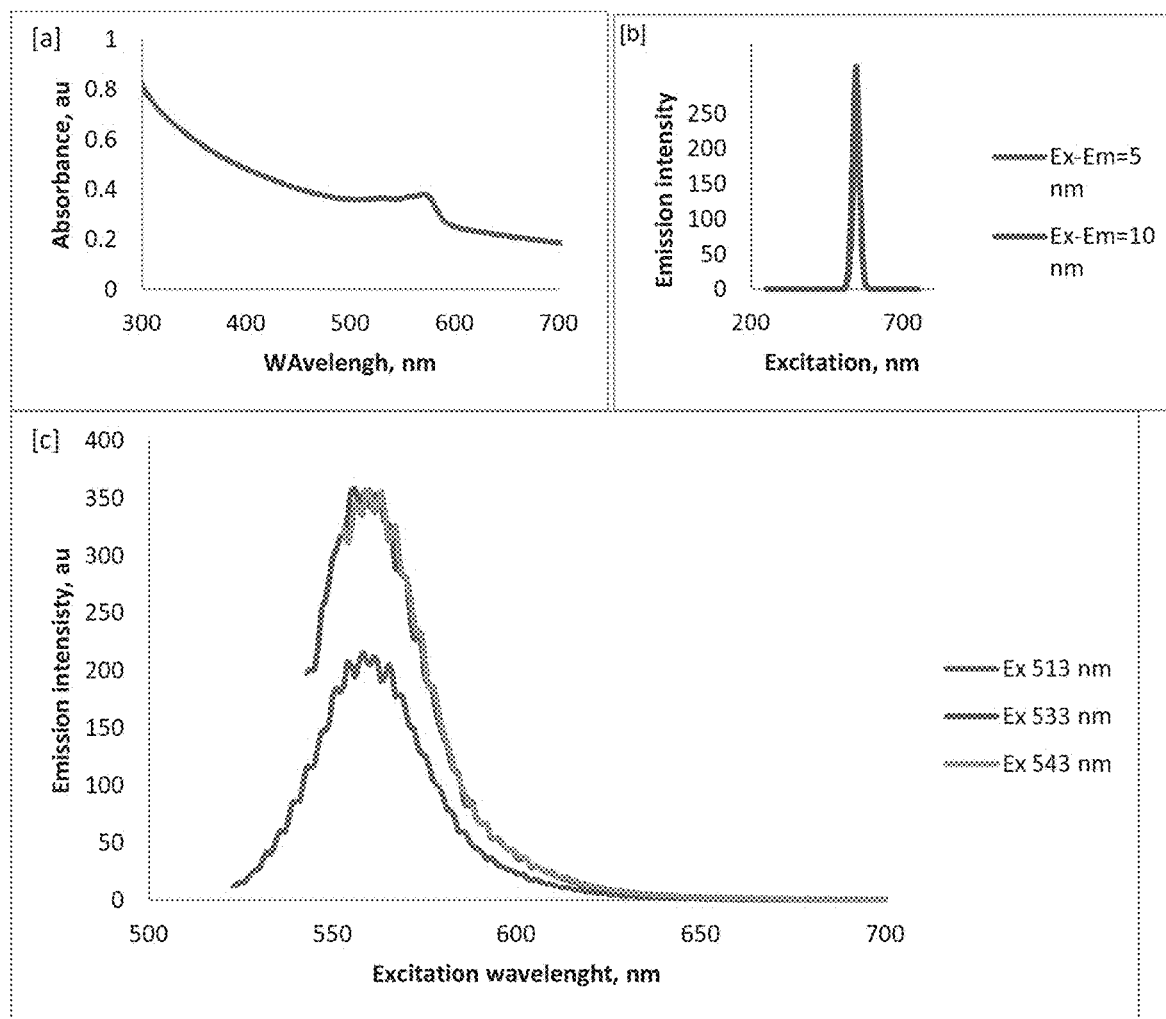
FIGS. 28a-28c are graphical illustrations of absorbance and intensity values of various PAA films.

FIGS. 28a-28c illustrate excitation and wavelength data. Specifically, UV-vis, Synchronous fluorescence of Rhodamine 6G (R6G) embedded PAA membranes. (a) UV-vis of PAA-R6G, (b) Synchronous fluorescence of PAA-R6G and (c) Emission of PAA-R6G.

Even though UV-vis gave peak at 570 nm, the best quantum yield was obtained for Ex 533 nm. While R6G in ethanol solution as shown in FIGS. 14a and 14b provides very smooth emission curve, R6G in PAA shows repeating ups and downs. This could be related to that R6G within the PAA might have different microenvironments where R6G behaves different than how it behaves in solution. The obtained quantum yield for PAA-R6G varies between 0.78 and 0.82; keeping 90% of quantum yield in comparison to pure R6G can make this type of membranes usable for fluorescent labeled membrane applications. Since, the membrane was rinsed with excess water, it can be said that there was no fluorescence come from R6G stays on the membrane.

1.4 Solvent Resistance Properties

Film lengths and widths were 2.5 cm while thicknesses were between 0.00128-0.00512 cm. The following buffers were used; 50 mM Acetate (pH 4.5) buffer, 50 mM PBS buffers (pH 6.8/7.0/7.4), 50 mM (pH 8.0) Tris-HCl and 50 mM (pH 9.6) carbonate buffer. All the buffers were prepared from their salts and pH was adjusted with 1M HCl and/or 1M NaOH. Glacial acetic acid, 30% hydrochloric acid, 100% sulfuric acid, 1 M sodium hydroxide and 37% NH4. The following organic solvents were employed for solubility testing": ethanol, methanol, tetrahydrofuran, hexane, ethylacetate, dimethyl formamide, dimethyl acetamide, dichloromethane, p-xylene, aceticanhydride, dimethyl-sulfoxide and acetone. The solvent resistance properties of various films is discussed in the data below.

PAA films are soluble in complex media such as protein and carbohydrate containing media and polar organic solvents. Therefore, it is essential to show the material will not live a problem of dissolvation during contact to food and possible chemical contaminants or the chemicals from food-itself.

Solvent resistance of the synthesized PAA membranes showed close relation to mostly GA condition and the small molecule. The findings are listed as below.

Aged GA made the membranes soluble for all small molecules PAA-copolymers in the case of FIG. 1bi/ii in strong organic polar solvents include DMF, DMAC, DMSO and buffers pH over 7.4. However, FIG. 1b ii membranes showed different character such as L-Tryptophan methyl ester individually, or the other amino acids combined with sulfanilic acid make the membranes non-soluble in DMAC and all the buffers tested in the study.

Fresh GA made the membranes of the small molecules PAA co-polymers synthesized according to FIG. 1b non-soluble in all the solvents tested here except the membranes containing pAS, pAB, 5AS, PC1 over 1 mg/mL.

Sulfanilic acid (SA) advanced solvent resistance character of all the membranes synthesized according to FIG. 1b. However, extra-GA must be added to the PAA solution prior to SA addition.

Tryptophan methyl ester-PAA-GA copolymers formed non-soluble membranes in the cases of that GA was fresh; methanol addition is required, or GA addition to the PAA solution could be beneficial to make the membranes non-soluble.

Membranes synthesized according to FIG. 1a except PAA-A-GA were soluble in strong polar organic solvents include DMAC, DMSO, DMF, and the buffers include 50 mM pH 8.0 PBS. Also, the most aggressive solvent for the most resistant membranes were ammonium-hydroxide.

Solubility of all the membranes did not show dependence on pH as shown in the figures and discussed below.

Figure 29:
FIG. 29 is a photograph of the solubility of ternary PAA membranes in basic solutions.

FIG. 29 shows the solubility of ternary PAA membranes in basic solutions. Solubility is not related to pH, because pH 4.5 50 mM Acetate buffer, 1M NaOH, 1M HCl, Glacial acetic acid, pH 8.00 50 mM PBS buffer, pH 6.0 1M PBS did not dissolve the membrane. But 29% $NH_4OH$ totally dissolved the Ile-PAA-GA membrane in less than 1 h under no agitation. This is important because ammonia is produced during food-purification.

Figure 30:
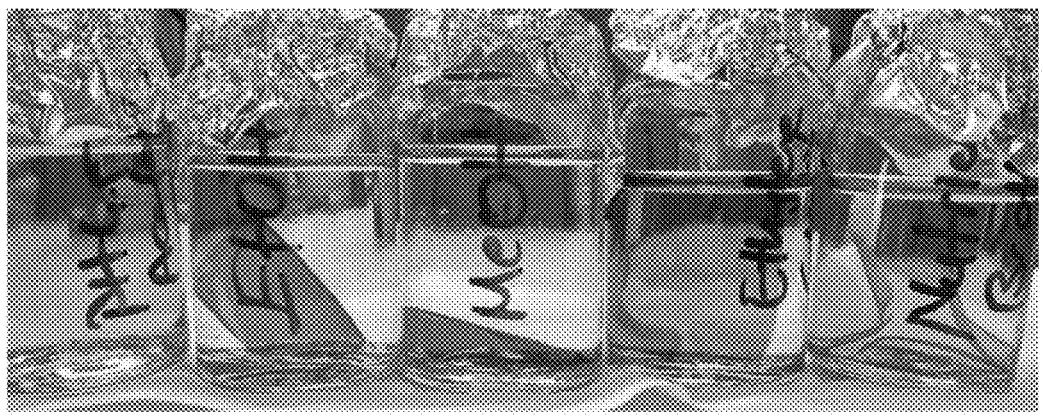
FIG. 30 is a photograph of the color changes of ternary PAA membranes in response to alcohol exposure.

Color changes of ternary PAA membranes in response to alcohol exposure is shown in FIG. 30. Color change related to exposure to alcohol using ternary PAA membranes. Ile-PAA; normally the membrane is greenish yellow. Alcohol turns the color into chestnut color as it was shown for Ethanol, Methanol and Ethylene Glycol.

Figure 31:
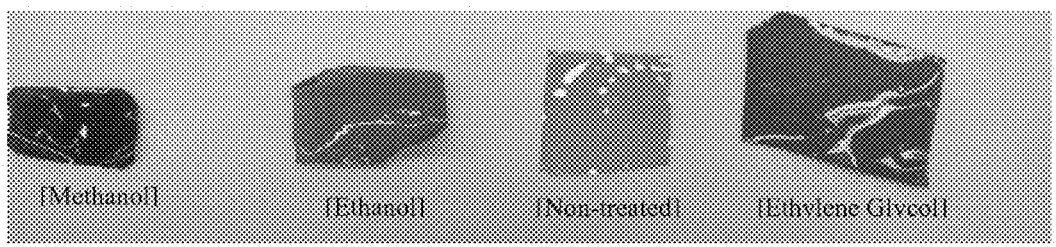
FIG. 31 is a photograph of various PAA films.

Color changes of PAA membranes in response to alcohol treatment is shown in FIG. 31. All of the membranes change their color different intensities of red in response to alcohol treatment. Color change is accompanied with new peak formation in UV-Vis Spectrum. While peak change in response to Methanol and Ethylene Glycol is more characteristics at around 520-550 nm, the new peak formation is less characteristics at around 560 nm and 250 nm. Speed of color changes is dependent on the membrane composition. In the case of L-isoleucine enhanced membranes, the color change becomes visible in less than 6 h while L-alanine and p-aminosalicylic acid conjugated PAA membranes show the color change within 12 h and 120 h, respectively. The synthesized hybrid PAA films can determine the onset of alcohol (or microbial degradation) production. The intelligent properties of the PAA were assessed by monitoring changes in reversible and irreversible properties of the membranes. Changes in voltage and color in response to microbial development and/or food decomposition would provide real-time monitoring of food condition. Color changes by alcohols are important findings for intelligent food packaging material of the synthesized membranes. Ethanol is the most common byproducts of microbial development, and can be seen from FIG. 31, color changes can be seen with bare eyes and does not need to be monitored using any sophisticated tools.

Color change in response to exposure alcohol is achieved in all types of PAA films, but when the membrane is very dark (low transparency), the change takes a comparatively longer time. Among the membranes, Ile containing membranes gave the response fastest; while Ile enhanced PAA-GA membrane gave color change within 30 min, pAS enhanced PAA-GA membrane required 2-4 h to give color change.

Color changes in response to alteration in environmental conditions can be further advanced with pH-dependent dyes. Here bromophenol blue (BPB) was simply tested, with the results shown in FIG. 32.

Figure 32:
FIG. 32 is a photograph of color changes in response to alteration in environmental conditions that can be further advanced with pH-dependent dyes.

In FIG. 32, pH dependence of bromophenol blue supported PAA ternary membrane. PAA-BPB-GA (aged) was prepared according to FIG. 1b. All of the membranes were 4 cm×2 cm×0.05 cm (length/width/thickness). (a) 50 mM pH 6.00 PBS; (b) 50 mM pH 6.5 PBS; (c) 50 mM pH 7.1 PBS; (d) 50 mM pH 7.6 PBS and (e) 50 mM pH 8.0 PBS buffer. Color changes started within 30 min for c, d and e vials while color change was seen for a and b for up to 6 h (test was completed in 6 h). End of 6 h incubation, the membranes were removed from the vials, and no visible color change was seen for a and b (f and g, respectively) while the color has changed for c, d and e (h, f and k, respectively). The membranes were also tested for 50 mM pH 4.5 Acetate buffer, and no color change was observed.

Figure 33:
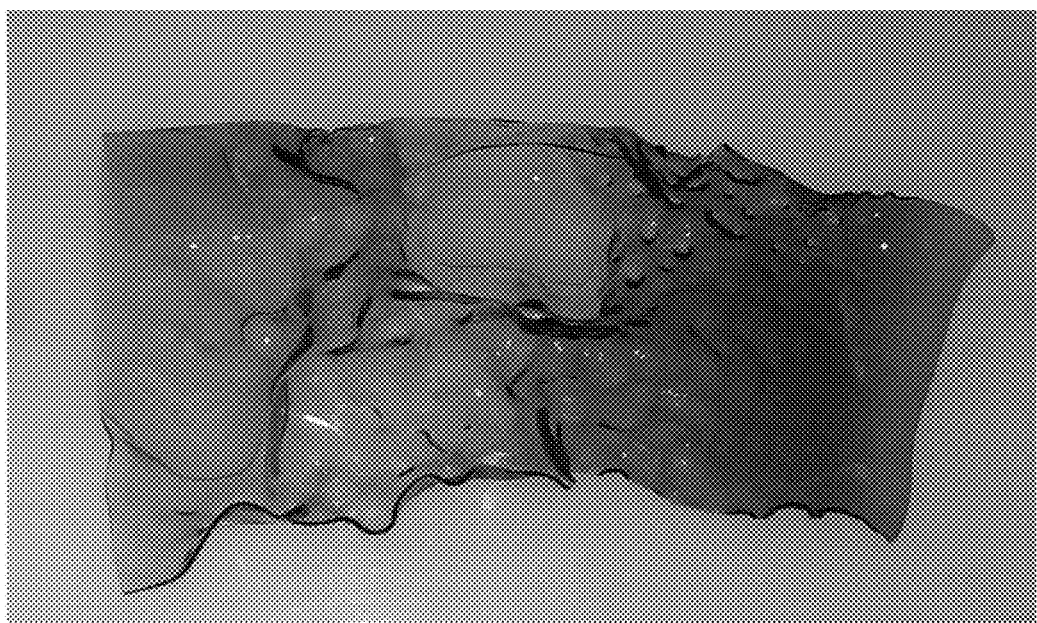
FIG. 33 is a photograph of an aged PAA film.

Further color change is shown in FIG. 33. In FIG. 33 at the end of 6 h incubation, PAA-BPB-GA (aged) membrane was taken out from the vial. As it is seen, the top part kept its yellowish color, because the part was not submerged into the buffer, while the rest of the membrane was turned into pale greenish form.

This section was to entrap BPB within PAA-GA, and release the BPB into the medium when there is a change in pH and/or ionic strength; when the PAA is treated with aged GA it doesn't have insoluble form for harsh environment such as high pH, strong organic solvents and so on. The color change of the membrane itself might be resulting from certain amount of BPB crosslinked to PAA. Actually, using fresh GA can advance BPB cross-linking to PAA, which could also a possible way of monitoring pH changes.

1.5 Mechanical Characterizations

The mechanical strengths of the membranes were determined using Instron® Tension Testers run by Merlin Project Software (Norwoon, Mass.). The strength tests were evaluated using maximum load, tensile strength and modulus of elasticity.

Mechanical properties of food-packaging materials are a parameter in assessing their relevance as packaging materials. This is because packaging materials must protect the containment against possible exposure to physical pressures during transportation and storage. Maximum load, modulus elasticity, break elongation and tensile strength are common parameters to evaluate mechanical properties of a packaging material. Different approaches have been applied to advance the properties such as combination of biopolymers and chemicals, composites or nanomaterials (i.e. chitosan and graphene, whey protein-zein).

TABLE J illustrates Mechanical properties of FIG. 1a Films

| Film-Type | Maximum load (kg) | Modulus elasticity (MPa) | Break Elongation % | Tensile Strength (MPa) |
|---|---|---|---|---|
| Composite[a] | 12.75 | 180 | 24.3 | 13.79 |
| PAA-C-GA[b] | 5.13 | 406.89 | 13.4 | 32.41 |
| PAA-A-GA[b] | 3.86 | 1096.55 | 10.9 | 24.14 |
| PAA-GA[c] | 1.81 | 13.79 | 29.6 | 2.07 |
| PAA-CS-GA | 7.39 | 37.24 | 139.5 | 6.21 |
| PAA-G-GA | 6.08 | 45.52 | 83.1 | 8.97 |
| PAA-W-GA | 2.95 | 31.03 | 42.9 | 4.14 |
| PAA-I-GA | 5.67 | 24.14 | 181.3 | 8.97 |
| PAA-R-GA | 4.68 | 26.89 | 79.8 | 6.89 |
| PAA-K-GA | 6.21 | 35.86 | 73.9 | 9.66 |
| PAA-T-GA | 2.31 | 164.14 | 28.8 | 3.45 |
| PAA-E-GA | 5.67 | 58.62 | 67.9 | 8.28 |

TABLE J-continued illustrates Mechanical properties of FIG. 1a Films

| Film-Type | Maximum load (kg) | Modulus elasticity (MPa) | Break Elongation % | Tensile Strength (MPa) |
|---|---|---|---|---|
| PAA-CA-GA | 10.61 | 86.89 | 115.4 | 15.86 |
| PAA-DA-GA | 6.4 | 121.3 | 7.2 | 11.73 |
| PAA-GA[d] | 8.62 | 485.52 | 38.8 | 43.45 |
| PAA-GA[e] | 9.03 | 232.41 | 63.6 | 45.52 |
| PAA-GA[f] | 12.47 | 232.41 | 126.4 | 63.49 |
| PAA-A-GA[h] | 9.48 | 821.38 | 8 | 28.97 |
| PAA-S-GA[h] | 5.72 | 697.24 | 30 | 43.45 |
| PAA-A-CS-GA | 4.04 | 72.41 | 8.56 | 6.21 |
| PAA-C-GA | 14.51 | 920 | 48.3 | 73.79 |

All of these films were at 0.18M PAA concentration, but some of the membranes were at 0.20 M concentrations. [a]PAA-GA was casted onto glass, and then non-GA treated W was added onto the PAA-GA. [b]GA treated PAA-C incubated overnight after being casted on the glass; 3-week old membrane. [b]GA treated PAA incubated overnight after being casted on the glass; 2 h old membrane. [d]GA was first diluted in dry DMAC and then applied to PAA solution. PAA membranes were casted on clean glass and incubated overnight. After incubation, DMAC was eliminated from the membranes by soaking them in pure water. The thickness of PAA membrane is important for its modulus elasticity and % break elongation; [e]while thicker one has higher % break elongation, its modulus elasticity is lower [i.e. thicker one has %63.6 and 273.79 MPa while one was %38.8 and 485.2 MPa. Altering the incubation time was also an important factor as seen in [f]which has lower incubation time. [h]GA was dissolved in dry DMAC and then directly applied to PAA-A solution. The length and width of all membranes were 2.52 cm while thickness of the membranes was between 0.025-0.1 mm:

Maximum-load bearing capacities of the membranes mostly showed relation with the thickness of the membrane. For example, PAA-CA, Composite membrane, PAA[f], PAA-CS were relatively thicker than PAA-T, PAA-A[b] and PAA-R which showed lower maximum-load bearing potential. However, PAA-C, PAA[e] and PAA[h] which were relatively thinner but could withstand high load, which is a sign of how small molecule affects the membrane's mechanical properties. Modulus elasticity and break elongation were dependent on the procedure and the small molecule combined with PAA. L-Cysteine and L-Alanine were by far best membranes in FIG. 1a. In terms of L-alanine, two different concentrations (1 mg/mL and 2 mg/mL) were tested; we however found that the concentration was not so important ion but the thickness of the crystal L-alanine residues applied on the membrane makes a difference in terms of modulus of elasticity. Larger crystals make the membrane weaker. However, manipulations in the procedure results in alterations of the mechanical properties.

New membranes were prepared according to FIG. 1b, and the mechanical results are discussed below.

TABLE K

Mechanical properties of FIG. 1b films

| Film Type | Maximum load (kg) | Tensile strength (MPa) | Break strength, (MPa) | Break Elongation (%) | Modulus elasticity (Mpa) |
|---|---|---|---|---|---|
| Combined[1, 2] | 5.25 | 26.89 | 24.68 | 3.4 | 1043.87 |
| PAA-A[1, 3, 4] | 3.13 | 47.57 | 22.27 | 6.1 | 1750.58 |
| PAA-A[1, 3, 5] | 2.54 | 19.3 | 16.55 | 2.2 | 930.79 |
| PAA[1, 3, 6] | 4.49 | 68.26 | 41.85 | 11.6 | 1872.62 |
| PAA-A[1, 3, 7] | 4.13 | 62.74 | 19.72 | 8 | 2244.93 |
| PAA[1, 8] | 2.86 | 86.18 | 30.34 | 16.4 | 1552.69 |
| PAA[1, 3, 4, 8] | 2.18 | 66.19 | 41.58 | 23.8 | 1101.51 |
| PAA-CA[1, 3, 4, 8] | 4.13 | 62.74 | 55.85 | 24.7 | 1221.06 |
| PAA-A[4, 9, 10, 11] | 2.9937072 | 45.51724138 | 44.62068966 | 61.7 | 235.862069 |
| PAA-A[9, 10, 12] | 2.3586784 | 35.86206897 | 21.5862069 | 11.2 | 961.3793103 |
| PAA[7, 9, 13] | 2.79412672 | 84.82758621 | 65.65517241 | 13.8 | 2639.310345 |
| PAA-A[4, 9, 10, 14] | 3.9916096 | 30.34482759 | 27.86206897 | 9.1 | 1038.62069 |
| PAA-A[7, 9, 10, 14] | 1.8597272 | 57.24137931 | 47.37931034 | 8.4 | 2062.068966 |
| PAA-A[7, 9, 10, 11] | 1.7236496 | 52.4137931 | 1.103448276 | 11.9 | 1678.62069 |
| PAA-A[7, 9, 10, 15] | 3.9008912 | 29.65517241 | 29.44827586 | 7.4 | 1031.724138 |
| PAA-A[7, 9, 10, 15] | 4.3544832 | 33.10344828 | 27.31034483 | 8.6 | 866.2068966 |
| PAA[8, 9, 11] | 2.2226008 | 33.79310345 | 25.86206897 | 6.2 | 1193.793103 |
| PAA-A[7, 16, 17] | 2.5854744 | 39.31034483 | 34.89655172 | 6.3 | 1382.758621 |
| PAA-A[7, 13, 18] | 4.4905608 | 33.79310345 | 33.03448276 | 14.6 | 1264.137931 |
| PAA-A[7, 8, 18] | 1.9504456 | 29.65517241 | 27.24137931 | 4.9 | 1400 |
| PAA[7, 8, 19] | 3.2205032 | 48.96551724 | 41.31034483 | 14.2 | 1397.931034 |
| PAA[7, 8, 19] | 3.40194 | 51.72413793 | 48.13793103 | 29.4 | 1823.448276 |
| PAA-DC[8, 9, 20, 21] | 2.1772416 | 65.51724138 | 35.86206897 | 9.7 | 2185.517241 |
| PAA-A[8, 9, 20] | 2.2226008 | 66.89655172 | 48.27586207 | 5.8 | 2762.068966 |
| PAA-W[8, 9, 20] | 1.4968536 | 46.20689655 | 42.48275862 | 9 | 1848.27586 |
| PAA-W[8, 9, 20] | 1.7690088 | 53.79310345 | 43.31034483 | 12.7 | 1880 |
| PAA-W[8, 9, 20] | 2.9029888 | 55.17241379 | 49.79310345 | 37.4 | 1615.172414 |
| PAA-BB[8, 9, 22] | 2.26796 | 68.96551724 | 58.68965517 | 40.9 | 2177.241379 |
| PAA-DA[8, 9, 20] | 2.0865232 | 63.44827586 | −10.48275862 | 30.4 | 1725.517241 |
| PAA-PCl[8, 9, 23, 24] | 0.8164656 | 31.03448276 | −12.27586207 | 11.8 | 1315.172414 |
| PAA-PCl[8, 9, 23, 25] | 2.4493968 | 46.89655172 | 32.48275862 | 6.6 | 1368.275862 |
| PAA-pAS-SA (4 mg/mL)[26, 27] | 6.25 | 95.147 | 88.942 | 58 | 4101.62 |
| PAA-T-pAS-SA[26, 27] | 4.8 | 48.95 | 47.44 | 63.3 | 1793.33 |
| PAA[26, 27, 28] | 3.22 | 48.95 | 48.95 | 5.7 | 2255.28 |
| PAA-SA[26, 29] | 3.26 | 33.1 | 31 | 63.8 | 1245.88 |
| PAA-pAS-SA-A[26, 29] | 3.49 | 35.16 | 31.44 | 37.3 | 1531.3 |
| PAA-pAS-W[26] | 3.76 | 38.61 | 31.78 | 27.1 | 1490 |
| PAA-SA[26, 30] | 9.66 | 85.49 | 68.12 | 10.4 | 2590 |
| PAA-SA[26, 30, 31] | 4.35 | 32.6 | 33.1 | 18.4 | 1530 |
| PAA-IZ[26] | 4.94 | 30.34 | 24.2 | 51.6 | 1170 |
| PAA-SA[26, 28, 30, 31] | 3.99 | 30.34 | 23.99 | 54.7 | 1400 |
| PAA-SA-SN-pAS[26, 28, 30, 31] | 5.3 | 32.4 | 32.4 | 45.3 | 2367 |
| PAA-SA(4 mg/mL)-pAS-5AS-GA[25, 26, 28] | 5.6 | 91.2 | 84.76 | 57 | 3850 |

All GA concentrations were between 0.035-0.1% if not otherwise mentioned. In the cases of Sulfanilic acid (SA), GA was directly added to the SA for pre-crosslinking, flowed added to the PAA solution. [1]PAA concentrations were 0.18M with FIG. 1b; [2]Viscous PAA was casted on Glass, followed by 0.1 mg/mL GA added PAA introduced on top of the already casted PAA; [3]MeOH was directly added to the system right after GA addition, or GA-small molecule addition; [4]40 µL/mL MeOH added; [5]80 µL/mL MeOH added; [6]10 µL/mL MeOH added; [7]20 µL/mL MeOH added; [8]FIG. 1b ii; [9]PAA concentration is 0.16M; [10]FIG. 1b i; [11]Glass-surface was rinsed with dry DMAC; [12]10 min incubation at 72° C.; [13]4 mg/mL imidazole was used as cross-linker; [14]Glass-surface is rinsed with dry MeOH; [15]Glass-surface and membrane surface were rinsed with DMAC; [16]FIG. 1a iii; [17]Glass-surface and membrane surface were rinsed with MeOH; [18]Glass-surface and membrane surface with EtOH; [19]Glass-surface was rinsed with EtOH; [20]20 µL/mL MeOH was added to the PAA solution before cross-linker addition; [21]4 mg/mL Diphenolcarbazide [DC]; [22]4 mg/mL 2-Benzylbenzoyl; [23]4 mg/mL 4-amino-2-chlorobenzoic acid; [24]The casted solution directly incubated under-hood for overnight; [25]4 h incubation in room temperature, and then incubated under-hood for overnight;

[26] 0.12 M PAA, [27] 4 months old; [28] PAA prepared in 35% DMAC in Ethanol; [29] 1-3 days old; [30] 7-10 days old; [31] GA dissolved in DMAC was added in addition to GA in water. In Table K, BB refers to 2-benzylbenzoyl.

Among the synthesized films, sulfanilic acid supported membranes provided the highest mechanical property. Increasing the concentration of sulfanilic acid from 2 mg/mL to 4 mg/mL improved the advanced mechanical properties by up to 3 times as shown in Table K. Among the small molecules incorporated to PAA, sulfanilic acid is the only small molecule containing —SOOOH group, this could be the main reason of why sulfanilic acid improved mechanical properties. The compound readily forms diazo compounds and is used to make dyes and sulpho-drugs.

1.6 Contact Angle Characterization

Pure-water contact angles of PAA membranes were tested with CAM Contact Angle Meter [KSV Instrument, CT] run by CAM100 image recorder software.

Contact angle is the parameters typically used to evaluate hydrophilicity of food-packaging materials. It provides information on the tendency of the material to absorb water. A good contact angle, which refers to over hydrophobic range (i.e. over 65°), can substantially eliminate water-vapor absorption that may trigger microbial development on or within the packaging material.

TABLE L

Contact angle of PAA membranes

| Membrane Type | Procedure of FIG. 1a Top/Bottom | Membrane Type | Procedure of FIG. 1b Top/Bottom |
|---|---|---|---|
| PAA-GA | 55.87/51.27 | PAA-GA[b] | 61.73/74.66 |
| PAA-CS-GA | 62.07/53.6 | PAA-PCl-GA | 80.54/72.10 |
| PAA-DA-GA | 62.35/55.7; 45.3/47.3 | PAA-pAB-GA | 91.49/73.63 |
| PAA-CA-GA | 87.26/95.16; 81.09/79.77* | PAA-AN-GA[c] | 57.74/59.21 |
| PAA-K-GA | 47.81/54.89 | PAA-pAB-GA[d] | 73.45/50.75 |
| PAA-A-GA | 80.88/57.02; 56.58/63.7* | PAA-CA-AcOH-GA | 65.91/66.78 |
| PAA-W-GA | 47.05/65.32 | PAA[e]-AcOH-GA | 88.19/80.56 |
| PAA-R-GA | 44.03/51.54 | PAA[f]-AcOH-GA | 82.84/79.88 |
| PAA-C-GA | 57.07/41.89; 67.37/51.2* | PAA[g]-AcOH-GA | 80.98/78.43 |
| PAA-T-GA | 63.91/84.67 | PAA-GA[g] | 80.23/79.20 |
| PAA-I-GA | 47.23/55.65 | PAA-GA[h] | 62.20/66.25 |
| PAA-G-GA | 66.53/69.1; 65.11/62.5* | PAA-A-pAS-GA[h] | 75.60/74.20 |
| PAA-E-GA | 78.78/59.09 | PAA-I-pAS-GA[h] | 77.25/78.30 |
| PAA-S-GA | 97.33/62.48; 74.27/61.5* | PAA-S-GA | 52.62/60.53 |
| Composite[a] | 95.27/80.7 | PAA-SA-pAS-GA | 82.56/84.3 |

In Table L * refers to 0.5-1% GA concentration and overnight incubation. The remaining membranes were consistent with 0.1-0.2% GA concentration and 6 h incubation: [a] GA treated PAA casted on the glass, and then non-GA treated PAA-W and PAA-CA was added onto the PAA-GA and left 6 h incubation. [b] membrane was phase-inverted under hood; [c] AN refers to Amonium Nitrate; [d] Formaldehyde was used for cross-linking; [e] 20 μL/mL olive oil; [f] 40 μL/mL olive oil; [g] 100 μL/mL olive oil; [h] 0.12 M PAA. Standard deviations out of 3-runs were less than 6% for all membranes developed.

Contact angle of the membranes synthesized according to FIGS. 1a and 1b did not indicate a substantial difference.

For FIG. 1a membranes, when the membranes includes a shiny surface with having amorphous inner part gave the highest contact angle. However, the membranes containing L-lysine (K) and L-arginine (R) gave the lowest contact angle even though they were fully amorphous; these K and R containing membranes were somewhat porous.

For FIG. 1b membranes, adding acetic acid to PAA before introducing GA advanced the contact angle from 65 to 88, but increasing olive-oil concentration into the PAA decreased the observed contact angle. Typically, oil is thought of as hydrophobic; probably acetic-acid making oil causing pore-opening which results in enhances water-membrane interaction. However, adding oil into the PAA without acetic acid, it advances the contact angle. Among FIG. 1b membranes, p-aminobenzoic acid (pAB) containing glutaraldehyde (GA) treated PAA membranes gave the highest contact angle; this could be related to that GA eliminate free amino-groups on pAB, which decreases hydrophilic properties of PAA.

In all cases, the present films contain sulfanilic acid, p-aminosalicylic acid and glutaraldehyde The obtained contact angle was over 65°, thus, the small molecule incorporated within the PAA film can serve as good-packaging materials due to the contact angle data.

1.7 Electrochemical Characterization

Figure 34:
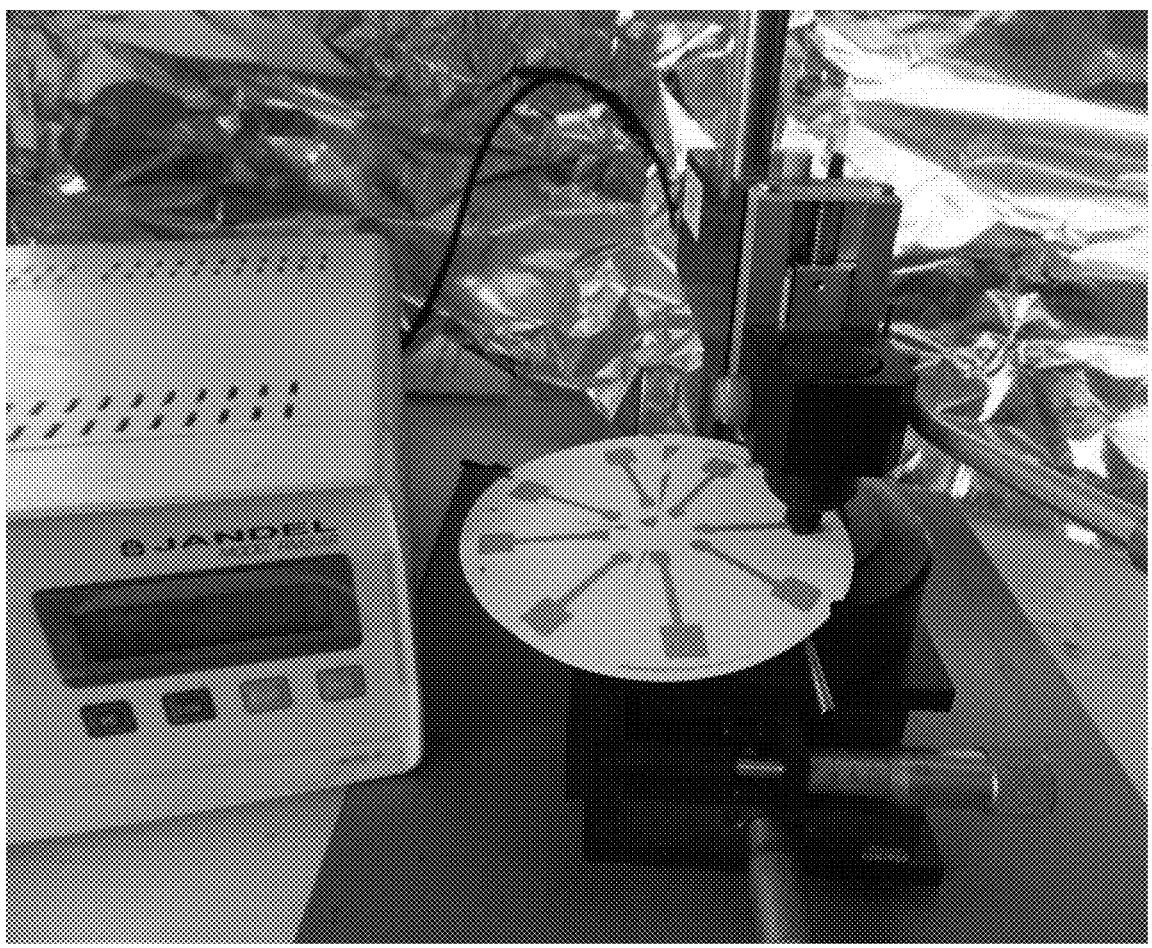
FIG. 34 is a photograph of a four-probe and Ohm meter for characterization of electronics properties.

Four-probe and Ohm meters were utilized for characterization of the electronics properties of the membranes, as shown in FIG. 34. In this figure a Jandel-brand four-point probe is shown. The technique is widely used to measure resistivity of thin conducting layers. In this system, current and voltage were measured simultaneously. The system has two current and two voltage probes; it gives information about probe resistance, contact resistance and semiconductor resistance. The results obtained from the four-probe was more accurate than simple voltmeter reading because the contact resistance is negligible in the four-point probe systems.

According to 4-probe and ohmmeter, none of the films was found to be conductive. The multimeter can go up to 200 MΩ and the scale was not sufficient to measure the resistance of the membranes, therefore the membranes were accepted as insulators.

Figures 35A, 35B, 35C:
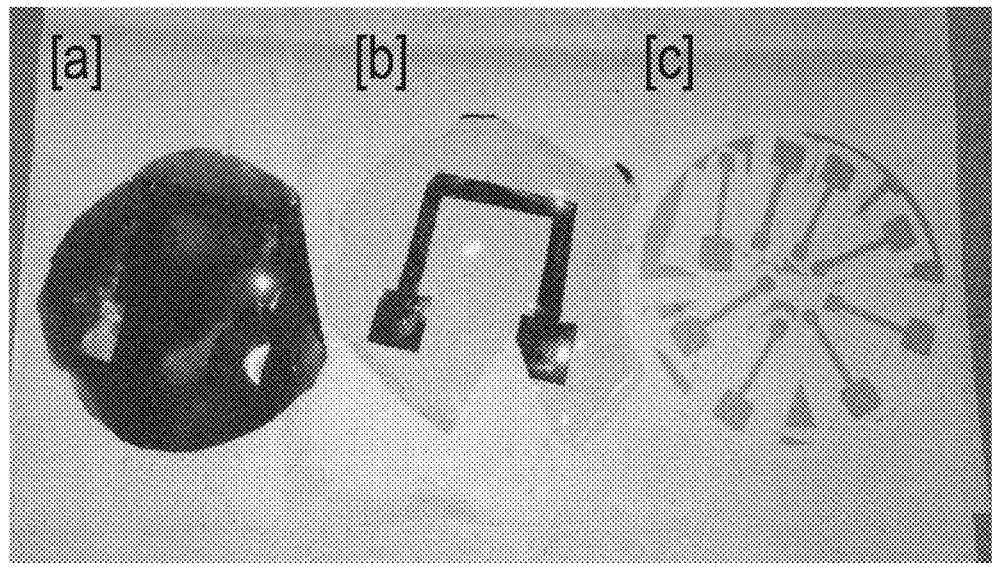
FIGS. 35a-35c is a photograph of PAA films.

Then the films were utilized as support material for gold-coating, ash shown in FIGS. 35a-35c. FIGS. 35a-35c include digital images of E-beamed gold on PAA ternary films and Whatman® paper. As seen from "a" and "b", 100 nm gold layer was coated on two different PAA membranes via E-beam under the current of 0.104 A. Similarly, 100 nm gold layer was coated on Whatman® paper (c) under same conditions.

Figures 36A, 36B:
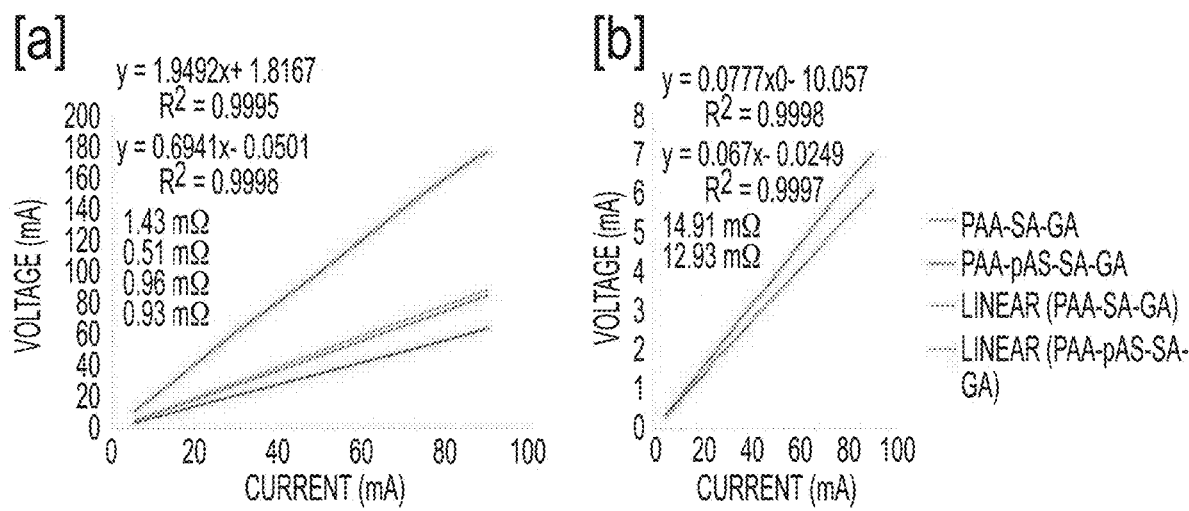
FIGS. 36a-36b are graphical illustrations of voltage vs. current of various PAA films.

Four-point probe resistivity of gold e-beamed PAA ternary membrane and Whatman® paper. FIG. 36a shows the current-voltage graphic of the coated gold from 4-probe test at 4-different sections on the paper; FIG. 36b shows current-voltage graphic of the coated gold from 4-probe test on PAA-SA and PAA-pAS-SA membranes. The obtained voltages demonstrates the difference of over 50% for the paper electrode, while the coated gold on different PAA membranes did show difference of less than 15%. However, the difference from different sections of the coated gold on same-membrane was obtained at less than 5%. When a multimeter was used to determine the resistance of the coated gold from one end to other end, the measured conductivity was 7.4Ω. The membrane itself was found to be a total insulator; the multimeter reading went beyond the calibrated level of 200 MΩ, and the instrument showed that the resistance was beyond the limit.

Figures 37A, 37B:
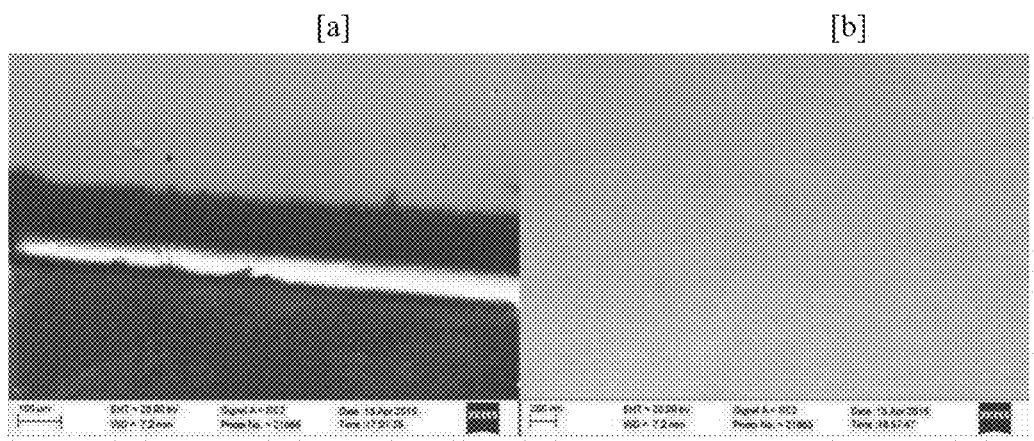
FIGS. 37a and 37b are SEM images of PAA films.
Figures 38A, 38B, 38C, 38D, 38E, 38F, 38G, 38H:
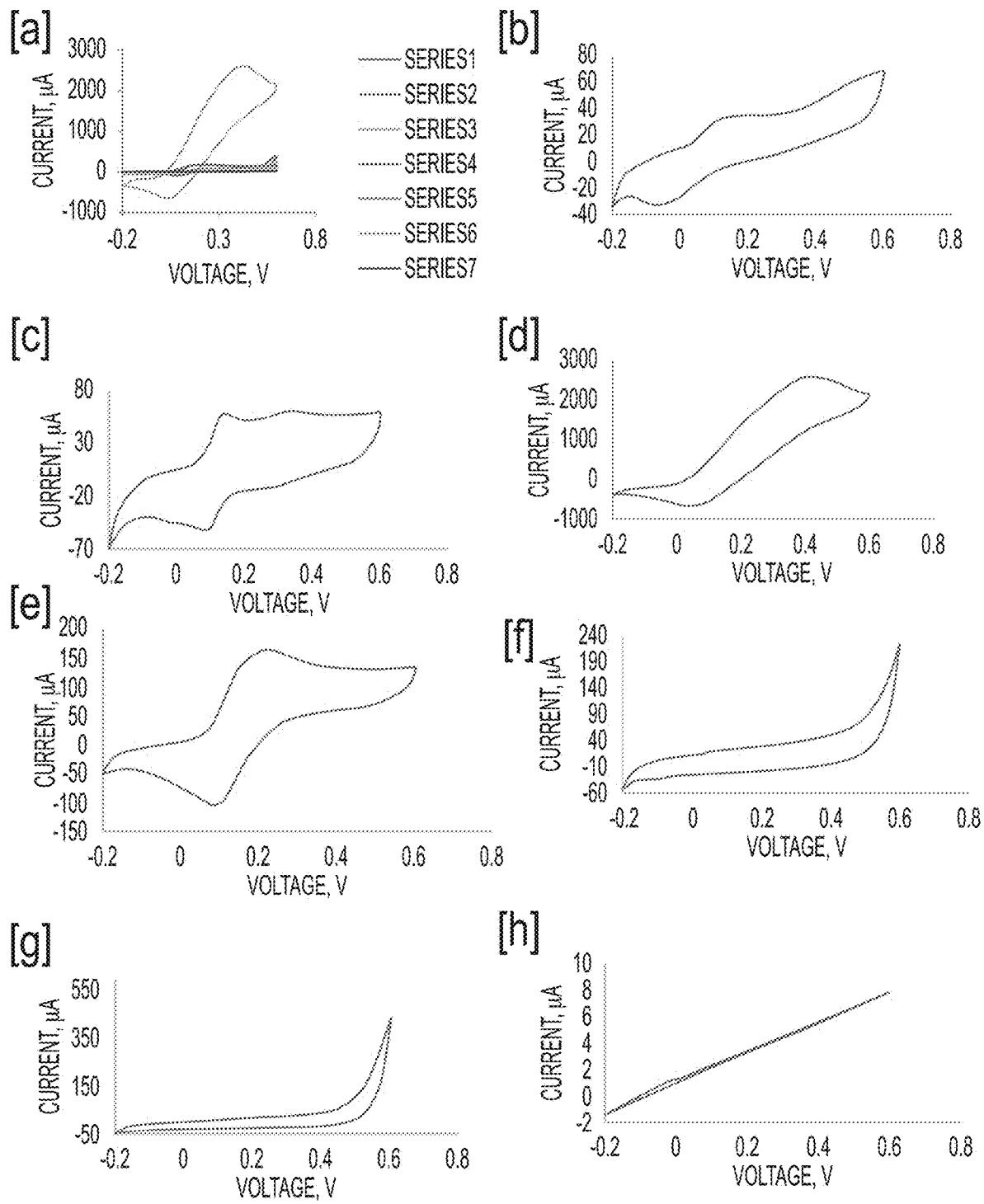
FIGS. 38a-38h are graphical illustrations of voltage vs. current of various PAA films.

SEM images at 10000 and 100000 magnification of gold e-beamed PAA ternary membrane and Whatman® paper are shown in FIGS. 37a and 37b. FIGS. 37a and 37b indicate that the coated gold on the PAA-SA was uniform and even. This could be the reason of the characteristic stable resistance recorded. The obtained resistance was 15-times larger than that noted on the Whatman® paper, which could be related to the fact that some gold could be embedded into the PAA membrane.

Since the membranes were determined to be non-conductive according to the 4-probe conductivity measurement, cyclic-voltammetry was further utilized to determine any possible electro-activity of the PAA membranes. All of the experiments were performed in 50 mM pH 7.4 PBS buffer. Platinum and silver wires were used as auxiliary and reference electrodes, respectively. Working electrodes were 200 nm gold-coated (via e-beam) Whatman® papers. Scanning rate was 50 mV, and the range was 200-600 mV.

Cyclic voltammetry results of ternary PAA membranes is shown in FIGS. 38a-38h. (38a) Series 1-7 are PAA, PAA-GA (aged GA), PAA-PDA, PAA-W-GA, PAA-pAS-GA (longer drying), PAA-pAS-GA, PAA-GA (aged) longer drying, respectively. (38a a) overlapped of all types of PAA membranes; (38a b) PAA, (38a c) PAA-GA (aged GA), (38a d) PAA-PDA, (38a e) PAA-W-GA, (38a f) PAA-pAS-GA (longer drying), (38a g) PAA-pAS-GA, (38a h) PAA-GA (aged) longer drying, respectively. Ternary PAA membranes were loaded on gold surface on e-beamed Whatman® paper. Longer drying refers to over 12 h drying, and while the rest were dried at than 6 h. All the tests were performed in pH 7.0 (50 mM) phosphate buffer in the presence of silver-wire as reference electrode and platinum wire as auxiliary electrode.

TABLE M

Summary of the Electrochemical Characterization of PAA Membranes

| Membrane | Peaks for oxidation (mV) | Peaks for reduction (mV) | Reversibility |
|---|---|---|---|
| PAA | −50 | 150 | Quasi-reversible |
| PAA-GA | −50/100/295 | 130/320/470 | Quasi-reversible |
| PAA-PDA | 55 | 410 | Irreversible |
| PAA-W-GA | 100 | 220 | Quasi-reversible |
| PAA-pAS-GA | −75 | 34 | Quasi-reversible |
| PAA-pAS-GA | No peak | No peak | NA |
| PAA-GA | No peak | No peak | NA |

Conductivity of the PAA co-polymers showed dependence on aged GA and the small molecule type, including the time of incubation. PAA-PDA-GA provided the highest oxidation reduction potentials (see the scale on the y-axis for FIG. 38b), followed by PAA-W-GA and PAA-GA. Overnight incubation under hood made PAA-GA non-conductive under the tested conditions. Similarly, PAA-pAS-GA (8 h incubation under hood) lost conductivity when it was incubated overnight under the hood. Even though there was no peak for PAA-pAS-GA, recorded current seems to be 10-times higher than PAA. As seen from Table M, PDA and W additions masked the peaks coming from PAA itself. PAA-PDA-GA provided the highest oxidation/reduction peaks while PAA-W-GA gave the closest distance for oxidation and reduction potentials, 110 mV. GA added two extra reduction and oxidation peaks to the membrane, and pulled PAA's reduction to 130 mV from 150 mV which could be a sign that the electroactive nature of the aged GA and/or GA-crosslinked PAA requires less potential for reduction. GA, as shown elsewhere affects the oxidation/reduction peaks of PAA and CS, and showed the existence of additional new peak that was not sharp in PAA-GA and PAA-CS-GA because of that the GA was fresh and much diluted.

Even though PDA provides good conductivity, PDA-PMDA based PAA membranes did not provide strong mechanical properties and durability, so GA was subsequently introduced. PDA was first dissolved in DMAC, followed by cross-linking with GA for 30 sec; the polymerized PDA was then directly introduced to PAA solution. The resulting PAA-PDA-GA was casted on gold-coated Whatman® paper, followed by drying under hood for 6 h with further rinsing in pure water. Similarly, all of the PAA coated electrodes were rinsed in pure water before they were exposed to cyclic voltammetry.

1.8 Water, Water-Vapor and Oil Permeability

Figure 39:
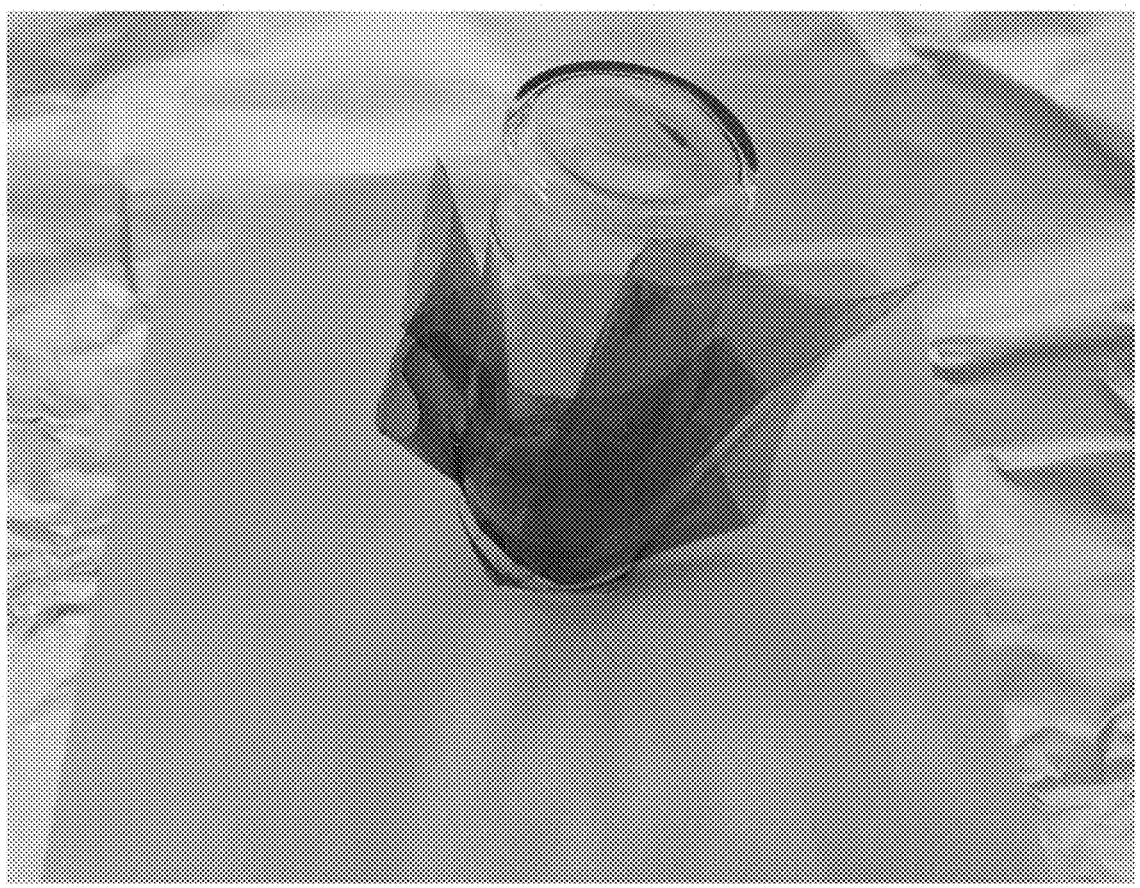
FIG. 39 is a digital image of the oil-permeability test.

FIG. 39 is a digital image of the oil-permeability test used in gathering the below data. This test was performed with the protocol of: 5 mL Extra virgin olive oil was put into a vial whose interior diameter and outer diameter were 20 mm and 24 mm, respectively. The tested membranes were used to cover the open part of the vial; the vial was placed upside down on top of a Whatman® paper [Sigma-Aldrich, MO] as shown in the digital image in FIG. 39. The membranes were incubated for 14 days at 37° C. with 95% humidity. The experiment was discontinued after 14 days.

Figure 40:
FIG. 40 is a digital image of the water-vapor permeability test.

FIG. 40 is a digital image of the water-vapor permeability test used in gathering the data below. This test was performed by the following method; measuring the weight changes of the vial containing 5 g dry desiccant. The tested membranes were used to cover the vial entrance, and the vial was incubated at 37° C. incubator, 5% $CO_2$ and 95% humidity. Incubation was conducted for 7 days. In addition to this, water permeability of the membrane was tested with Millipore Lab-scale TFF System 115V (Millipore, Billerica Mass.); the pressure was kept under 30 psi, and eluent-side was observed for wetness testing.

Resistance to oil and water-vapor penetration are important for keeping a containment fresh and for preventing the loss of taste and flavor. Different approaches have been applied to provide resistant surface to oil and water vapor transfer.

Due to the good mechanical properties, FIG. 1b membranes were used in these tests. PAA-A-GA and PAA-GA were used for both tests. It was proven that oil does not pass through the membranes. The tests were carried out in buffers and strong polar and apolar solvents including PBS buffer, DMF and hexane.

The water vapor permeability takes thickness as a parameter to determine the power of membrane against vapor permeability by which both the quality of membrane and the importance of thickness can be evaluated more objectively.

Certain membranes can be used to cover the top of the vial without requiring an adhesives for which only thin string or parafilm is enough. However, in some cases such as sulfanilic acid enhanced or 2BB co-polymerized PAA membranes are not easily attached with a thin string or parafilm since they are harder plastic.

Further, PAA-I-GA, PAA-I-pAS-GA and PAA-A-pAS-GA were tested, and no transfusion was observed. These results showed that the membranes synthesized according to FIG. 1b were better than those reported ones such as glycerol enhanced-cellulose sulfate.

Since sulfanilic acid (SA), sulfanilamide (SN), p-aminosalicylic acid (pAS) and 5-aminosalicylic acid (5AS) were used as the main molecules in the developed membranes, PAA-pAS-5AS-SA-GA and PAA-pAS-5AS-SN membranes were tested as well. Membranes at different thickness were tested. Thickness and texture did not affect the membranes resistant to oil-permeability.

1.9 Biodegradability and Toxicity Characterization

The synthesized membranes were heavily cross-linked with glutaraldehyde, and co-polymerized with intrinsic antimicrobial agents (i.e. sulfanilic acid, p-aminosalicylic acid). The biodegradability of these films is determined below. However, the introduction of these antimicrobial agents made the resulting membranes to be biodegradable. Therefore, it was required to test biodegradability of the PAA membranes.

For the below data microorganisms were obtained from rotten sticks from American Elm (*Ulmus Americana*) in the University's garden, Binghamton-NY. $^1$H NMR, $^1$H-correlation spectroscopy (COSY), and $^1$H-$^{13}$C-heteronuclear single quantum coherence (HSQC). The fungus chunk was directly introduced to the bioreactor without any selection. Pre-selected fungus and fungus chunk were characterized with molecular biological techniques. The plasticized PAA membranes showed dramatic differences in terms of physical characteristics than the membranes designed elsewhere, so it required further biodegradation testing of the new membranes.

Characterization of the isolated fungi species were done in the Department of Sustainable Bioproducts, College of Forest Resources, Mississippi State University, Starkville, Miss., USA.

FIG. 1a/1b membranes were used in biodegradation studies because if these membranes can be degraded, the rest of PAA membranes synthesized in this study can be degraded as they have lower degree of cross-linking. PAA-GA and PAA-CS-GA have been shown to degrade in less than two months by the ascomycete fungus. *Fusarium oxysporum*.

The bioreactor contained 25 mg/mL YPD medium, 0.1 mg/mL D-glucose, 1% L-glutamine, 25 µL/mL trace-metal solution and 5 mg/mL Peptone, which only contains the fungi chunk that was later identified as *Trichaptum biforme*. The pH of the medium was adjusted to pH 5.7 before autoclave. The bioreactor volume was 100 mL, and the membranes were from 50 mg PAA-A-GA of FIGS. 1a i and 50 mg FIG. 1a ii PAA-GA. It also includes 50 mg PAA-A-pAS-GA and 50 mg PAA-SA-GA of FIG. 1b.

The membranes were not crushed, and put into the medium as they were. The blank bioreactor was cultured under same conditions without the membranes. Disintegration was monitored by visual decreases in the membrane size while structural degradation was monitored via NMR. Disintegration was not able to be monitored when microbial biomass totally covered the membrane surface. In this experimental design, there were four main differences from previous designs:

The starting fungus inoculum was prepared by dissecting the fungi chunk, and taken the inner part as the starting biomass, which was later on characterized as *Trichaptum biforme*.

Cells were not acclimatized before they were used to degrade the films of FIGS. 1a and 1b.

Trace metal solution was used at 25 µL/mL to enhance overall activation of laccases and manganese peroxidases to advance PAA degradation Fed-batch process was used instead of combination of fed-batch and continuous process For each NMR run, 1 mL of solution from the bioreactors was put into 1.5 mL polypropylene microcentrifuge tube. The sample was kept in −20° C. overnight, and then lyophilized for 24 h. The resulted solid sample was dissolved in 0.9 mL $D_2O$. The dissolved sample was then left for precipitation of non-dissolved sample for 15 min; the final volume was between 0.75-0.8. mL. Degradation of the membranes was monitored via $^1$H NMR, $^1$H COSY and $^1$H $^{13}$C HSQC NMR techniques.

"The trace metals solution" contained 20 mM $FeSO_4 7H_2O$, 2 mM $CuSO_4 5H_2O$, 5 mM $ZnCl_2$, 20 mM $MnSO_4 H_2O$, 6 µM $CoCl_2 6H_2O$, 1 mM $NiCl_2 6H_2O$, and 1 mM $MoCl_3$.

Both *Trichaptum biforme*, a white rot fungus, belonging to Basidiomycota division of Fungi kingdom and *Trichaptum biforme*, similar to *Fusarium oxysporum* can degrade aliphatic and cyclic organic pollutants were used. Basidiomycetes are among the higher fungi that can develop multicellular mycelium. They are mainly found in rotten trees where they degrade lingo-cellulosic polymers via extracellular enzymes including manganese peroxidases, laccase peroxidase and so on.

Figures 41A, 41B, 41C:
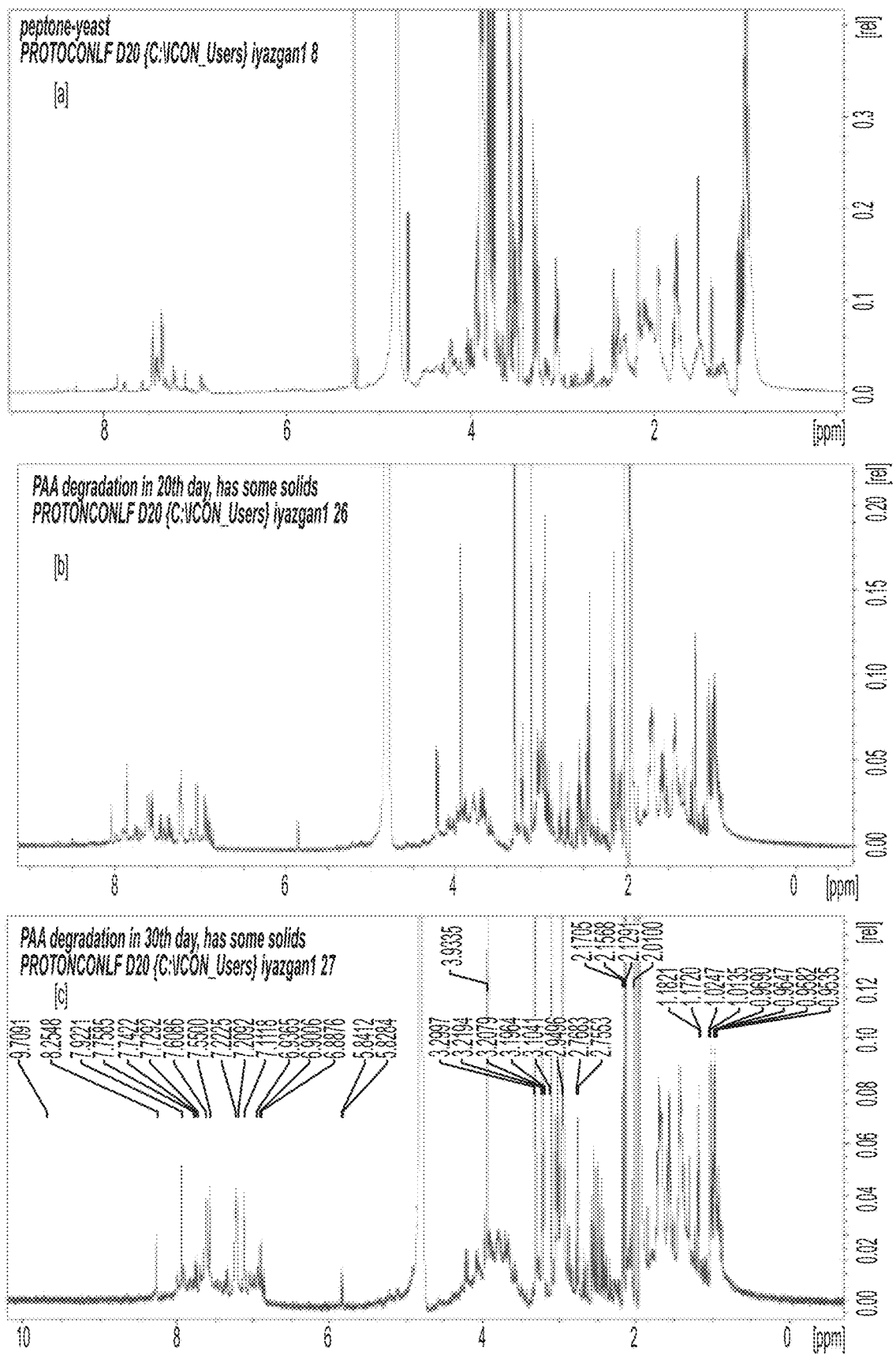
FIGS. 41a-41j are illustrations of NMR data.
Figures 41D, 41E, 41F:
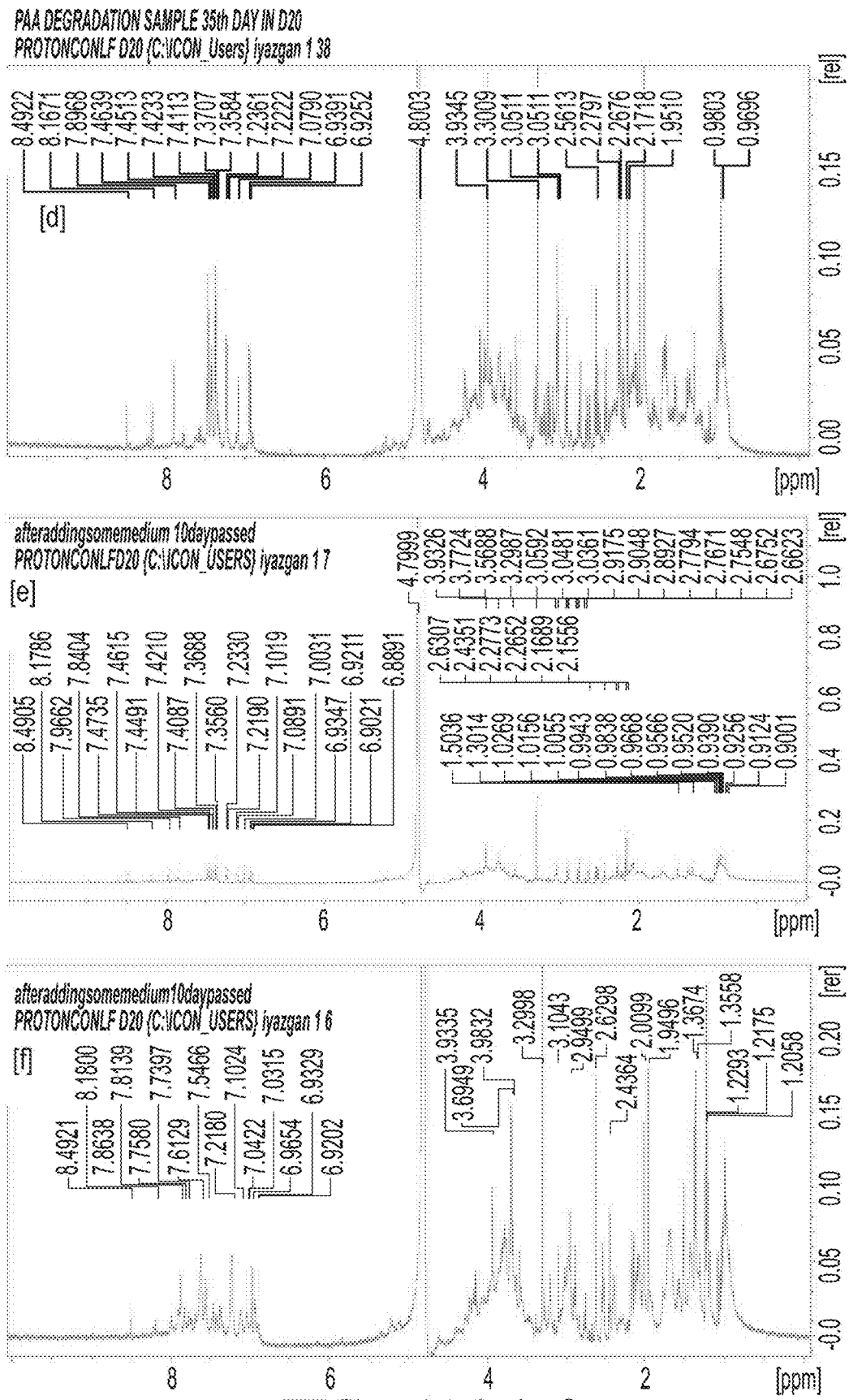
Figure 41G:
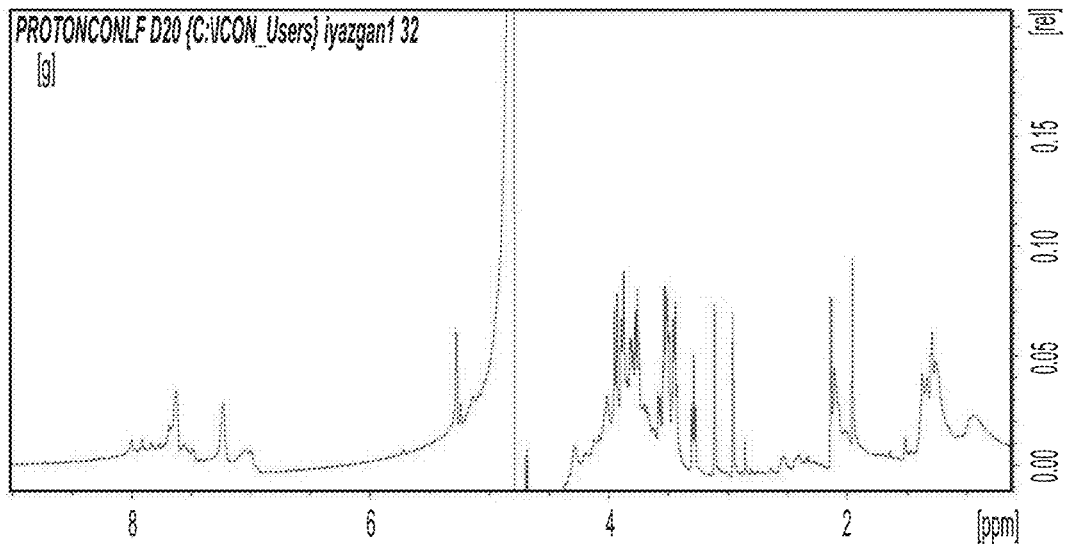
Figure 41H:
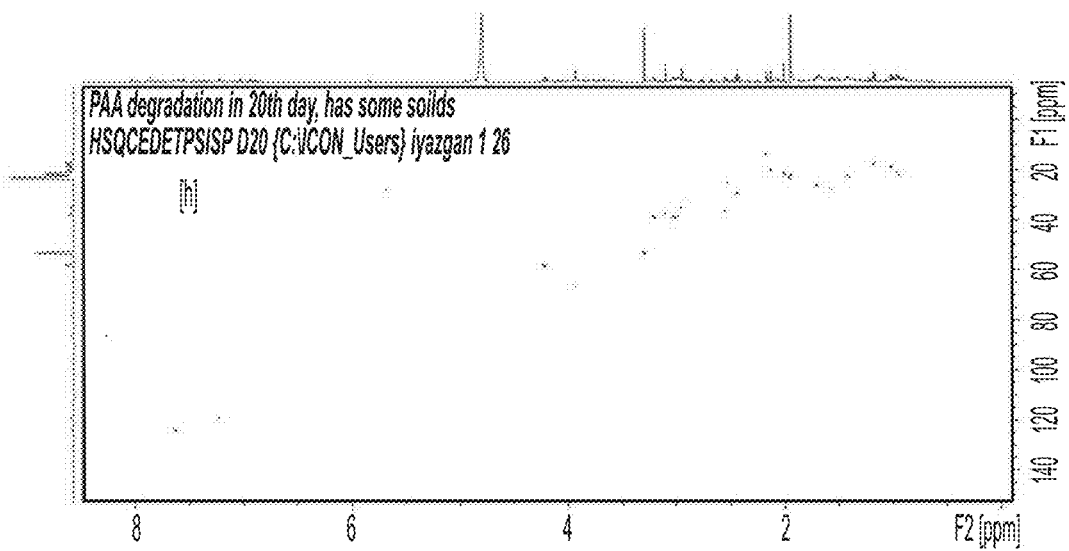
Figures 41I, 41J:
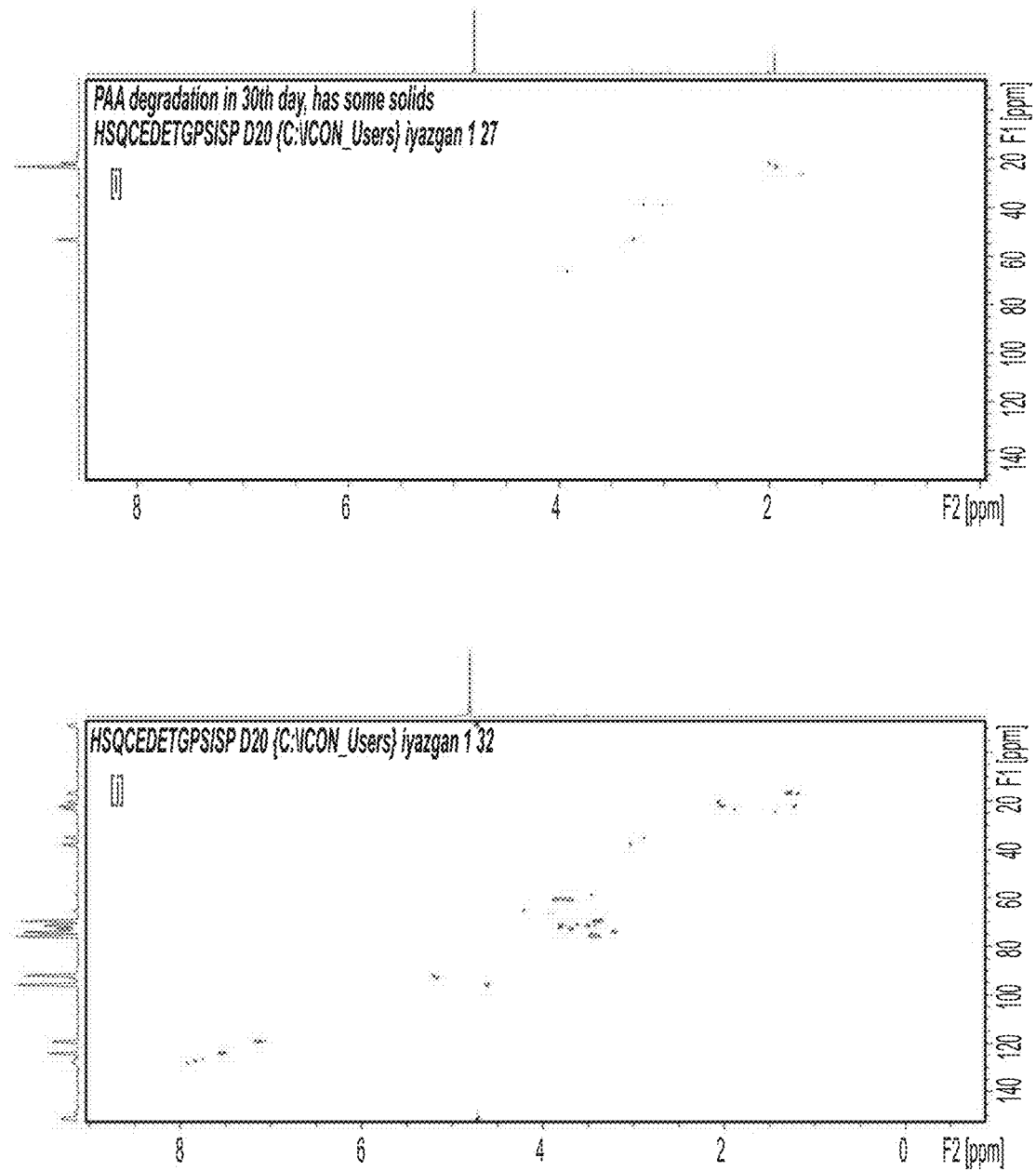

Full $^1$H spectra of the PAA for peptone-yeast medium (FIG. 41a), at day $20^{th}$ (FIG. 41b), $30^{th}$ (FIG. 41c), $35^{th}$ (FIG. 41d), $40^{th}$ (FIGS. 41e) and $50^{th}$ (FIG. 41f), and (FIG. 41g) $120^{th}$. Degradation of the plasticized PAA membranes were monitored by examining the aromatic peaks belonging to PAA. The three peaks between 2-3 ppm [2.13, 2.53 and 3.10 ppm] were observed which could be thought to belong to DMAC. However, as seen in FIG. 41j, DMAC gave three peaks in $^1$H $^{13}$C HSQC; at $120^{th}$ day $^1$H $^{13}$C HSQC, these peaks were confirmed as also belonging to DMAC. This could be related to that addition of high amount of PAA membranes resulted in partial dissolution of the polymers which were surrounded by the metabolites or peptides/proteins released into the medium. This could then prevent the release of DMAC into the medium.

DMAC is a volatile organic-solvent, and is supposed to evaporate from the system upon overnight lyophilization. NMR sample was prepared via freeze-and thawing procedure where overnight-lyophilization was applied to eliminate all the solvents coming from the biodegradation media. Disintegration of the membranes was completed within 20 days. That was why the $20^{th}$ day was selected as the first day of sampling. Aromatic regions in $^1$H NMR spectra at $20^{th}$ and $30^{th}$ days showed strong similarities; the doublets and triplets are quite similar. Aromatic regions in NMR spectra at $35^{th}$ and $40^{th}$ days showed largely triplets in contrast to $20^{th}$ and $30^{th}$ days; $35^{th}$ day still showed some doublets and singlets which signifies the presence of PAA. However, the aromatic regions in $^1$H NMR spectrum of $40^{th}$ day did not show any clear evidence of the presence of PAA. Interestingly, the aromatic regions in $^1$H NMR spectra at $20^{th}$ and $40^{th}$ days showed strong similarities for the presence of triplets. For the $20^{th}$ and $30^{th}$ days, a doublet was seen at 5.82 ppm which could be a sign of fragmentation of the PAA molecule, which was then consumed because at $35^{th}$ and later-days the peak disappeared.

TABLE N

Characteristic peaks related to PAA degradation

| Day incubation | Aromatic range, ppm | Aliphatic range, ppm |
| --- | --- | --- |
| 20 | Doublets of PAA, 6.9-8.1 | |
| 30 | Doublets of PAA, 6.9-8.1 | |
| 35 | Triplets, no sign of PAA | |
| 40 | Triplets, no sign of PAA | |
| 50 | Doublets of PAA (6.9-8.1), and triplets from degradation/metabolites | |
| 120 | Overwhelmingly doublets of PAA, 6.9-8.1 | Peaks of DMAC (1.95, 2.7 and 3.2) |

Since PAA is composed of aromatic groups, it is not expected to show any triplet. The triplets at aromatic region are a strong sign of partial or total saturation of the rings found in PAA. Then 50 mg of PAA-pAS-GA and PAA-SA-GA were added to the system at $40^{th}$ day, which was then analyzed at $50^{th}$ day. During this period, only 0.2 mg/mL sugar was added to the medium at $40^{th}$ day. Then, the system was run in continuous mode. From 6.5 to 8.5 ppm range of $50^{th}$ and $120^{th}$ day was overlapped to see the changes in PAA degradation. Analyzing the $50^{th}$ day data we found that the aromatic region in $^1$H NMR revealed the peaks of PAA and the triplets which are the signs of saturation of aromatic groups in PAA and/or the newly formed cyclic groups. Then, 100 mg of PAA-pAS-GA were added to the medium, and the mixture was incubated for additional 70 without adding any sugar or peptone to the system. Then, at $120^{th}$ day, $^1$H NMR of the bioreactor was carried out; but only the PAA related peaks were found.

When the $^1$H NMR spectra were compared the followings were observed; Peptone yeast NMR possesses doublets and triplets between 3.27-3.94 ppm, which is not found in any other; a singlet at 3.10 ppm, which is slightly larger at 20th and 30th days, while very small at 35th and 50th days; a singlet at 3.30 ppm is relatively larger at $20^{th}$, $30^{th}$ and $35^{th}$ days while it is smaller at $40^{th}$ and $50^{th}$ days; the peak is not clear for peptone-yeast medium; a singlet at 3.93 ppm probably found in all of them but not found in peptone-yeast medium; three singlets between 2.75-2.78 ppm in all, but not in peptone yeast; the triplet at 2.43 ppm found in all; a singlet 2.12 found in $20^{th}$ and $30^{th}$ days, might be in $50^{th}$ day; but it was not found in peptone-yeast medium, $35^{th}$ and $40^{th}$ days; a singlet at 2.01 ppm is found in 20th, 30th, 35th and 50th days, but not in peptone yeast and 40th days, this peak is relatively bigger for 20th and 30th days; a peak at 1.95 ppm for 20th, 30th, 35th days which is very small for 50th day while it was not found in $40^{th}$ day and peptone-yeast medium; a singlet found in all, except 30th day at 8.49 ppm; the singlets found at 8.37 and 8.29 ppm only for peptone-yeast medium; the singlet at 7.84 is only for peptone-yeast and 40th days; they are quite similar; the two singlets at 7.6 and 7.7 are only for peptone-yeast medium; there is a triplet at 7.46 ppm found in peptone yeast medium, $20^{th}$, $35^{th}$ and $40^{th}$ days; slight presence of the peak is in $50^{th}$ day while it was not in 30th day; the singlet at 7.10 ppm is only for peptone yeast medium; the doublet (for $35^{th}$ and $40^{th}$ days) or the broad peak (for $20^{th}$, $30^{th}$ and $50^{th}$ days) at 7.22 ppm where peptone yeast medium has a triplet. However, the doublet is relatively bigger for $30^{th}$ day. There are 4 broad (or doublet) and a one singlet on upper field of this peak. These are the sign of presence of PAA. However, it is not easy to say that they are present in 30th and 35th days; the broad peak at 7.61 ppm for $20^{th}$, $30^{th}$ and $50^{th}$ days, which is not included in $35^{th}$ and $40^{th}$ days; the singlet peaks between 6.5 to 8.5 ppm shifted during from $20^{th}$ to $50^{th}$ days, could be related to the biodegradation of PAA; the triplet at 7.56 ppm for $20^{th}$, $30^{th}$ and $35^{th}$ days where $40^{th}$ day has nothing; peptone yeast medium has a doublet and $50^{th}$ day has a singlet. This shows there is a degradation of PAA, but at $50^{th}$ day intact PAA polymers or PAA polymers protected their back-bone structure are present in the media; the two triplets and a doublet between 7.3-7.5 ppm found in $20^{th}$, $30^{th}$, $35^{th}$ and $40^{th}$ day look similar, but that is not possible to say they are from peptone or sugar since the peaks between 2-4 ppm showed no similarity. Actually, the shapes of these triplets don't look alike; when $50^{th}$ and $120^{th}$ days compared, there is no improvement rather the triplet at 7.46 and the doublets 7.41 and 7.35 went away for $120^{th}$ day, and the singlet at 8.49 ppm went away as well.

Biodegradation of the membranes (PAA-CS-GA and PAA-GA) showed some-differences such as PAA was fragmented into little fragment which was seen as that integrals of the four-peaks between 6.9 to 7.2 ppm became similar with time. For example, at $15^{th}$ day, the major peak was overwhelmingly larger while at $30^{th}$ day they were all the same. Also, at $30^{th}$ day, the triplets appeared; the sign of saturation of the double bonds in PAA and/or conversion of the groups. However, for $15^{th}$ to $27^{th}$ days, the triplets were not seen or could be very low. Therefore, it can be said that the fungi degraded the PAA-CS-GA and PAA-GA polymers into two steps; first degraded the larger PAA polymers into small PAA polymers. In the second step, the fungi quickly degraded the smaller-sized PAA polymers.

In contrast to this, as seen from the FIGS. 41a-41j, consumption of the PAA membranes synthesized in this chapter were done without requiring fragmenting the larger PAA polymers into smaller PAA polymers. These results are summarized in Table N above, as a function of time of degradation. As seen from Table N, at the $35^{th}$ day, all the PAA was consumed by the fungi.

Characterization of the Fungi Responsible for PAA Degradation Using Molecular Biological Techniques Genomic DNA Isolation-Genomic DNA was isolated from dried mycelium by use of the NucleoSpin® Plant II Kit (MACHEREY-NAGEL GmbH & Co. KG). The dried weight of the mycelium was 0.05 g for sample A and 0.07 g form sample B. Mycelium was washed with 95% ethanol for 2 hours. The mycelium was transferred to tubes with 2 mm glass bead sand homogenized with CTAB lysis buffer (2% cis-trimethyl ammonium boric acid, 100 mM Tris, 20 mM Na2 EDTA, 1.4 M NaCL, and 1% polyvinylpyrolidine). The extract was treated with RNase A (200 ng/ul, incubate at 65° C. for 10 min) followed by Proteinase-K and incubated at 65° C. for 1 hour. The remainder of the extraction followed the kit instructions for isolation of DNA from fungi. DNA was eluted with 50 μl buffer PE heated to 65° C. The concentration was measured on a Nanodrop 1000 spectrophotometer. The purity of the DNA was evaluated in gel electrophoresis on a 1% agarose gel in 1×SBA (Sodium Boric Acid).

PCR Amplification

The Internal transcribed spacer (ITS) region of the fungi was amplified using primers ITS1-F (5'-CTT GGT CAT TTA GAG GAA GTA A-3') (SEQ ID NO: 1), which is specific for the higher fungi (Gardes et al. 1993), and ITS4 (5'-TCC TCC GCT TAT TGA TAT GC-3') (SEQ ID NO: 2), the universal primer. Amplifications were performed in Eppendorf Mastercycler® with the following settings: an initial hot start at 98° C. for 2 min (DNA template only), melting at 95° C. for 45 s, annealing at 52° C. for 45 s, and extension at 72° C. for 2 min, and final extension at 72° C.

for 10 min for 35 cycles. After the initial hot start, a master mix containing 10 mM reaction buffer, 25 mM MgCl$_2$, 10 mM Forward and 10 mM Reverse primers, 10 mM deoxynucleotide triphosphates (dNTPs), 10 mg/ml Bovine Serum Albumin (BSA), between 100-200 ng/µl total DNA isolated from samples, deionized water, and 2.5 U/µl Tag polymerase was added to each sample.

PCR products were separated by electrophoresis in 1% (wt/vol) agarose gels in 1×SBA buffer (Sodium Boric Acid) with RedGel (100 ng/ml) and running buffer; DNA bands were visualized by the fluorescence of the intercalated RedGel under UV light and photographed.

Sequence Analysis

The amplified fragments were inserted into the pGEM-T easy vector (Promega, Madison, Wis.) for sequencing, and the sequence of ITS regions were confirmed by sequencing at least three individual recombinant colonies using a Beckman Coulter (Brea, Calif.) CEQ8000 DNA sequencer. The sequence data were assembled and analyzed by the use of CEQ sequencing analysis software and MegAlign (Lasergene®) and were then searched by using the ITS-1F and ITS4 primer sequences to define the ITS region. Each sequence was analyzed into the ITS region and was then separately used to perform the individual nucleotide-nucleotide searches with the BLASTn algorithm at the NCBI website. The outputs from the BLAST searches were sorted on the basis of the maximum identity and were recorded. Sequence-based identities with a cutoff of 99% or greater were considered significant in this study, and the best hit was defined as the sequence with the highest maximum identity to the query sequence.

TABLE O

The consensus sequence of sample A and sample B

| | Consensus sequences |
|---|---|
| Sample A | AGTTGGGGTTTAACGGCGTGGCCGCGACGATTACCAGTAA CGAGGGCTTTACTACTACGCTATGGAAGCTCGACGTGACC GCCAATCAATTTGAGGACAGGCATGCCCGCCAGAATACTG GCGGGCGCAATGTGCGTTCAAAGATTCGATGATTCACTGA ATTCTGCAATTCACATTACTTATCGCATTTTGCTGCGTTC TTCATCGATGCCAGAACCAAGAGATCCGTTGTTGAAAGTT TTGATTTATTTATGGTTTTACTCAGAAGTTACATATAGAA ACAGAGTTTTAGGGGTCCTCTGGCGGGCCGTCCCGTTTTA CCGGGAGCGGGCTGATCCGCCGAGGCAACAAGTGGTATGT TCACAGGGGTTTGGGAGTTGTAAACTCGGTAATGATCCCT CCGCTGGTTCACCAACGGAGACCT (SEQ ID NO: 3) |
| Sample B | CCCGGGGCAAGGGGCGGGCGGCGTTGGATTTTGCGGGACC CTTAACACCCGCTTCAGCCGCAGCGGGCGCCGCCGCCCCG AGGCCCGGCGCCGATCTAACAAGTAATACATCTCAAAGGT GTCCAACCGTATCCAACCAGTGGACGTCCGAGGGTCGCGC CGTTTGAGTGTCATGTTAATATCAACTCTGATGGTTTTTT GTTAATCATTGGATGTTGGACTTGGGGATCCCGTCACAGT CGACTACTGATGAGTACTATAGACTACGCATCGCGCAGCT GATATATTTAATGTCTACGTATATCAATCCATTAATAAA (SEQ ID NO: 4) |

Figure 42:
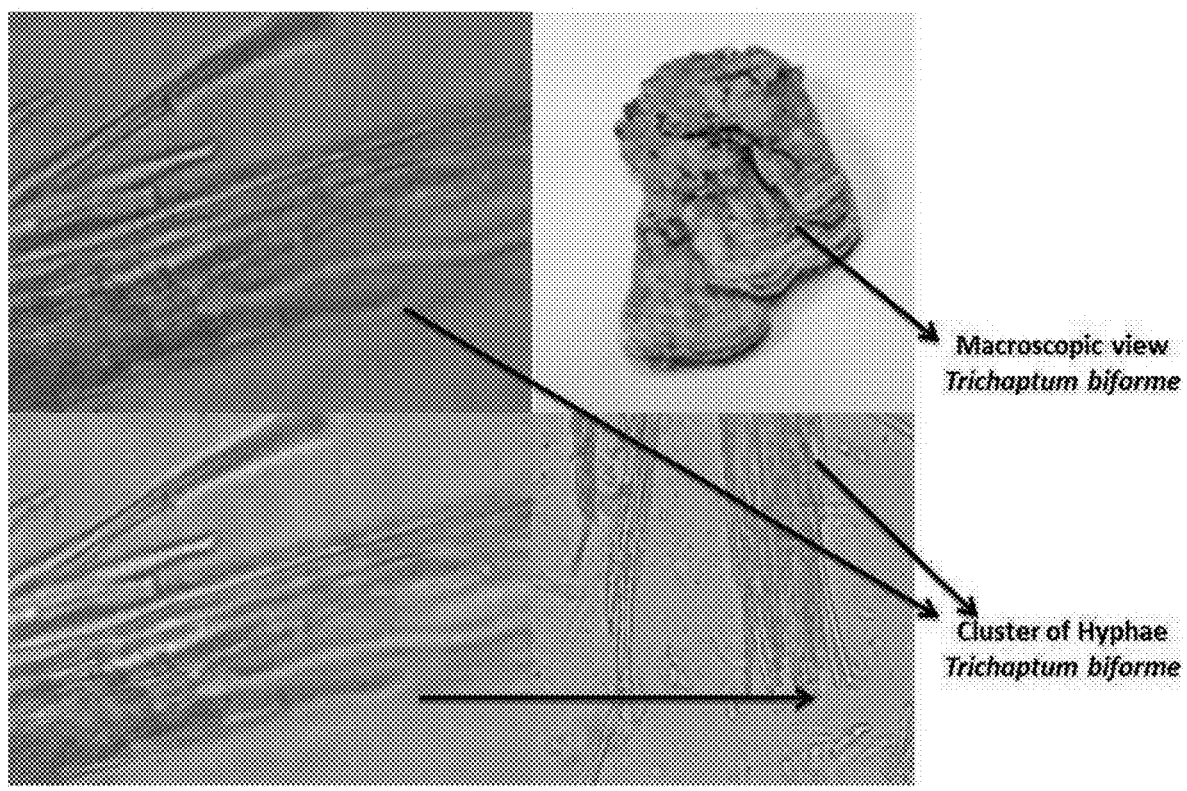
FIG. 42 is a picture of a macroscopic and four microscopic pictures of *Trichaptum biforme*.

FIG. 42 shows pictures of a macroscopic and four microscopic pictures of *Trichaptum biforme* (Picture of 1000× Oil Immersion).

Figure 43:
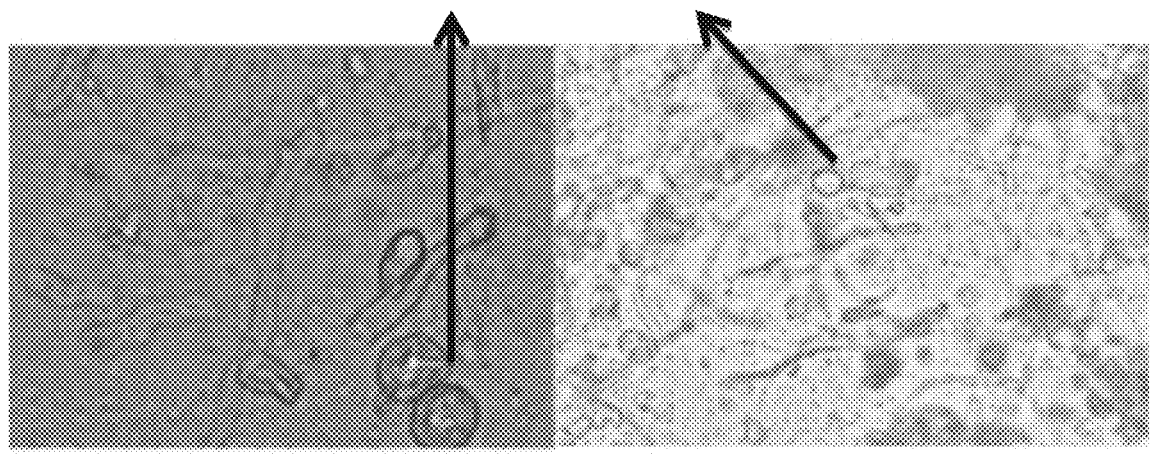
FIG. 43 is microscopic pictures of *Fusarium oxysporum*.

FIG. 43 is microscopic pictures of *Fusarium oxysporum* (Picture of 1000× Oil Immersion).

Raw sequence data for the samples are listed below:

Sample A-1 Forward
(SEQ ID NO: 5)
CCGCGNGGAGGTTTCTGGACCGCTGTCCGACCGCGCCGCTCCGTTC

GGCGCCGAGTTCCACTTTGTCCCCTCATTNATATTGTCAATTACGCGGGT

ATTCCACCGATTCCAGGTCACTTCGAAGTTGGGGTTTAACGGCGTGGCCG

CGACGATTACCAGTAACGAGGGTTTTACTACTACGCTATGGAAGCTCGAC

GTGACCGCCAATCAATTTGAGGAACGCGAATTAACGCGAGTCCCAACACC

AAGCTGTGCTTGAGGGTTGAAATGACGCTCGAACAGGCATGCCCGCCAGA

ATACTGGCGGGCGCAATGTGCGTTCAAAGATTCGATGATTCACTGAATTC

TGCAATTCACATTACTTATCGCATTTTGCTGCGTTCTTCATCGATGCCAG

AACCAAGAGATCCGTTGTTGAAAGTTTTGATTTATTTATGGTTTTACTCA

GAAGTTACATATAGAAACAGAGTTTTAGGGGTCCTCTGGCGGGCCGTCCC

GTTTTACCGGGAGCGGGCTGATCCGCCGAGGCAACAAGTGGTATGTTCAC

AGGGGTTTGGGAGTTGTAAACTCGGTAATGATCCCTCCGCTGGTTCACCA

ACGGAGACCTGTNACAACTTTNACTCCCTCTAATGACAAAATCACTANTG

AATCCCGCCGCCGCAGTCACATATGGGAGAGCTCCCACGCGTGGATCTAN

CTGAGTATCTATANGTCACCTAATACTGGCGTATCTGGTATACCGTCCCG

GTAATGTTATCCCCCATTCCCCACTCACCGAACTAATGTAACGGGTCA

Sample A-1 Reverse
(SEQ ID NO: 6)
CCCTCTTTNAAATTCTTTTTAGGGGGGGGCGACTTCCCGGCGGGGCT

ACTCAGTCATGGATCTCTGGATGCAATAANATATTAGCGATCTTCGCCNG

TGAACCACGAGGAGGATCACNAGTGCAACCCCAAACCCCTGTGAACATAC

CACTTGTTGCCGCGCCGATNCGNCCGCCCCCGTAAAACGGGACGGCCCGC

CAGAGGACCCCTAAAACTCTGTTTCTATATGTAACTTCTGAGTAAAACCA

TAAATAAATCAAAACTTTCAACAACGGATCTCTTGGTTCTGGCATCGATG

AAGAACGCAGCAAAATGCGATAAGTAATGTGAATTGCAGAATTCAGTGAA

TCATCGAATCTTTGAACGCACATTGCGCCCGCCAGTATTCTGGCGGGCAT

GCCTGTTCGAGCGTCATTTCAACCCTCAAGCACAGCTTGGTGTTGGGACT

CGCGTNAATTCGCGTNCCCTCAAATTGATTGGCGGTCACGTCAAGCTTCC

ATAGCGTAATAGTAAAAACCCTCGTTACTGGTAATCTCCGGCCACGCCGT

AACCCCACTTTGAATGTGACCCGATCGGTAGGATACCGCGAACTAACTAT

ATACGAGA

Sample A-2 Forward
(SEQ ID NO: 7)
CCGGGCGGGAGGTTTNGTTAGGGATCCCGTCGCTCGACGCGCGCCG

CGCCGGTCGGCGCGCGAGTGGCCATCGGTGTCCGCCTCATTCAGTATNGT

CAAGTGTGACGCGGGTATTCCTCACCCGATTCCAGGTGCACTTCCAGAAG

TTGGGGTTTAACGGCGTGGCCGCGACGATTACCAGTAACGAGGGCTTTAC

TACTACGCTATGGAAGCTCGACGTGACCGCCAATCAATTTGAGGAACGCG

AATTAACGCGAGTCCCAACACCGAGCTGTGCTTGAGGGTTGAAATGACGC

TCGAACAGGCATGCCCGCCAGAATACTGGCGGGCGCAATGTGCGTTCAAA

-continued
GATTCGATGATTCACTGAATTCTGCAATTCACATTACTTATCGCATTTTG

CTGCGTTCTTCATCGATGCCAGAACCAAGAGATCCGTTGTTGAAAGTTTT

GATTTATTTATGGTTTTACTCAGAAGTTACATATAGAAACAGAGTTTTAG

GGGTCCTCTGGCGGGCCGTCCCGTTTTACCGGGAGCGGGCTGATCCGCCG

AGGCAACAAGTGGTATGTTCACAGGGGTTTGGGAGTTGTAAACTCGGTAA

TGATCCCTCCGCTGGTTCACCAACGGAGACCTTGTTACGACTTTTACTTC

CTCTAAATGACCAAGAATCACTAGTGAATTCGCGGCCGCCTGCAGGTCAA

CATATGGAGAGCTCCACCCGTGGATGCATANCTGAGTATCTATAGTGTCC

CTAATACTTGGCGTATCATGGCATACCGGTTCCGTGTGAAATGTTATCGC

TCACCATCCAACAAATACNACCCGAAACTTAANGTTAACCGGGGGTCCTA

ATAGTGACCACCCATTANTGCNTTGCC

Sample A-2 Reverse
(SEQ ID NO: 8)
CGGAGGTTTTTTGGGNCNCCGTCGCGACNAGGGCCCTCACTTGGAG

CTCCGACCGGNCGCGCCAATTAACTCATGGATTTCGGGGATTTAGAGGAA

GTAAAAGTTTTAACAGGTGTCCCGTTGGTGAACCAGCGGAGGGATCTTAC

CGAGTTTACACTCCCAAACCCCTGTGAACATACCACTTGTTGCCTCGGCG

GATCAGCCCGCTCCCGGTAAAACGGGACGGCCCGCCAGAGGACCCCTAAA

ACTCTGTTTCTATATGTAACTTCTGAGTAAAACCATAAATAAATCAAAAC

TTTCAACAACGGATCTCTTGGTTCTGGCATCGATGAAGAACGCAGCAAAA

TGCGATAAGTAATGTGAATTGCAGAATTCAGTGAATCATCGAATCTTTGA

ACGCACATTGCGCCCGCCAGTATTCTGGCGGGCATGCCTGTTCGAGCGTC

ATTTCAACCCTCAAGCACAGCTCGGTGTTGGGACTCGCGTTAATTCGCGT

TCCTCAAATTGATTGGCGGTCACGTCGAGCTTCCATAGCGTAGTAGTAAA

GCCCTCGTTACTGGTAATCGTCGCGGCCACGCCGTTAAACCCCAACTTCT

GAATGTTGACCTCGGATCAGGTAGGAATACCCGCTGAACTTAAGCATATC

AATAAGCGGAGGAAATCGAATTCCGCGGGCGCCATGGCGGCCGGAACATC

AACTTCGGCCAATCCCTATATATGTATACATCCTGGCGNTTNACAACTG

GACGGGAAACGCGTACCACTATCCTGCNCATCCCTTCCCCGGCTATTCAA

GCCCCCACCCTCCAATGCCCCAATGG

Sample A-3 Forward
(SEQ ID NO: 9)
CCGGAGGTNAGNCAGCACCCGCCCCTNGGAACCCNCCCATATTCTA

CCTGTNACCCATTTAGGCATACAATTGGGTGAACGCTGGCCCACATACCT

AACAGGGCTACACTACCATGGAAGCCACTGACCGCCATCATTTGAGGAAC

GCAATTAACGCGAGTCCCAACACCGAGCTGTGCTTGAGGGTTGAAATGAC

GCTCGAACAGGCATGCCCGCCAGAATACTGGCGGGCGCAATGTGCGTTCA

AAGATTCGATGATTCACTGAATTCTGCAATTCACATTACTTATTCGCATT

TTGCTGCGTTCTTCATCGATGCCAGAACCAAGAGATCCGTTGTTGAAAGT

TTTGATTTATTTATGGTTTACTCAGAAGTTACATATAGAAACAGAGTTTT

AGGGGTCCTCTGGCGGGCCCGTCCCGTTTTACCGGGAGCGGGCTGATCCG

CCNAGCAACAAGTGGTATGTTACAGGGGTTGGGAGTTGTAACCGTAAT

Sample A-3 Reverse
(SEQ ID NO: 10)
GGGCGTTATATCTTGTGGTCTCCCGCGCTTGAGGAGCTCTCCCATAT

GTGTCGACCTGCAGGCGGCCGCGAATTCACTAGTGATTCTTGGTCATTTA

GAGGAAGTAAAAGTCGTAACAAGGTCTCCGTTGGTGAACCAGCCGGAGGG

ATCATTACCGAGTTTACAACTCCCAAACCCCTGTGAACATACCACTTGTT

GCCTCGGCGGATCAGCCCGCTCCCGGTAAAACGGGACGGCCCGCCAGAGG

ACCCCTAAAACTCTGTTTCTATATGTAACTTCTGAGTAAAACCATAAATA

AATCAAAACTTTCAACAACGGATCTCTTGGTTCTGGCATCGATGAAGAAC

GCAGCAAAATGCGATAAGTAATGTGAATTGCAGAATTCAGTGAATCATCG

AATCTTTGAACGCACATTGCGCCCGCCAGTATTCTGGCGGGCATGCCTGT

TCGAGCGTCATTTCAACCCTCAAGCACAGCTCGGTGTTGGGACTCGCGTT

AATTCGCGTTCCTCAAATTGATTGGCGGTCACGTCGAGCTTCCATAGCGT

AGTAGTAAAGCCCTCGTTACTGGTAATCGTCGCGGCCACGCCGTTAAACC

CCAACTTCTGAATGTTGACCTCGGATCAGGTAGGAATACCCGCTGAACTT

AAGCATATCAATAAGCGGAGGAAATCGAATTCCGCCGGCCGCCATGGCGG

CCGGGAGCATGCGAAGTCGGGCCCAATTCGCCCTATAGTGAGTTTTATTA

CAATTCACTGGCCCGTCTTTTACAAACNTTGTGACTGGG

Sample B-1 Forward
(SEQ ID NO: 11)
GGATCGCGCCGGGGTGGGGCGGGGCCTTAAGATTTTACGAGAATT

AGGTTAGAGATTTTGTCTTAGATCGAGACAGACTCAAGAATAGTTCATGG

TCAAGAGTAGGATCTAACAAGTAATACATCTCAAAGGTGTCCAACCGTAT

CCAACCAGTGGACGGATCTTNACCGAGTGGTGCGCAGGGGGCGCATCCCC

TTGTCGAACCCACTACCCCTGGATGGCTCGTAGCTCCATCGGACGGGTGC

CGGGGGGGATCGCGTCACTGTCGANTACTGATGNGAACTATAGACTATN

GATCCGGGCAGCTGATATATCCNANATCTATGTATATNAATCCATNAATA

AA

Sample B-1 Reverse
(SEQ ID NO: 12)
NNNNTGTTTTTCGGGCGCGTCGCGCGGGGCCCTCTCTGGGGAGCGT

CCGCCGGNCGTCCGCCGNTTACACTAAGATGNATTTGCGAGCACGNGCTA

ACATGAGATAGTTATAGGCGTTNCGAGTCTTTCTACGNGAGCTCAAATCC

CCTAGNTCACTGAGNCTCCCCAGCACGNGCTACAGNCCTCCTTGCAGAGA

GGGGCGCTCTCTTTCGGGATCAGAATATNTACACGGGCGAAAAAAGAGGG

CCCCCNTNATANCNANACNCGAGACAGTGCGACAGNCTGGACNCNGNTAC

ACAGGTTCTGAGAGTCGNTGGNGNGGAAGACAGTGAGACGGGNCAAACAG

GGAAAACCANANAGNTCGAGTTTGTNCNGCNGTGGTNCNCNATNGGAAA

AANCTCATCCCGTNGAAGGGCCCACCGANGAGCCCCNACNAAAATNCTN

GGGGTTGGGCCCGGCNCTNGTTCCNACCAAAAANGTNATNGTTCTNCTTG

TAATNTCTGGGGGGGGNGTGCCCGCCCCCNGTNCANGAATTNTANCANT

ANGANCGNAANAGNNTGNTGGGCAAAAACGGAGGTTCCCTCNACNCTNGA

ATATTAACATATTTCCCCCCCCACCAAAATATTGGTTCCTCCCACCCCGC

```
CCCCCTTTTGTGGGGCCCCCGCGGGTTTGGGGTTTCCAATTCCCTCGGCC

TNTNTTGGCCAGAAGGAAGGTGGGGGGCNGCNGANGAAAAAAANTCCGCA

AANANGGCCANGTNCAAGTTGCNACNGCNAATNGTGGGGCCTNATTTTTG

GAAACCANCAATTGGGGT

Sample R-2 Forward
                                        (SEQ ID NO: 13)
CCGGGGCNGCCGGGGCGCGTCGCCGGCNGNCNGCGGCNCNTNGGC

NGCCCGCNGCGCGAGCGCAGCGNGCCGGTGGTGCNCGCGCNCACCTCCCG

TCCCACCTCCTTCGCGCTCGNTGCGCNCANCTCTATANTANGTNAGAGNA

GATNGAATACTAGNACTATACNTATACNTATAGCACGTAGGACGANGNAA

GNGANTCNCGANATTTTTATTTGGCCGATTNTCCTATANTGNANANGGGG

AAAANGGNAGNAATTTTTGAA

Sample B-2 Reverse
                                        (SEQ ID NO: 14)
CGGCGGTGGGTTTGGCTCGTGGGCCNCCCGTGCGCGGGGGGCGCCG

CCTCCCTTTTTGCGGACGCGTCCNGCCCGGGCGCGCCCGNCGCGGTANAC

GGCTANAGTGGAGTGTGTTGCAGTGCACGNGCTATACATGGTAGTAGTTA

TAGGCAGTTGGGCNTGAGTACTGCTCTGTACNGGGAGNCTCAAATCCCAT

GAGTCCCGTGGAGGCTCCCCGACACGGGCGTACAGGCCCTCCTTTGAGAG

AGGGGGCGCTCTCTTTCCGGACAGANATATACGCGGGCGAAAANGAGGGC

CCNCNTTTNTNTCGGNACNCNAGGGTCANGTNCNGAGCANGNTCNTAGNA

CCCCCCGGGGAAACAACANGGTTTTNCTCGACGAAAGTNCGNGTGGGGGC

GGGGGGAAAGAACCAAGTNGAAAGAACGGGGGCCCANTAACAGGAGGAAA

AACCCAAAGANGANTCNGAATTTGTNCCNCNGTGGTNAACCNATNGGAAN

GANCTTATNCNGTNGAAGGGCCNACNGANGAGCCCCCNACNGACATNCTT

GGGGGTTGGGCCCGGCNCTNGTTCCCAACCAANACCGGTTAATNGTTCCT

CCCTTGTTTAATNTCTGGGGGGGGGTNNGTGCCCCGGCCCCCCCCTCGG

TTCAAAAGAAATTTNTAACCAAANAAGGAACGCAAAAAAGNNTGNGTGCC

AAAAACCGNAGGTTCCCTCNACNCTNGAATTANACNNATTCCCNCGCCAC

CAAANATTTGTTCCTCAACNCGGCCCCCTTTTGTGGGGCCCCGGGGTTT

GGTGTTTCTAAATTCCTTGGC

Sample B-3 Forward
                                        (SEQ ID NO: 15)
CCCGGCGAATGTTTTATGGGGTCATGTTCGACCGCGCCGTCCGGTTG

GCGGAGTTNCATTTTCGTGATCTANAAGAGATAAAATGGCTAAACAGGTT

TACCGTAGGTTATTANCCGCGGAAGGATCTTAACAGTTTTGAAGTGGGCT

TGATGCTGGCTTGTAACAGAGCACTGTGCTCAGTCCCGCTCCAATCCATT

CAACCCCTGTGCACTATTCGGAGTGTTGCAAGCTAAGACAATGTGGGGAG

TGGTCCCGGTTGTATTTCTAATGCGACTTGGGCTTACTTTCAAACGGTCA

AGGCTTGTCCTCCGGTTTATATACAAACACTTTTATTGTCTTGTCGAATG

TATTAGCCTCTCGTTAGGCGAAATTTAAATACAACTTTCAACAACGGATC

TCTTGGCTCTCGCATCGATGAAGAACGCAGCGAAATGCGATAAGTAATGT

GAATTGCAGAATTCAGTGAATCATCGAATCTTTGAACGCACCTTGCGCTC

CTTGGCTATTCCGAGGAGCATGCCTGTTTGAGTGTCATGTTAATATCAAC

TCTGATGGTTTTTTGTTAATCATTGGATGTTGGACTTGGAGGTTCGTGCT

GGCTGCAAAGTCGGCTCCTCTTGNATGCATTAGCTTGGACCTGTGCGCGT

TTGCTAGCGGTGTAATACATTTAATTCACCACGGGCCGTGTCACTATTAG

GGTCTGCTTCTATTCGTCCTACCGGACAATAATAACTTATGACCTGACTC

AATAGGTAGACACCCCGACTAACTTAATACCGAGAATCANTATCCGCCCG

CGTACATGAAA

Sample B-3 Reverse
                                        (SEQ ID NO: 16)
CCAGAAGGATTTNATGAAACAAGATAAGCAGAGGTCCCTCATCTTN

GGACTCCGACGGCGNCGCCATATAACTCATGATTTCCCGCTCTATTGATA

TGCTAAGTTTTTAGCGGGTAGTCCACCGATTTGAGGTCAGAGTCATAAAG

TTTATTATTGTCCGGTAAGGACGATTAGAAGCAGACCCTAATAGTGACAC

GGCCCGTGGTGAATAAAATGTATTACACCGCTAGCAAACGCGCACAGGTC

CAAGCTAATGCATTCAAGAGGAGCCGACTTTGCAGCCAGCACGAACCTCC

AAGTCCAACATCCAATGATTAACAAAAACCATCAGAGTTGATATTAACAT

GACACTCAAACAGGCATGCTCCTCGGAATAGCCAAGGAGCGCAAGGTGCG

TTCAAAGATTCGATGATTCACTGAATTCTGCAATTCACATTACTTATCGC

ATTTCGCTGCGTTCTTCATCGATGCGAGAGCCAAGAGATCCGTTGTTGAA

AGTTGTATTTAAATTTCGCCTAACGAGAGGCTAATACATTCGACAAGACA

ATAAAAGTGTTTGTATATAAACCGGAGGACAAGCCTTGACCGTTTGAAAG

TAAGCCCAAGTCGCATTAAAAATACAACCGGGACCACTCCCCACATTGTC

TTAGCTTGCAACACTCCGAATAGTGCACAGGGGTTGAATGATGGAACGGA

CTGACACAGTGCTCTGTACAGCCACATAAGCCACTCAACTCGTATGATCT

TCCGCAGTACTACGAACTGTACATTTATTCCCTATACA
```

The Sample B fungus used in this study was taken from a rotted-elm tree in Binghamton University Garden, Binghamton-New York. Sample A fungus was isolated semi-selectively from sample B which was grown on Nutrient Broth Medium, Trametes defined medium, and *Candida albicans* selective medium. The candidate fungi A and B were submitted for molecular characterization to the Molecular Biology lab in the Department of Sustainable Bioproducts at Mississippi State University.

TABLE P

Comparison of GenBank top hits for the ITS region

| Isolate | Organism ITS identified | % ITS identity | No. of ITS matches/ no. identified in Gen Bank |
|---|---|---|---|
| Sample A | *Fusarium oxysporum* | 100% | 328/328 |
| Sample B | *Trichaptum biforme* | 99% | 551/558 |

The characterization results showed that the fungi selection in the previous study lead selection of *Fusarium oxysporum* over *Trichaptum biforme*; it should be noted the fungi chunk can have some impurities.

Polycyclic organics can be degraded by *Fusarium oxysporum* and *Trichaptum biforme*, as well as, *Penicillium italicum* (*P.italicum*), *Glomerella cingulata* (*G.cingulata*),

*Aspergillus flavus, Colletotrichum alatae, Fusarium solani, Ceriporiopsis carnegieae*, and *Xenoacremonium falcatus*. The type of extracellular enzymes released to the medium by these fungi, and their growth pattern and performance have an impact on their PAA degradation, which might be the reason for the time required to achieve full degradation of the membranes.

Full degradation refers to when the fungi have completely consumed the PAA membrane. As seen from the Table N above, 1H NMR did not show any peak related to PAA polymers and the polymer has been totally, or nearly totally, degraded.

Cytotoxicity Characterization of Ternary PAA Membranes

PAA membranes did not show any cytotoxic effects on non-cancerous and cancerous cell lines. Since the membranes synthesized here are different, their cytotoxicity on non-cancerous IEC6 and cancerous A549 cell lines were tested as well. Two different membranes from FIG. 1a and 4 membranes from FIG. 1b were used.

Figure 44A:
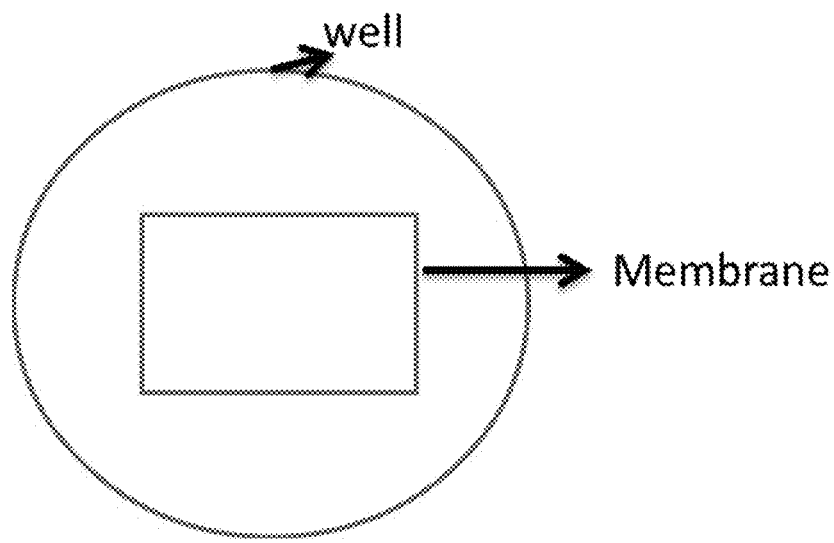
FIGS. 44a-44b are graphical illustrations of membrane loading in a well and cytotoxicity.
Figure 44B:
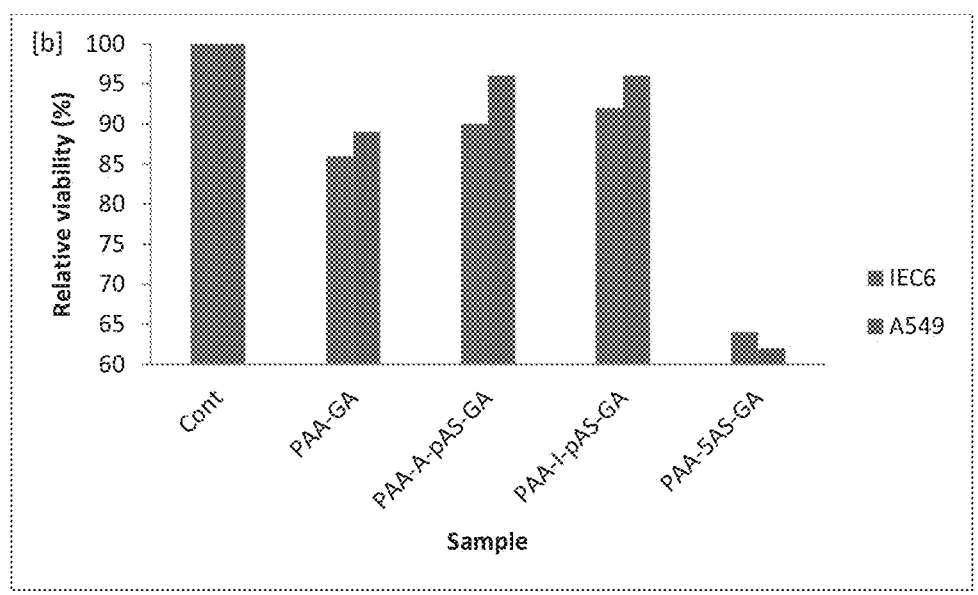

FIG. 44a is an illustration of membrane loading in a well. As seen from the graphics in FIG. 44b, PAA-GA of FIG. 1a, and PAA-A-pAS-GA, PAA-I-pAS of FIG. 1b did not show any significant cytotoxicity, while PAA-5AS-GA of FIG. 1b showed significant cytotoxicity, for which viability decreased at nearly 40%. However, it should be mentioned that low concentration of 5AS (below 0.3 mg/mL) was not toxic to the cells.

PAA-A-GA of FIG. 1a and PAA-W-GA of FIG. 1b membranes showed unexpected results; cells did not only grow in the wells, but also they grew on the membranes. SEM images of the membranes are seen below. The surfaces were either woven-like or micro-porous, which can allow cells to grow on them. 3D cell culture provides unique environment for seeded cells to recapitulate in vivo conditions. Biocompatibility, porosity and hydrophilicity are important for 3D cell culture materials. High-mass transport, ease of process, flexibility and good-mechanical strength is the desired properties of 3D cell culture material, which limit choice of 3D cell culturing materials.

Good 3D cell culturing supports possess high transparency and low-background fluorescence ability for high quality light microscopy and fluorescence imaging. Stiffness of the support material is a factor for proper cell migration because cells must apply cytoskelatal forces for movement instead of passive-movement driven by fluidity of the support material or the system. This is possible by providing solid stiff support materials.

Antimicrobial Activity of the Films

The featureless membranes synthesized according to FIG. 1b were utilized characterized for antimicrobial studies. *Staphylococcus epidermidis* ATCC® 12228™, *Escherichia coli* ATCC® 25922™ and *Citrobacter frenduii* ATCC® 8090 were cultured in Mueller-Hinton broth at room temperature for 24 hrs. The viable cell number was determined by conventional agar plate. The resulting figures were Detailed explanations were given under related figures.

Figures 45A, 45B, 45C, 45D:
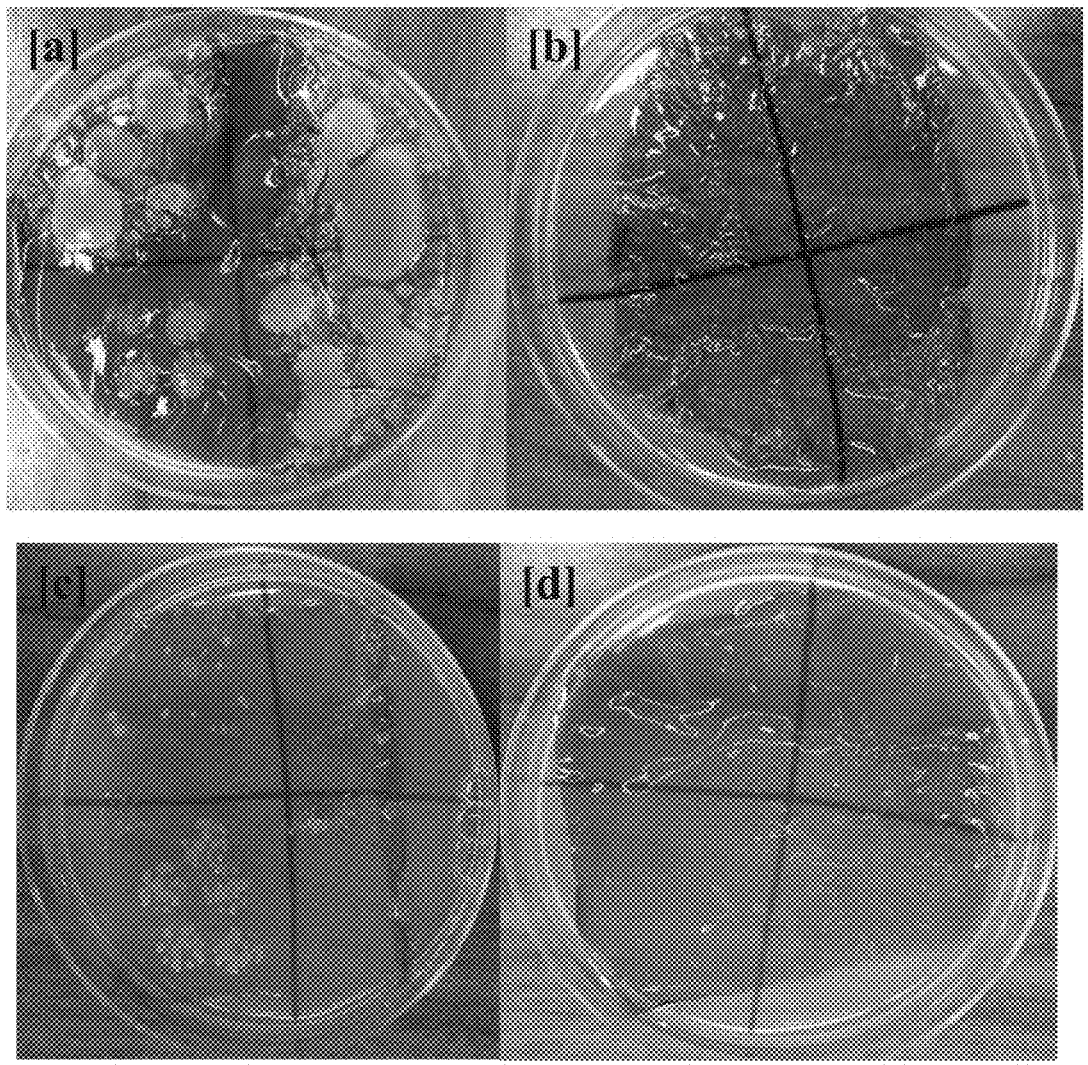
FIGS. 45a-45av are photographs of various PAA films.

Antibacterial activity of ternary PAA membranes. FIG. 45a 0.2 mg/mL Ile was dissolved in GA and then added to 0.16 M PAA. Overall GA concentration was %0.1. FIG. 45b 3 mg/mL 5AS was dissolved in 0.16 M GA, and then %0.2 GA was added to the system. Both membranes were incubated at RT for 12, and then membranes were peeled off. $10^4$ cfu/mL for one area and $10^6$ cfu/mL for the three sections were inoculated for both membranes. While Ile did not show any antibacterial activity, 5AS did not allow bacterial development. Incubation was 72 h. FIG. 45c 0.2 mg/mL PCAM sugar was dissolved in 0.16 M PAA, followed by 0.2 mg/mL Ile was dissolved in GA and then added to 0.16 M PAA-PCAM. Overall GA concentration was %0.2. FIG. 45d 3 mg/mL PAS was dissolved in 0.16 M GA, and followed by W addition [1 mg/mL W dissolved GA was added to the system]. Overall GA concentration was %0.2. Both membranes were incubated at RT for 12, and then membranes were peeled off. 1500, 150, 15 and 1.2 cfu/mL added to the different area. While Ile-PCAM did not show high antibacterial activity [600 colonies formed out of 1500 cfu, and 26 cfu out of 150 cfu], PAA-W/GA-PAS did not allow bacterial development. Incubation was 24 h for FIGS. 45c and 72h for FIG. 45d.

The introduction of pAS or 5AS was found to advance the antibacterial activity of the disclosed films. Antibacterial activity refers to the fact that the disclosed film will not cause the growth of bacterial and hence will preserve contained food.

To visualize bacterial development, plate counting method was utilized. Incubations were made up to three days, and no bacterial colonies were observed. The disclosed films provide about a 99.999% reduction of bacterial growth.

Similarly, 5AS, pAS and pAB enhanced PAA membranes showed good antibacterial activity against *Aeromonas hydrophila, Pseudomonas aeruginosa, Escherichia coli* DH5alfa, *Listeria monocytogenes* strains F2365 and HCC7. Good antibacterial activity of the PAA membranes can also be displayed against other gram-positive and/or gram-negative bacterial species. Gram-positive species other than *Listeria monocytogenes*, can include *Staphylococcus epidermidis*. Gram-negative species other than *Escherichia coli, Aeromonas hydrophila*, can include *Enterobacter aerogenes* and *Citrobacter freundii*.

Virulent type strain *L. monocytogenes* were grown in a rich medium such as brain heart infusion (BHI). Lysogeny broth (LB), a nutritionally rich medium agar also used for the maintenance of the tested *E. coli*. The bacteria were taken from the culture collection unit −80° C. freezer in department of Basic Science, College of Veterinary Medicine, Mississippi State University Mississippi-USA.

Even though 5AS enhanced-PAA membranes showed that good antimicrobial activity includes showing antifungal activity, it disrupted membrane mechanical properties with over 0.5 mg/mL usage while pAS can be used up to 2 mg/mL for PAA membrane preparation. So, the packaging membrane can contain 0.5 mg/mL pAS and 0.1 mg/mL 5AS, which provides good physical and antimicrobial properties. However, it should be mentioned that selection of antibacterial molecule is also affecting the color, so instead of pAS/5AS, pAS and 5AS can be used independently at different concentrations.

As seen from FIGS. 45a-45k, pAB can be used instead of pAS since it showed similar antibacterial activity. $2\times10^7$ cfu of *E. coli* and *S.epidermidis* in 20 µL were dropped on the agars shown in FIGS. 45e-45h and FIGS. 45j-45k. 0.2 mg/mL Ampicillin were dissolved in agar placed in well FIG. 45e while same amount of ampicillin was put on left side of well FIG. 45h; combination of 0.1 mg/mL 5AS and 0.2 mg/mL pAS were dissolved in agar placed in well FIG. 45f while same composition was put on left side of well FIG. 45j; combination of 0.1 mg/mL 5AS and 0.2 mg/mL pAB were dissolved in agar placed in well FIG. 45g while same the composition was put on left side of well FIG. 45k.

Figures 45E, 45F, 45G, 45H, 45I, 45J, 45K:
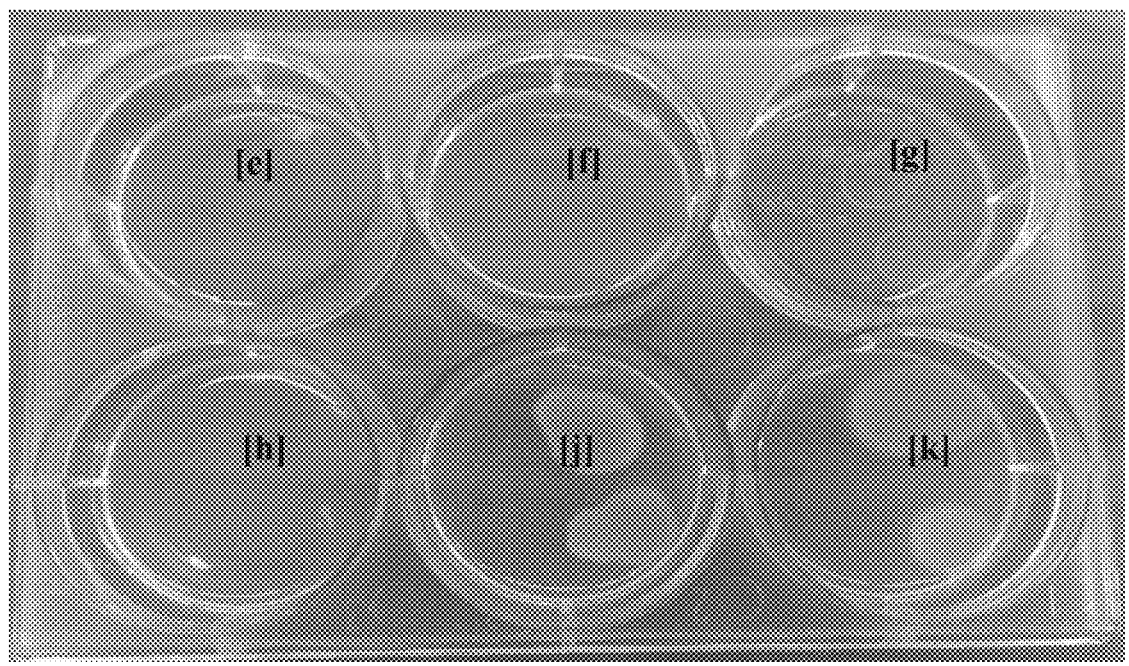

For well FIG. 45h, slight bacterial growth was observed in comparison to well FIG. 45j and FIG. 45k; this could be related to that ampicillin dissolved in agar while combination of 5AS and pAS or 5AS and pAB did not dissolve.

When ampicillin was dissolved in agar, no bacterial formation was observed. Similarly, combination of 5AS and pAS eliminated all the bacteria while combination of 5AS and pAB did only wipe out 99.99%. Therefore, the good antibacterial activity of 5AS/pAS and 5AS/pAB modified membranes was obtained in comparison to non-antibiotic containing PAA membranes. However, in the case of sulfanilamide based membranes, utilization of pAS, 5AS or pAB are not required at higher levels since sulfanilamide membranes showed antibacterial activities.

Figures 45L, 45M, 45N, 45O, 45P, 45Q, 45R:
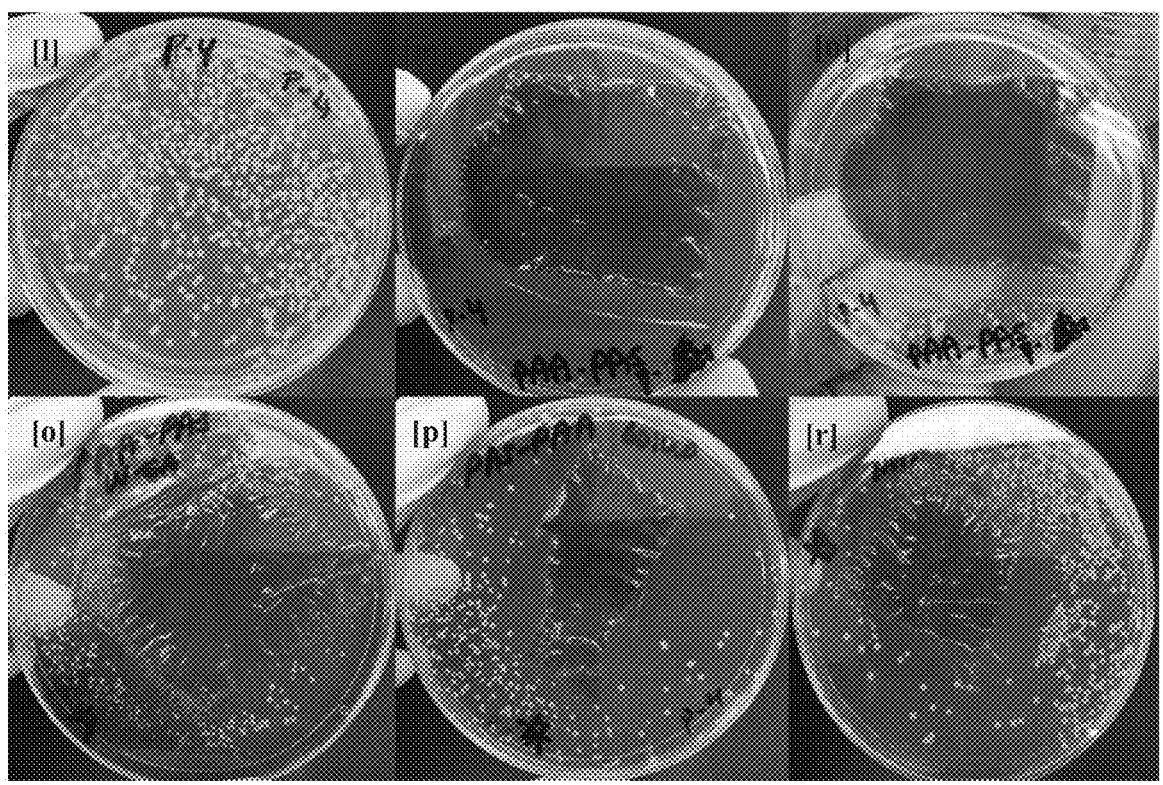

For the well in FIG. 45l, a control of *Pseudomonas aeruginosa* in agar is shown, while FIG. 45m contains PAA-SA-pAS-5AS-GA and FIG. 45n PAA-SA-pAS-GA and FIG. 45o PAA-SA-pAS-W-GA for the membranes prepared according in DMAC. FIG. 45p PAA-pAS-5AS-GA and FIG. 45r PAA-SA-pAS-GA membranes prepared in 60:40, Ethanol/DMAC, solvent. All of the membranes showed strong suppressing effect (cidal effect was well) on *Pseudomonas aeruginosa*; synthesizing the membranes in ethanol:DMAC mixture did not show any negative effect on membrane's duty. Here, another important results were observed that introduction of 5AS to the membrane enhanced its antibacterial activity which was observed as smaller colony formation in contrast to only pAS containing membranes.

Figures 45A, 45S:
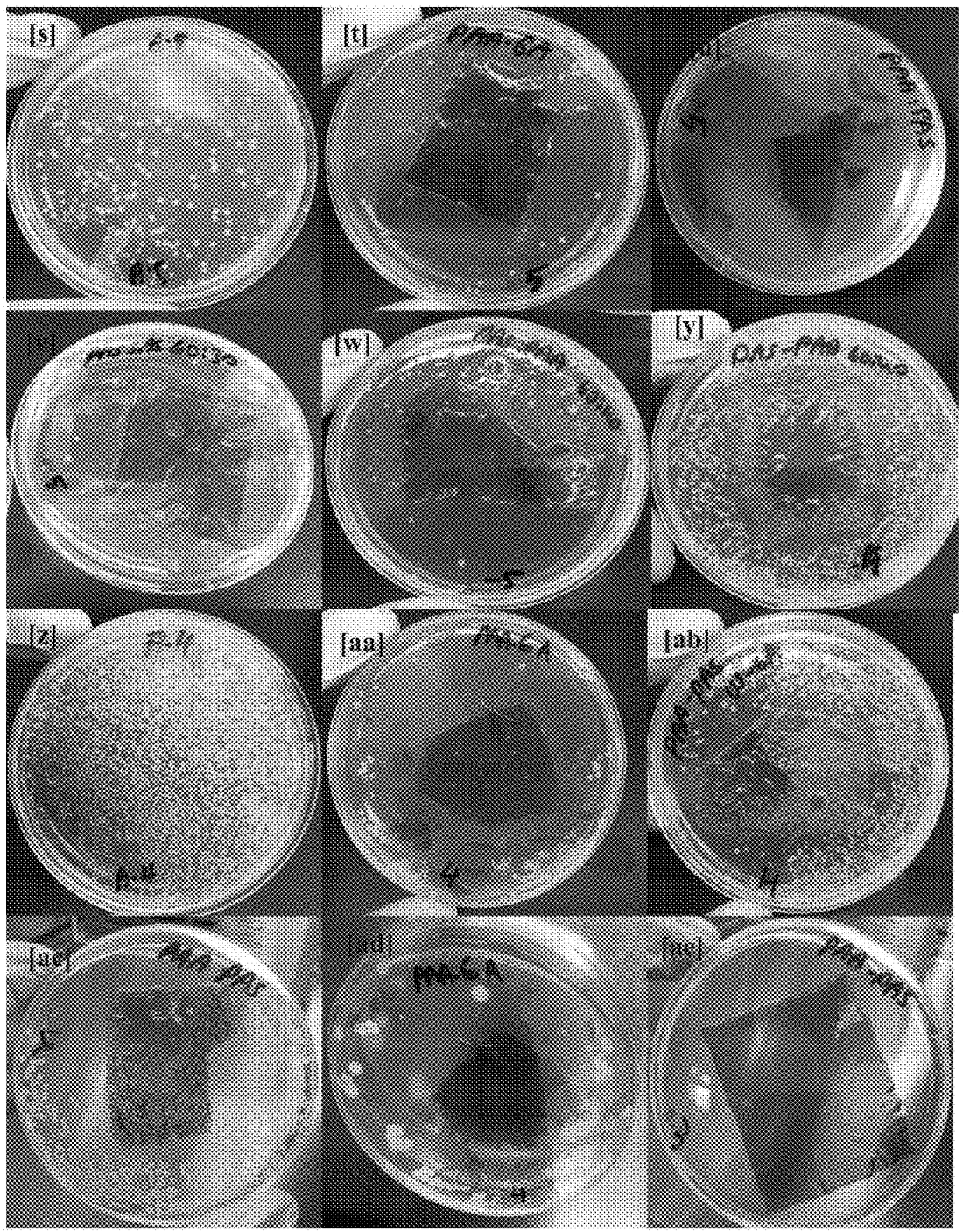
Figure 45A:
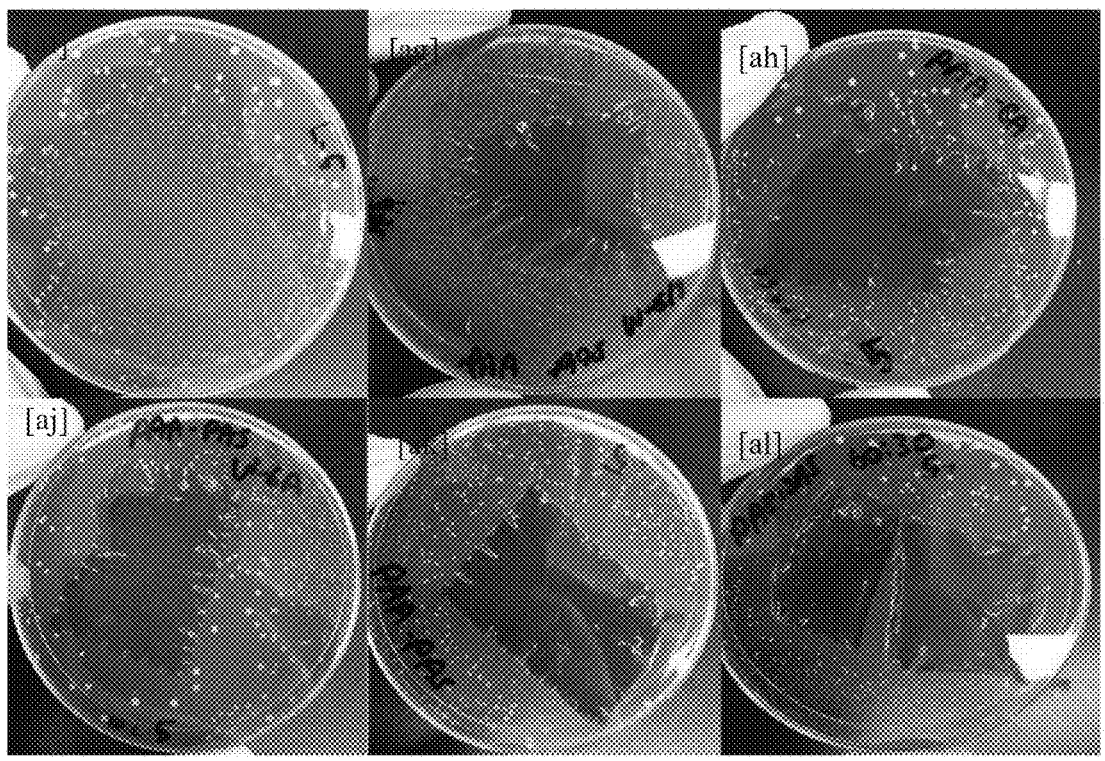
Figure 45A:
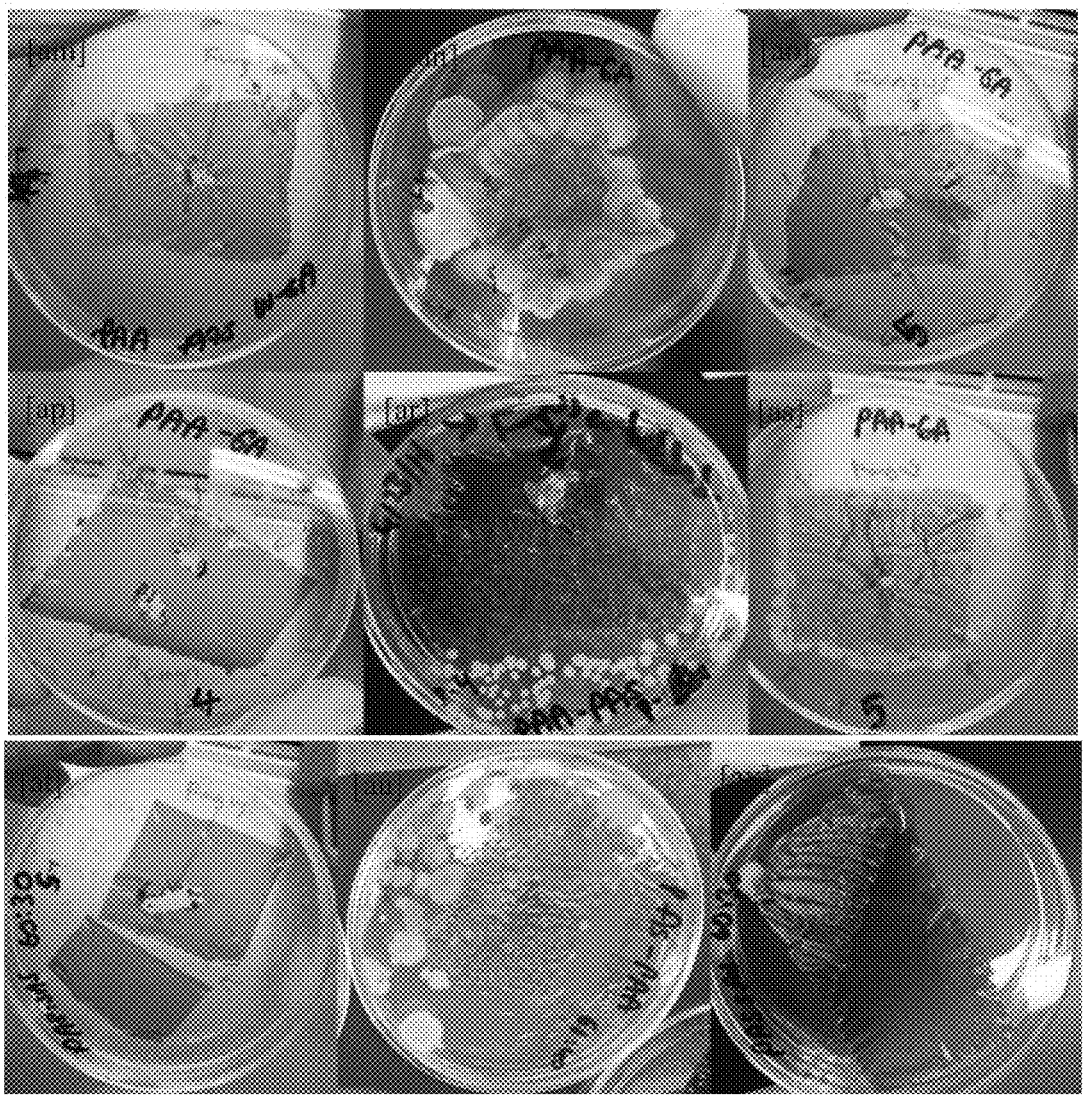

*Aeromonas hydrophila* was tested on membranes for 24 h and 48 h incubation. For FIGS. 45s-y, incubation period was 24 h. FIG. 45s is control for 24 incubation period; FIG. 45t PAA-SA-pAS-5AS-GA; FIG. 45u PAA-pAS-5AS-GA; FIG. 45v PAA-SA-pAS-GA (solvent 65:35, Ethanol:DMAC); FIG. 45w PAA-SA-pAS-5AS-GA (solvent 60:40, Ethanol:DMAC); FIG. 45y PAA-SA-pAS-GA (solvent 60:40, Ethanol:DMAC). For the membrane FIG. 45y, the bacteria did not grow on membrane, but around the membrane microbial colonies were observed. For FIG. 45z-ae, incubation period was 48 h. FIG. 45z is control for 48 h incubation; FIG. 45aa PAA-SA-pAS-5AS-GA membrane; FIG. 45ab PAA-SA-pAS-W-GA membrane: in the cases of losing membranes integrity causing *A.hydrophila* grow on membrane while the protected area of the membrane did not allow bacterial growth. Thus, it appears that the antibacterial activities of the membranes were not coming from releases of pAS or 5AS into the media.

As a note, as seen from FIGS. 45f and g, free pAS and 5AS were wiped out both gram (+) and gram (−) bacteria. So, it can be said that GA might cross-link pAS and 5AS, and when they were released into the media, they do not show strong antibacterial activity while when they were bonded to the PAA, they were more active. FIG. 45ac PAA-SA-pAS-5AS-GA membrane; likewise, FIG. 45ab, when the membrane lost its integrity, the membrane allowed bacterial growth. FIG. 45ad PAA-SA-pAS-5AS-GA membrane while FIG. 45ae PAA-SA-pAS-GA membrane. Membranes eliminated *A.hydrphila* development strongly as long as the membrane protected its structure.

FIG. 45af is a control of *Listeria monocytogenes* for 24 h incubation; FIG. 45ag PAA-SA-pAS-W-GA: *L.monocytogenes* showed growth on some sections of the membrane where the membrane integrity got lost; FIG. 45ah PAA-SA-pAS-5AS-GA;

FIG. 45af PAA-pAS-SA-GA; FIG. 45ak PAA-pAS-5AS-GA; FIG. 45al PAA-SA-pAS-GA (solvent 65:35, Ethanol:DMAC).

Antifungal activity of some ternary PAA membranes is shown in FIGS. 45am-45ay. The fungi used here was *Aspergillus nidulans*. Incubation period was 6 days for all these membranes. FIG. 45am PAA-SA-pAS-W-GA; FIG. 45an PAA-SA-pAS-GA; FIG. 45ap PAA-SA-pAS-5AS-GA; FIG. 45ar PAA-pAS-5AS-GA; FIG. 45as PAA-SA-pAS-GA; FIG. 45at PAA-SA-pAS-5AS-GA (65:35, Ethanol:DMAC solvent); FIG. 45au PAA-SA-pAS (60:40, Ethanol:DMAC solvent); FIG. 45av PAA-SA-pAS-5AS-GA. For all the membranes, where there was disintegration, the fungi showed growth pattern. However, the growth was not all over the membrane. For FIG. 45ar, *S.aerugenosa* and *A.nidulans* were inoculated together; while the fungus showed growth at the edge of the membrane, the bacteria did not show any growth. For FIG. 45av, when there is distortion on the membrane, development of fungus was observed while the protected side of the membrane did not allow fungus development.

Poly(amic)acid polymer has been synthesized from 4,4-oxydianiline (ODA) and pyromellitic dianhydride (PMDA) in anhydrous N,N-dimethylacetamide. Three procedures have been applied to develop antibacterial and antifungal PAA membranes and thin films. (i) entrapping p-aminosalyclic acid (1 mg/mL) into PAA thin film, (ii) polymerizing p-aminosalyclic acid (1 mg/mL) via glutaraldehyde, followed by introduced to the PAA thin-film, and (iii) entrapping p-aminosalyclic acid (1 mg/mL) in PAA membrane. Thin films were prepared via controlled solvent evaporation method while membrane was prepared via coagulation-based phase inversion where 2 h controlled evaporation under hood was applied to increase pore-size. 1 mg/mL p-aminosalicyclic acid was shown to eliminate both *E. coli* and *S.epidermidis* under the testing conditions.

Figures 46A, 46B:
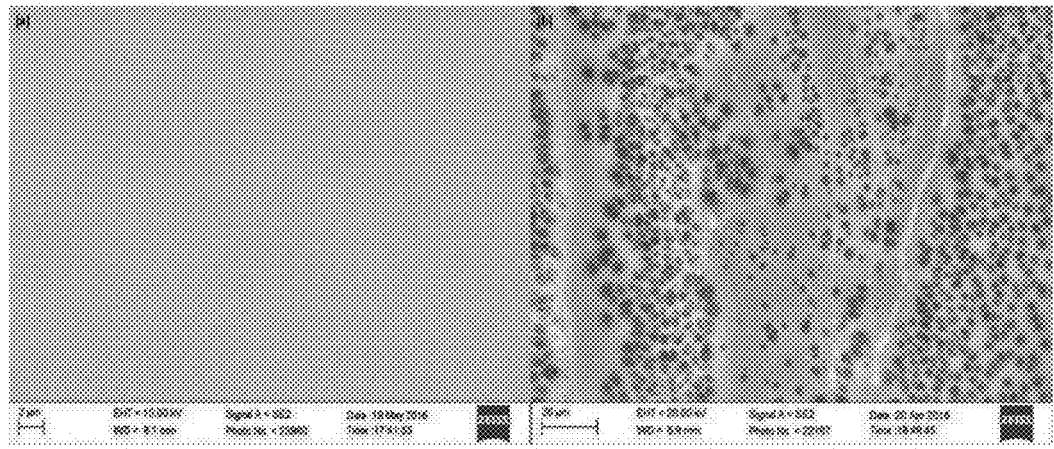
FIGS. 46a-46b are SEM images of various PAA films.

Scanning Electron Microscope (SEM) images of FIG. 46a PAA thin film and FIG. 46b PAA membrane which contains p-aminosalyclic acid cross-linked with GA and p-aminosalyclic acid molecules, are shown respectively.

Figures 47A, 47B, 47C, 47D, 47E, 47F, 47G, 47H:
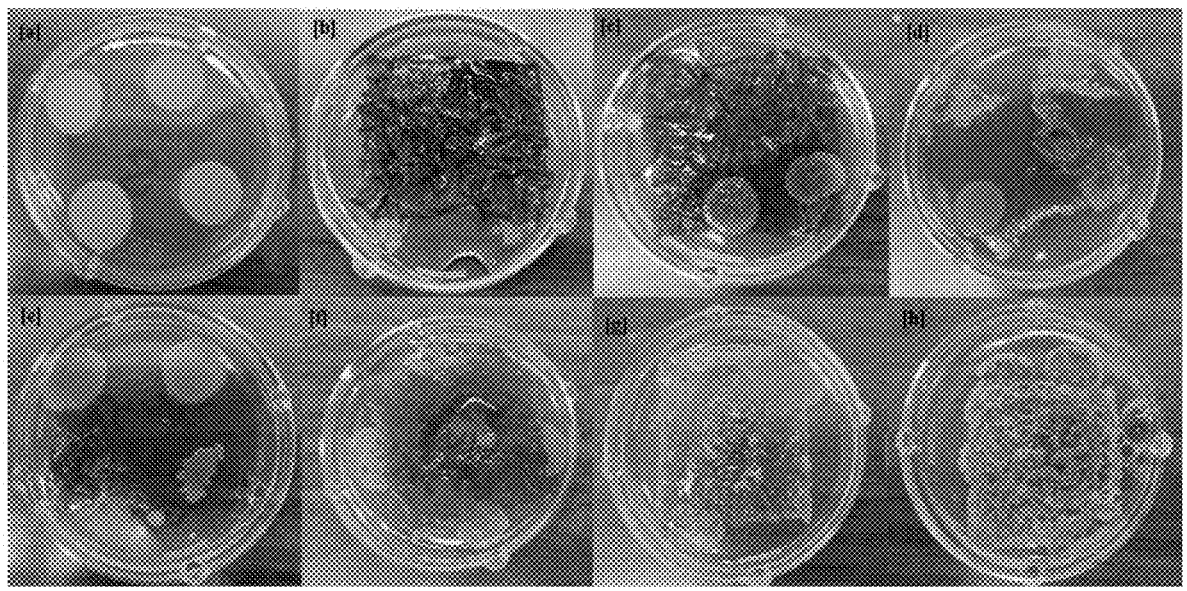
FIGS. 47a-47h are photographs of various PAA films.

Antibacterial activity of p-aminosalyclic acid supported PAA thin films and membranes on *Escherichia coli* ATCC 25922 (*E. coli*, gram −) and *Staphylococcus epidermidis* ATCC 12228 (*S.epidermidis*, gram +) are shown in FIGS. 47a-47h. FIG. 47a is a control of *E. coli* and *S.epidermidis*; FIG. 47b *E. coli* and FIG. 47c *S.epidermidis* inoculated onto the PAA film which contains p-aminosalyclic acid was cross-linked with glutaraldehyde, followed by rinsed and dried in anhydrous methanol to quench further cross-linking; FIG. 47d *E. coli* and FIG. 47e and FIG. 47f *S.epidermidis* inoculated onto the PAA film which entraps p-aminosalyclic acid; FIG. 47g *E. coli* and FIG. 47h *S.epidermidis* inoculated onto the PAA porous membrane which entraps p-aminosalyclic acid.

The results indicate that capturing p-aminosalicyclic acid in PAA membranes did not show a descent antibacterial activity towards both *E. coli* and *S.epidermidis*. However, as seen from FIG. 47f, suppression of bacterial development is shown; the film was thinner in comparison to the film of FIG. 47e, which depicts that thinner film was more prone to release its containment to show its antibacterial activity. As seen from FIG. 47b and FIG. 47c, bacterial growth for *E. coli* and *S.epidermidis* were suppressed, particularly the thin film didn't allow much bacteria to grow on the thin film, but still *S.epidermidis* grew on the membrane. In contrast to the thin films, nanostructured PAA membrane showed high antibacterial activity (i.e. up to about 90%) towards both *E. coli* and *S.epidermidis*.

The results indicate that thickness of PAA thin film and eligibility of the molecule to transfer from inside of the membrane to the media (PAA membrane), and possible non-covalent modifications done on thin film enhances their antibacterial capability.

1.10 Surface Characterization

Surface characterization of the membranes synthesized according to FIGS. 1a and 1b are provided together. Description of the membranes and procedures are given under the related figures.

Figures 48A, 48B:
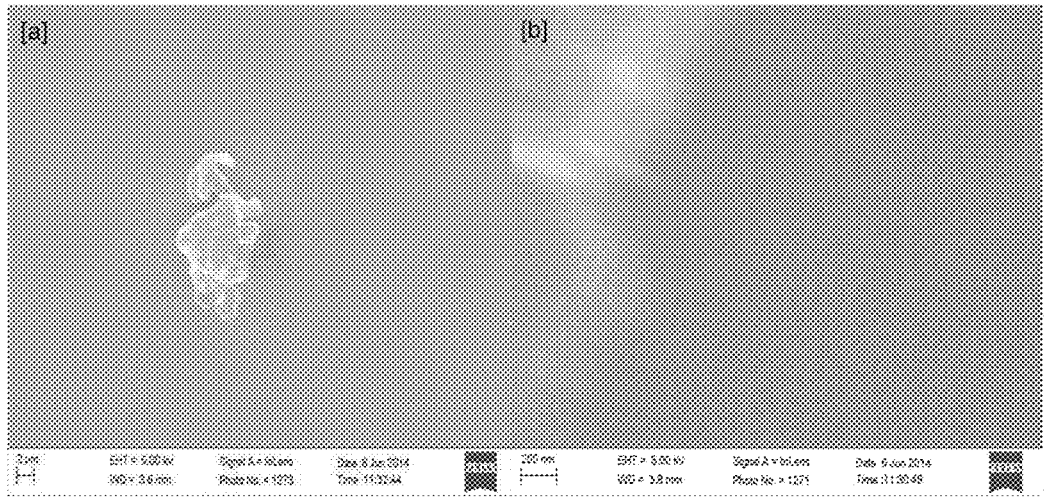
FIGS. 48a-48b are SEM images of various PAA films.

SEM image of PAA membrane of FIG. 1a are shown in FIGS. 48a and 48b. FIG. 48a top and FIG. 48b bottom phases of PAA. This membrane synthesized as followed; the viscous solution from 0.18 M PAA solution was casted on glass and incubated in air-tight cabinet for 6 h, and then phase-inverted under hood for 12 h (FIG. 1a-ii).

Figures 49A, 49B:
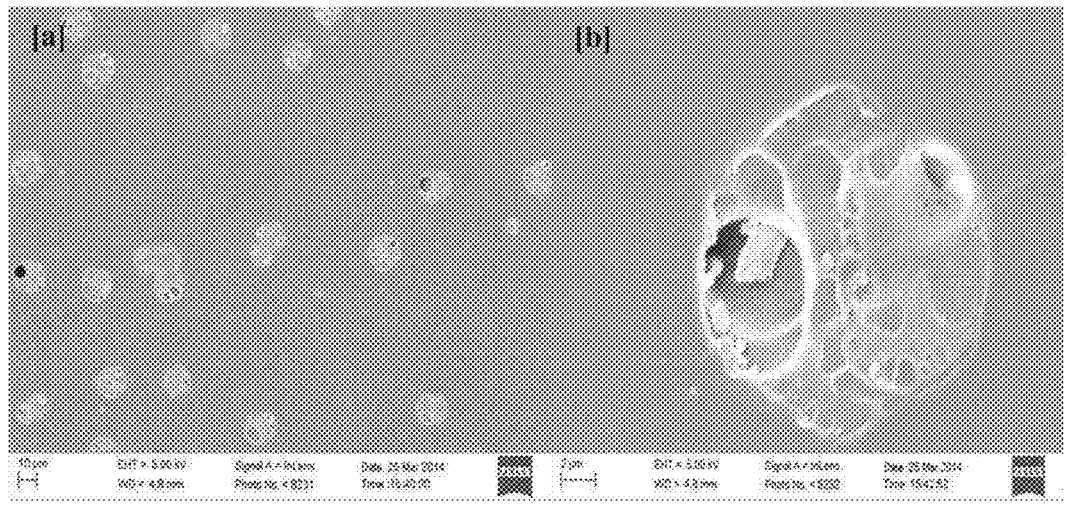
FIGS. 49a-49b are SEM images of various PAA films.

SEM image of PAA-A-GA membrane of FIG. 1a are show in FIGS. 49a and 49b. FIG. 49a top and FIG. 49b bottom phases of the membrane. This membrane synthesized as followed; 0.25 mg/mL GA was added to 0.20 M PAA containing 1 mg/mL A, and stirred for 2 min. Then the viscous solution was casted on glass and incubated in air-tight cabinet for 6 h, followed by 3 h incubation in hood and then phase-inverted in pure water for 3 h. It is clear that the localized pores or deposits possibly from L-alanine couple to PAA via GA; this is characteristics of the membranes prepared according to FIG. 1a. However, when the molecules totally dissolved in PAA viscous solution of FIG. 1a, they provided featureless surface.

Figures 50A, 50B:
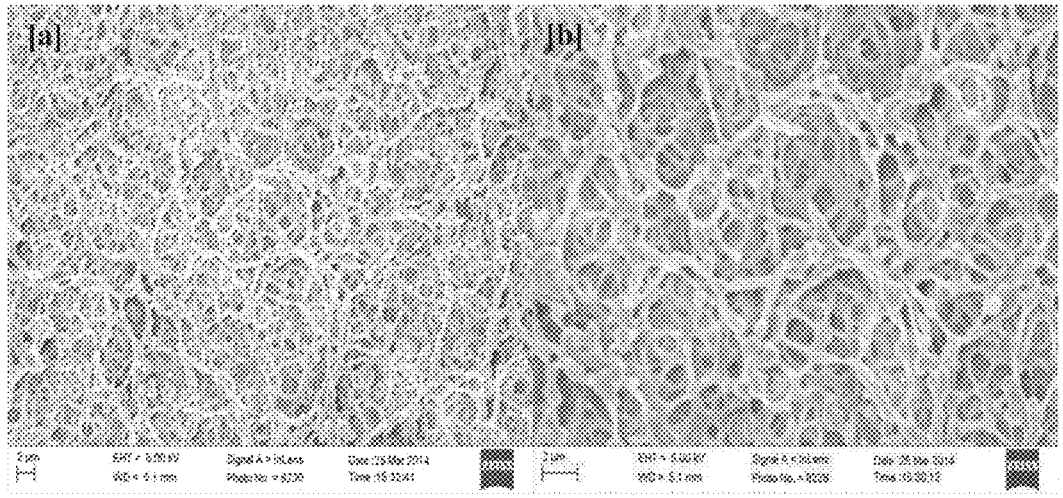
FIGS. 50a-50b are SEM images of various PAA films.

SEM image of PAA-A-GA membrane of FIG. 1a-ii are shown in FIGS. 50a and 50b. FIG. 50a top and FIG. 50b bottom of the membrane. This membrane synthesized as followed; 0.25 mg/mL GA was added to 0.20 M PAA containing 1 mg/mL A, and stirred for 2 min. Then the viscous solution was casted on glass and incubated in air-tight cabinet for 6 h, and then phase-inverted in anhydrous ethanol for 2 h, followed by 3 h phase-inversion in pure water. FIG. 1a-ii, this membrane did not require sonication, however sonication is possible.

Figures 51A, 51B:
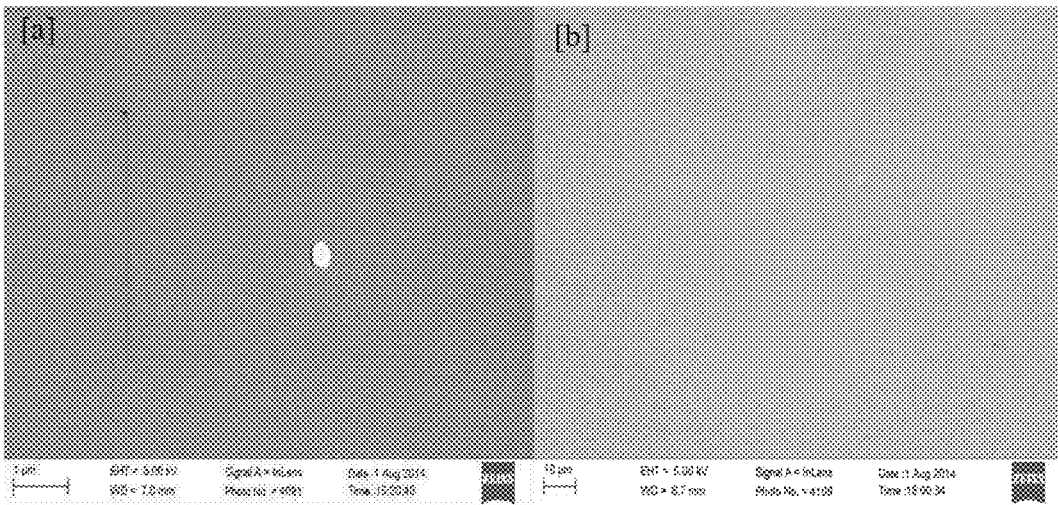
FIGS. 51a-51b are SEM images of various PAA films.

SEM image of PAA-A-GA of FIG. 1b-ii are shown in FIGS. 51a and 51b. FIG. 51a is top face, and FIG. 51b is bottom face of the membrane. 2 mg/mL Alanine was added to the PAA solution. 100 μL/mL GA from 25% GA was introduced to 5 mL PAA solution. 20 μL/mL methanol was introduced to the 0.18 M PAA solution The glass surface was then wetted with dry methanol, and then the solution was casted on the glass on which methanol was then spreaded, then incubated at room temperature for 6 h. Finally, the membrane was dried under hood for 12 h. Both faces have no pores. FIG. 1b-ii, the major difference of this PAA-A-GA membrane from other PAA-A-GA membranes was that A was pre-dissolved and treated in GA-water, which resulted in elimination of localized porous-area formations.

Figures 52A, 52B:
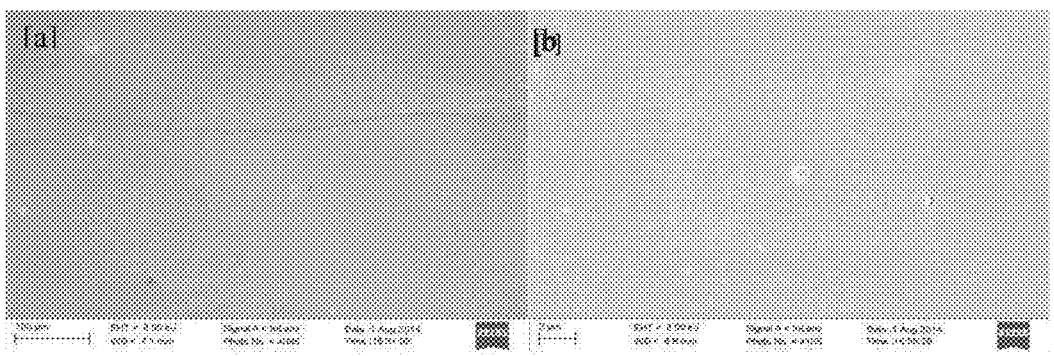
FIGS. 52a-52b are SEM images of various PAA films.

SEM image of PAA-CA-GA of FIG. 1b are shown in FIGS. 52a and 52b. FIG. 52a is the top face and FIG. 52b is the bottom face of the membrane. 2 mg/mL cellulose acetate was added to the 0.18M PAA solution. 100 μL/mL GA from 25% GA was introduced to 5 mL PAA solution. 40 μL/mL ethanol was introduced to the PAA solution The glass surface was then wetted with dry ethanol, and then the solution was casted on the glass on which ethanol was then spreaded, then incubated at room temperature for 6 h. Finally, the membrane was dried under hood for 12 h. Both faces have no pores. FIG. 1b-ii.

Figures 53A, 53B:
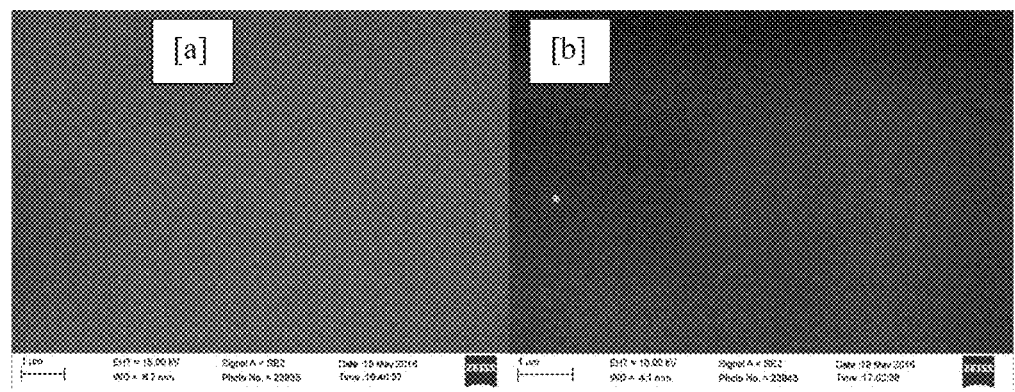
FIGS. 53a-53b are SEM images of various PAA films.

SEM image of PAA-SA-pAS-GA membrane of FIG. 1b are shown in FIGS. 53a and 53b. FIG. 53a top and FIG. 53b bottom phases of the membrane. Both of the surfaces are featureless.

Figures 54A, 54B, 54C, 54D:
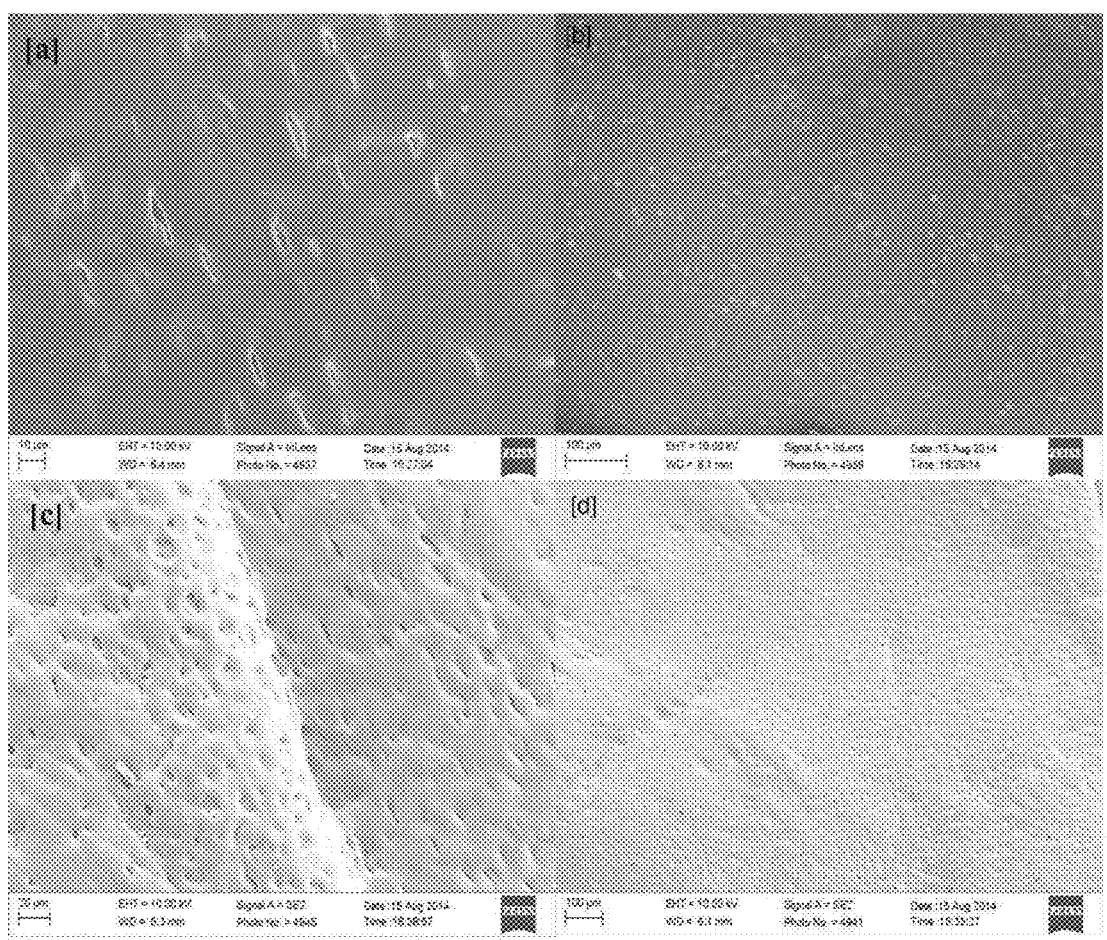
FIGS. 54a-54d are SEM images of various PAA films.

SEM images of PAA-W-GA membrane are shown in FIGS. 54a-54d. 10 mg Trp (W) is dissolved in 100 μL GA from 25% GA stock. The Tip was incubated for 20 sec for polymerization with the help of GA. Then, the Trp-GA solution was introduced to 0.16 M PAA (or 0.12 M) solution at 5 drops, and 5 second interval was followed each consecutive drops. 3 min stirring after last drop of Trp-GA, the PAA solution was casted on glass. 4 h incubation at room temperature, followed by 12 h incubation under-hood. Finally, the membrane was sonicated in anhydrous methanol for 20 min, which was then dried under hood. FIGS. 54a and 54b are images were taken with inlens detector, while FIG. 54c and FIG. 54d images were taken with SE2 detector. Sonication of the same membrane in pure water, 20% MeOH and 50% MeOH did not provide any pore-formation. However, 80% EtOH allows pore-formation.

Figures 55A, 55B, 55C, 55D, 55E, 55F:
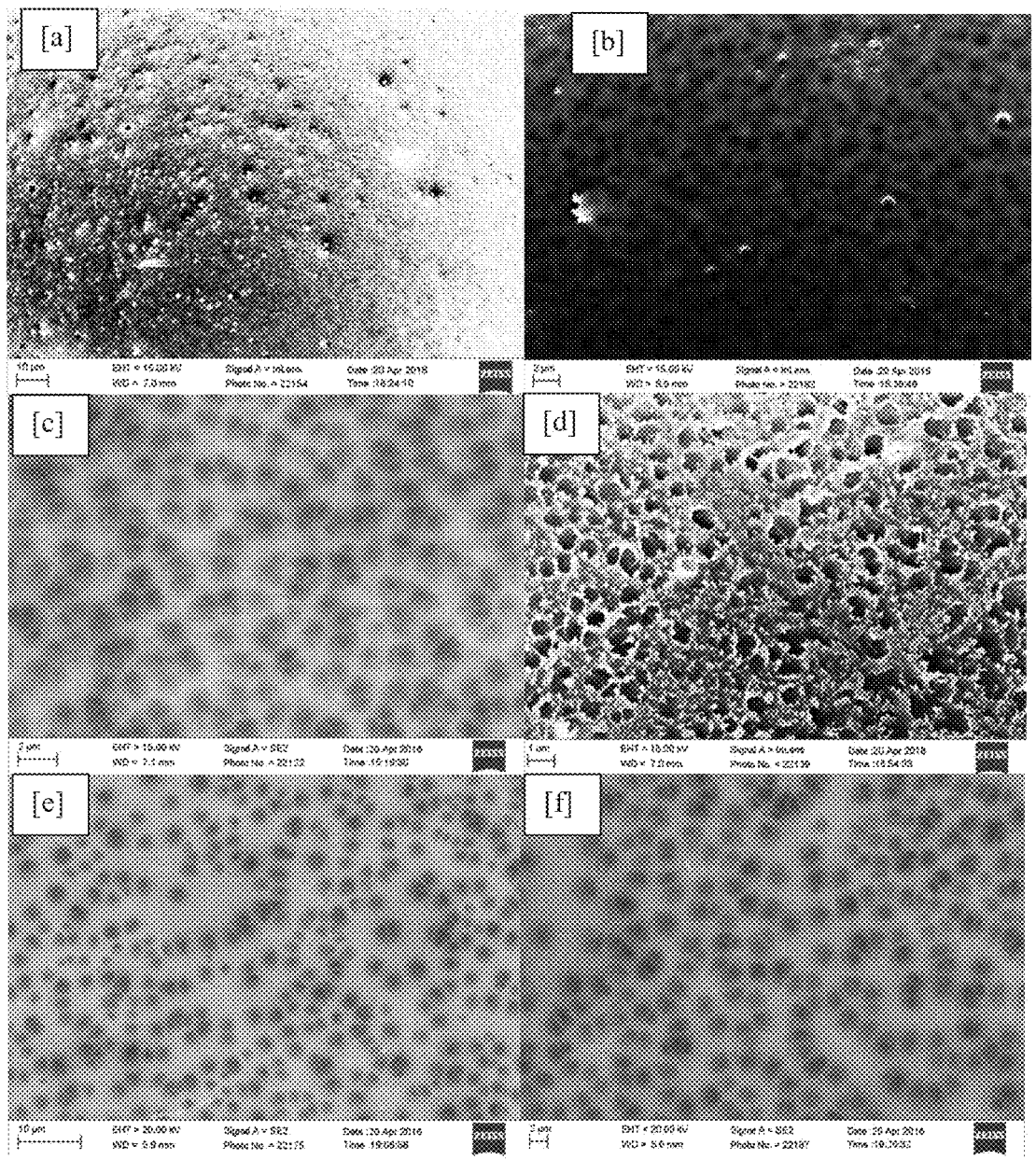
FIGS. 55a-55f are SEM images of various PAA films.

SEM images of PAA-W-GA and PAA-SA-GA membranes are shown in FIGS. 55a-55f. FIG. 55a top and FIG. 55b bottom of the PAA-SA was incubated at room temperature for 4 h, followed by incubated in 70% Ethanol in water for 2 h. FIG. 55c top and FIG. 55d bottom of the PAA-W was incubated at room temperature for 4 h, followed by 2 h incubation in 70% Methanol. FIG. 55e top and FIG. 55f bottom of the PAA-SA was incubated at room temperature for 4 h, followed by 2 h incubation in 70% Methanol. PAA-SA gets solidified faster than PAA-W; so it is normal to see less porous surface for PAA-SA. As seen from all of the FIGS. 54a-54d and FIGS. 55a-55f, the surfaces of the membrane are porous enough for cell adhesion; since both sides showed pores, transfer of wastes resulted from cellular metabolism is possible.

Surface characteristics of all synthesized PAA membranes did not show any difference in response to alteration in PAA concentration (from 0.08 M to 0.20 M range), GA concentration and small molecule and its concentration. However, at macro-scale all parameters affected the eye-visible membrane surface. Addition of organic solvents include methanol, ethanol and tetrahydrofuran did not make any difference on surface characteristics. Here, the most dramatic change in surface characteristics were seen in parallel to changes in procedure. Here, three major surface types were obtained; featureless, macro-porous and woven-like surfaces. Nearly all the procedures provided featureless membrane surface; pore-free surfaces can be a good barrier against penetration of oil, water-vapor and gas transfers.

Figures 56A, 56B:
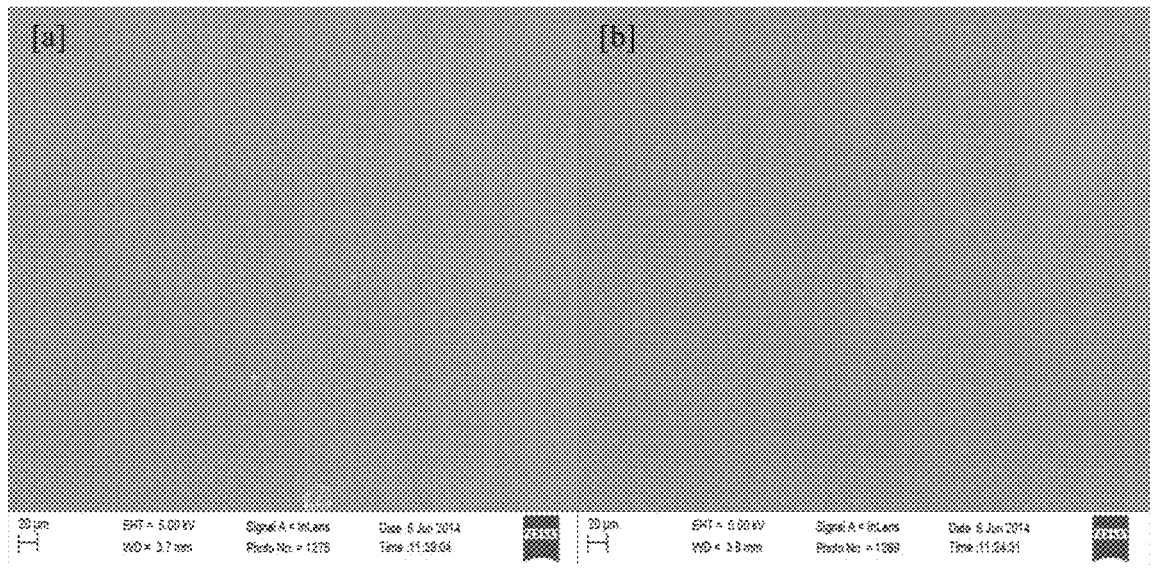
FIGS. 56a-56b are SEM images of various PAA films.

SEM image of PAA-GA are shown in FIGS. 56a and 56b; FIG. 56a top and FIG. 56b bottom phases of PAA-GA membrane. This membrane synthesized as followed; 0.25 mg/mL GA from stock was added to 0.18M PAA solution and stirred for 3 min, and then the viscous solution was casted on glass and incubated in air-tight cabinet for 12 h, and then further incubated under hood for 6 h. The membranes synthesized according to FIG. 1a-i.

Figures 57A, 57B:
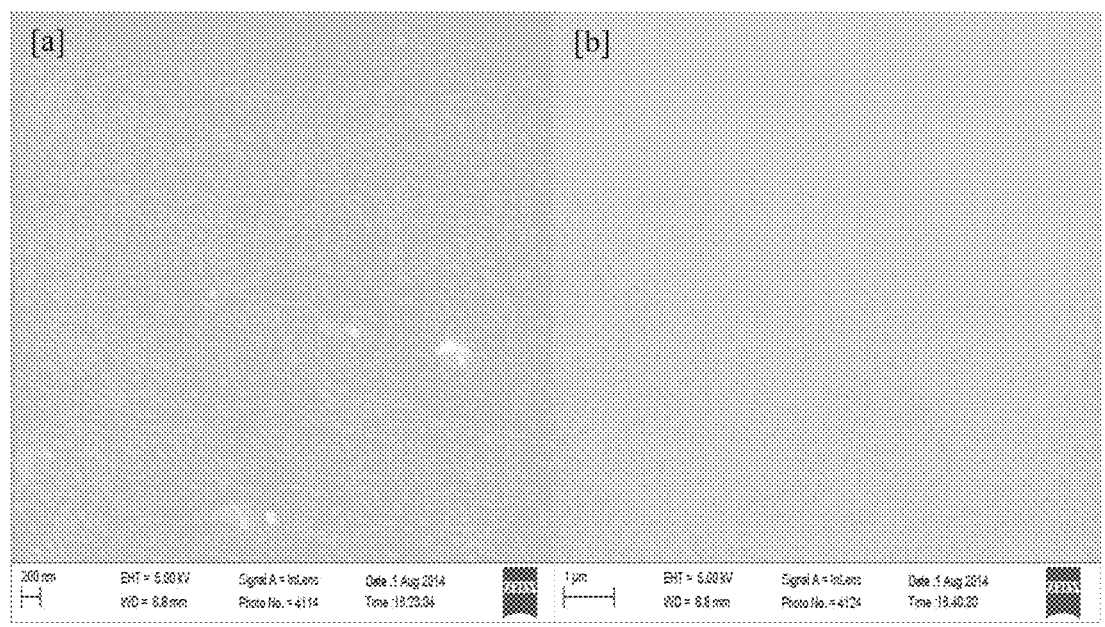
FIGS. 57a-57b are SEM images of various PAA films.

The right figure is top face FIG. 57a, and left one FIG. 57b is bottom face of the membrane. 5 mg Alanine was dissolved in 100 μL of 25% GA solution. The cross-linked L-Alanine was then introduced to 5 mL 0.18 M PAA solution. 40 μL/mL methanol was introduced to the system. The glass surface was then wetted with dry DMAC, the PAA solution was casted on the glass and then incubated at room temperature for 6 h. Finally, the membrane was dried under hood for 12 h. Bottom is nearly featureless while the top has recognizable numbers of defects. FIG. 1b-ii.

As illustrated and discussed above, both FIG. 1a and FIG. 1b can provide featureless surface if the small molecule or cross-linker are dissolved in PAA solution properly.

1.10 PAA Concentrations

PAA concentration was selected as 0.16, 0.18, 0.20 and 0.25 M based on the pore size of pure PAA membrane obtained via phase-inversion. PAA solution's viscosity was not measured with an instrument; if the viscosity is low enough to be stirred with stirring magnet at high speed, the concentration was accepted as good. The following optimizations were obtained from FIG. 1a. 0.18 M was selected as best concentration for FIG. 1a subsequent membrane preparation.

In addition to viscosity, other parameters were considered including the ratio of ODA to PMDA, temperature of the medium and the speed of stirring showed great impact on PAA formation; in optimum conditions, the PAA concentration is 0.08 M in the cases of 1.00:1.03 ODA:PMDA ratio at 40° C. under mild mixing (i.e. between 400-600 rpm). The mixing should be enough to totally dissolve PMDA at less than 120 seconds but no earlier than 30 sec. In the case of 0.12 M, ODA:PMDA a good ratio was found to be between 1.00:1.04 at 40° C. under mild mixing to obtain viscous PAA solution. However, the formed PAA solution was highly viscous.

In the case of high temperature such as 70° C., PMDA was dissolved in seconds and the resulting 0.12 M PAA solution was not as viscous at 1.1:1.0 ODA:PMDA ratio. Similar results were observed for 1:1 ODA:PMDA ratio at high temperatures. At 40° C., 1.00:1.10 ODA:PMDA ratio, 0.12 M PAA became less viscous than 1:1 ratio. So, it can be concluded that a good PAA concentration is 0.08 M or 0.12 M for FIG. 1b membranes.

TABLE Q

Summary of optimization of ODA:PMDA ratio, stirring speed and temperature needed to produce viscous PAA solution.

| ODA:PMDA ratio | Stirring speed | Temperature | Time | Observation (viscosity low, high, same? |
|---|---|---|---|---|
| 1.00:1.00 | 400 | 25° C. | Overnight | Mild |
| 1.00:1.01 | 400 | 25° C. | Overnight | Mild |
| 1.00:1.02 | 400-600 | 40° C. | Overnight | High |
| 1.00:1.02 | 400 | 50° C. | Overnight | Very high |
| 1.00:1.02 | 400 | 60° C. | Overnight | Mild |
| 1.00:1.02 | 1200 | 70° C. | Overnight | Very low |
| 1.00:1.02 | 400-600 | 70° C. | Overnight | Low |
| 1.00:1.04 | 400 | 40° C. | Overnight | Mild |
| 1.00:1.05 | 400 | 40° C. | Overnight | Low |
| 1.2:1.0 | 400 | 25° C. | Overnight | Very low |

The choice of appropriate solvent depends on three parameters as (i) environmental-friendliness, (ii) chemistry such as reaction yield and (iii) engineering which is more of scalability and ease of down-stream process. Environmental aspects of solvents are regulated by US Environmental Protection Agency (EPA). Chemistry and engineering are defined by the process itself and aim of the study.

The solvents aim to meet the following requirements: the solvent must be neutral to all members of the reaction mixture, including reactants, products as well as catalysts; if the solvent is a provider of any group such as —O, —H, that should be just a carrier; the solvent must be liquid at the reaction condition such as if the reaction is happening at room temperature the solvent should not require higher degrees to be liquid; if the phase split is required for the solvent that should be preferred; the solvent should provide the desirable solubility for the reactants as well as products if it is required; the solvent should not undergo association or dissociation; and the solvent should selectively dissolve reactants or the possible products if it is desired.

In order to obtain "greener" membranes (those with a smaller ecological impact), DMAC was combined with ethanol at varying ratios. Ethanol is generally accepted as a "green" solvent. However, the criteria listed above were taken into account in the selection. The goal was to use as high a percentage of ethanol as possible while minimizing the volume of DMAC employed. Ultimately, an optimum condition is sought that will provide the highest benefit. Determining the possible highest Ethanol:DMAC ratio was done using only two parameters; (i) the physical properties of the membrane and (ii) the aim of application of the membrane.

The observed characteristics of the membrane were (i) durability, (ii) resistance against solvents and (iii) mechanical properties. 65:35 Ethanol:DMAC ratio was accepted as a good ratio to develop 0.12 M PAA membrane with 1.00:1.03 ODA:PMDA ratio at 50° C. medium temperature under mild mixing. However, the PAA polymer formed in 65:35 Ethanol:DMAC ratio did not form fluorescent active membrane, so it is not advised for fluorescent active membrane formation. Actually, introducing ethanol into PAA solution prepared in only DMAC still disrupting formation of fluorescent active membrane formation.

TABLE R

Determining good conditions for Ethanol:DMAC ratios in membrane preparation.

| Mixture | Observation |
|---|---|
| 50:50, DMAC: EtOH | Viscosity high, require warming up (i.e 50° C.), and forming membranes that are strong but hard to obtain different colors |
| 35:65, DMAC: EtOH | Viscosity mild, require warming up (i.e 50° C.), and forming membranes that are strong, but hard to obtain different colors |
| 35:65, DMAC: EtOH | Viscosity mild, require warming up (i.e 50° C.), and forming membranes are strong, require the addition of 2% water to obtain desired colors |
| 25:75, DMAC: EtOH | Viscosity acceptable, require warming up (i.e 60° C.), and forming membranes that are strong, but hard to obtain different colors |
| 35:50:15, DMAC: EtOH:Water | Viscosity acceptable, require warming up (i.e 60 ° C.), and require special care to form good membranes, but provide desired different colored membranes |
| 30:50:20, DMAC: EtOH:Water | Viscosity low, require warming up (i.e 60° C.) and require care to form good membranes, but provide desired different colored membranes |
| 60:40, DMAC: Water | Did not form PAA viscous solution |
| 60:30:10, DMAC: Water: AcOH | Did not form PAA viscous solution |

*PAA concentration employed was 0.12 for all experimental conditions indicated.

Water:Ethanol:DMAC and Ethanol:DMAC mixtures were tested as well. In all cases, PAA concentration was kept constant at 0.12 M. The following solvent mixtures were obtained a good reachable ratio as 15:50:35 (water:ethanol: DMAC) and 75:25 (Ethanol:DMAC). However, it was shown that 20:50:30 (water:ethanol:DMAC) ratio is possible, but the PAA solution should be used within 2 days, otherwise PAA precipitates in the solution due to presence of high water content and low DMAC ratio.

However, it was noted that introduction of water to the solvent system eliminates the ethanol effect of preventing colorful and fluorescent PAA membrane formation. Methanol was not tested with combination of DMAC; ethanol is less toxic in comparison to methanol. However, methanol, ethanol and water containing 0.1 M hydrochloric acid (HCl) were tested individually, but viscous PAA solutions were not obtained.

Optimization of Small Molecule Concentrations

Optimization of the small molecule concentrations were performed for the membranes synthesized according to FIG. 1a. Since the small molecules used were mostly insoluble in viscous PAA solution. Therefore, it was a goal to find good concentrations of the molecules in order to form uniform and stand-alone membranes. Changes in viscosity related to small molecule addition was not tested with an instrument, rather the viscosity was described as low, mild, high and very high in relation to membrane preparation; and ease of spread onto the glass substrate prior to phase inversion. low and very high viscous PAA-small molecules were not be able to cast on glass surface to form even membranes.

However, for the membranes synthesized according to FIG. 1b, the small molecules were pre-dissolved before being introduced to the viscous PAA solution, hence optimization of the concentrations was performed mostly with respect to the aspect of mechanical strength and antimicrobial activity.

Figures 58A, 58B, 58C, 58D, 58E, 58F, 58G, 58H, 58I, 58J, 58K, 58L, 58M:
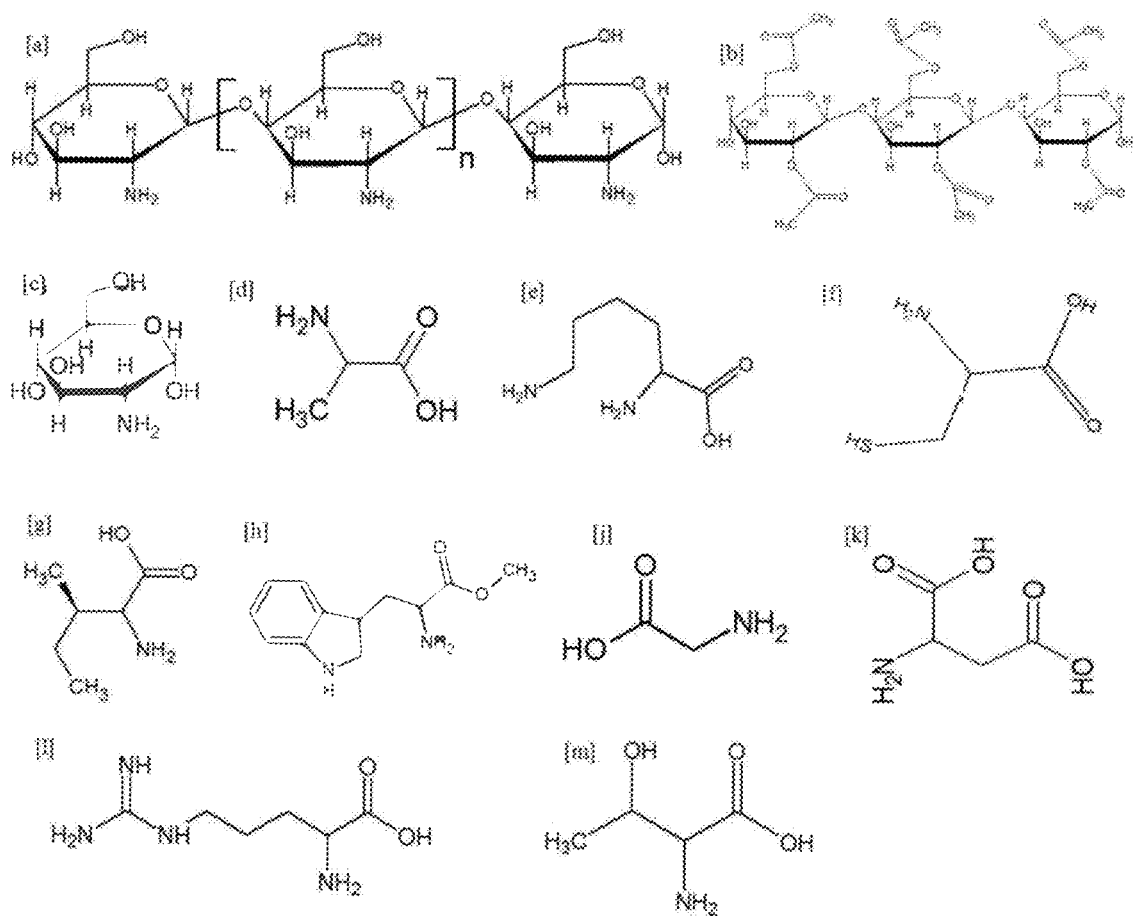
FIGS. 58a-58m are illustrations of different chemical structures.

Structures of the small molecules used in FIG. 1a membranes are shown in FIGS. 58a-58m. FIG. 58a Chitosan, FIG. 58b cellulose acetate, FIG. 58c glucosamine, FIG. 58d L-alanine, FIG. 58e L-lysine, FIG. 58f L-cysteine, FIG. 58g L-isoleucine, FIG. 58h L-tryptophane methylester, FIG. 58j glycine, FIG. 58k glutamic acid, FIG. 58l L-arginine and FIG. 58m L-threonine.

For all PAA concentration, 2 mg/mL chitosan (CS) [Low-molecular weight chitosan, Sigma-Aldrich] concentration can be used. CS mediated increase in the viscosity of PAA solution showed distinct characteristics; At 0.5 mg/mL, 1 mg/mL and 3 mg/mL of CS, PAA solution became highly viscous. From observations, CS is insoluble in DMAC; so it is clear that yellowish CS flanks are in PAA solution, which causes un-uniformity.

Cellulose acetate (100 kDa molecular weight) completely dissolved resulting in a clear solution when mixed with PAA solution despite the fact that cellulose has similar structure to CS. PAA and PAA-CA solutions exhibit similar color and uniformity with no air bubble in PAA-CA unlike PAA-CS mixture. The formation of the air bubbles resulted from combination of insolubility of the small molecule and high viscosity. When the PAA-small molecule mixture was stirred at 100 rpm for 10-30 min, the air-bubbles disappeared. Interestingly, CA at 1 mg/mL concentration makes PAA solution highly viscous which is like solid, so it is concentration should be used less than 0.5 mg/mL. Even at 0.5 mg/mL concentration, PAA-CA solution became viscous which made it eligible for membrane preparation by waterbath mediated phase inversion.

D-glucosamine (DA) is one of the two monomers in chitosan molecule, so they were expected to possess similar properties. Similar to CS, DA was not soluble in DMAC. However, when 1 mg/mL concentration of DA was dissolved in PAA solution, the resulting mixture became highly viscous resulting in even higher viscous solution than PAA-CA. Hence the optimum concentration of DA needed should be less than 0.5 mg/mL concentration in 0.20 M PAA, but 1 mg/mL works for 0.18 M PAA.

L-Alanine (A) can be used at 1 mg/mL concentration; higher concentrations were not tested because 1 mg/mL gave desirable viscosity even at 0.20M PAA solutions. A does not dissolve in DMAC, its insoluble crystals are visible in PAA-A solution; however it is possible some of A dissolved because in terms of mechanical properties PAA-A membrane was good. Its plastic-like structure did not turn brittle even at six months' exposure in the hood. Similar characteristics were observed for 3 weeks with PAA/PAA-W/PAA-CA composite membranes; when prepared using layer-by-layer casting on glass. In order to develop more durable membranes based on FIG. 1a, PAA was incubated with GA, and PAA-W and PAA-CA were sequentially casted on PAA. The aim was to observe if GA moves to PAA-CA solution.

Based on contact angle measurements data, this composite produced the highest hydrophobicity among FIG. 1a membranes. This layer-by-layer casting is not similar to the technique used to prepare polyelectrolyte multilayer membranes which relies on charge-charge interactions of different layers.

L-lysine (K) shows similar pattern to A, but it makes PAA solution much more viscous at the same concentration. A good concentration should be less than 1 mg/mL at 0.18 M PAA. At 0.20 M PAA concentration, 0.5 mg/mL of K produced a highly viscous PAA-K solution.

L-Cysteine (C) was selected because it has a free —SH group. Introducing C to CS membrane via GA makes CS membrane very flexible. Like-wise K, C is not soluble in DMAC. Interestingly, it was observed that C forms fibrils in DMAC and during membrane preparation these fibrils resulted in blocks within the PAA-C membrane shown in FIGS. 62a-62g. Therefore, highly heterogeneous PAA was formed, but these membranes protect the plasticized form [FIG. 1a i] more than the others except PAA-A [stable for around 3 months]. However, stirring PAA-C solution at very high speed minimized the fibril formation. It was observed that cysteine makes wrinkled PAA membranes, however its mechanical strength was still high in comparison to phase-inverted PAA membranes. When GA concentration was 0.21% in PAA-C solution, it did not result in plasticized PAA-C membrane but it resulted in shiny and relatively stronger membranes than individual PAA membranes. So, for preparation of PAA-C membranes, the optimum GA concentration should be between about 0.21 to about 0.35%.

For the amino-acids of FIG. 66 and the other molecules utilized to prepare the disclosed PAA films, the GA concentration can be up to about 2%. However, the concentration of GA depends on the formula and composition of the membrane.

L-isoleucine (I) can be used at less than 1 mg/mL concentration, at which concentration desirable PAA-I viscosity can be obtained. In this study, 0.5 mg/mL-3 mg/mL were tested at 0.20M PAA solution, and in all cases the extremely high viscosity of the mixture did not allow membrane formation. However, 0.5 mg/mL I was a good concentration at 0.18 M PAA solution for desired fluidity during membrane preparation.

Likewise, L-Tryptophane-methyl ester (W) can be used at less than 0.5 mg/mL concentration, at which concentrations desirable PAA-W viscosity could be obtained. In this study, 0.2 mg/mL-1 mg/mL were used at 0.20 M PAA solution, and in all cases extremely high viscosity did not allow membrane preparation. However, 0.5 mg/mL W could be used at 0.18 M PAA solution to get the desired fluidity. For the same concentrations, PAA-W gave the highest viscosity. W, gave unexpected results for FIG. 1b membranes as well.

Glycine (G) and L-Aspartic Acid (D) exhibit similar pattern to A, but makes PAA solution much less viscous at the same concentration, hence the optimum concentration should be at about 1 mg/mL at 0.18 M PAA.

After PAA-W, PAA-R (L-Arginine (R)) has the second highest viscosity [these are just based on observations]. 0.2 mg/mL R can be used with 0.20 and 0.23 M PAA; 0.25 M PAA. 0.5 mg R was observed to give a good concentration at 0.18 M PAA solution. However, the formed membranes did not provide durable membranes; keeping the membrane at room temperature for 2 days made the membrane brittle.

L-Threonine (T) can be used at 0.5 mg/mL for 0.20 M PAA and 0.18 M PAA solutions. However, similar to L-arginine, T made the PAA membrane brittle within 3 days after drying.

All these amino acids were introduced to the PAA solution immediately after the formation of PAA solution as described in FIG. 1a. However, these biomolecules were added to the system at the same time with ODA. The resulting PAA solutions showed similar characteristics. All these characterizations were made for FIG. 1a membranes; the concentrations of these amino acids can be increased up to 2 mg/mL in FIG. 1b. However, thiol containing amino acids and other molecules did not lead to the formation of membranes when FIG. 1b were employed.

Optimization of Cross-Linker Concentrations

Optimization of GA Concentration:

For desirable PAA membranes, the following parameters were found to be factors: Concentration of GA stock [Sigma-Aldrich, 70% Glutaraldehyde] solutions, the final concentration of GA when mixed with PAA solutions, age and temperature of GA added to the PAA solutions are highly important in terms of obtaining desirable PAA membranes. Age of GA is a term used here to describe what type of pre-treatment was applied to GA before it was introduced to PAA solution. Temperature of GA refers to that at which temperature GA was incubated before it was introduced to PAA solution.

There are similar procedures to age GA, but the way of aging in this study is not related to time, rather it is related to temperature. Aged GA, in general, provides distinct results than fresh GA during crosslinking. General rules in optimization of GA can be listed as below: concentration of GA stock is a factor in terms of how much water is introduced to the PAA solution; even though water provides a working microenvironment to GA, it can disrupt the cross-linked PAA membrane formation and also cause localized phase inverted PAA membrane formation in the PAA solution's vial, or during the membrane formation. So, it is advisable to use high stock concentration if the FIG. 1a iii is used to prepare the membranes.

Concentration of GA added to the PAA solutions should not be over the concentration at which it makes pure 0.16 M or 0.12 M PAA solutions solid less than 15 min and 30 min, respectively. Beyond this point, the leads to the formation of easily breakable PAA membranes. Similar observation was shown for PAA-CS. Further optimization can be performed for each molecule accompanied with PAA. However, it should be noted that incubation time also matters in defining the degree of cross-linking. When GA is less than 0.35%, the resulting PAA membranes are in between pure water phase inverted PAA membrane resulting in plasticized form. However, higher GA concentrations such as 2% GA convert PAA solution into completely non-fluidic within 3 min, which was observed in FIG. 1a iii and FIGS. 1bi and 1bii.

Age of GA defines its active individual GA molecule and degree of auto-polymerization. NMR characterization and further explanations are provided above.

GA stock vial should be kept in the hood until before being placed at room temperature for approximately 10-20 min; when the GA stock has been left at 4° C. needs 10 min, and it is then transitioned into room temperature, its viscosity decreases and becomes highly fluidic (for 25% or less forms), which was concluded based on observations through preparing different concentrations from 70% stock. When it is introduced directly from the refrigerator, it forms localized phase-inverted PAA membranes using the PAA solution.

Another point with respect to GA is that it must be thoroughly mixed with dry-DMAC before introducing it to PAA viscous solution. Moreover, there are two observations in this application as (i) adding GA into DMAC containing vial causes heat formation. In that respect, DMAC should be added slowly to the GA containing vial [note: the resulting heat may not increase the temperature up to flash point of DMAC but being cautious is advisable because mixing 25% stock GA with DMAC releases heat causes over 40° C.]. Increase in heat is possibly related to water-DMAC interaction since the same amount of GA in less water content added to the DMAC released less heat. The second observation (ii) is that using the stock solution of GA is different than GA that has been mixed in water. Pretreating GA with DMAC gives better membranes and causes no local membrane formation in PAA viscous solution. The PAA membranes prepared using FIG. 1a ii were found to be more stable for months when even kept under hood and at room temperature. Simple-treatment of GA in DMAC prior to the introduction into the PAA solution can bring a change in the resulting membrane.

The overall result of addition of GA to PAA viscous solutions from stock GA [FIG. 1a iii] makes the PAA membranes [except PAA-Cys and PAA-A] brittle after drying. This could be related to the kinetics of membrane formation according to FIG. 1a. It should be noted that the membranes described here were synthesized according to the procedure described in FIG. 1 a iii. However, the PAA membranes can be stored in pure water which protects their mechanical properties or prevents them from being brittle. However, PAA-A and PAA-Cys membranes were found to be strong and more durable even up to months. Addition of pre-diluted GA stock with dry DMAC to PAA solutions make PAA membranes strong and durable.

Optimization of 1, 1'-Diimidazole 1, 1'-diimidazole (IZ) was employed as a solid by slowly adding the solid particles into PAA solutions. Introducing over 1 mg/mL IZ to the PAA solutions at once causes localized orange color solid formation. However, IZ's original color is pale-yellow. Besides; IZ-treated PAA forms heterogeneous membrane, for instance the inner part looked similar to the non-cross-linker treated PAA membranes while the outer layer looks more like a plastic [Synthesized as described in FIG. 1 a iii]. In order to eliminate formation of non-even membranes, IZ should be used at low amounts and under good mixing.

IZ works slower than GA for membrane formation; while GA requires less than 3 min to increase the viscosity up to the desired level, IZ requires 15 min at 0.16 M PAA while 45 min requires at 0.12M PAA. The final membrane is physically similar to GA-treated PAA membrane. In order to prepare a totally plasticized-membrane, 3 mg/mL IZ should be added to the system under FIG. 1a iii. Besides, imidazole was dissolved in anhydrous DMAC and then applied to the PAA and PAA-small molecule viscous solutions. However, there was no difference between direct addition of solid imidazole and DMAC-dissolved imidazole. Beside 1,1'-diimidazole, N,N'-dicyclohexylcarbodiimide [DCC] was tested, and similar membranes were obtained with longer incubation times. DCC mediated membranes gave similar colored membranes as obtained with IZ. However, EDC/NHS did not work either direct solid addition, or dissolved in water.

Likewise, EDC/NHS, the use of glutaric acid [Sigma-Aldrich, MO] did not provide any plastic-like membranes. However, glutaric acid simply enhanced the IZ's activity to make PAA solutions' viscosity high enough to be prepared membrane relatively quick. It should be emphasized that plastic-like structure does not mean just being a transparent membrane, which is common for evaporation mediated phase inversion, but that means formation cross-linker mediated membranes. Neither carbodiimidazoles nor glutaraldehyde required EDC/NHS to modify PAA molecules. These combinations did not require EDC/NHS for crosslinking. Extensive tests were performed for GA, and NMR data show that GA covalently binds to PAA without the use of any EDC/NHS intermediate (discussed above).

Treating PAA with DCC until the PAA solution became solid resulted in vibrating solid which was seen for GA treated CS solution. This effect was not seen for GA treated PAA, and was observed for relatively lower in the cases of IZ treated PAA. For IZ, it could be related to lower and localized solubility of IZ in viscous PAA solution. The vibration property was not tested with an instrument; it was visually observed.

Time-Dependent Alterations in Membrane Physical Characteristics.

Incubation of PAA with a cross-linker alters its physical and chemical characteristics. These changes both depend on the type of cross-linker and the biomolecule used to modify PAA. Glutaraldehyde is highly active molecule, and it is not easy to control its diverse binding to PAA and other small molecules. Immediately after the phase-inversion, most of the PAA membranes protect their flexible natures. The membranes other than L-cysteine, L-alanine and chitosan modified PAA membranes did not protect their plasticized nature after about a week. However, the mentioned three membranes protected their plasticized nature well over 6 months. Measurement did not exceed 6 months. However, in parallel to increase in phase inversion incubation in water they become brittle, which takes weeks to months [Synthesized as described in FIGS. 1ai and 1aii].

Phase inversion or the process of transformation from solution state to solid state is a technique in preparation of membranes. It is used from micro-filtration to gas separation applications. Four main approaches have been described for phase inversion; (i) coagulation bath mediated phase inversion, (ii) heat triggered phase inversion, (iii) precipitation from vapor phase and (iv) evaporation in non-solvent.

Pore formation on the top layer of membrane through coagulation-bath mediated phase inversion forms due to flow of non-solvent into the membrane while the thickness of membrane's skin layer depends on flow of solvent from inner part of membrane into the coagulation bath. However, open-pore formation also requires coalescence in the polymer-poor area which is right under the top-layer. The relation between solvent and polymer itself, and solvent and non-solvent are also important in determining the characteristics of the pores. For example, in the presence of high affinity solvent and non-solvent, macrovoids are formed.

Figure 59:
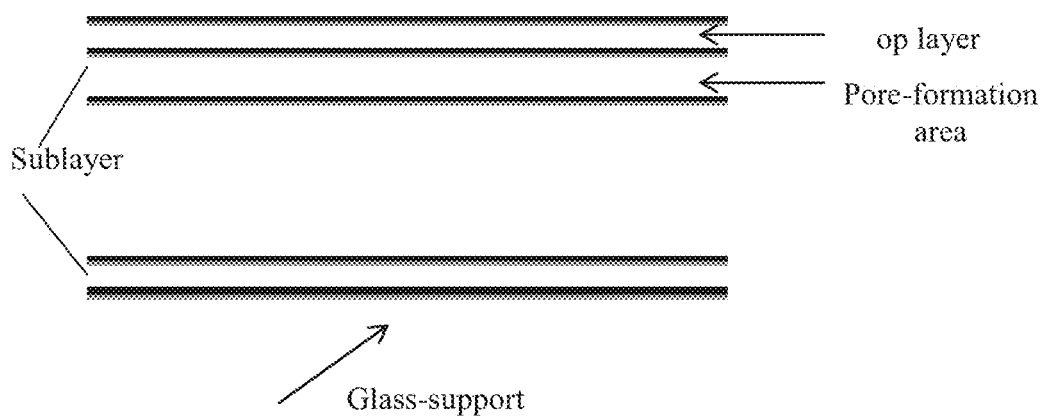
FIG. 59 is a graphical illustration of phase-inversion in coagulation-bath.

FIG. 59 is an illustration of phase-inversion in coagulation-bath (immersion precipitation).

Solvent refers to the solvent used to prepare membrane solution while non-solvent refers to the solvent used in the coagulation bath (which is also not supposed to be main solvent for the membrane). The solvent can be any suitable solvent capable of dissolving other substances, such as ethanol, methanol, and combinations thereof. The non-solvent can be any suitable material that is not capable of substantially dissolving other substances, such as water.

Besides altering the non-solvent, addition of non-solvent into solvent (casting solution) also makes difference in pore formation. While a very fast desolvation of solvent into non-solvent forms finger like structures and cause no or rare pore formation, addition of solvent into non-solvent allows porous surface formation because this situation reduces solvent desolvation into the non-solvent. However, addition of non-solvent into the solution before it is casted, less porous surface with a less dense surface forms. The solvation power of solvent also possesses strong effect on pore formation for instance a less solvation power provides more pores on membrane surface.

The membrane formation process here is mostly driven by combination of glutaraldehyde, evaporation and coagulation-bath/glutaraldehyde evaporation. When there is no glutaraldehyde in the system, even the speed of stand-alone membrane formation through evaporation is reduced. However, it should be mentioned that this does not mean that GA enhances solvent evaporation. Faster formation of stand-alone membrane implies that GA cross-links individual polymers leading into macro-polymeric systems by which stand-alone membrane formation eliminates high percentage of DMAC removal from the system.

In the method used herein glutaraldehyde is not only functioning as a cross linker, it is also transforming the resulted PAA into optically active form such as fluorescence active forms. These bindings alter the membrane formation; the very basic alteration is the rate of solvent evaporation. Here, encrossslinking was used to refer extensive crosslinking.

As explained for PAA-GA, PAA-CS-GA, PAA-A-GA, PAA-DA-GA and PAA-C-GA, the concentration and activity of GA (i.e. heat treatment and pre-treatment with DMAC) showed dramatic effect on the resulting PAA membranes synthesized according to FIG. 1a, in which coagulation bath was used as the final step of the phase-inversion.

For some small molecules, the membrane showed thin inner solid layer which was then disappeared when the membrane was incubated under hood for 6 h or more, which refers to a continuing progress of membrane formation. However, in the cases of higher GA concentrations and/or enhanced activity of GA, formation of plastic-like and transparent membrane surface didn't show any requirement to sonication in methanol/ethanol or drying under hood. It is evident that GA alters the kinetics of membrane formation; additives were shown a role-player in the kinetics. In the cases of the membranes synthesized according to FIG. 1b, all of the membranes are plastic-like and transparent, and don't form any solid amorphous layer even they are submerged into water or other solvents.

In FIG. 1a membranes, there is no pore formation in the cases of water bath becomes the final phase-inversion step. Therefore, the speed of DMAC releases into water bath is too fast to form porous surface, but the surface becomes shiny and plastic-like which can be assigned to the activity of GA. However, when the final step of phase-inversion was performed in methanol, the surface lost its shiny structure and formed woven-like structures (as discussed above) which can be explained through DMAC having a relatively lower tendency to diffuse into methanol.

Similarly, losing the shiny outer surface appearance can be explained by the quenching activity of methanol on the activity of GA crosslinking. However, when methanol/ethanol bath was accompanied with sonication, membranes then can be synthesized porous. In the cases of high GA concentrations, the membranes can also be made porous if they are sonicated in methanol/ethanol bath. In essence, surface patterns of FIG. 1a membranes depend on the final step of phase-inversion while the texture of them is mostly dependent on concentration and treatment of GA. However, it should be noted that small molecule also makes difference in formation of the membrane such as PAA-C-GA, PAA-W-GA and PAA-A-GA are more of on the plastic-like surface forming co-polymers while chitosan and glucosamine urge the membranes become more of amorphous.

Another test was performed to determine how glutaraldehyde, small molecule and the final step of phase-inversion affect the final texture of PAA membranes. The co-polymers were left in a vial overnight and the resulted PAA co-polymers were sticky gels. Then, they were exposed to evaporation under hood, phase-inversion in water-bath, methanol, methanol-water mixture, and ethanol and ethanol-water mixtures. PAA-W-GA and any other PAA co-polymers enhanced with sulfanilic acid provided plastic-like membrane surfaces under all final phase inversion conditions, but only sonication in organic solvent (i.e. methanol and ethanol) made the membranes fully plastic-like; as shown for FIG. 1b membranes, high amount of residual DMAC in PAA makes it possessing solid amorphous layer.

This is evidence that the speed of solvent removal from the inner part of the membrane is one of the parameters in order to form totally plastic-like membranes. Besides, sonication allowed the membranes possess porous surfaces in organic solvents; even though ethanol works better such as 80% ethanol is enough for porous surfaces while methanol can be 100%, methanol bath treated membranes showed better durability. Besides, introduction of organic solvents such as ethanol, hexane and others into co-polymerization media did not affect the pore formation as well. Introducing solvent into coagulation bath was shown a parameter to make flat membranes porous, but the approach did not work for the membranes synthesized according to FIG. 1a.

Classical pore preserving agents include PEG 400 or any other agents weren't tested to make the membranes porous since the goal was just to understand how membrane formation progresses under different conditions.

Preparation of Ternary PAA Membranes

Figures 60A, 60B, 60C, 60D, 60E, 60F, 60G, 60H:
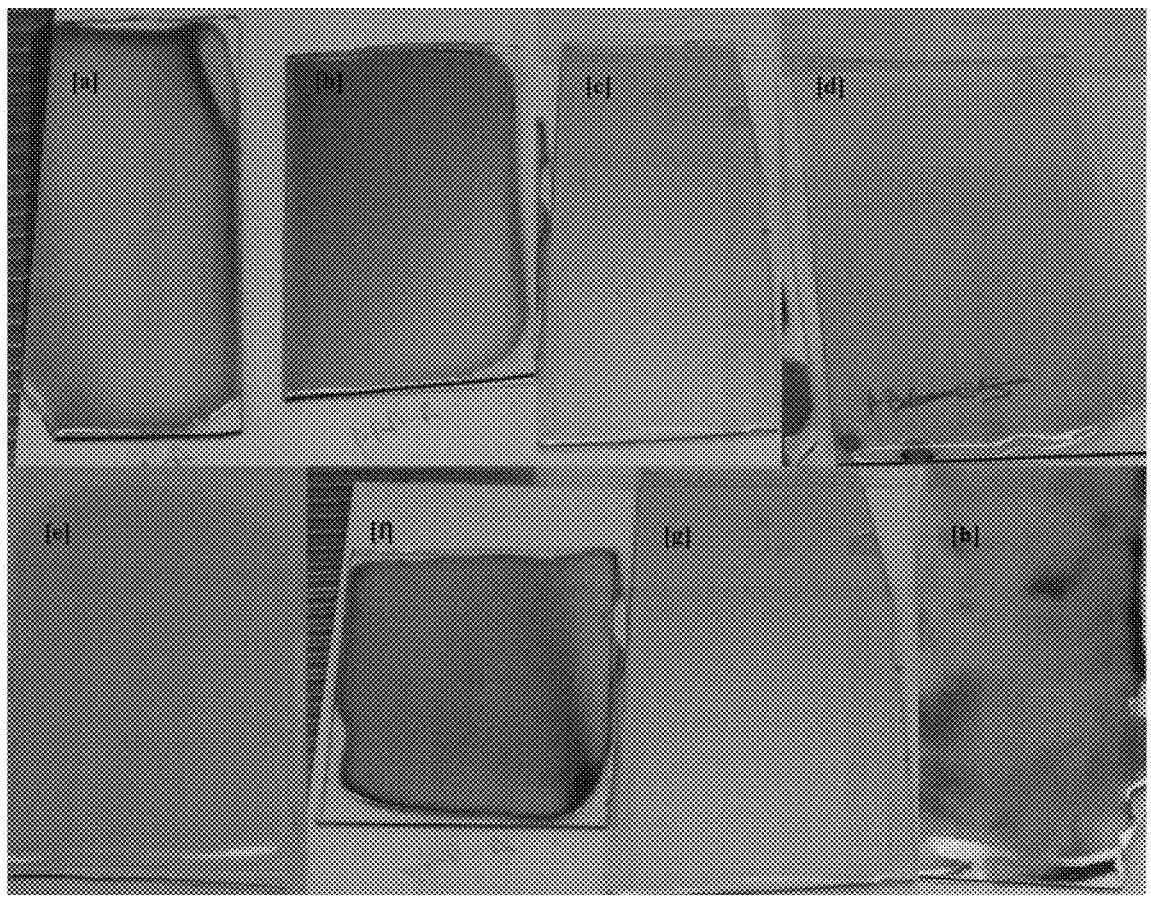
FIGS. 60a-60p are photographs of various PAA films.

Images of several films are shown in FIGS. 60a-60h. FIG. 60a: PAA-CS-GA; FIG. 60b: PAA-A-GA; FIG. 60c: PAA-A-GA; FIG. 60d: PAA-A-GA; FIG. 60e: PAA-GA; FIG. 60f: PAA-A-GA; FIG. 60g: PAA-GA and FIG. 60h: PAA-CS-GA. All of these digital images were taken between 30-60 min right-after castings on the glasses. Steps of the phase-inversion according to FIG. 1a resulted in different surface-properties.

The casted solutions shown in FIGS. 60a-60h underwent different final phase-inversion process, by which different surface properties of same types of membranes were obtained. FIGS. 60i-60p illustrates -PAA-CS-GA FIG. 60a was incubated for 6 h at room temperature, followed by incubated at 70° C. for 20 min. The resulted membrane turned into brownish colored transparent and brittle membrane FIG. 60i. PAA-A-GA FIG. 60a was incubated at room temperature for overnight FIG. 60j. PAA-A-GA FIG. 60c was incubated at room temperature for 6 h, followed by incubated at 70° C. for 1 h.

Figures 60I, 60J, 60K, 60L, 60M, 60N, 60O, 60P:
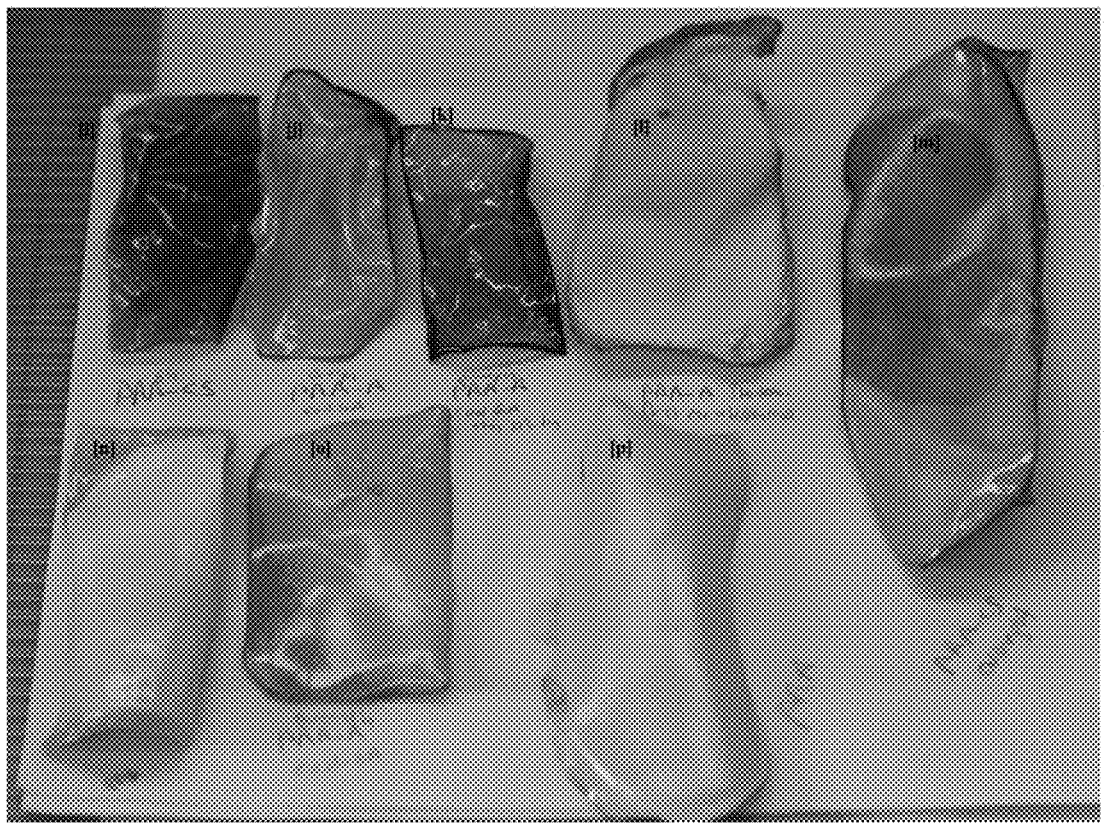

The resulted membranes showed quite-similar characteristics with PAA-CS-GA membrane FIG. 60i. PAA-A-GA FIG. 60d was incubated at room-temperature for 3 h, followed by incubated in 100% methanol for 1 h. The resulted membrane FIG. 60l showed opaque and non-shiny surface with possessing plastic-like edges. PAA-CS-GA FIG. 60h was incubated overnight at room temperature, and the resulted membrane possessed slightly shinny surface FIG. 60m. Since the thickness was over 0.3 mm, total transparency was not obtained.

PAA-GA FIG. 60e was incubated at room temperature for 6 h, and the resulted PAA-GA FIG. 60n showed shinny surface. PAA-A-GA was incubated at room temperature for overnight, and the resulted membrane FIG. 60o showed slightly shiny color. PAA-GA FIG. 60g was incubated at room temperature overnight at room-temperature, and the resulted membrane FIG. 60p showed shiny surface. This membrane did not show any plastic-like surface how it was seen for the membrane FIG. 60n, which can be attributed that the edges of FIG. 60n was thinner while the center was thicker. However, for the PAA-GA membrane FIG. 60p, the solution was evenly distributed. All of these membranes were prepared according to FIG. 1a, which means the last step of phase-inversion took place in pure water if not specified otherwise.

Figures 61A, 61B, 61C, 61D, 61E:
FIGS. 61a-61e are photographs of various PAA films.

FIGS. 61a-61e includes several images. FIG. 61a PAA-A-GA (0.25%); FIG. 61b PAA-A-GA (0.75%); FIG. 61c PAA-C-GA (0.25%); FIG. 61d PAA-CS-GA (0.3%), FIG. 61e PAA-GA (0.25%). 70% stock GA was pre-dissolved in DMAC if not mentioned otherwise. All of the membranes prepared according to FIG. 1a.

Figures 62A, 62B, 62C, 62D, 62E, 62F, 62G:
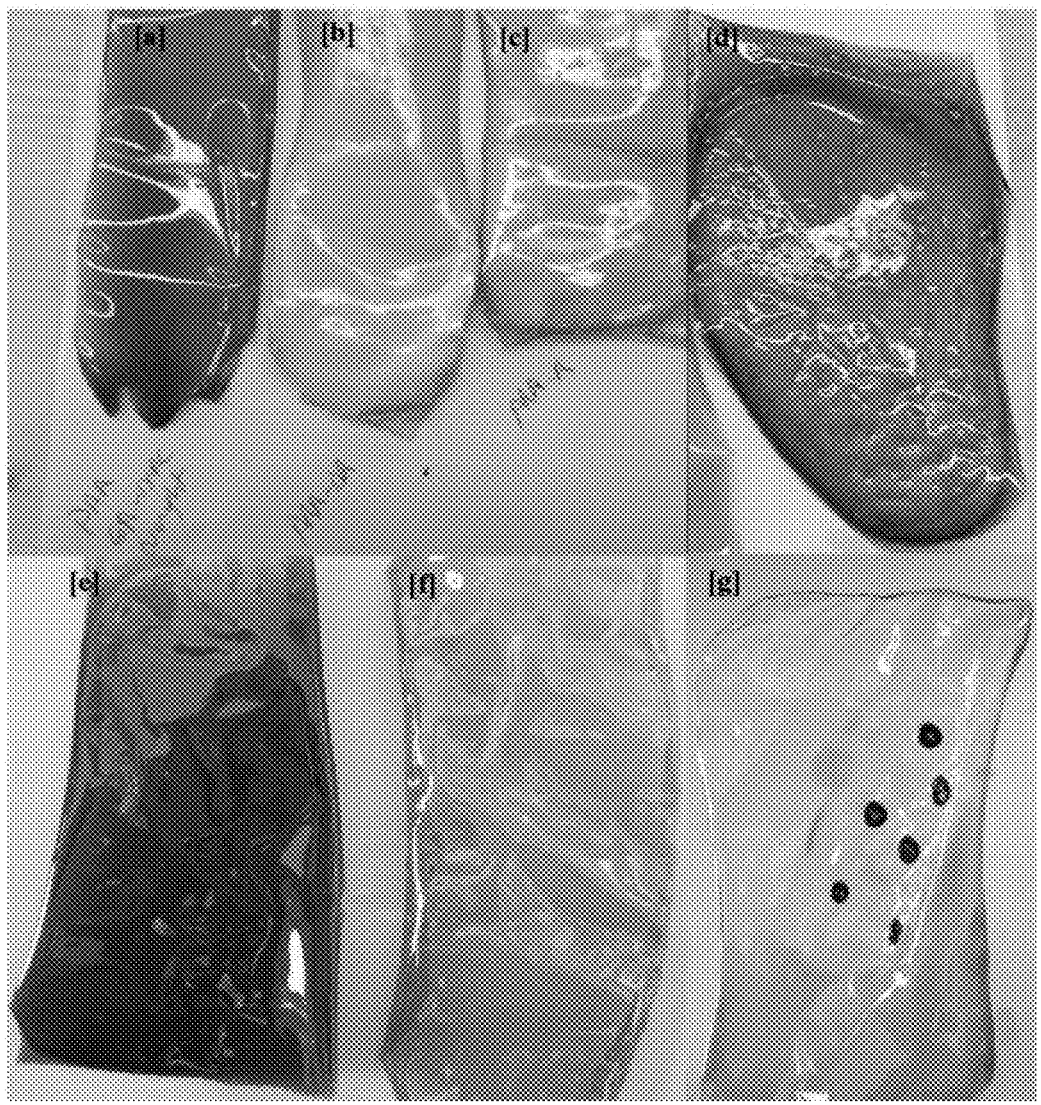
FIGS. 62a-62g are photographs of various PAA films.

FIGS. 62a-62g includes several images. FIG. 62a-PAA-GA; FIG. 62b-PAA-DA-GA; FIG. 62c-PAA-A-GA; FIG. 62d: PAA-DA-GA (direct from 70% stock); FIG. 62e-PAA-A-GA was first incubated in 70° C. for 30 min, followed by overnight incubation at room temperature; FIG. 62f-PAA-A-GA similar to c but higher GA concentration (%0.9); FIG. 62g-PAA-C-GA. 70% stock GA was pre-diluted in DMAC if not mentioned otherwise, followed by introduced to the membrane formation processes at the concentration of 0.3% if not mentioned otherwise.

GA concentration and its form are important in terms of membrane characteristics. Besides, viscosity of PAA solution is important. As seen in FIG. 60g, PAA-DA gave some blue region but the rest is yellowish. Interestingly, increased incubation time and high GA concentration make the membranes plastic like-structures and colorful. However, this is not clear during phase-inversion. When they are getting dry, their transparent natures become visible. At low GA concentration and short-incubation time, the membranes don't turn into transparent form, but a thin layer forms on top of the membranes. The bottom of the membrane is mostly not-shinny. It should be mentioned that the way of GA application is important in membranes' mechanical and optical properties. For example, while PAA-CS forms strong-green color membrane with FIG. 1aii, it does form pale chestnut color with FIG. 1ai. For example, FIG. 13a illustrates UV/Visible spectroscopy for several disclosed films. The Y-axis in the data is referred to as Optical Density, or DO, with a comparatively good number between 0.1 and 0.9. The larger the number the stronger the color intensity.

Figures 63A, 63B, 63C, 63D, 63E, 63F, 63G, 63H, 63I, 63J, 63K:
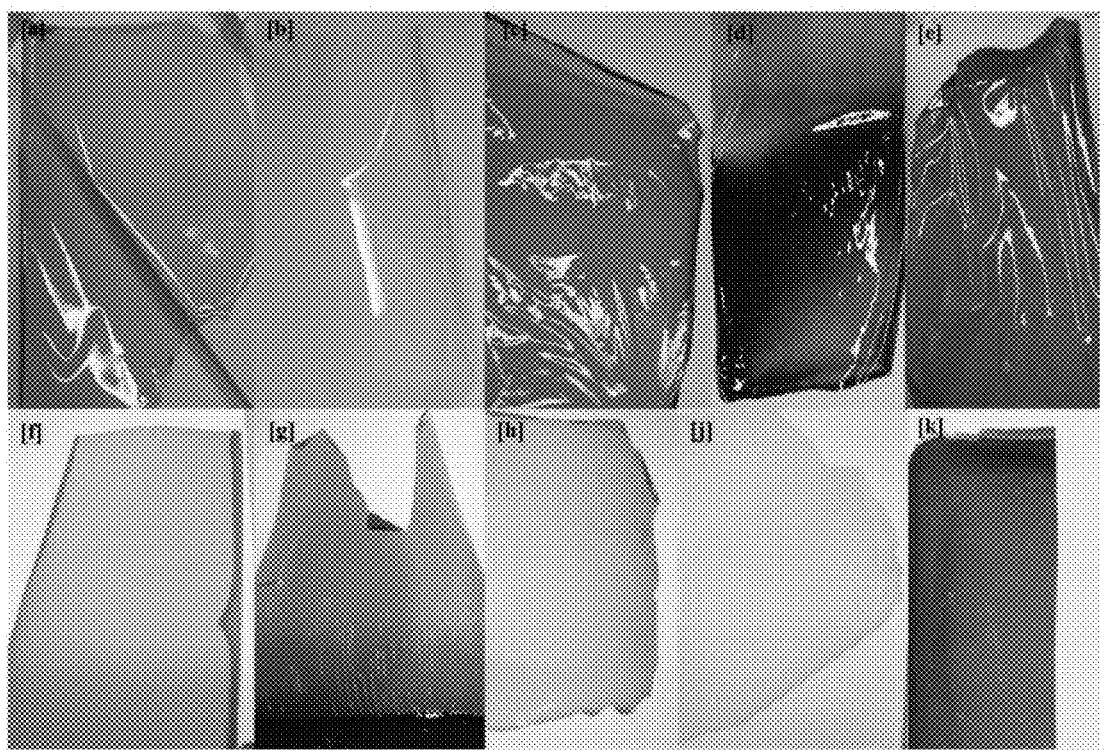
FIGS. 63a-63k are photographs of various PAA films.

FIGS. 63a-63k are images of the following films: FIG. 63a: PAA-pAS-GA; FIG. 63b: PAA; FIG. 63c: pAB-PAA-GA; FIG. 63d: pAB-DMAC-GA-PAA; FIG. 63e: W-GA (long incubation)-PAA; FIG. 63f: W-GA-PAA; FIG. 63g: pAB-DMAC-GA-PAA (30 min incubation); FIG. 63h: PAA-pAS-W-GA; FIG. 63j: pAS-DMAC-GA-PAA; FIG. 63k: PAA-pAB-GA. All of the membranes prepared according to FIG. 1b.

Figures 64A, 64B, 64C, 64D:
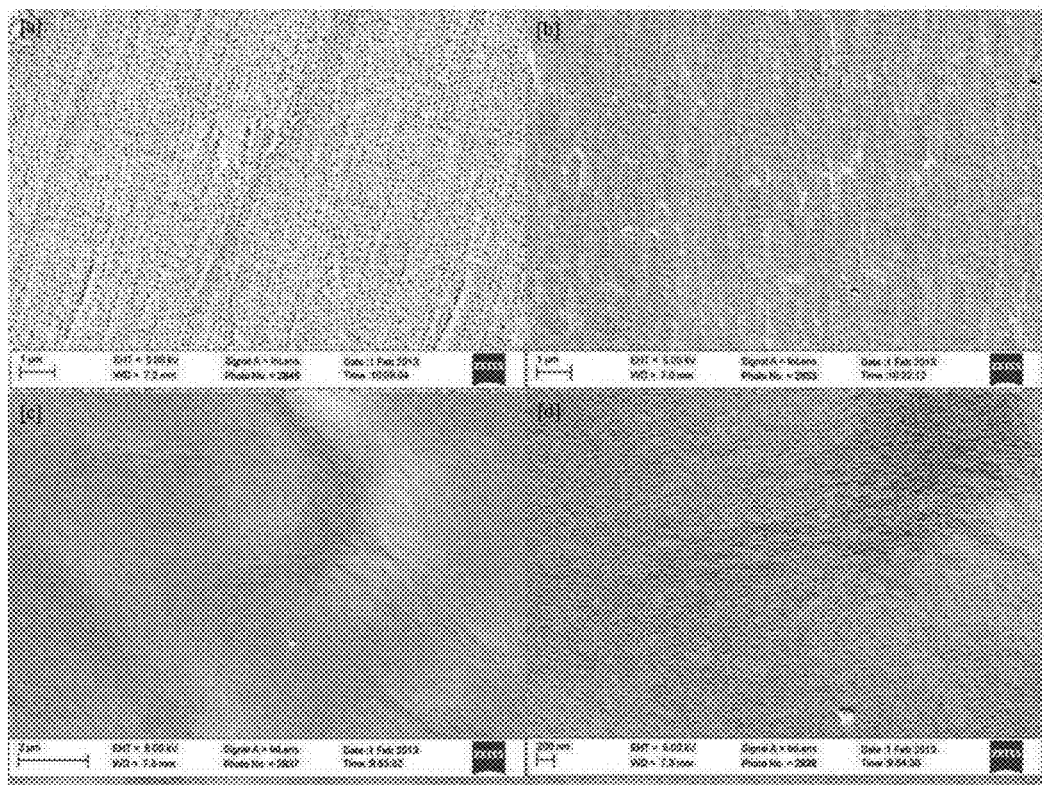
FIGS. 64a-64d are SEM images of various PAA films.

0.32 M highly viscous (no fluidity) was treated with 0.25% GA for 6 h at room temperature, followed by casted on glass and phase-inverted according to FIG. 1a. The resulting films are shown in FIG. 64a final steps of phase inversion were in 100% Ethanol, FIG. 64b 50% Ethanol:

water and (FIGS. 64c/d) and nano-pure water. All of the membranes prepared according to FIG. 1a.

PAA-GA

As seen from FIG. 60e and FIG. 60g, GA (aged) treated PAA showed similar transparent-view while they ended up showing distinct surfaces in response to alteration in the final step of phase-inversion (FIGS. 60n and 60p respectively). Both of the membranes were synthesized according to FIG. 1a iii, but completion of the phase inversion was performed in methanol (FIGS. 60 g/p) in addition to water-bath (membrane shown in FIGs. e/n). Thinner regions of the membrane FIG. 60n showed fully-plastic-like structure while the thicker regions showed two different characters; the outer part was fully plasticized while the inner part was amorphous. However, the membrane shown in FIG. 60p was more of amorphous membrane and no plastic-like outer layer was seen. Contact angles of the membranes showed difference as well; they were 67 and 61 for the membranes shown in FIGS. 60n and 60p, respectively. However, when PAA-GA showed total plastic-like such as the edges of the membrane FIG. 60n was 58. When the GA was diluted in DMAC before it was applied to PAA solution brought strong impact on membrane formation (shown in FIG. 60a). GA from 70% stock was pre-dissolved in. DMAC, followed by introduced to the PAA solution. The membrane was prepared according to FIG. 1a ii with 0.9% GA. The resulted PAA gave durable and fully plastic-like membrane. Even though, the PAA-GA (0.25%) membrane shown in FIG. 61e was prepared according to FIG. 1a ii, the resulted membrane showed totally different character; outer layer and thinner regions were plastic like while the center was amorphous because of the thickness.

PAA-CS-GA:

Here three different PAA-CS-GA were shown how glutaraldehyde affected color formation and formation of plastic-like structure. As seen from FIGS. 60a and 60h, both PAA-CS-GA were transparent. (FIG. 60a) PAA-CS-GA (%0.25) was first incubated under hood for 6 h, followed by incubated at room temperature for overnight (~14 h). However, (FIG. 60h) PAA-CS-GA (%0.5) was only incubated at room temperature for overnight (~20 h). Phase-inversion of both membranes was finalized in water-bath, followed by dried under hood for 2 h. As seen from FIG. 60i, the membrane (FIG. 60a) resulted in a brownish plastic-like membrane while the membrane (FIG. 60h) resulted in greenish amorphous membrane (FIG. 60m). For both of these membranes, aged-GA was directly introduced to the membrane formation process. However, GA from 70% stock was pre-diluted in DMAC, followed by warmed for 10 min at 70° C., which was then introduced to PAA-CS solution seen in FIG. 61d. The membrane (FIG. 61d) was incubated at room temperature for 15 h, and phase inversion was completed in water-bath for 2 h followed by dried under hood for 2 h. The resulted PAA-CS-GA membrane (FIG. 61d) was durable, strong and resistant to the organic solvents while the membrane (FIG. 61m) became brittle within three days. The membrane (FIG. 61m) did not turn into plastic-like membrane within 2 weeks, but rather the membrane became brittle. The membrane (FIG. 61d) did not form a transparent greenish membrane at once, rather it took over 2 h to form the transparent membrane; at first it was opaque and within time it turned into transparent form.

PAA-A-GA

FIGS. 60b, 60c, 60d and 60f are showing the membranes before they underwent final step of the phase-inversion. Even though same GA (stock 25%) was used for these four membranes, heat treatment and alteration in final step of phase-inversion showed strong impact on physical properties of final membrane. Heat treatment at 70° C. for 1 h was applied to the casted PAA-A-GA solution before it underwent incubation at room temperature. The resulted membrane showed fully plastic-like reddish structure (FIG. 60k), but it was not durable and became brittle within a week. When the completion of phase-inversion took place in methanol/water mixture, the resulted PAA-A-GA (FIG. 6l) was opaque. In contrast to this, outer layer of the PAA-A-GA (FIG. 60k) was plastic-like and shiny. However, when the membrane was thick, the outer layer did not provide similar plastic-like view, rather it gave a shiny surface (FIG. 60o). When 70% GA was dissolved in DMAC, followed by introduction to PAA-A solution, it affected membrane formation; before the membrane formation underwent incubation at room temperature, it was warmed at 70° C. for 10 min. The resulted membrane (FIG. 61a) showed thicker plastic-like outer layer in comparison to the membrane shown in FIG. 61b. Similarly, low GA concentration and short incubation (6 h total) resulted in non-plastic like membrane formation (FIG. 62c). The edges of PAA-A-GA (FIG. 61a) are totally transparent, and the overall durability of the membrane is better than FIG. 60j membrane. When GA concentration was increased (0.75%), the resulted PAA-A-GA became transparent and brownish (FIG. 62b); the membrane was durable and strong. Similarly, when the GA concentration was increased from 0.75% to 0.9%, the resulted membrane became yellowish (FIG. 62f) and better transparency in comparison to the PAA-A-GA membrane shown in FIG. 61b. Heat treatment allowed PAA-A-GA (FIG. 62e) totally shiny and plastic-like view, which was also durable in comparison to heat treated-PAA-GA (has similar color).

PAA-C-GA and PAA-DA-GA

Dilution of GA in DMAC totally altered the view of PAA-DA-GA even though same GA concentration was used. PAA-DA-GA (FIG. 62d) showed plastic-like outer layer and stronger and durable membrane. However, as shown in FIG. 60m, fully plastic-like membrane can be obtained if PAA-DA-GA was heated for 20 min as of first step incubation at 70° C. Heat treatment allowed PAA-C-GA (FIG. 60i) membrane became totally plastic-like structure, but not very transparent. When there is no heat treatment and high GA level, PAA-C-GA (FIG. 60m) did not end up forming transparent membrane. Glucosamine might react with GA first over C1-OH in addition to amino group, followed by introduced to PAA through amino groups on PAA. This could be a type of Maillard reaction, which gives brown-color formation (FIG. 62d).

PAA-pAB-GA, PAA-W-GA, PAA-pAS-GA pAB is also another small molecule altered overall view of PAA. In all cases, aged GA was used for preparation of PAA-pAB-GA membranes. As seen from the FIG. 63c, PAA-pAB-GA is bluish with 0.25% GA concentration while the PAA-pAB-GA (FIG. 63k) is more of brownish with 0.5% GA, which unexpectedly became brittle within a month. Similar to high GA concentration, incubation of pAB with GA in DMAC before they were introduced to PAA solution resulted in color changes of PAA-pAB-GA membranes; pAB was pre-treated with GA in DMAC for 10 min and 20 min for the membranes seen in FIGS. 63d and 63g. Similarly, W was pre-treated with GA for 20 min and 30 min before they were added to PAA solutions resulted in yellowish (FIG. 63f) and reddish membrane formation (FIG. 63e), respectively. pAS was pretreated with GA in DMAC, followed by added to PAA solution, gave yellowish view (FIG. 63j) while PAA-pAS-GA (FIG. 63a) gave light purple view. However, when GA treated pAS and GA treated W were simultaneously added to PAA solution, the membrane gave light yellowish view (FIG. 63h) which resembles to PAA membrane phase-inverted under hood (FIG. 63b). All of these membranes were synthesized according to FIG. 1b.

Figures 65A, 65B, 65C, 65D:
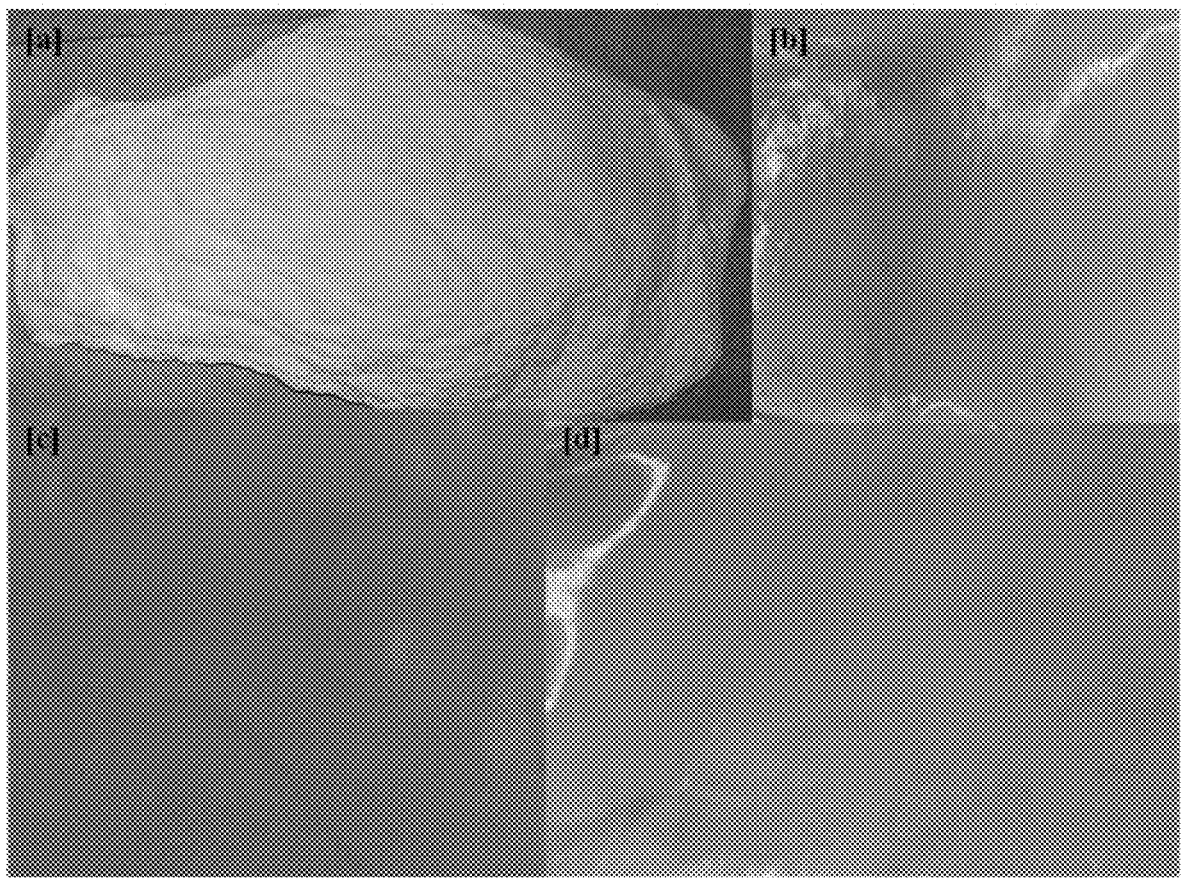
FIGS. 65a-65d are photographs of various PAA films.

FIGS. 65a-65d are images of: FIG. 65a PAA (ODA+PMDA)-GA-SA 1 h incubation at room temperature, followed by phase-inversion in pure water; FIG. 65b PAA (PDA+PMDA)-GA-SA 1 h incubation at room temperature, followed by phase-inversion in pure water; FIG. 65c PAA (ODA+PMDA)-GA-W 1 h incubation at room temperature, followed by phase-inversion in pure water; FIG. 65d PAA (PDA+PMDA)-GA-SA 30 min incubation at room temperature, followed by phase-inversion in pure water. In order to get transparent membranes, in the cases of PDA as amine sources less time required due to the fact that PDA has more reactive amino groups than ODA because of conjugation. Small molecule such as W resulted in bluish non-transparent while SA provided highly transparent membrane; PAA-SA-GA gave glassy brittle membrane while PAA-W-GA gave amorphous durable membrane.

1.13 Application of PAA Membranes for Food Packaging

Cheese, pepperoni, apple and walnut were used to test packaging properties of the membranes.

Figures 67A, 67B, 67C, 67D, 67E:
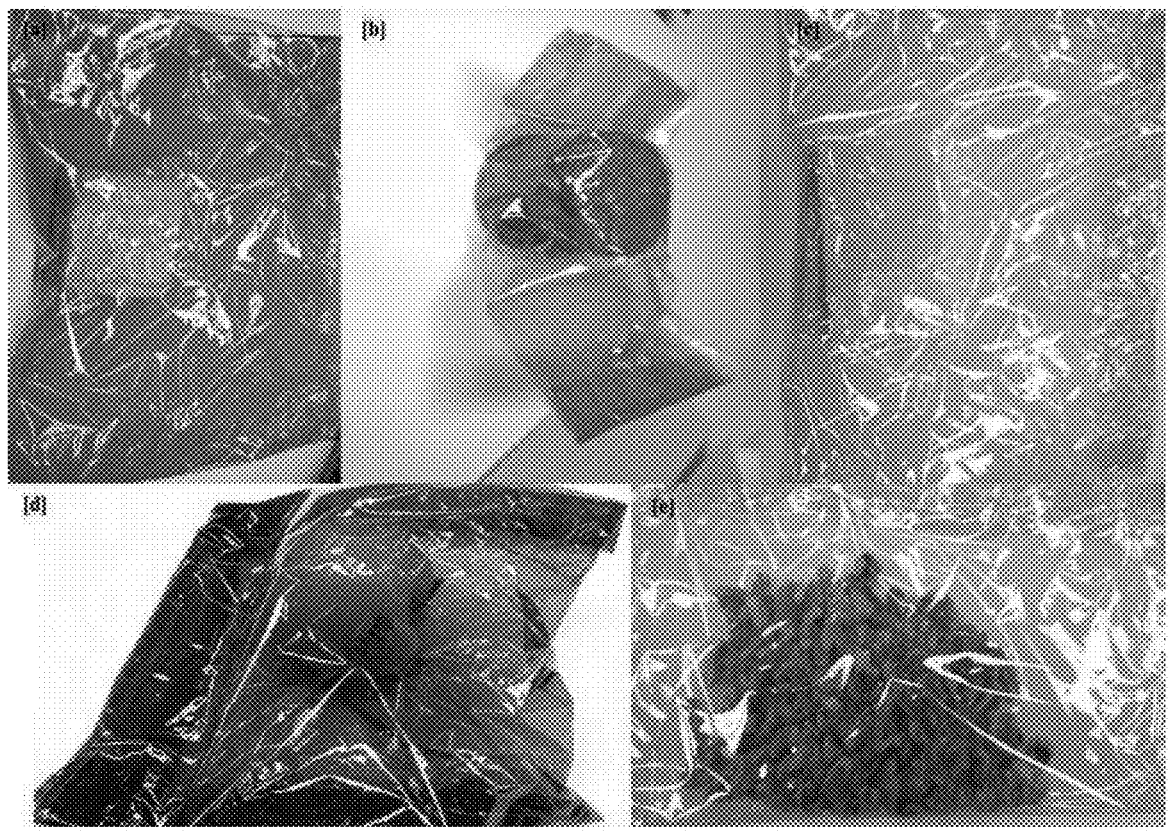
FIGS. 67a-67e are photographs of various PAA films covering various foods.

The formed films are shown in FIGS. 67a-67e, with FIG. 67a POLLY-O part-skim mozzarella cheese (Campbell, N.Y.); FIG. 67b Merve pepperoni (NJ); FIG. 67c Cabot extra sharp cheddar cheese (Cabot, Vt.); FIG. 67d Green apple (WalMart, Jonson City N.Y.) and FIG. 67e Diamond walnut (CA). PAA-A-GA, PAA-A-pAS and PAA-I-pAS membranes were used for packaging, respectively.

The films were sterilized rinsing 70% Ethanol, followed by rinsing with excess pure water (18.2 MΩ), which were finally treated with 1 h UV light. Food samples were kept in fridge at 4° C. Cheeses and pepperoni protected their stability for the tested period, 3-6 months.

Figure 68A:
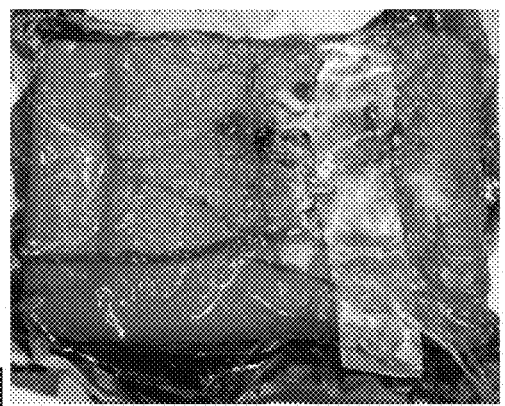
FIGS. 68a-68c are photographs of various PAA films covering various foods.
Figure 68B:
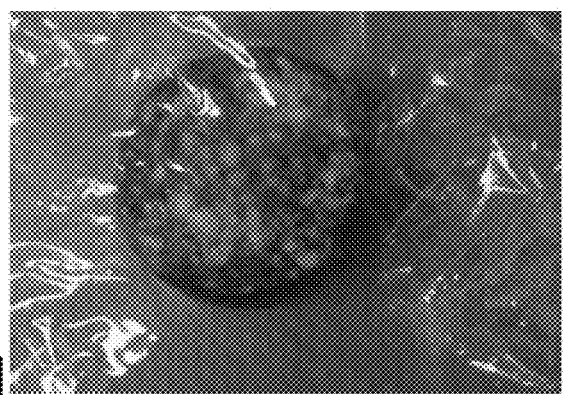
Figure 68C:
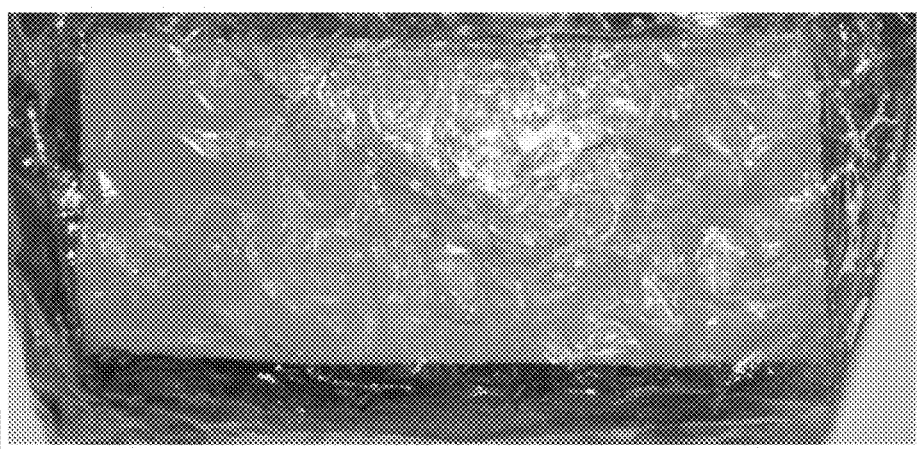

FIGS. 68a-68c are images of the stored foods of FIGS. 67a-67c. FIGS. 68a and 68c are images of cheeses stored for 10-11 months. As it is seen, the microbial growth is localized in FIG. 68a, which was intentionally pierced.

FIG. 68c is an image of pepperoni after 15 months incubation. No microbial growth was observed.

Figure 69:
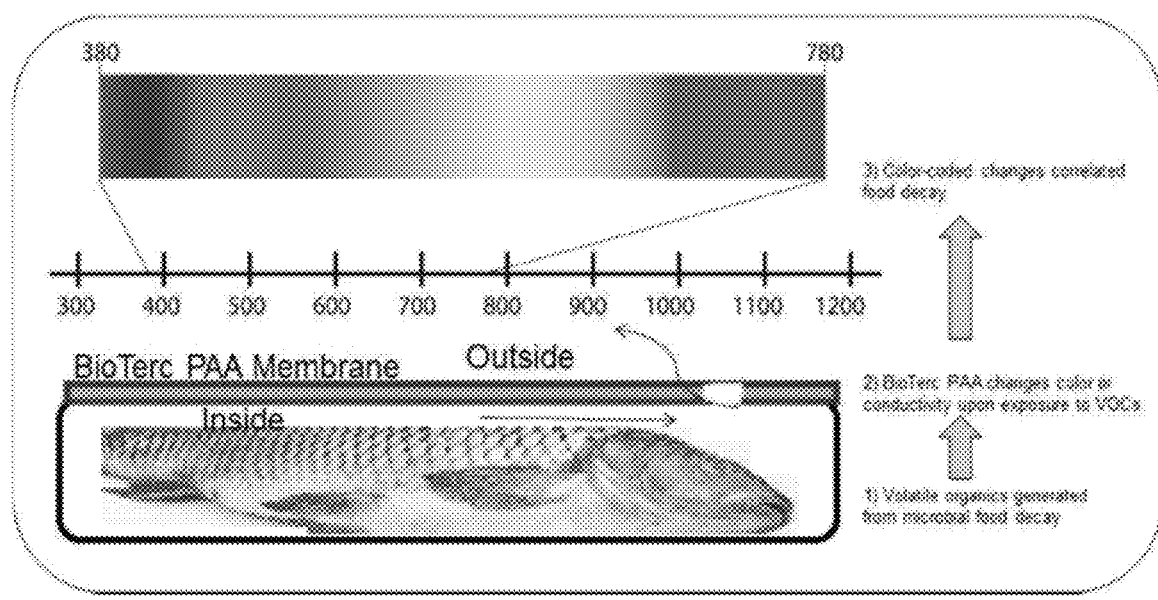
FIG. 69 is a graphical illustration of a color change of a PAA film.

FIG. 69 illustrates the disclosed film concept for both detection and packaging. Step 1: air packed or vacuum packed food sample produces volatile organic compounds or other compounds; (ii) the VOC interacts with PAA, (ii) this results in color-change that is visually detected or electronically detected.

The disclosed films can be used as a packaging material but at least a portion of the film makes no direct contact with the food sample. Any volatile or semivolatile organic vapor that is produced as a result of food spillage is drawn on to the sensor/packaging PAA. The sensor responds via a visible color change and a measurable change in conductivity using an optional conductivity monitor that is placed on the package. The concentration of the emission of volatile organic compounds (VOCs—e.g., sulfur compounds, acetone, methyl ethyl ketone, toluene, ethylbenzene, m,p-xylene, styrene, and o-xylene) largely increased over the storage time and should be correlated with the total number of microbial numbers. This should allow a rapid detection of food spoilage and may also allow consumers to visually determine food freshness. The PAA film can also detect pH-related changes in the air around the food (e.g. ammonia, alcohol).

1.14 Thermoplastic Examples

This example includes formulations that are capable of forming a PAA film that i) softens when heated (thus allowing the film to be molded to different shapes and sizes); ii) is flexible and undergoes crystallization transitions by incorporating sulfur-containing monomers, fatty acids, ionic salts and liquids, and plasticizers between the different functional groups; and iii) is resistant to shrinking while retaining good strength and chemical stability.

In this example, these films can exclude, wholly or partially, the formation of covalent bonds while increasing ionic properties, mechanical strength and dissolution. The resultant film in this example is referred to as "Thermoplastic PAA".

Unlike a "thermoset" PAA polymer that is held together via irreversible chemical bonds, Thermoplastic PAA is relatively weakly held together through electrostatic interactions and Van der Walls forces. These relatively weak bonds in the thermoplastic polymers allow them to be re-usable, relatively soft when heated, and to be molded and remolded one or more times.

This ability to reuse thermoplastic typically means a higher recyclability. Also, other properties such as good strength and a tendency to resist shrinking is realized by these Thermoplastic PAA films.

These Thermoplastic PAA films can be made more thermoplastic by reacting sulfur containing monomers (e.g. 4,4'-thiodianiline; an analogue of 4,4'-oxydianiline) in a stoichiometric ratio of acid/amine functionality and other additives. Examples of Thermoplastic PAA Films include but are not limited to those shown in Table S.

Table S

Examples of Proposed Thermoplastic PAA Film Formulations

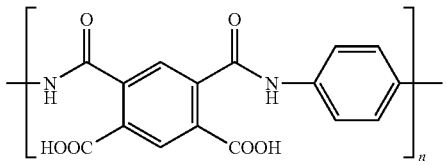

Poly (pyromellitic dianhydride-p-phenylenediamine) (PPDD) from PMDA + PDA

Table S-continued
Examples of Proposed Thermoplastic PAA Film Formulations
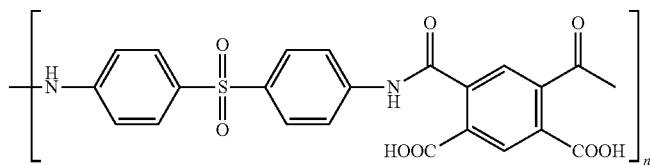
Pyromellitic dianhydride (PMDA) + diaminodiphenyl sulfone (DDS
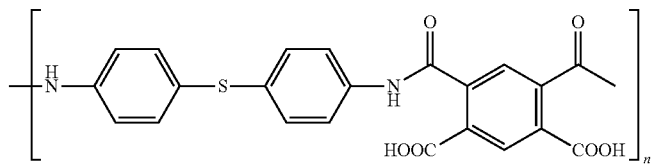
Pyromellitic dianhydride (PMDA) + 4,4'-thiodianiline (TDA)
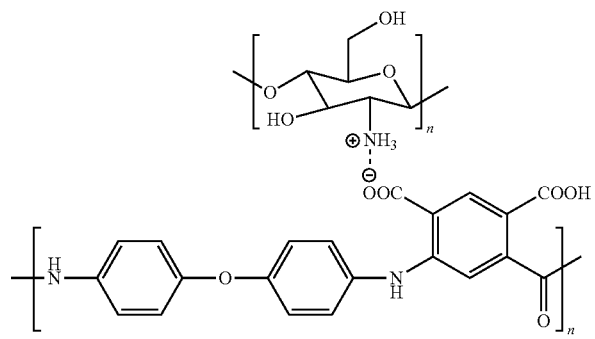
PAA/chitosan or PPDD/chitosan
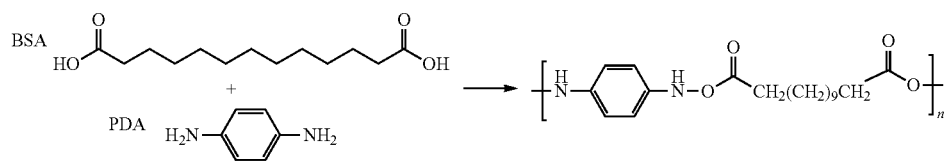
(PDA) makes polyamide
Brassylic acid (BSA) + phenylene diamine
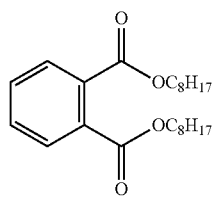
DIOP
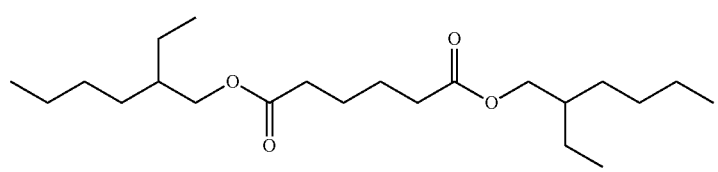 [SMILES: CCCCC(CC)COC(=O)CCCCC(=O)OCC(CC)CCCC]
DOA Table S-continued Examples of Proposed Thermoplastic PAA Film Formulations

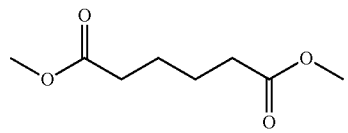

DMAD
External plasticization by adding dioctyl adipate (DOA) or dimethyl adipate (DMAD) to PAA

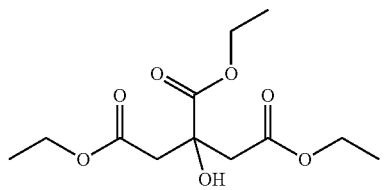 [SMILES: CCOC(=O)CC(O)(CC(=O)OCC)C(=O)OCC]

External plasticization by adding tributyl citrate plasticizer to PAA.
citrate plasticizers are safer with better biodegradability

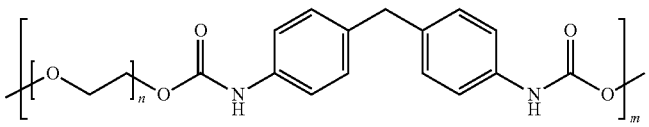

Poly(ethylene glycol) + 4,4'-methylenebis(phenyl isocyanate) (makes polyurethane)

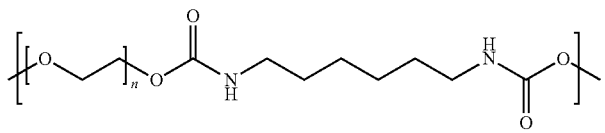

Poly(ethylene glycol) + hexamethylene diisocyanate (makes polyurethane)

Various Thermoplastic PAA films can be developed using various calculated concentrations of acid/amine, plasticizers, and monomers. These concentrations can be derived using the concept of critical branching coefficient. Mixtures of Thermoplastic PAA films can incorporate plasticizers (e.g. adipates, phthalates, and citrates) and/or two polymer chains (e.g PAA and chitosan) interacting via hydrogen bonding and electrostatic forces. The main polymer chains can move freely using these formulations.

Additional formulations can include the use of shorter or longer alkyl chains and a range of other dicarboxylic acids (e.g. oleic acids, palmitoleic acid, sapienic acid, and linoleic acid). Other materials to be added for the formation of the Thermoplastic PAA films can include low to high polarity esters (e.g. nitriles, polychloroprene, chlorinated polyethylene and epichlorohydrins) in order to decrease the attraction between polymer chains to make them more flexible. A range of esters (e.g. sabacates, terephthalates, gluterates and azelates) are options. These polymers can be synthesized in environmentally-friendly solvents.

The Thermoplastic PAA films can be analyzed in several ways, for example their structures can be characterized using 1H and 13C Nuclear Magnetic Resonance (1H NMR) Spectroscopy and Heteronuclear Single Quantum Coherence (HSQC) spectroscopy of the 1H-13C system. The polymerization can be validated via Infrared Spectroscopy (IR) by analyzing changes in the functional groups. The molecular weights can be determined via size exclusion chromatography. Also, Differential Scanning calorimetry (DSC) can be used to study the thermal transitions of the polymers.

These Thermoplastic PAA films exhibit a decrease in the glass transition temperature (Tg) for the films containing plasticizers in their DSC curves. For all formulations, the appearance of a crystallization temperature (Tc) peak is evident in the DSC curves. This peak indicates the crystallinity of the polymers upon cooling, which also suggests thermoplasticity. Also, these films have an increase in plasticity and a reduction in rigidity due to an absence or a relatively low amount of covalent crosslinking.

Throughout the application the following acronyms are used when discussing PAA films. The meaning of these abbreviations appears below:
PAA: Poly(amic) acid
GA: Glutaraldehyde
A-alanine
W-tryptophane
CS-Chitosan
SA-Sulfanilic acid
I-isoleucine
K-L-Lysine
CA-cellulose acetate
pAS-p-aminoscalicylic acid
PDA-PAA-p-phenylenedianiline+pyromellitic dianhydride PAA
IZ-Carbodiimizole
pAB-: p-aminobenzoic acid
PCL-3-chloro-4-aminobenzoic acid
C-cysteine
BB-2 benzoylbenzoic acid 5AS-5-aminosalycylic acid
4AS-p-aminoscalicylic acid
Ser-L-Serin
DA-D-glucosamine
SN-sulfanilamide
T-L-Threonine The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

The invention claimed is:

1. A method of packaging a food material, the method comprising:
   covering at least a portion of the food material with a film, the film comprising polyamic acid (PAA); glutaraldehyde (GA); and a small molecule selected from the group consisting of 2-benzylbenzoyl (BB), polycaprolactone (PCl), D-glucosamine (DA), dipropylene glycol (DP), p-aminosalicylic acid (pAS), sulfanilic acid (SA), and 5-aminosalicylic acid (5AS).

2. The method of claim 1, wherein the film is provided on a roll, the film provided with a predetermined width and a predetermined length.

3. The method of claim 1, wherein the small molecule is 2-benzylbenzoyl (BB).

4. The method of claim 1, wherein the small molecule is polycaprolactone (PCl).

5. The method of claim 1, wherein the small molecule is D-glucosamine (DA).

6. The method of claim 1, wherein the small molecule is dipropylene glycol (DP).

7. The method of claim 1, wherein the small molecule is p-aminosalicylic acid (pAS).

8. The method of claim 1, wherein the small molecule is sulfanilic acid (SA).

9. The method of claim 1, wherein the small molecule is 5-aminosalicylic acid (5AS).

10. A method of monitoring food spoilage of a food product, the method comprising:
    applying a polyamic acid (PAA) film to at least a portion of the food product, wherein the film comprises a small molecule selected from the group consisting of 2-benzylbenzoyl (BB), polycaprolactone (PCl), D-glucosamine (DA), dipropylene glycol (DP), p-aminosalicylic acid (pAS), sulfanilic acid (SA), and 5-aminosalicylic acid (5AS); and
    monitoring the film for a change in at least one of a color of the film and a conductivity of the film.

11. The method of claim 10, wherein the small molecule is 2-benzylbenzoyl (BB).

12. The method of claim 10, wherein the small molecule is polycaprolactone (PCl).

13. The method of claim 10, wherein the small molecule is D-glucosamine (DA).

14. The method of claim 10, wherein the small molecule is dipropylene glycol (DP).

15. The method of claim 10, wherein the small molecule is p-aminosalicylic acid (pAS).

16. The method of claim 10, wherein the small molecule is sulfanilic acid (SA).

17. The method of claim 10, wherein the small molecule is 5-aminosalicylic acid (5AS).

* * * * *

```
                             SEQUENCE LISTING

<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
cttggtcatt tagaggaagt aa                                                  22

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tcctccgctt attgatatgc                                                     20

<210> SEQ ID NO 3
<211> LENGTH: 424
<212> TYPE: DNA
<213> ORGANISM: Fusarium oxysporum

<400> SEQUENCE: 3
agttggggtt taacggcgtg gccgcgacga ttaccagtaa cgagggcttt actactacgc         60
tatggaagct cgacgtgacc gccaatcaat ttgaggacag gcatgcccgc cagaatactg        120
gcgggcgcaa tgtgcgttca aagattcgat gattcactga attctgcaat tcacattact        180
tatcgcattt tgctgcgttc ttcatcgatg ccagaaccaa gagatccgtt gttgaaagtt        240
ttgatttatt tatggtttta ctcagaagtt acatatagaa acagagtttt aggggtcctc        300
tggcgggccg tcccgtttta ccgggagcgg gctgatccgc cgaggcaaca agtggtatgt        360
tcacaggggt ttgggagttg taaactcggt aatgatccct ccgctggttc accaacggag        420
acct                                                                     424

<210> SEQ ID NO 4
<211> LENGTH: 319
<212> TYPE: DNA
<213> ORGANISM: Fusarium oxysporum

<400> SEQUENCE: 4
cccggggcaa ggggcgggcg gcgttggatt ttgcgggacc cttaacaccc gcttcagccg         60
```

```
cagcgggcgc cgccgccccg aggcccggcg ccgatctaac aagtaataca tctcaaaggt      120
gtccaaccgt atccaaccag tggacgtccg agggtcgcgc cgtttgagtg tcatgttaat      180
atcaactctg atggttttt gttaatcatt ggatgttgga cttggggatc ccgtcacagt       240
cgactactga tgagtactat agactacgca tcgcgcagct gatatattta atgtctacgt     300
atatcaatcc attaataaa                                                    319

<210> SEQ ID NO 5
<211> LENGTH: 794
<212> TYPE: DNA
<213> ORGANISM: Fusarium oxysporum
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t

<400> SEQUENCE: 5
ccgcgnggag gtttctggac cgctgtccga ccgcgccgct ccgttcggcg ccgagttcca       60 cttttgtcccc tcattnatat tgtcaattac gcgggtattc caccgattcc aggtcacttc    120
gaagttgggg tttaacgcg tggccgcgac gattaccagt aacgagggtt ttactactac      180
gctatggaag ctcgacgtga ccgccaatca atttgaggaa cgcgaattaa cgcgagtccc     240
aacaccaagc tgtgcttgag ggttgaaatg acgctcgaac aggcatgccc gccagaatac    300
tggcgggcgc aatgtgcgtt caaagattcg atgattcact gaattctgca attcacatta   360
cttatcgcat tttgctgcgt tcttcatcga tgccagaacc aagagatccg ttgttgaaag   420
ttttgattta tttatggttt tactcagaag ttacatatag aaacagagtt ttaggggtcc    480
tctggcgggc cgtcccgttt taccgggagc gggctgatcc gccgaggcaa caagtggtat   540
gttcacaggg gtttgggagt tgtaaactcg gtaatgatcc ctccgctggt tcaccaacgg   600
agacctgtna caactttnac tccctctaat gacaaaatca ctantgaatc ccgccgccgc    660
agtcacatat gggagagctc ccacgcgtgg atctanctga gtatctatan gtcacctaat    720
actggcgtat ctggtatacc gtcccggtaa tgttatcccc cattcccac tcaccgaact     780 aatgtaacgg gtca                                                      794

<210> SEQ ID NO 6
<211> LENGTH: 605
<212> TYPE: DNA
```

<213> ORGANISM: Fusarium oxysporum
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t

<400> SEQUENCE: 6

```
ccctctttna aattcttttt agggggggc gacttcccgg cggggctact cagtcatgga    60
tctctggatg caataanata ttagcgatct tcgccngtga accacgagga ggatcacnag   120
tgcaacccca aaccctgtg aacataccac ttgttgccgc gccgatncgn ccgccccgt    180
aaaacgggac ggcccgccag aggacccta aaactctgtt tctatatgta acttctgagt    240
aaaaccataa ataaatcaaa actttcaaca acggatctct tggttctggc atcgatgaag   300
aacgcagcaa aatgcgataa gtaatgtgaa ttgcagaatt cagtgaatca tcgaatcttt   360
gaacgcacat tgcgccccgcc agtattctgg cgggcatgcc tgttcgagcg tcatttcaac   420
cctcaagcac agcttggtgt tgggactcgc gtnaattcgc gtncctcaa attgattggc    480
ggtcacgtca agcttccata gcgtaatagt aaaaaccctc gttactggta atctccggcc   540
acgccgtaac cccactttga atgtgacccg atcggtagga taccgcgaac taactatata   600
cgaga                                                               605
```

<210> SEQ ID NO 7
<211> LENGTH: 873
<212> TYPE: DNA
<213> ORGANISM: Fusarium oxysporum
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (829)..(829)
<223> OTHER INFORMATION: n is a, c, g, or t
<220> FEATURE:
<221> NAME/KEY: misc_feature
<222> LOCATION: (864)..(864)
<223> OTHER INFORMATION: n is a, c, g, or t
<220> FEATURE:
<221> NAME/KEY: misc_feature
<222> LOCATION: (868)..(868)
<223> OTHER INFORMATION: n is a, c, g, or t

<400> SEQUENCE: 7

```
ccgggcggga ggtttngtta gggatcccgt cgctcgacgc gcgccgcgcc ggtcggcgcg      60
cgagtggcca tcggtgtccg cctcattcag tatngtcaag tgtgacgcgg gtattcctca     120
cccgattcca ggtgcacttc cagaagttgg ggtttaacgg cgtggccgcg acgattacca     180
gtaacgaggg ctttactact acgctatgga agctcgacgt gaccgccaat caatttgagg     240
aacgcgaatt aacgcgagtc ccaacaccga gctgtgcttg agggttgaaa tgacgctcga     300
acaggcatgc ccgccagaat actggcgggc gcaatgtgcg ttcaaagatt cgatgattca     360
ctgaattctg caattcacat tacttatcgc attttgctgc gttcttcatc gatgccagaa     420
ccaagagatc cgttgttgaa agttttgatt tatttatggt tttactcaga agttacatat     480
agaaacagag ttttaggggt cctctggcgg gccgtcccgt tttaccggga gcgggctgat     540
ccgccgaggc aacaagtggt atgttcacag gggtttggga gttgtaaact cggtaatgat     600
ccctccgctg gttcaccaac ggagaccttg ttacgacttt tacttcctct aaatgaccaa     660
gaatcactag tgaattcgcg gccgcctgca ggtcaacata tggagagctc cacccgtgga     720
tgcatanctg agtatctata gtgtccctaa tacttggcgt atcatggcat accggttccg     780
tgtgaaatgt tatcgctcac catccaacaa atacnacccg aaacttaang ttaaccgggg     840
gtcctaatag tgaccaccca ttantgcntt gcc                                  873
```

<210> SEQ ID NO 8
<211> LENGTH: 822
<212> TYPE: DNA
<213> ORGANISM: Fusarium oxysporum
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (736)..(736)
<223> OTHER INFORMATION: n is a, c, g, or t
<220> FEATURE:
<221> NAME/KEY: misc_feature
<222> LOCATION: (739)..(739)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t

<400> SEQUENCE: 8

```
cggaggtttt tgggncncc gtcgcgacna gggccctcac ttggagctcc gaccggncgc    60
gccaattaac tcatggattt cggggattta gaggaagtaa aagttttaac aggtgtcccg   120
ttggtgaacc agcggaggga tcttaccgag tttacactcc caaacccctg tgaacatacc   180
acttgttgcc tcggcggatc agcccgctcc cggtaaaacg ggacggcccg ccagaggacc   240
cctaaaactc tgtttctata tgtaacttct gagtaaaacc ataaataaat caaaactttc   300
aacaacggat ctcttggttc tggcatcgat gaagaacgca gcaaaatgcg ataagtaatg   360
tgaattgcag aattcagtga atcatcgaat ctttgaacgc acattgcgcc cgccagtatt   420
ctggcgggca tgcctgttcg agcgtcattt caaccctcaa gcacagctcg gtgttgggac   480
tcgcgttaat tcgcgttcct caaattgatt ggcggtcacg tcgagcttcc atagcgtagt   540
agtaaagccc tcgttactgg taatcgtcgc ggccacgccg ttaaacccca acttctgaat   600
gttgacctcg gatcaggtag gaatacccgc tgaacttaag catatcaata agcggaggaa   660
atcgaattcc gcgggcgcca tggcggccgg aacatcaact tcggccaatc ccctatatat   720
gtatacatcc tggcgnttna caactggacg ggaaacgcgt accactatcc tgcncatccc   780
ttccccggct attcaagccc ccaccctcca atgccccaat gg                     822
```

<210> SEQ ID NO 9
<211> LENGTH: 494
<212> TYPE: DNA
<213> ORGANISM: Fusarium oxysporum
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t

<400> SEQUENCE: 9

```
ccggaggtna gncagcaccc gccccctngga acccnccccat attctacctg tnacccattt   60
aggcatacaa ttgggtgaac gctggcccac ataccctaaca gggctacact accatggaag   120
ccactgaccg ccatcatttg aggaacgcaa ttaacgcgag tcccaacacc gagctgtgct   180
tgagggttga aatgacgctc gaacaggcat gcccgccaga atactggcgg gcgcaatgtg   240
cgttcaaaga ttcgatgatt cactgaattc tgcaattcac attacttatt cgcattttgc   300
tgcgttcttc atcgatgcca gaaccaagag atccgttgtt gaaagttttg atttatttat   360
ggtttactca gaagttacat atagaaacag agttttaggg gtcctctggc gggcccgtcc   420
cgttttaccg ggagcgggct gatccgccna gcaacaagtg gtatgttaca ggggttggga   480
gttgtaaccg taat                                                     494
```

<210> SEQ ID NO 10
<211> LENGTH: 785
<212> TYPE: DNA
<213> ORGANISM: Fusarium oxysporum
<220> FEATURE:
<221> NAME/KEY: misc_feature
<222> LOCATION: (774)..(774)
<223> OTHER INFORMATION: n is a, c, g, or t

<400> SEQUENCE: 10

| | | | | | |
|---|---|---|---|---|---|
| gggcgttata | tcttgtggtc | tcccgcgctt | gaggagctct | cccatatgtg | tcgacctgca | 60 |
| ggcggccgcg | aattcactag | tgattcttgg | tcatttagag | gaagtaaaag | tcgtaacaag | 120 |
| gtctccgttg | gtgaaccagc | ggagggatca | ttaccgagtt | tacaactccc | aaacccctgt | 180 |
| gaacatacca | cttgttgcct | cggcggatca | gcccgctccc | ggtaaaacgg | gacggcccgc | 240 |
| cagaggaccc | ctaaaactct | gtttctatat | gtaacttctg | agtaaaacca | taaataaatc | 300 |
| aaaactttca | acaacggatc | tcttggttct | ggcatcgatg | aagaacgcag | caaaatgcga | 360 |
| taagtaatgt | gaattgcaga | attcagtgaa | tcatcgaatc | tttgaacgca | cattgcgccc | 420 |
| gccagtattc | tggcgggcat | gcctgttcga | gcgtcatttc | aaccctcaag | cacagctcgg | 480 |
| tgttgggact | cgcgttaatt | cgcgttcctc | aaattgattg | gcggtcacgt | cgagcttcca | 540 |
| tagcgtagta | gtaaagccct | cgttactggt | aatcgtcgcg | gccacgccgt | taaaccccaa | 600 |
| cttctgaatg | ttgacctcgg | atcaggtagg | aatacccgct | gaacttaagc | atatcaataa | 660 |
| gcggaggaaa | tcgaattccg | ccggccgcca | tggcggccgg | gagcatgcga | agtcgggccc | 720 |
| aattcgccct | atagtgagtt | ttattacaat | tcactggccc | gtcttttaca | aacnttgtga | 780 |
| ctggg | | | | | | 785 |

<210> SEQ ID NO 11
<211> LENGTH: 348
<212> TYPE: DNA
<213> ORGANISM: Trichaptum biforme
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (334)..(334)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t

<400> SEQUENCE: 11

```
ggatcgcgcc gggggtgggg cggggcctta agattttacg agaattaggt tagagatttt      60
gtcttagatc gagacagact caagaatagt tcatggtcaa gagtaggatc taacaagtaa     120
tacatctcaa aggtgtccaa ccgtatccaa ccagtggacg gatcttnacc gagtggtgcg     180 caggggcgc atccccttgt cgaacccact acccctggat ggctcgtagc tccatcggac      240
gggtgccggg ggggatcgc gtcactgtcg antactgatg ngaactatag actatngatc      300
cgggcagctg atatatccna natctatgta tatnaatcca tnaataaa                  348
```

<210> SEQ ID NO 12
<211> LENGTH: 813
<212> TYPE: DNA
<213> ORGANISM: Trichaptum biforme
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t -continued

```
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (265)..(265)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (387)..(387)
```

```
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (409)..(409)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (461)..(461)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t
<220> FEATURE:
<221> NAME/KEY: misc_feature
<222> LOCATION: (482)..(482)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t
<220> FEATURE:
<221> NAME/KEY: misc_feature
<222> LOCATION: (491)..(491)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (512)..(512)
<223> OTHER INFORMATION: n is a, c, g, or t
<220> FEATURE:
<221> NAME/KEY: misc_feature
<222> LOCATION: (526)..(526)
<223> OTHER INFORMATION: n is a, c, g, or t
<220> FEATURE:
<221> NAME/KEY: misc_feature
<222> LOCATION: (529)..(529)
<223> OTHER INFORMATION: n is a, c, g, or t
<220> FEATURE:
<221> NAME/KEY: misc_feature
```

```
<222> LOCATION: (532)..(532)
<223> OTHER INFORMATION: n is a, c, g, or t
<220> FEATURE:
<221> NAME/KEY: misc_feature
<222> LOCATION: (538)..(538)
<223> OTHER INFORMATION: n is a, c, g, or t
<220> FEATURE:
<221> NAME/KEY: misc_feature
<222> LOCATION: (541)..(541)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (559)..(560)
<223> OTHER INFORMATION: n is a, c, g, or t
<220> FEATURE:
<221> NAME/KEY: misc_feature
<222> LOCATION: (563)..(563)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (593)..(593)
<223> OTHER INFORMATION: n is a, c, g, or t
<220> FEATURE:
<221> NAME/KEY: misc_feature
<222> LOCATION: (697)..(697)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (727)..(727)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t
<220> FEATURE:
<221> NAME/KEY: misc_feature
<222> LOCATION: (739)..(739)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<220> FEATURE:
```

<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (788)..(788)
<223> OTHER INFORMATION: n is a, c, g, or t
<220> FEATURE:
<221> NAME/KEY: misc_feature
<222> LOCATION: (803)..(803)
<223> OTHER INFORMATION: n is a, c, g, or t

<400> SEQUENCE: 12
nnnntgtttt tcgggcgcgt cgcgcggggc cctctctggg gagcgtccgc cggncgtccg      60
ccgnttacac taagatgnat ttgcgagcac gngctaacat gagatagtta taggcgttnc     120
gagtctttct acgngagctc aaatccccta gntcactgag nctccccagc acgngctaca     180
gncctccttg cagagagggg cgctctcttt cgggatcaga atatntacac gggcgaaaaa     240
agagggcccc cntnatancn anacncgaga cagtgcgaca gnctggacnc ngntacacag     300
gttctgagag tcgntggngn ggaagacagt gagacgggnc aaacagggaa aaccananag     360
ntcgagtttg tncngcngtg gtncncnatn ggaaaaanct catcccgtng aagggcccac     420
cgangagccc ccnacnaaaa tnctngggt tgggcccggc nctngttccn accaaaaang     480
tnatngttct ncttgtaatn tctggggggg gngtgcccgc ccccngtnc angaattnta     540 ncantangan cgnaanagnn tgntgggcaa aaacggaggt tccctcnacn ctgaatatt     600 aacatatttc cccccccacc aaaatattgg ttcctcccac cccgccccc ttttgtgggg     660 cccccgcggg tttggggttt ccaattccct cggcctntnt tggccagaag gaaggtgggg     720
ggcngcngan gaaaaaaant ccgcaaanan ggccangtnc aagttgcnac ngcnaatngt     780
ggggcctnat ttttggaaac cancaattgg ggt                                 813

<210> SEQ ID NO 13
<211> LENGTH: 266
<212> TYPE: DNA
<213> ORGANISM: Trichaptum biforme
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t -continued

```
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (149)..(149)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (167)..(167)
```

```
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t

<400> SEQUENCE: 13
ccggggcngc cggggcgcgt cgccggcngn cngcggcncn tnggcngccc gcngcgcgag      60
cgcagcgngc cggtggtgcn cgcgcncacc tcccgtccca cctccttcgc gctcgntgcg     120
cncanctcta tantangtna gagnagatng aatactagna ctatacntat acntatagca    180
cgtaggacga ngnaagngan tcncganatt tttatttggc cgattntcct atantgnana    240 ngggggaaaan ggnagnaatt tttgaa                                          266

<210> SEQ ID NO 14
<211> LENGTH: 817
<212> TYPE: DNA
<213> ORGANISM: Trichaptum biforme
```

-continued

```
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (184)..(184)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (325)..(325)
<223> OTHER INFORMATION: n is a, c, g, or t
<220> FEATURE:
<221> NAME/KEY: misc_feature
<222> LOCATION: (328)..(328)
```

```
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (338)..(338)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (457)..(457)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t
<220> FEATURE:
<221> NAME/KEY: misc_feature
```

```
<222> LOCATION: (491)..(491)
<223> OTHER INFORMATION: n is a, c, g, or t
<220> FEATURE:
<221> NAME/KEY: misc_feature
<222> LOCATION: (496)..(496)
<223> OTHER INFORMATION: n is a, c, g, or t
<220> FEATURE:
<221> NAME/KEY: misc_feature
<222> LOCATION: (499)..(499)
<223> OTHER INFORMATION: n is a, c, g, or t
<220> FEATURE:
<221> NAME/KEY: misc_feature
<222> LOCATION: (505)..(505)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (563)..(563)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (624)..(625)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
```

```
<221> NAME/KEY: misc_feature
<222> LOCATION: (687)..(688)
<223> OTHER INFORMATION: n is a, c, g, or t
<220> FEATURE:
<221> NAME/KEY: misc_feature
<222> LOCATION: (691)..(691)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (716)..(716)
<223> OTHER INFORMATION: n is a, c, g, or t
<220> FEATURE:
<221> NAME/KEY: misc_feature
<222> LOCATION: (719)..(719)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (732)..(733)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (766)..(766)
<223> OTHER INFORMATION: n is a, c, g, or t

<400> SEQUENCE: 14
cggcggtggg tttggctcgt gggccncccg tgcgcggggg gcgccgcctc ccttttgcg      60 gacgcgtccn gcccgggcgc gcccgncgcg gtanacggct anagtggagt gtgttgcagt    120
gcacgngcta tacatggtag tagttatagg cagttgggcn tgagtactgc tctgtacngg    180
gagnctcaaa tcccatgagt cccgtggagg ctcccccgaca cgggcgtaca ggccctcctt    240
tgagagaggg ggcgctctct ttccggacag anatatacgc gggcgaaaan gagggcccnc    300
ntttntntcg gnacncnagg gtcangtncn gagcangntc ntagnacccc ccggggaaac    360
aacanggttt tnctcgacga aagtncgngt gggggcgggg ggaaagaacc aagtngaaag    420
aacgggggcc cantaacagg aggaaaaacc caaagangan tcngaatttg tnccncngtg    480
gtnaaccnat nggaanganc ttatncngtn gaagggccna cngangagcc cccnacngac    540
atncttgggg gttgggcccg gcnctngttc ccaaccaana ccggttaatn gttcctccct    600
tgtttaatnt ctgggggggg ggtnngtgcc ccggcccccc cctcggttca aaagaaattt    660
ntaaccaaan aaggaacgca aaaaagnntg ngtgccaaaa accgnaggtt ccctcnacnc    720
tngaattana cnnattcccn cgccaccaaa natttgttcc tcaacncggc cccctttgt    780 ggggcccccg gggtttggtg tttctaaatt ccttggc                              817

<210> SEQ ID NO 15
<211> LENGTH: 808
<212> TYPE: DNA
<213> ORGANISM: Trichaptum biforme
```

```
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (787)..(787)
<223> OTHER INFORMATION: n is a, c, g, or t

<400> SEQUENCE: 15
cccggcgaat gttttatggg gtcatgttcg accgcgccgt ccggttggcg gagttncatt      60
ttcgtgatct anaagagata aaatggctaa acaggtttac cgtaggttat tanccgcgga    120
aggatcttaa cagttttgaa gtgggcttga tgctggcttg taacagagca ctgtgctcag    180
tcccgctcca atccattcaa ccctgtgca ctattcggag tgttgcaagc taagacaatg     240
tggggagtgg tcccggttgt atttctaatg cgacttgggc ttactttcaa acggtcaagg    300
cttgtcctcc ggtttatata caaacacttt tattgtcttg tcgaatgtat tagcctctcg    360
ttaggcgaaa tttaaataca actttcaaca acggatctct tggctctcgc atcgatgaag    420
aacgcagcga aatgcgataa gtaatgtgaa ttgcagaatt cagtgaatca tcgaatcttt    480
gaacgcacct tgcgctcctt ggctattccg aggagcatgc ctgtttgagt gtcatgttaa    540
tatcaactct gatggttttt tgttaatcat tggatgttgg acttggaggt tcgtgctggc    600
tgcaaagtcg gctcctcttg aatgcattag cttggacctg tgcgcgtttg ctagcggtgt    660
aatacattta attcaccacg ggccgtgtca ctattagggt ctgcttctat tcgtcctacc    720
ggacaataat aacttatgac ctgactcaat aggtagacac cccgactaac ttaataccga    780
gaatcantat ccgcccgcgt acatgaaa                                       808

<210> SEQ ID NO 16
<211> LENGTH: 784
<212> TYPE: DNA
<213> ORGANISM: Trichaptum biforme
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 16
ccagaaggat ttnatgaaac aagataagca gaggtccctc atcttnggac tccgacggcg     60
ncgccatata actcatgatt tcccgctcta ttgatatgct aagttttttag cgggtagtcc   120 accgatttga ggtcagagtc ataaagttta ttattgtccg gtaaggacga ttagaagcag    180
accctaatag tgacacggcc cgtggtgaat aaaatgtatt acaccgctag caaacgcgca    240
caggtccaag ctaatgcatt caagaggagc cgactttgca gccagcacga acctccaagt    300
ccaacatcca atgattaaca aaaaccatca gagttgatat taacatgaca ctcaaacagg    360
```

-continued

```
catgctcctc ggaatagcca aggagcgcaa ggtgcgttca aagattcgat gattcactga    420
attctgcaat tcacattact tatcgcattt cgctgcgttc ttcatcgatg cgagagccaa    480
gagatccgtt gttgaaagtt gtatttaaat ttcgcctaac gagaggctaa tacattcgac    540
aagacaataa aagtgtttgt atataaaccg gaggacaagc cttgaccgtt tgaaagtaag    600
cccaagtcgc attaaaaata caaccgggac cactccccac attgtcttag cttgcaacac    660
tccgaatagt gcacaggggt tgaatgatgg aacggactga cacagtgctc tgtacagcca    720
cataagccac tcaactcgta tgatcttccg cagtactacg aactgtacat ttattcccta    780
taca                                                                 784
```